US008741881B2

(12) United States Patent
Malladi et al.

(10) Patent No.: US 8,741,881 B2
(45) Date of Patent: *Jun. 3, 2014

(54) TESTOSTERONE GEL AND METHOD OF USE

(71) Applicants: Unimed Pharmaceuticals, LLC, North Chicago, IL (US); Besins Healthcare Luxembourg SARL, Luxembourg (LU)

(72) Inventors: Ramana Malladi, Marietta, GA (US); Jodi Stahlman, Smyrna, GA (US)

(73) Assignees: Unimed Pharmaceuticals, LLC, Marietta, GA (US); Besins Healthcare Luxembourg, SARL, Charlotte (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/831,231

(22) Filed: Mar. 14, 2013

(65) Prior Publication Data

US 2013/0210791 A1   Aug. 15, 2013

Related U.S. Application Data

(63) Continuation of application No. 13/180,327, filed on Jul. 11, 2011, now Pat. No. 8,466,137, which is a continuation of application No. 11/549,083, filed on Oct. 12, 2006, now abandoned.

(60) Provisional application No. 60/725,276, filed on Oct. 12, 2005.

(51) Int. Cl.
| A61K 31/56 | (2006.01) |
| A61K 31/568 | (2006.01) |
| C07J 1/00 | (2006.01) |
| C07C 49/00 | (2006.01) |

(52) U.S. Cl.
USPC ............ 514/177; 514/178; 552/638; 568/369

(58) Field of Classification Search
USPC .................... 514/177, 178; 552/638; 568/369
See application file for complete search history.

(56) References Cited

U.S. PATENT DOCUMENTS

| 2,155,658 A | 4/1939 | Herrman et al. |
| 2,232,508 A | 2/1941 | Bonanno |
| 3,068,188 A | 12/1962 | Beste et al. |
| 3,121,042 A | 2/1964 | Ercoli |
| 3,164,520 A | 1/1965 | Huber |
| 3,218,283 A | 11/1965 | Miller |
| 3,887,699 A | 6/1975 | Yolles |
| 3,888,995 A | 6/1975 | Katz et al. |
| 3,913,789 A | 10/1975 | Miller |
| 3,939,111 A | 2/1976 | Schollenberger et al. |
| 3,989,816 A | 11/1976 | Rajadhyaksha |
| 4,009,254 A | 2/1977 | Renold |
| 4,078,060 A | 3/1978 | Benson |
| 4,083,973 A | 4/1978 | Van der Vies |
| 4,161,948 A | 7/1979 | Bichon |
| 4,197,316 A | 4/1980 | Yu et al. |
| 4,299,826 A | 11/1981 | Luedders |
| 4,346,709 A | 8/1982 | Schmitt |
| 4,424,363 A | 1/1984 | Plath et al. |
| 4,440,777 A | 4/1984 | Zupan |
| 4,442,094 A | 4/1984 | Atkinson et al. |
| 4,447,562 A | 5/1984 | Ivani |
| 4,478,822 A | 10/1984 | Haslam et al. |
| 4,496,455 A | 1/1985 | Linder et al. |
| 4,496,556 A | 1/1985 | Orentreich |
| 4,557,934 A | 12/1985 | Cooper |
| 4,563,473 A | 1/1986 | Hofman et al. |
| 4,615,697 A | 10/1986 | Robinson |
| 4,631,188 A | 12/1986 | Stoy et al. |
| 4,663,157 A | 5/1987 | Brock |
| 4,683,242 A | 7/1987 | Poser |
| 4,690,775 A | 9/1987 | Schott et al. |
| 4,695,465 A | 9/1987 | Kigasawa et al. |
| 4,699,779 A | 10/1987 | Palinczar |
| 4,704,282 A | 11/1987 | Campbell et al. |
| 4,725,439 A | 2/1988 | Campbell et al. |
| 4,745,160 A | 5/1988 | Churchill et al. |
| 4,767,627 A | 8/1988 | Caldwell et al. |
| 4,780,320 A | 10/1988 | Baker |
| 4,788,062 A | 11/1988 | Gale et al. |
| 4,791,099 A | 12/1988 | Aroonsakul |
| 4,820,724 A | 4/1989 | Nimni |
| 4,855,305 A | 8/1989 | Cohen |
| 4,861,764 A | 8/1989 | Samour et al. |
| 4,863,911 A | 9/1989 | Anderson et al. |
| 4,863,970 A | 9/1989 | Patel et al. |
| 4,867,982 A | 9/1989 | Campbell et al. |
| 4,906,169 A | 3/1990 | Chien et al. |
| 4,919,937 A | 4/1990 | Mauvais-Jarvis et al. |
| 4,920,203 A | 4/1990 | Tang et al. |
| 4,946,870 A | 8/1990 | Partain et al. |
| 4,954,487 A | 9/1990 | Cooper et al. |
| 4,981,696 A | 1/1991 | Loomis et al. |
| 4,994,265 A | 2/1991 | White |
| 5,013,553 A | 5/1991 | Southard et al. |
| 5,023,252 A | 6/1991 | Hseih |

(Continued)

FOREIGN PATENT DOCUMENTS

| AU | 4998490 | 9/1990 |
| AU | 9141391 | 6/1992 |

(Continued)

OTHER PUBLICATIONS

U.S. Appl. No. 13/781,849, filed Mar. 2013, Dudley et al.*
U.S. Appl. No. 13/902,035, filed May 2013, Dudley et al.*
Co-pending U.S. Appl. No. 13/831,189, filed Mar. 14, 2013.
Co-pending U.S. Appl. No. 13/831,207, filed Mar. 14, 2013.
Co-pending U.S. Appl. No. 13/831,217, filed Mar. 14, 2013.
Notice of Allowance for U.S. Appl. No. 13/180,316 dated Feb. 21, 2013 (15 pages).
Notice of Allowance for U.S. Appl. No. 13/180,327 dated Feb. 19, 2013 (16 pages).
Notice of Allowance for U.S. Appl. No. 13/253,848 dated Feb. 20, 2013 (14 pages).

(Continued)

*Primary Examiner* — Kara R McMillian
(74) *Attorney, Agent, or Firm* — Lisa V. Mueller; Michael Best & Friedrich LLP

(57) ABSTRACT

The present invention relates to an improved transdermal hydroalcoholic testosterone gen formulation that provides, among other things, a desirable pharmacokinetic hormone profile, and methods of use.

29 Claims, 6 Drawing Sheets

(56) References Cited

U.S. PATENT DOCUMENTS

| | | |
|---|---|---|
| 5,026,692 A | 6/1991 | Kuno et al. |
| 5,036,100 A | 7/1991 | Deboeck et al. |
| 5,053,227 A | 10/1991 | Chiang et al. |
| 5,059,603 A | 10/1991 | Rubin |
| 5,071,657 A | 12/1991 | Oloff et al. |
| 5,073,545 A | 12/1991 | Arima et al. |
| 5,116,828 A | 5/1992 | Miura et al. |
| 5,122,519 A | 6/1992 | Ritter |
| 5,152,997 A | 10/1992 | Ebert et al. |
| 5,200,190 A | 4/1993 | Azuma et al. |
| 5,208,013 A | 5/1993 | Klein |
| 5,223,261 A | 6/1993 | Nelson et al. |
| 5,231,087 A | 7/1993 | Thornfeldt |
| 5,231,382 A | 7/1993 | Tanaka |
| 5,232,703 A | 8/1993 | Blank |
| 5,238,933 A | 8/1993 | Catz et al. |
| 5,238,944 A | 8/1993 | Wick et al. |
| 5,256,652 A | 10/1993 | El-Rashidy |
| 5,324,521 A | 6/1994 | Gertner et al. |
| 5,326,566 A | 7/1994 | Parab |
| 5,326,790 A | 7/1994 | Thornfeldt |
| 5,332,577 A | 7/1994 | Gertner et al. |
| 5,340,584 A | 8/1994 | Spicer et al. |
| 5,340,585 A | 8/1994 | Pike et al. |
| 5,340,586 A | 8/1994 | Pike et al. |
| 5,346,901 A | 9/1994 | Bell et al. |
| 5,362,497 A | 11/1994 | Yamada et al. |
| 5,362,886 A | 11/1994 | Berglund |
| 5,413,794 A | 5/1995 | Suzuki et al. |
| 5,436,634 A | 7/1995 | Kanazawa |
| 5,446,025 A | 8/1995 | Lu |
| 5,446,070 A | 8/1995 | Mantelle |
| 5,460,820 A | 10/1995 | Ebert et al. |
| 5,482,970 A | 1/1996 | Kim et al. |
| 5,487,898 A | 1/1996 | Lu et al. |
| 5,550,107 A | 8/1996 | Labrie |
| 5,589,498 A | 12/1996 | Mohr |
| 5,607,691 A | 3/1997 | Hale et al. |
| 5,610,150 A | 3/1997 | Labrie |
| 5,629,019 A | 5/1997 | Lee et al. |
| 5,629,021 A | 5/1997 | Wright |
| 5,639,743 A | 6/1997 | Kaswan et al. |
| 5,641,504 A | 6/1997 | Lee et al. |
| 5,643,899 A | 7/1997 | Elias et al. |
| 5,648,350 A | 7/1997 | DeLignieres |
| 5,651,973 A | 7/1997 | Moo-Young et al. |
| 5,654,337 A | 8/1997 | Roentsch et al. |
| 5,656,286 A | 8/1997 | Miranda et al. |
| 5,662,925 A | 9/1997 | Ebert et al. |
| 5,665,377 A | 9/1997 | Gonella |
| 5,676,956 A | 10/1997 | Duffy et al. |
| 5,686,112 A | 11/1997 | Liedtke |
| 5,708,038 A | 1/1998 | Davis |
| 5,716,638 A | 2/1998 | Touitou |
| 5,719,197 A | 2/1998 | Kanios et al. |
| 5,723,114 A | 3/1998 | Thornfeldt et al. |
| 5,725,874 A | 3/1998 | Oda et al. |
| 5,730,987 A | 3/1998 | Omar |
| 5,731,303 A | 3/1998 | Hsieh |
| 5,731,339 A | 3/1998 | Lowrey |
| 5,744,162 A | 4/1998 | Okabe et al. |
| 5,760,096 A | 6/1998 | Thornfeldt et al. |
| 5,769,274 A | 6/1998 | Behar |
| 5,770,606 A | 6/1998 | El-Rashidy et al. |
| 5,776,923 A | 7/1998 | Labrie |
| 5,780,050 A | 7/1998 | Jain et al. |
| 5,783,208 A | 7/1998 | Venkateshwaran et al. |
| 5,785,991 A | 7/1998 | Burkoth et al. |
| 5,788,983 A | 8/1998 | Chien et al. |
| 5,788,984 A | 8/1998 | Guenther et al. |
| 5,807,568 A | 9/1998 | Cody et al. |
| 5,807,849 A | 9/1998 | Labrie |
| 5,807,957 A | 9/1998 | Samour et al. |
| 5,837,289 A | 11/1998 | Grasela et al. |
| 5,844,103 A | 12/1998 | Au et al. |
| 5,847,128 A | 12/1998 | Martin et al. |
| 5,849,729 A | 12/1998 | Zoumas et al. |
| 5,855,905 A | 1/1999 | Oettel et al. |
| 5,855,920 A | 1/1999 | Chein |
| 5,859,006 A | 1/1999 | Daugan |
| 5,863,560 A | 1/1999 | Osborne |
| 5,874,074 A | 2/1999 | Smith |
| RE36,138 E | 3/1999 | Suzuki et al. |
| 5,877,216 A | 3/1999 | Place et al. |
| 5,880,117 A | 3/1999 | Arnold |
| 5,881,926 A | 3/1999 | Ross |
| 5,882,676 A | 3/1999 | Lee et al. |
| 5,891,462 A | 4/1999 | Carrara |
| 5,894,019 A | 4/1999 | Hesse et al. |
| 5,902,603 A | 5/1999 | Chen et al. |
| 5,906,830 A | 5/1999 | Farinas et al. |
| 5,908,619 A | 6/1999 | Scholz |
| 5,908,638 A | 6/1999 | Huber et al. |
| 5,926,953 A | 7/1999 | Behar |
| 5,932,227 A | 8/1999 | Higo et al. |
| 5,935,949 A | 8/1999 | White |
| 5,942,545 A | 8/1999 | Samour et al. |
| 5,952,000 A | 9/1999 | Venkateshwaran et al. |
| 5,955,455 A | 9/1999 | Labrie |
| 5,962,021 A | 10/1999 | Hughes, Jr. et al. |
| 5,968,919 A | 10/1999 | Samour et al. |
| 5,972,377 A | 10/1999 | Jona et al. |
| 5,981,542 A | 11/1999 | Bigg et al. |
| 6,007,837 A | 12/1999 | Enscore et al. |
| 6,010,716 A | 1/2000 | Saunal et al. |
| 6,019,988 A | 2/2000 | Parab et al. |
| 6,019,997 A | 2/2000 | Scholz et al. |
| 6,024,974 A | 2/2000 | Li |
| 6,036,977 A | 3/2000 | Drizen et al. |
| 6,037,346 A | 3/2000 | Doherty, Jr. et al. |
| 6,046,244 A | 4/2000 | Buyuktimkin et al. |
| 6,051,555 A | 4/2000 | Hadley |
| 6,071,531 A | 6/2000 | Jona et al. |
| 6,075,028 A | 6/2000 | Graham |
| 6,077,841 A | 6/2000 | Sui et al. |
| 6,087,362 A | 7/2000 | El-Rashidy |
| 6,087,368 A | 7/2000 | Macor et al. |
| 6,103,765 A | 8/2000 | Neal |
| 6,117,446 A | 9/2000 | Place |
| 6,124,461 A | 9/2000 | Shoemaker |
| 6,127,363 A | 10/2000 | Doherty et al. |
| 6,132,760 A | 10/2000 | Hedenstrom et al. |
| 6,133,320 A | 10/2000 | Yallampalli et al. |
| 6,139,873 A | 10/2000 | Hughes, Jr. et al. |
| 6,143,746 A | 11/2000 | Daugan et al. |
| 6,146,662 A | 11/2000 | Jao et al. |
| 6,156,753 A | 12/2000 | Doherty et al. |
| 6,165,491 A | 12/2000 | Grasset et al. |
| 6,172,088 B1 | 1/2001 | Simpkins et al. |
| 6,187,750 B1 | 2/2001 | Chein |
| 6,190,693 B1 | 2/2001 | Kafrissen et al. |
| 6,200,591 B1 | 3/2001 | Hussain et al. |
| 6,200,593 B1 | 3/2001 | Place |
| 6,207,694 B1 | 3/2001 | Murad |
| 6,221,379 B1 | 4/2001 | Place |
| 6,224,573 B1 | 5/2001 | Yeager et al. |
| 6,225,299 B1 | 5/2001 | Golbs et al. |
| 6,228,852 B1 | 5/2001 | Shaak |
| 6,238,284 B1 | 5/2001 | Dittgen et al. |
| 6,241,529 B1 | 6/2001 | Place |
| 6,248,363 B1 | 6/2001 | Patel et al. |
| 6,251,436 B1 | 6/2001 | Drizen et al. |
| 6,266,560 B1 | 7/2001 | Zhang et al. |
| 6,267,984 B1 | 7/2001 | Beste et al. |
| 6,267,985 B1 | 7/2001 | Chen et al. |
| 6,277,884 B1 | 8/2001 | de Tejada |
| 6,284,234 B1 | 9/2001 | Niemiec et al. |
| 6,284,263 B1 | 9/2001 | Place |
| 6,294,192 B1 | 9/2001 | Patel et al. |
| 6,294,550 B1 | 9/2001 | Place et al. |
| 6,299,900 B1 | 10/2001 | Reed et al. |
| 6,306,841 B1 | 10/2001 | Place et al. |
| 6,309,663 B1 | 10/2001 | Patel et al. |
| 6,319,913 B1 | 11/2001 | Mak et al. |

(56) References Cited

U.S. PATENT DOCUMENTS

| | | |
|---|---|---|
| 6,323,242 B1 | 11/2001 | Mueller |
| 6,331,543 B1 | 12/2001 | Garvey et al. |
| 6,342,246 B2 | 1/2002 | Johnson et al. |
| 6,342,250 B1 | 1/2002 | Masters |
| 6,395,744 B1 | 5/2002 | Adams et al. |
| 6,436,950 B1 | 8/2002 | Achari et al. |
| 6,469,016 B1 | 10/2002 | Place et al. |
| 6,472,425 B1 | 10/2002 | Garvey et al. |
| 6,503,894 B1 | 1/2003 | Dudley et al. |
| 6,506,765 B2 | 1/2003 | Gupta et al. |
| 6,562,369 B2 | 5/2003 | Luo et al. |
| 6,562,370 B2 | 5/2003 | Luo et al. |
| 6,579,865 B2 | 6/2003 | Mak et al. |
| 6,582,724 B2 | 6/2003 | Hsu et al. |
| 6,586,000 B2 | 7/2003 | Luo et al. |
| 6,593,313 B2 | 7/2003 | Place et al. |
| 6,818,226 B2 | 11/2004 | Reed et al. |
| 6,980,566 B2 | 12/2005 | Melick et al. |
| 7,030,104 B2 | 4/2006 | Gray et al. |
| 7,097,853 B1 | 8/2006 | Garbe et al. |
| 7,320,968 B2 | 1/2008 | Gyurik |
| 7,611,727 B2 | 11/2009 | Taravella et al. |
| 2001/0018073 A1 | 8/2001 | Dittgen et al. |
| 2001/0023261 A1 | 9/2001 | Ryoo et al. |
| 2001/0033870 A1 | 10/2001 | Luo et al. |
| 2001/0036483 A1 | 11/2001 | Luo et al. |
| 2001/0051166 A1 | 12/2001 | Luo et al. |
| 2001/0051656 A1 | 12/2001 | Place et al. |
| 2002/0004065 A1 | 1/2002 | Kanios |
| 2002/0013304 A1 | 1/2002 | Wilson et al. |
| 2002/0034554 A1 | 3/2002 | Hsu et al. |
| 2002/0128176 A1 | 9/2002 | Forssmann et al. |
| 2002/0183296 A1 | 12/2002 | Dudley et al. |
| 2003/0018085 A1 | 1/2003 | Raoof et al. |
| 2003/0022877 A1 | 1/2003 | Dudley |
| 2003/0027804 A1 | 2/2003 | Van der Hoop |
| 2003/0050292 A1 | 3/2003 | Dudley et al. |
| 2003/0087885 A1 | 5/2003 | Masini-Eteve et al. |
| 2003/0139384 A1 | 7/2003 | Dudley |
| 2003/0175329 A1 | 9/2003 | Azarnoff et al. |
| 2003/0232072 A1 | 12/2003 | Dudley et al. |
| 2004/0001881 A1 | 1/2004 | Selzer et al. |
| 2004/0002482 A1 | 1/2004 | Dudley et al. |
| 2004/0044086 A1 | 3/2004 | Schulze et al. |
| 2004/0072810 A1 | 4/2004 | Masini-Eteve et al. |
| 2004/0110732 A1 | 6/2004 | Masini-Eteve et al. |
| 2005/0020552 A1 | 1/2005 | Aschkenasy et al. |
| 2005/0025833 A1 | 2/2005 | Aschkenasy et al. |
| 2005/0042268 A1 | 2/2005 | Aschkenasy et al. |
| 2005/0049233 A1 | 3/2005 | Dudley |
| 2005/0054623 A1 | 3/2005 | Dudley |
| 2005/0112181 A1 | 5/2005 | Dudley et al. |
| 2005/0113353 A1 | 5/2005 | Dudley et al. |
| 2005/0118242 A1 | 6/2005 | Dudley et al. |
| 2005/0142173 A1 | 6/2005 | Dudley et al. |
| 2005/0152956 A1 | 7/2005 | Dudley |
| 2005/0158388 A1 | 7/2005 | Le Nestour et al. |
| 2005/0276842 A1 | 12/2005 | Zhang et al. |
| 2006/0088579 A1 | 4/2006 | Shastri et al. |
| 2006/0211664 A1 | 9/2006 | Dudley |
| 2006/0280783 A1 | 12/2006 | Dipietro et al. |
| 2007/0065494 A1 | 3/2007 | Anigbogu et al. |
| 2007/0082039 A1 | 4/2007 | Jones et al. |
| 2007/0088012 A1 | 4/2007 | Seo |
| 2007/0154533 A1 | 7/2007 | Dudley |
| 2007/0189977 A1 | 8/2007 | Zhang et al. |
| 2007/0190124 A1 | 8/2007 | Zhang et al. |
| 2007/0196323 A1 | 8/2007 | Zhang et al. |
| 2007/0196453 A1 | 8/2007 | Zhang et al. |
| 2007/0237822 A1 | 10/2007 | Malladi |
| 2007/0254036 A1 | 11/2007 | Brennan et al. |
| 2008/0058299 A1 | 3/2008 | Dudley |
| 2008/0220068 A1 | 9/2008 | Masini-Eteve et al. |
| 2008/0261937 A1 | 10/2008 | Dudley et al. |
| 2008/0317844 A1 | 12/2008 | Dudley |
| 2009/0011041 A1 | 1/2009 | Musaeva et al. |
| 2009/0258063 A1 | 10/2009 | Udagawa et al. |
| 2010/0048526 A1 | 2/2010 | Taravella et al. |
| 2011/0172196 A1 | 7/2011 | Dudley |
| 2011/0201586 A1 | 8/2011 | Dudley |
| 2011/0269729 A1 | 11/2011 | Malladi et al. |
| 2011/0306582 A1 | 12/2011 | Dudley |
| 2011/0306583 A1 | 12/2011 | Malladi et al. |
| 2012/0028946 A1 | 2/2012 | Malladi et al. |
| 2012/0028948 A1 | 2/2012 | Malladi et al. |
| 2012/0058981 A1 | 3/2012 | Dudley |

FOREIGN PATENT DOCUMENTS

| | | |
|---|---|---|
| CA | 2141690 | 3/1994 |
| CA | 2220358 | 11/1996 |
| CA | 2419573 | 3/2002 |
| CA | 2420895 | 3/2002 |
| CA | 2451725 | 1/2003 |
| CA | 2502607 | 5/2004 |
| CA | 2624788 | 4/2007 |
| CN | 1470239 | 1/2004 |
| DE | 3836862 | 5/1990 |
| DE | 19825856 | 12/1999 |
| EP | 0043738 | 1/1982 |
| EP | 0183492 | 6/1986 |
| EP | 0189861 | 8/1986 |
| EP | 0196769 | 10/1986 |
| EP | 0248885 | 12/1987 |
| EP | 0271983 | 6/1988 |
| EP | 0332147 | 9/1989 |
| EP | 0364211 | 4/1990 |
| EP | 0386960 | 9/1990 |
| EP | 0491076 | 6/1992 |
| EP | 0513832 | 11/1992 |
| EP | 0581587 | 2/1994 |
| EP | 0483105 | 6/1995 |
| EP | 0672422 | 9/1995 |
| EP | 0698393 | 2/1996 |
| EP | 0197753 | 10/1996 |
| EP | 0737477 | 10/1996 |
| EP | 0857488 | 8/1998 |
| EP | 0552405 | 11/1998 |
| EP | 0563813 | 12/1999 |
| EP | 1043020 | 1/2000 |
| EP | 1005831 | 6/2000 |
| EP | 0815871 | 7/2002 |
| EP | 0811381 | 5/2003 |
| EP | 1634583 | 3/2006 |
| EP | 2450041 | 5/2012 |
| FR | 2518879 | 7/1983 |
| FR | 2519252 | 7/1983 |
| GB | 916778 | 1/1963 |
| GB | 941634 | 1/1963 |
| GB | 1158283 | 7/1969 |
| GB | 2109231 | 6/1983 |
| JP | 01138288 | 5/1989 |
| JP | 62011675 | 8/1994 |
| JP | H7-82147 | 3/1995 |
| JP | H9-176049 | 7/1997 |
| JP | H10-087488 | 4/1998 |
| JP | 2000-212080 | 8/2000 |
| JP | 2002087964 | 3/2002 |
| JP | 2002212105 | 7/2002 |
| KR | 2002013248 | 5/1999 |
| RU | 2122396 | 11/1998 |
| WO | WO8703473 | 6/1987 |
| WO | WO9207586 | 5/1992 |
| WO | WO9207590 | 5/1992 |
| WO | WO9215289 | 9/1992 |
| WO | WO9325168 | 12/1993 |
| WO | WO9408590 | 4/1994 |
| WO | WO9409778 | 5/1994 |
| WO | WO9421230 | 9/1994 |
| WO | WO9421271 | 9/1994 |
| WO | WO9424125 | 10/1994 |
| WO | WO9428902 | 12/1994 |
| WO | WO9629988 | 3/1996 |
| WO | WO9616644 | 6/1996 |

(56) References Cited

FOREIGN PATENT DOCUMENTS

| | | |
|---|---|---|
| WO | WO9616657 | 6/1996 |
| WO | WO9620699 | 7/1996 |
| WO | WO9627372 | 9/1996 |
| WO | WO9636339 | 11/1996 |
| WO | WO9637201 | 11/1996 |
| WO | WO9703985 | 2/1997 |
| WO | WO9724148 | 7/1997 |
| WO | WO9739743 | 10/1997 |
| WO | WO9740792 | 11/1997 |
| WO | WO9741865 | 11/1997 |
| WO | WO9743989 | 11/1997 |
| WO | WO9806404 | 2/1998 |
| WO | WO9808547 | 3/1998 |
| WO | WO9817215 | 4/1998 |
| WO | WO9818417 | 5/1998 |
| WO | WO9824451 | 6/1998 |
| WO | WO9830198 | 7/1998 |
| WO | WO9831368 | 7/1998 |
| WO | WO9832465 | 7/1998 |
| WO | WO9834621 | 8/1998 |
| WO | WO9837871 | 9/1998 |
| WO | WO9840076 | 9/1998 |
| WO | WO9850016 | 11/1998 |
| WO | WO9855076 | 12/1998 |
| WO | WO9913812 | 3/1999 |
| WO | WO9920257 | 4/1999 |
| WO | WO9921558 | 5/1999 |
| WO | WO9924041 | 5/1999 |
| WO | WO9932107 | 7/1999 |
| WO | WO9933859 | 7/1999 |
| WO | WO9966870 | 12/1999 |
| WO | WO9966909 | 12/1999 |
| WO | WO0001351 | 1/2000 |
| WO | WO0006144 | 2/2000 |
| WO | WO0024362 | 5/2000 |
| WO | WO0040230 | 7/2000 |
| WO | WO0045795 | 8/2000 |
| WO | WO0066870 | 8/2000 |
| WO | WO0067708 | 11/2000 |
| WO | WO0074684 | 12/2000 |
| WO | WO0076522 | 12/2000 |
| WO | WO0105400 | 1/2001 |
| WO | WO0143775 | 6/2001 |
| WO | WO0151053 | 7/2001 |
| WO | WO0152823 | 7/2001 |
| WO | WO0154699 | 8/2001 |
| WO | WO0164146 | 9/2001 |
| WO | WO0164167 | 9/2001 |
| WO | WO0172307 | 10/2001 |
| WO | WO0176608 | 10/2001 |
| WO | WO0211768 | 2/2002 |
| WO | WO0217926 | 3/2002 |
| WO | WO0217927 | 3/2002 |
| WO | WO0217967 | 3/2002 |
| WO | WO03002123 | 1/2003 |
| WO | WO03088974 | 10/2003 |
| WO | WO2004037173 | 5/2004 |
| WO | WO2005076899 | 8/2005 |
| WO | WO2006023526 | 3/2006 |
| WO | WO2006027278 | 3/2006 |
| WO | WO2006113227 | 10/2006 |
| WO | WO2006113505 | 10/2006 |
| WO | WO2007044976 | 4/2007 |
| WO | WO2007119151 | 10/2007 |

OTHER PUBLICATIONS

Notice of Allowance for U.S. Appl. No. 13/253,867 dated Mar. 4, 2013 (15 pages).
Notice of Opposition of Unimed Pharmaceuticals LLC et al.'s European Patent No. 1937276 dated Aug. 21, 2013 by Andreas Oser.
Brookfield DV-II+ Pro EXTRA Programmable Rheometer Operating Instructions Manual No. M/09-166, (12.07) p. 1-79.
Physicians' Desk Reference, Medical Economics Co., 55th edition (2001) p. 304, 339, 535-538, 3218-3220, Androgel 1% and Testoderm TTS.
Physicians' Desk Reference, Thomson PDR, 58th edition (2004) p. 337, 3239-3241, Androgel 1%.
Labeling for Androgel 1% (testosterone gel) Product (2002).
Labeling for Testim 1% (testosterone gel) CIII Product (2002).
Co-pending U.S. Appl. No. 13/942,245, filed Jul. 15, 2013.
Non-final Office Action for U.S. Appl. No. 13/831,189 dated Jun. 20, 2013 (25 pages).
Non-final Office Action for U.S. Appl. No. 13/902,035 dated Aug. 2, 2013 (29 pages).
Non-final Office Action for U.S. Appl. No. 13/831,207 dated Jun. 27, 2013 (26 pages).
Non-final Office Action for U.S. Appl. No. 13/831,217 dated Jun. 26, 2013 (27 pages).
Co-pending U.S. Appl. No. 13/965,499, filed Aug. 13, 2013.
US 6,214,374, 04/2001, Schmirler et al. (withdrawn).
U.S. Appl. No. 09/703,753, filed Nov. 1, 2000, (abandoned).
U.S. Appl. No. 09/892,981, filed Jun. 27, 2001, (abandoned).
U.S. Appl. No. 10/033,101, filed Oct. 19, 2001, (abandoned).
U.S. Appl. No. 10/046,454, filed Oct. 19, 2001, (abandoned).
U.S. Appl. No. 10/098,232, filed Mar. 15, 2002, (abandoned).
U.S. Appl. No. 10/099,725, filed Mar. 15, 2002, (abandoned).
U.S. Appl. No. 10/153,468, filed May 21, 2002, (abandoned).
U.S. Appl. No. 10/248,267, filed Jan. 3, 2003, (abandoned).
U.S. Appl. No. 10/273,484, filed Oct. 18, 2002, (abandoned).
U.S. Appl. No. 10/456,868, filed Jun. 6, 2003.
U.S. Appl. No. 10/531,526, filed Feb. 8, 2006.
U.S. Appl. No. 10/787,071, filed Feb. 25, 2004, (abandoned).
U.S. Appl. No. 10/825,540, filed Apr. 15, 2004, (abandoned).
U.S. Appl. No. 10/828,678, filed Apr. 20, 2004, (abandoned).
U.S. Appl. No. 10/829,618, filed Apr. 20, 2004.
U.S. Appl. No. 10/867,435, filed Jun. 14, 2004.
U.S. Appl. No. 10/867,445, filed Jun. 14, 2004.
U.S. Appl. No. 10/925,421, filed Aug. 24, 2004.
U.S. Appl. No. 11/399,642, filed Apr. 6, 2006.
U.S. Appl. No. 11/402,682, filed Apr. 11, 2006.
U.S. Appl. No. 11/402,986, filed Apr. 11, 2006.
U.S. Appl. No. 11/549,083, filed Oct. 12, 2006.
U.S. Appl. No. 11/662,339, filed Sep. 24, 2007.
U.S. Appl. No. 11/925,421, filed Oct. 26, 2007.
U.S. Appl. No. 12/052,337, filed Mar. 20, 2008.
U.S. Appl. No. 12/543,541, filed Aug. 19, 2009.
U.S. Appl. No. 12/609,473, filed Oct. 30, 2009.
U.S. Appl. No. 13/071,264, filed Mar. 24, 2011.
U.S. Appl. No. 13/071,276, filed Mar. 24, 2011.
U.S. Appl. No. 13/165,545, filed Jun. 21, 2011.
U.S. Appl. No. 13/180,316, filed Jul. 11, 2011.
U.S. Appl. No. 13/180,327, filed Jul. 11, 2011.
U.S. Appl. No. 13/253,848, filed Oct. 5, 2011.
U.S. Appl. No. 13/253,867, filed Oct. 5, 2011.
U.S. Appl. No. 13/275,232, filed Oct. 17, 2011.
U.S. Appl. No. 13/430,862, filed Mar. 27, 2012.
U.S. Appl. No. 13/648,694, filed Oct. 10, 2012.
U.S. Appl. No. 09/651,777, Jan. 16, 2002 Supplemental Amendment.
U.S. Appl. No. 09/651,777, Feb. 6, 2002 Declaration of Robert E. Dudley dated (submitted with the Supplemental Amendment II dated Feb. 8, 2002), 9 pages.
U.S. Appl. No. 09/651,777, Feb. 8, 2002 Supplemental Amendment II, 46 pages.
U.S. Appl. No. 09/651,777, Mar. 27, 2007 Decision Granting Petition to Correct Inventorship under 37 CFR §1.324.
U.S. Appl. No. 09/651,777, Apr. 1, 2002 Letter in response to Mar. 28, 2002 Examiner Interview, 4 pages.
U.S. Appl. No. 09/651,777, Apr. 30, 2007 Certificate of Correction.
U.S. Appl. No. 09/651,777, May 7, 2002 Non-Final Rejection, 6 pages.
U.S. Appl. No. 09/651,777, May 20, 2002 Response after Non-Final Action, 12 pages.
U.S. Appl. No. 09/651,777, May 22, 2007 Certificate of Correction—Correction of Inventors.
U.S. Appl. No. 09/651,777, Jun. 12, 2003 Request for Certificate of Correction under 37 CFR §1.322 (2 pages of corrections).
U.S. Appl. No. 09/651,777, Jun. 12, 2003 Request for Certificate of Correction under 37 CFR §1.323 (1 page of corrections).

(56) References Cited

OTHER PUBLICATIONS

U.S. Appl. No. 09/651,777, Jun. 19, 2001 Non-Final Rejection, 10 pages.
U.S. Appl. No. 09/651,777, Jul. 23, 2002 Supplemental Response After Interview, 2 pages.
U.S. Appl. No. 09/651,777, Jul. 23, 2002 Declaration of Michele Alm, 5 pages.
U.S. Appl. No. 09/651,777, Jul. 23, 2002 Declaration of Sandy Faulkner, 7 pages.
U.S. Appl. No. 09/651,777, Jul. 24, 2002 Supplemental Amendment, 7 pages.
U.S. Appl. No. 09/651,777, Aug. 1, 2002 Supplemental Amendment, 5 pages.
U.S. Appl. No. 09/651,777, Aug. 13, 2002 Notice of Allowance, 6 pages.
U.S. Appl. No. 09/651,777, Aug. 20, 2002 Protest under 37 CFR §1.291(a).
U.S. Appl. No. 09/651,777, Oct. 17, 2003 Certificate of Correction.
U.S. Appl. No. 09/651,777, Oct. 29, 2001 Declaration of Jean-Louis Anspach, 4 pages.
U.S. Appl. No. 09/651,777, Oct. 29, 2001 Response after Non-Final Action, 23 pages.
U.S. Appl. No. 09/651,777, Nov. 29, 2004 Petition to correct inventorship under 35 USC §256, 37 CFR §1.324, and M.P.E.P. §1481 (a certificate of correction is submitted).
U.S. Appl. No. 09/651,777, Dec. 21, 2001 Supplemental Amendment, 15 pages.
U.S. Appl. No. 09/703,753, Jan. 15, 2003 Non-Final Rejection, 10 pages.
U.S. Appl. No. 09/703,753, Feb. 22, 2002 Notice of Appeal and Amendment/Argument after Notice of Appeal, 7 pages.
U.S. Appl. No. 09/703,753, Mar. 22, 2002 Advisory Action, 4 pages.
U.S. Appl. No. 09/703,753, Apr. 9, 2003 Response after Non-Final Action, 33 pages.
U.S. Appl. No. 09/703,753, Apr. 24, 2001 Non-Final Rejection, 12 pages.
U.S. Appl. No. 09/703,753, Jun. 5, 2002 Non-Final Rejection, 9 pages.
U.S. Appl. No. 09/703,753, Jun. 19, 2003 Response after Non-Final Action, 16 pages.
U.S. Appl. No. 09/703,753, Aug. 24, 2001 Response after Non-Final Action, 8 pages.
U.S. Appl. No. 09/703,753, Aug. 26, 2003 Final Rejection, 15 pages.
U.S. Appl. No. 09/703,753, Oct. 21, 2002 Response after Non-Final Action, 7 pages.
U.S. Appl. No. 09/703,753, Nov. 23, 2001 Final Rejection, 11 pages.
U.S. Appl. No. 09/892,981, Feb. 8, 2002 Non-Final Office Action, 8 pages.
U.S. Appl. No. 09/892,981, Feb. 9, 2004 Advisory Action, 3 pages.
U.S. Appl. No. 09/892,981, Feb. 24, 2005 Response to Non-Final Office Action, 5 pages.
U.S. Appl. No. 09/892,981, Feb. 26, 2003 Non-Final Office Action, 12 pages.
U.S. Appl. No. 09/892,981, Mar. 15, 2005 Notice of Non-Responsive Amendment.
U.S. Appl. No. 09/892,981, Mar. 28, 2006 Non-Final Office Action, 6 pages.
U.S. Appl. No. 09/892,981, Apr. 8, 2005 Response to Non-Final Office Action, 2 pages.
U.S. Appl. No. 09/892,981, Apr. 16, 2004 RCE and Response to Final Office Action.
U.S. Appl. No. 09/892,981, Jun. 7, 2002 Response to Non-Final Office Action, 11 pages.
U.S. Appl. No. 09/892,981, Jun. 21, 2005 Final Office Action, 7 pages.
U.S. Appl. No. 09/892,981, Jul. 25, 2003 Response to Non-Final Office Action, 14 pages.
U.S. Appl. No. 09/892,981, Aug. 25, 2004 Non-Final Office Action, 7 pages.
U.S. Appl. No. 09/892,981, Aug. 27, 2002 Final Office Action, 11 pages.
U.S. Appl. No. 09/892,981, Sep. 28, 2006 Response to Non-Final Office Action, 6 pages.
U.S. Appl. No. 09/892,981, Oct. 16, 2003 Final Office Action, 11 pages.
U.S. Appl. No. 09/892,981, Nov. 26, 2002 RCE and Response to Final Office Action, 17 pages.
U.S. Appl. No. 09/892,981, Dec. 11, 2006 Final Office Action, 7 pages.
U.S. Appl. No. 09/892,981, Dec. 16, 2003 Response to Final Office Action, 8 pages.
U.S. Appl. No. 09/892,981, Dec. 16, 2005 RCE and Response to Final Office Action, 3 pages.
U.S. Appl. No. 10/033,101, Jan. 10, 2003 Non-Final Rejection, 12 pages.
U.S. Appl. No. 10/033,101, May 12, 2003 Response after Non-Final Action, 16 pages.
U.S. Appl. No. 10/033,101, Jun. 3, 2003 Supplemental Amendment and Request for Interview, 16 pages.
U.S. Appl. No. 10/033,101, Jun. 30, 2003 Supplemental Amendment B, 18 pages.
U.S. Appl. No. 10/033,101, Oct. 21, 2003 Final Rejection, 13 pages.
U.S. Appl. No. 10/046,454, Jan. 27, 2003 Notice of Allowance, 5 pages.
U.S. Appl. No. 10/046,454, Jun. 13, 2003 Request for Continued Examination (RCE), Petition to Withdraw, and Supplemental amendment, 9 pages.
U.S. Appl. No. 10/046,454, Jun. 18, 2003 Petition Decision of Granted to Withdraw from Issue, 1 page.
U.S. Appl. No. 10/046,454, Jul. 11, 2003 Supplemental Amendment B, 16 pages.
U.S. Appl. No. 10/046,454, Sep. 10, 2002 Non-Final Rejection, 8 pages.
U.S. Appl. No. 10/046,454, Sep. 20, 2002 Response after Non-Final Action, 8 pages.
U.S. Appl. No. 10/046,454, Oct. 16, 2003 Non-Final Rejection, 7 pages.
U.S. Appl. No. 10/046,454, Dec. 9, 2002 Supplemental amendment, 5 pages.
U.S. Appl. No. 10/098,232, Jul. 31, 2003 Preliminary Amendment, 8 pages.
U.S. Appl. No. 10/098,232, Oct. 20, 2003 Non-Final Rejection, 8 pages.
U.S. Appl. No. 10/098,232, Nov. 14, 2007 Request under Rule 48 correcting inventorship, 7 pages.
U.S. Appl. No. 10/099,725, Jan. 29, 2003 Non-Final Office Action.
U.S. Appl. No. 10/099,725, Sep. 29, 2003 Notice of Abandonment.
U.S. Appl. No. 10/099,725, Oct. 1, 2002 Office Action.
U.S. Appl. No. 10/153,468, Feb. 24, 2004 Non-Final Rejection, 17 pages.
U.S. Appl. No. 10/153,468, Aug. 24, 2004 Response after Non-Final Action, 2 pages.
U.S. Appl. No. 10/153,468, Nov. 17, 2004 Final Rejection, 17 pages.
U.S. Appl. No. 10/248,267, Dec. 15, 2003 Non-Final Rejection, 17 pages.
U.S. Appl. No. 10/273,484, Dec. 15, 2003 Non-Final Rejection.
U.S. Appl. No. 10/436,380, Jan. 2, 2008 Final Office Action, 12 pages.
U.S. Appl. No. 10/436,380, Jan. 3, 2007 Amendment and Reply to Office Action, 11 pages.
U.S. Appl. No. 10/436,380, Jan. 23, 2009 Final Office Action, 18 pages.
U.S. Appl. No. 10/436,380, Apr. 22, 2009 Response to Final Office Action, 13 pages.
U.S. Appl. No. 10/436,380, May 2, 2008 RCE and Response to final Office Action, 18 pages.
U.S. Appl. No. 10/436,380, May 13, 2009 Notice of Allowance, 5 pages.
U.S. Appl. No. 10/436,380, May 28, 2008 Non-Final Office Action, 17 pages.
U.S. Appl. No. 10/436,380, Jun. 8, 2010 Certificate of Correction—Post Issue Communication, 1 page.

(56) References Cited

OTHER PUBLICATIONS

U.S. Appl. No. 10/436,380, Jul. 3, 2006 Non-Final Office Action, 13 pages.
U.S. Appl. No. 10/436,380, Jul. 17, 2007 Non-Final Office Action, 11 pages.
U.S. Appl. No. 10/436,380, Jul. 23, 2009 Amendment After Notice of Allowance, 5 pages.
U.S. Appl. No. 10/436,380, Aug. 5, 2009 Response to Amendment under Rule 312, 2 pages.
U.S. Appl. No. 10/436,380, Oct. 28, 2008 Declaration of Olivier Raux, 4 pages.
U.S. Appl. No. 10/436,380, Oct. 28, 2008 Declaration of Russel Potts, 30 pages.
U.S. Appl. No. 10/436,380, Oct. 28, 2008 Response to Non-Final Office Action, 16 pages.
U.S. Appl. No. 10/436,380, Nov. 19, 2007 Response to Non-Final Office Action, 10 pages.
U.S. Appl. No. 10/456,868, Jan. 12, 2006 Non-final Office Action, 13 pages.
U.S. Appl. No. 10/456,868, Jan. 26, 2011 Response to Non-final Office Action, 13 pages.
U.S. Appl. No. 10/456,868, Feb. 4, 2010 Declaration under 37 CFR 1.131, 23 pages.
U.S. Appl. No. 10/456,868, Feb. 4, 2010 Response to Non-Final Office Action, 8 pages.
U.S. Appl. No. 10/456,868, Apr. 12, 2011 Final Rejection, 14 pages.
U.S. Appl. No. 10/456,868, Apr. 25, 2006 Response to Non-Final Office Action, 7 pages.
U.S. Appl. No. 10/456,868, Apr. 25, 2007 Declaration of Valerie Masini-Eteve, 3 pages.
U.S. Appl. No. 10/456,868, Apr. 25, 2007 RCE and Response to Final Office Action, 7 pages.
U.S. Appl. No. 10/456,868, May 11, 2010 Non-Final Office Action, 11 pages.
U.S. Appl. No. 10/456,868, Jun. 28, 2006 Final Office Action, 10 pages.
U.S. Appl. No. 10/456,868, Aug. 5, 2009 Non-Final Office Action, 8 pages.
U.S. Appl. No. 10/456,868, Aug. 11, 2010 Response to Non-final Office Action, 9 pages.
U.S. Appl. No. 10/456,868, Oct. 27, 2010 Non-Final Office Action, 12 pages.
U.S. Appl. No. 10/456,868, Nov. 28, 2006 Declaration of Valerie Masini-Eteve.
U.S. Appl. No. 10/456,868, Nov. 28, 2006 Response to Final Office Action, 5 pages.
U.S. Appl. No. 10/531,526, Feb. 2, 2011 Non-Final Rejection, 9 pages.
U.S. Appl. No. 10/531,526, Feb. 22, 2010 Final Rejection, 9 pages.
U.S. Appl. No. 10/531,526, Mar. 18, 2008 Non-Final Rejection, 8 pages.
U.S. Appl. No. 10/531,526, May 12, 2009 Request for Continued Examination (RCE) and Amendment, 13 pages.
U.S. Appl. No. 10/531,526, Jul. 9, 2009 Non-Final Rejection, 10 pages.
U.S. Appl. No. 10/531,526, Jul. 17, 2008 Response after Non-Final Action, 16 pages.
U.S. Appl. No. 10/531,526, Jul. 28, 2011 Response to Non-Final Rejection, 17 pages.
U.S. Appl. No. 10/531,526, Aug. 20, 2010 Request for Continued Examination (RCE) and Amendment, 8 pages.
U.S. Appl. No. 10/531,526, Sep. 12, 2011 Final Office Action, 24 pages.
U.S. Appl. No. 10/531,526, Nov. 17, 2008 Final Rejection, 8 pages.
U.S. Appl. No. 10/531,526, Dec. 8, 2009 Response after Non-Final Action, 17 pages.
U.S. Appl. No. 10/787,071, Feb. 1, 2008 Response after Non-Final Action, 15 pages.
U.S. Appl. No. 10/787,071, May 29, 2008 Final Rejection, 31 pages.
U.S. Appl. No. 10/787,071, Oct. 2, 2007 Non-Final Rejection, 23 pages.
U.S. Appl. No. 10/825,540, Jun. 20, 2008 Non-Final Rejection, 22 pages.
U.S. Appl. No. 10/828,678, Jun. 25, 2008 Non-Final Rejection, 23 pages.
U.S. Appl. No. 10/829,618, Jan. 17, 2012 Interview Summary, 3 pages.
U.S. Appl. No. 10/829,618, Feb. 5, 2009 Non-Final Rejection, 11 pages.
U.S. Appl. No. 10/829,618, May 14, 2008 Non-Final Rejection, 20 pages.
U.S. Appl. No. 10/829,618, Jun. 1, 2010 Response after Non-Final Action, 13 pages.
U.S. Appl. No. 10/829,618, Aug. 5, 2009 Response after Non-Final Action, 10 pages.
U.S. Appl. No. 10/829,618, Aug. 11, 2010 Notice of Allowance, 8 pages.
U.S. Appl. No. 10/829,618, Oct. 5, 2011 Non-Final Office Action, 16 pages.
U.S. Appl. No. 10/829,618, Nov. 12, 2010 RCE and Preliminary Amendment, 8 pages.
U.S. Appl. No. 10/829,618, Nov. 13, 2008 Response after Non-Final Action, 10 pages.
U.S. Appl. No. 10/829,618, Nov. 30, 2009 Non-Final Rejection, 10 pages.
U.S. Appl. No. 10/829,618, Dec. 28, 2010 Interview Summary, 4 pages.
U.S. Appl. No. 10/867,435, Mar. 11, 2009 Final Rejection, 11 pages.
U.S. Appl. No. 10/867,435, Jun. 4, 2010 Response after Non-Final Action, 15 pages.
U.S. Appl. No. 10/867,435, Jun. 9, 2008 Non-Final Rejection, 18 pages.
U.S. Appl. No. 10/86,7435, Aug. 13, 2010 Final Rejection, 10 pages.
U.S. Appl. No. 10/867,435, Sep. 11, 2009 Request for Continued Examination and Amendment, 13 pages.
U.S. Appl. No. 10/867,435, Oct. 11, 2011 Non-Final Office Action, 19 pages.
U.S. Appl. No. 10/867,435, Dec. 4, 2009 Non-Final Rejection, 10 pages.
U.S. Appl. No. 10/867,435, Dec. 9, 2008 Response after Non-Final Action, 19 pages.
U.S. Appl. No. 10/867,435, Feb. 14, 2011 Request for Continued Examination (RCE) and Amendment, 17 pages.
U.S. Appl. No. 10/867,445, Jan. 19, 2010 Non-Final Rejection, 11 pages.
U.S. Appl. No. 10/867,445, Mar. 11, 2008 Non-Final Rejection, 18 pages.
U.S. Appl. No. 10/867,445, Mar. 24, 2011 Request for Continued Examination and Amendment, 16 pages.
U.S. Appl. No. 10/867,445, Apr. 2, 2012 Response to Office Action, 15 pages.
U.S. Appl. No. 10/867,445, Apr. 10, 2009 Response after Non-Final Action, 99 pages.
U.S. Appl. No. 10/867,445, Jun. 24, 2008 Response after Non-Final Action, 20 pages.
U.S. Appl. No. 10/867,445, Jun. 28, 2012 Final Rejection, 22 pages.
U.S. Appl. No. 10/867,445, Jul. 15, 2009 Final Rejection, 11 pages.
U.S. Appl. No. 10/867,445, Jul. 19, 2010 Response after Non-Final Action, 17 pages.
U.S. Appl. No. 10/867,445, Sep. 24, 2010 Final Rejection, 10 pages.
U.S. Appl. No. 10/867,445, Oct. 10, 2008 Non-Final Rejection, 12 pages.
U.S. Appl. No. 10/867,445, Oct. 13, 2011 Office Action, 21 pages.
U.S. Appl. No. 10/867,445, Dec. 14, 2009 Request for Continued Examination and Amendment, 28 pages.
U.S. Appl. No. 10/925,421, Mar. 29, 2010 Response after Final Action and RCE, 13 pages.
U.S. Appl. No. 10/925,421, Apr. 12, 2011 Response after Non-Final Action, 14 pages.
U.S. Appl. No. 10/925,421, May 26, 2009 Response after Non-Final Action, 15 pages.
U.S. Appl. No. 10/925,421, Jun. 22, 2011 Final Rejection, 15 pages.

(56) References Cited

OTHER PUBLICATIONS

U.S. Appl. No. 10/925,421, Sep. 8, 2011 Response to Final Office Action, 10 pages.
U.S. Appl. No. 10/925,421, Sep. 29, 2009 Final Rejection, 17 pages.
U.S. Appl. No. 10/925,421, Oct. 12, 2010 Non-Final Rejection, 18 pages.
U.S. Appl. No. 10/925,421, Nov. 24, 2008 Non-Final Rejection, 16 pages.
U.S. Appl. No. 11/399,642, Feb. 8, 2010 Non-Final Office Action, 14 pages.
U.S. Appl. No. 11/399,642, Feb. 15, 2011 Request for Continued Examination (RCE) and Amendment, 13 pages.
U.S. Appl. No. 11/399,642, May 14, 2009 Final Office Action, 12 pages.
U.S. Appl. No. 11/399,642, Aug. 9, 2010 Response to Non-Final Office Action, 24 pages.
U.S. Appl. No. 11/399,642, Oct. 15, 2010 Final Office Action, 14 pages.
U.S. Appl. No. 11/399,642, Oct. 18, 2011 Office Action, 26 pages.
U.S. Appl. No. 11/399,642, Nov. 16, 2009 Response to Non-Final Office Action, 21 pages.
U.S. Appl. No. 11/402,682, Mar. 17, 2010 RCE and Response to Final Office Action, 11 pages.
U.S. Appl. No. 11/402,682, Jun. 2, 2009 Response to Non-Final Office Action, 13 pages.
U.S. Appl. No. 11/402,682, Sep. 17, 2009 Final Office Action, 13 pages.
U.S. Appl. No. 11/402,682, Dec. 2, 2008 Non-Final Office Action, 16 pages.
U.S. Appl. No. 11/402,986, Feb. 22, 2010 Response to Non-Final Office Action, 20 pages.
U.S. Appl. No. 11/402,986, May 14, 2010 Final Office Action, 25 pages.
U.S. Appl. No. 11/402,986, May 15, 2009 Response to Non-Final Office Action, 18 pages.
U.S. Appl. No. 11/402,986, Aug. 20, 2009 Non-Final Office Action, 30 pages.
U.S. Appl. No. 11/402,986, Nov. 15, 2010 RCE and Response to Final Office Action, 13 pages.
U.S. Appl. No. 11/402,986, Nov. 17, 2008 Non-Final Office Action, 21 pages.
U.S. Appl. No. 11/549,083, Jan. 8, 2010 Response to Notice of Non-Compliant Amendment, 6 pages.
U.S. Appl. No. 11/549,083, Jan. 14, 2009 Final Office Action, 10 pages.
U.S. Appl. No. 11/549,083, Mar. 25, 2010 Final Office Action, 7 pages.
U.S. Appl. No. 11/549,083, Apr. 1, 2009 RCE and Response to Final Office Action, 12 pages.
U.S. Appl. No. 11/549,083, Apr. 8, 2011 Non-Final Rejection, 7 pages.
U.S. Appl. No. 11/549,083, Apr. 24, 2008 Non-Final Office Action, 11 pages.
U.S. Appl. No. 11/549,083, Jun. 22, 2009 Non-Final Office Action, 9 pages.
U.S. Appl. No. 11/549,083, Sep. 27, 2010 RCE and Response to Final Office Action, 18 pages.
U.S. Appl. No. 11/549,083, Oct. 13, 2009 Declaration of Norman Weiner, 52 pages.
U.S. Appl. No. 11/549,083, Oct. 13, 2009 Response to Non-Final Office Action, 7 pages.
U.S. Appl. No. 11/549,083, Oct. 23, 2008 Declaration of Drs. Ramana Malladi and Jodi Miller (37 CFR 1.131), 9 pages.
U.S. Appl. No. 11/549,083, Oct. 23, 2008 Declaration of Norman Weiner, 62 pages.
U.S. Appl. No. 11/549,083, Oct. 23, 2008 Petition to Correct Inventorship, 5 pages.
U.S. Appl. No. 11/549,083, Oct. 23, 2008 Response to Non-Final Office Action, 12 pages.
U.S. Appl. No. 11/549,083, Dec. 6, 2007 Non-Final Office Action.
U.S. Appl. No. 11/662,339, Jan. 19, 2011 Final Office Action, 18 pages.
U.S. Appl. No. 11/662,339, Feb. 3, 2009 Non-Final Office Action, 19 pages.
U.S. Appl. No. 11/662,339, Feb. 22, 2010 Response to Non-Final Office Action, 13 pages.
U.S. Appl. No. 11/662,339, May 29, 2009 Response to Non-Final Office Action, 9 pages.
U.S. Appl. No. 11/662,339, Jun. 14, 2010 Non-Final Office Action, 15 pages.
U.S. Appl. No. 11/662,339, Sep. 22, 2009 Non-Final Office Action, 16 pages.
U.S. Appl. No. 11/662,339, Oct. 4, 2010 Response to Non-Final Office Action, 13 pages.
U.S. Appl. No. 12/052,337, Mar. 29, 2010 Final Office Action, 12 pages.
U.S. Appl. No. 12/052,337, May 15, 2009 Non-Final Office Action, 17 pages.
U.S. Appl. No. 12/052,337, Sep. 29, 2010 RCE and Response to Final Office Action, 7 pages.
U.S. Appl. No. 12/052,337, Nov. 16, 2009 Response to Non-Final Office Action, 12 pages.
U.S. Appl. No. 12/543,541, Jan. 28, 2010 Examiner Interview Summary Record, 2 pages.
U.S. Appl. No. 12/543,541, Feb. 2, 2010 Applicants' comments to Examiner-initiated interview summary, 2 pages.
U.S. Appl. No. 12/543,541, Feb. 5, 2010 Non-Final Rejection, 24 pages.
U.S. Appl. No. 12/543,541, Mar. 5, 2010 Response after Non-Final Action, 12 pages.
U.S. Appl. No. 12/543,541, Apr. 5, 2010 Final Rejection, 21 pages.
U.S. Appl. No. 12/543,541, Aug. 19, 2009 Petition for 12-month Accelerated Exam, Pre-examination search document; accelerated examination support document, 56 pages.
U.S. Appl. No. 12/543,541, Oct. 5, 2010 Request for Continued Examination (RCE) and Amendment, 11 pages.
U.S. Appl. No. 12/543,541, Nov. 9, 2010 Non-Final Rejection, 24 pages.
U.S. Appl. No. 12/543,541, Dec. 7, 2009 Petition for 12-month Accelerated Exam Decision—Granted, 4 pages.
U.S. Appl. No. 12/543,541, Dec. 9, 2010 Response after Non-Final Action, 6 pages.
U.S. Appl. No. 12/543,541, Dec. 30, 2010 Final Rejection, 20 pages.
U.S. Appl. No. 12/609,473, Apr. 29, 2011 Response after Non-Final Action, 11 pages.
U.S. Appl. No. 12/609,473, Jul. 20, 2011 Final Rejection, 15 pages.
U.S. Appl. No. 12/609,473, Dec. 7, 2010 Non-Final Rejection, 18 pages.
U.S. Appl. No. 13/071,264, Dec. 21, 2011 Non-Final Rejection, 23 pages.
U.S. Appl. No. 13/071,276, Jan. 6, 2012 Non-Final Rejection, 48 pages.
U.S. Appl. No. 13/165,545, Apr. 11, 2012 Non-Final Rejection, 22 pages.
U.S. Appl. No. 13/180,316, May 25, 2012 Non-Final Rejection, 24 pages.
U.S. Appl. No. 13/180,327, Jun. 15, 2012 Response After Non-final Rejection, 21 pages.
U.S. Appl. No. 13/180,327, Sep. 17, 2012 Final Rejection, 27 pages.
U.S. Appl. No. 13/180,327, Dec. 21, 2011 Non-Final Rejection.
U.S. Appl. No. 13/253,848, Mar. 29, 2012 Final Rejection, 52 pages.
U.S. Appl. No. 13/253,848, May 30, 2012CEce, Response to Final Rejection, 22 pages.
U.S. Appl. No. 13/253,848, Aug. 30, 2012 Non-Final Rejection, 34 pages.
U.S. Appl. No. 13/253,848, Dec. 22, 2011 Non-Final Rejection, 47 pages.
U.S. Appl. No. 13/253,867, Mar. 20, 2012 Response After Non-Final Rejection, 10 pages.
U.S. Appl. No. 13/253,867, Aug. 31, 2012 Final Rejection, 28 pages.
U.S. Appl. No. 13/253,867, Dec. 20, 2011 Non-Final Rejection, 22 pages.

(56) References Cited

OTHER PUBLICATIONS

U.S. Appl. No. 13/275,232, Mar. 2, 2012 Non-Final Rejection, 40 pages.
U.S. Appl. No. 13/275,232, Jun. 4, 2012 Response After Non-final Action, 15 pages.
U.S. Appl. No. 13/275,232, Sep. 17, 2012 Final Rejection, 30 pages.
U.S. Appl. No. 13/275,254, Mar. 22, 2012 Response After Non-final Action, 10 pages.
U.S. Appl. No. 13/275,254, Jul. 16, 2012 Final Rejection, 25 pages.
International Preliminary Examination Report—Application No. PCT/US2003/007910 (May 27, 2004).
International Search Report—Application No. PCT/US2003/032597 (May 19, 2004).
International Preliminary Examination Report—Application No. PCT/US2003/032597 (Jul. 8, 2004).
International Preliminary Report on Patentability I—Application No. PCT/US2006/013551 (May 29, 2007).
International Search Report—Application No. PCT/US2001/27202 (Jan. 29, 2002).
International Search Report—Application No. PCT/US2003/007910 (Oct. 17, 2003).
International Search Report and Written Opinion—Application No. PCT/EP2006/003974 (Sep. 4, 2006).
International Search Report and Written Opinion—Application No. PCT/US2006/013551 (Aug. 7, 2006).
International Preliminary Report on Patentability I—Application No. PCT/EP2006/003974 (Oct. 9, 2007).
International Preliminary Report on Patentability—Application No. PCT/US2006/040481 (Apr. 16, 2008).
International Search Report—Application No. PCT/US01/27199, Reference No. 01902267 (International Filing Date: Aug. 29, 2001).
International Search Report—Application No. PCT/US01/27205, Reference No. 01736544 (International Filing Date: Aug. 29, 2001).
International Search Report of PCT/US2006/040481 mailed Jul. 13, 2007.
Singapore Patent Application No. 200802644-5, Search Report and Written Opinion, Dec. 2, 2009.
International Search Report dated Dec. 12, 2002 and International Preliminary Report on Patentability I dated Apr. 2, 2004—Application No. PCT/US2002/020141.
International Search Report and Written Opinion dated Apr. 23, 2008 and International Preliminary Report on Patentability I dated Mar. 17, 2009—Application No. PCT/US2006/013550.
International Search Report and Written Opinion dated Feb. 29, 2008 and International Preliminary Report on Patentability I dated Feb. 29, 2009—Application No. PCT/EP2008/053372.
European Search Report mailed May 28, 2002 in application No. EP01403166 (corresponding to US 2003/0087885).
Search report for EP0672422, published Jul. 28, 1994.
USPTO Word Mark Search on "CPE-215", uspto.gov (searched Oct. 21, 2002).
Written Opinion of the International Searching Authority of PCT/US2006/040481, Jul. 13, 2007.
Opposition in Venezuela VE000537/03 dated Apr. 3, 2003.
Opposition to CL1026-2007 dated Sep. 5, 2008.
Opposition to CO08036312 dated Feb. 10, 2010.
Opposition to ECSP088363 dated Apr. 11, 2008.
Response to Opposition to ECSP088363 dated Apr. 7, 2009.
"Isopropyl myristate," Martindale (2011) 4 pages.
"Propylene glycol," Martindale (2011) 7 pages).
"Alza introduces Testoderm TTS for testosterone deficiency—survey finds key role of testosterone unknown to most men." Alza. Mar. 11, 1998. http://www.alza.com/print/p_957321395 (accessed Nov. 15, 2004).
"Androderm Watson Pharmaceuticals reacquires U.S. and Canadian marketing rights to A(R) testosterone transdermal system." Watson Pharmaceuticals Inc. May 17, 1999.
"AndroGel Offers New Option for Testosterone Replacement," The Body (Mar. 31, 2000), available at http://www.thebody.com/content/art2023.html.
"Besins Grants Schering Distribution Rights for Testogel in Europe," Espicom Business Intelligence (Jul. 8, 2002).
"Cellegy Pharmaceuticals Initiates Phase III Clinical Trial Using Transdermal Testosterone Gel." PR Newswire. Mar. 29, 2000.
"Cellegy Pharmaceuticals Market Opportunities." Cellegy Pharmaceuticals. http://www.cellegy.com/products/market.html (accessed Nov. 19, 1998).
"Delatestryl (testosterone enanthate): Prescribing Information." Revised Oct. 1995. http://www.delatestryl.com/prescribing.body.htm (accessed Dec. 16, 2004).
"Dermally applied testosterone gel ('androgel') appears effective and well tolerated," In Pharma (Feb. 1999) 1175, p. 12.
"Erratum." The Lancet. (1999);354:602.
"Hypogonadism: Schering acquires distribution rights for Testogel in Europe," Pain & Central Nervous System Week: 14 (Aug. 19, 2002).
"New Testosterone Replacement Gel, AndroGel®, Available Nationwide to Treat Men with Low Testosterone." Androgel.com. http://www.androgel.com/media/press_release000614.htm (Jun. 14, 2000).
"Observation study of T-gel (1%) in treatment of adolescent boys with hypogonadism," http://clinicaltrials.gov/NCT00193661 (2006).
"Products filed for marketing approval: androgel," Pharma Business (Jul./Aug. 1999) 29:72-73.
"Sandrena, a new estrogen gel, for the improvement of acceptability in menopause therapy", Organon press release, Copenhagen, Aug. 7, 1997.
"Schering Acquires Distribution Rights for Testogel(R) in Europe," PR Newswire (Jul. 2, 2002).
"Schering AG gets Euro Testogel Rights; Brief Article," Marketletter (Jul. 10, 2002).
"Schering Buys European Rights to Male HRT Product," Handelsblatt (English Version)(Jul. 3, 2002).
"Schering Buys European Rts for Hormone Therapy Testogel," Dow Jones International News (Jul. 2, 2002).
"Testosterone gel shows promise in phase III trial,"AIDS Alert (1999) 14:67.
"Unimed files NDA for androgel in USA," Pharma Market Letter (May 10, 1999) 26(19):23.
"Unimed forecasts steep rise in revenues," SCRIP No. 2338/39: 14 (May 27/29, 1998).
"Unimed Pharmaceuticals Completes Clinical Trial Enrollment for First Topical Testosterone Replacement Gel." Press Release. May 28, 1998.
"Unimed Pharmaceuticals files for FDA Approval of Androgel to Treat Low Testosterone Levels; Over 1 Mil Men in US Suffer from Hypogonadism," PharmaBusiness Issue 29 (Jul. 1999).
"Unimed Pharmaceuticals Licenses Testosterone Products." PR Newswire. Aug. 14, 1995.
"Unimed Pharmaceuticals Licenses Two Testosterone Products." Pharma Market letter. Aug. 21, 1995.
Abbasi A. Mattson DE, Cuisinier M, Schultz S, Rudman I, Drinka P, Rudman D: Hyposomatomedinemia and hypogonadism in hemiplegic men who live in nursing homes. Arch Phys Med Rehabil 75:594-9, 1994.
Abbasi AA, Drinka PJ, Mattson DE, Rudman D: Low circulating levels of insulin-like growth factors and testosterone in chronically institutionalized elderly men. J. Amer Geri Soc 41:975-82, 1993.
ABCNews.com: Testosterone Patch Increases Women's Sex Drive, http://abcnews.go.com/sections/living/DailyNews/testosterone990615.html. Sep. 8, 2000.
Abdu, et al., Coronary Risk in Growth Hormone Deficient Hypopituitary Adults: Increased Predicted Risk is Due Largely to Lipid Profile Abnormalities, Clinical Endocrinology, vol. 55, pp. 209-216 (2001).
Abitbol, et al., Sex Hormones and the Female Voice, J Voice, Sep. 1999; 13(3): 424-46.
Abraham G. E., Ovarian and adrenal contribution to peripheral androgens during the menstrual cycle, J. Clin. Endocrinol. Metab. 1974; 39:340-346.
Adami, et al., Effect of Hyperandrogenism and Menstrual Cycle Abnormalities Bone Mass and Bone Turnover in Young Women, Clinical Endocrinology (OXF), vol. 48, No. 2, 169-173 (Feb. 1998).

(56) References Cited

OTHER PUBLICATIONS

Adesuyi, et al., Coronary Heart Disease/Myocardial Infarction: Testosterone Increases Human Platelet Thromboxane A sub 2 Receptor Density and Aggregation Responses, Circulation, vol. 91, No. 11, pp. 2742-2747 (Jun. 1, 1995).
Adult female postmenopausal subject. Stedman's Medial Dictionary, 25th Edition, (1990).
Adult female premenopausal subject. Stedman's Medial Dictionary, 25th Edition, (1990).
Advance Collaborative Group, Intensive blood glucose control and vascular outcomes in patients with type 2 diabetes. N Engl J Med. Jun. 12, 2008;358(24):2560-72. (Epub Date Jun 6, 2008).
Agarwal, et al., Differential Response of Prostate Specific Antigen to Testosterone Surge after Luteinizing Hormone-Releasing Hormone Analogue in Prostate Cancer and Benign Prostatic Hyperplasia, BJU Intl., vol. 85, pp. 690-695 (2000).
Aguiar, A.J. et al., "Percutaneous absorption studies of chloramphenicol solutions," J. Pharm. Sci. (1969) 58(2):210-216.
Ahmed, et al., Transdermal Testosterone Therapy in the Treatment of Male Hypogonadism, J Clin Endocrinol Metab, Mar. 1988; 66(3): 546-51.
Akimoto, et al., Relationship Between Diurnal Rhythm of Serum Testosterone and Prostatic Markers (PSSA and PAP) in Untreated Prostate Cancer, Urology, Mar. 1994; 43(3): 337-41.
Alberti, I. et al., "Effect of ethanol and isopropyl myristate on the availability of topical terbinafine in human stratum corneum, in vivo," Int. J. Pharm. (2001) 219:11-19.
Albertson's, Inc. Enters Agreement with Men's Health Network to Support National Men's Health Awareness Campaign: 'Time Out for Men's Health' Encourages Men to be Checked by a Doctor More Regularly, Yahoo!Finance.com (Aug. 29, 2002).
Alexander, et al., Testosterone and Sexual Behavior in Oral Contraceptive Users and Nonusers: A Prospective Study, Hormones and Behavior, vol. 24, No. 3, pp. 388-402 (Sep. 1990).
Alexander, et al., Androgen-Behavior Correlations in Hypogonadal Men and Eugonadal Men, Hormones and Behavior, vol. 33, pp. 85-94 (1998).
Alexander, et al., Sex Steroids, Sexual Behavior, and Selection Attention for Erotic Stimuli in Women Using Oral Contraceptives, Psychoneuroendocrinology, 1993; 18(2): 91-102.
Alivizatos, et al., Update of Hormonal Treatment in Cancer of the Prostate, Anticancer Drugs, Jun. 1993; 4(3):301-9.
Allen, Methyltestosterone 6-mg/g Gel, Int'l J. Pharm. Compounding, vol. 2(1), p. 52 (1998).
Allen, Testosterone Topical Vaginal Cream, U.S. Pharmacist, pp. 54, 56, 58, (Jan. 22, 2000).
Almeida, Sex Playing with the Mind. Effects of Oestrogen and Testosterone Mood and Cognition, Arq Neuropsiquiatr, Sep. 1999; 57(3A): 701-6. [Abstract only].
Alternative to Viagra for Women!, www.mdhealthline.com (Downloaded Aug. 7, 2000).
American association of Clinical Endocrinologies (AACE) medical guidelines for clinical practices for the evaluation and treatment of hypogonadism in adult male patients—2002 update. Endocr Pract 2002; 8(6):439-456.
Anabolic Steroid Boosts Weight, GMHC Treatment Issues, vol. 10, No. 9 (Sep. 1996) (no authors listed).
Anabolic Steroids, Project Inform Hotline Handout, www.projinf.org. (Downloaded Oct. 8, 1998).
Anabolic Steroids, Project Inform, Anabolic Steroids Quick Sheet (Dec. 1997).
Anabolic Steroids—A Simple Facts Sheet From the Network, www.network/simple/steroids (Downloaded Oct. 27, 1998).
Anawalt, Potential Expanded Indications for Androgen Treatment, The Endocrine Society, No. 166 (ENDO 2000).
Anderson et al., The effects of exogenous testosterone on sexuality and mood of normal men, J. Clin. Endocrinol. Metab., 1992, 75(6):1503-7.
Anderson, et al., Haemostatic Effects of Supraphysiological Levels of Testosterone in Normal Men, pp. 693-697 (1995).

Andro Gel, Netrition, http://www.netrition.com/andro_gel_page.html (1997-1998).
Androderm®, Physician Desk Reference, pp. 2796-2798 (1998).
Androgel (testosterone gel 1%), A Double-Blind, Randomized, Placebo-controlled, Parallel Study to Evaluate the Efficacy and Safety of AndroGel, as and Adjunct to Hypoglycemic Therapy, in the Treatment of Hypogonadal and Low Testosterone Men with Type 2 Diabetes. Solvay Pharmaceuticals. Jun. 20, 2008.
Androgel 1% (testosterone gel) CIII, available at http://www.rxabbott.com/pdf/androgel_PI.pdf, pp. 1-2. (Sep. 2009).
Androgel and Andractim, General Information (1997).
Androgel, The Medical Letter on Drugs and Therapeutics, vol. 42 (Issue 1080), pp. 49-52 (Jun. 12, 2000).
AndroGel® (Testosterone Gel). CIII Physicians Desk Reference, Issued Dec. 2000.
Androgel® 1% (Testosterone Gel). Physicians Desk Reference, pp. 3239-3241 (2004).
Androgel® 1% (Testosterone Gel). Physician's Package Insert, pp. 1 and 11 (2004).
Androgel® 1% Package Insert, Dec. 2000.
Androgen Deficiency in Aging Men Questionnaire, Saint Louis University, available at www.slu.edu/adam (retrieved May 23, 2005).
Andropausal, Los Gatos Longevity Institute, http://www.antiaging.com/andropause.html (1998).
Andropause Added to Men's Health Risk Assessment Tool, America's Pharmacist (Alexandria, VA), Jan. 2002.
Andropause, National Public Radio, The Connection Online (Jul. 29, 2003).
AndrosteDERM, http://www.gethuge.net/androderm1.htm (Jun. 22, 2000).
Angold, et al., Pubertal Changes in Hormone Levels and Depression in Girls, Psychol Med Sep. 1999; 29(5): 1043-53.
Annual Report pursuant to Section 13 or 15(d) of the Securities Exchange Act of 1934 for the Fiscal Year Ended Dec. 31, 1998, by Unimed Pharmaceuticals, Inc.
Ansel et al., Transdermal Drug Delivery Systems, Pharmaceutical Dosage Forms and Drug Delivery Systems, pp. 263-278 (1999).
Ansel, H. Introduction to Pharmaceutical Dosage Forms.Psychiatry. 43(12):279-308 (1981) (Jun. 15, 1998).
Approved Products: From Pipeline to Market, R&D Directions (West Trenton, NJ), Jun. 2002.
Arellano, A. et al., "Influence of propylene glycol and isopropyl myristate on the in vitro percutaneous penetration of diclofenac sodium from carbopol gels," Eur. J. Pharm. Sci. (1998) 7:129-135.
Arisaka et al., Systemic effects of transdermal testosterone for the treatment of microphallus in children. Pediatrics International: Official Journal of the Japan Pediatric Society APR, 43(2):134-136 (2001).
Arsenieva. "Androgen therapy of patients suffering from climacteric neurosis." Soviet Medicine (1964). [in Russian with English Abstract].
Arver et al., Long-Term Efficacy and Safety of a Permeation-Enhanced Testosterone Transdermal System in Hypogonadal Men, Clinical Endocrinology, vol. 47, pp. 727-737 (1997).
Arver, et al., Improvement of Sexual Function in Testosterone Deficient Men Treated for 1 Year with a Permeation Enhanced Testosterone Transdermal System, J Urol, May 1996; 155(5): 1604-8.
Asbill CS, et al., "Enhancement of transdermal drug delivery: chemical and physical approaches," Crit Rev Ther Drug Carrier Syst. (2000);17(6):621-58.
Asscheman H. Scrotal testosterone patches: a good addition to therapeutic options for hypogonadal men. Ned Tijdschr Geneeskd. Apr. 29, 2000;144(18):847-50.
Aungst, "Structure/effect studies of fatty acid isomers as skin penetration enhancers and skin irritants," Pharmaceutical Research (1989); 6(3):244-247.
Aungst, B.J., "Fatty acids as skin permeation enhancers," Chapter 9.1 of Percutaneous Penetration Enhancers, E.W. Smith, Editor, CRC Press (1995) 277-287.
Auxilium Pharmaceutical, Inc. Citizen's Petition Decision, Aug. 26, 2009, Docket No. FDA-2009-P-0123.

(56) References Cited

OTHER PUBLICATIONS

Aversa, et al., Androgens and Penile Erection: Evidence for a Direct Relationship Between Free Testosterone and Cavernous Vasodilation in Men with Erectile Dysfunction, Clinical Endocrinology, vol. 53, pp. 517-522 (2000).
Baarends, E. M., A. M. W. J. Schols, W. D. van Marken Lichtenbelt, and E. F. M. Wouters. Analysis of body water compartments in relation to tissue depletion in clinically stable patients with chronic obstructive pulmonary disease. Am. J. Clin. Nutr. 65: 88-94 (1997).
Baba, et al., Delayed Testosterone Replacement Restores Nitric Oxide Synthase-Containing Nerve Fibres and the Erectile Response in Rat Penis, BJU Intl., vol. 85, pp. 953-958 (2000).
Bachmann et al., Female androgen insufficiency: the Princeton consensus statement on definition, classification, and assessment, Fertility and Sterility, vol. 77, No. 4, Apr. 2002, pp. 660-665.
Bagatel et al., Metabolic & Behavioral Effects of High-Dose, Exogenous Testosterone in Healthy Men, J. Clinical Metabolism & Endocrinology 79:561-567 (1994).
Bagatell et al., Androgens in Men—Uses and Abuses. New England Journal of Medicine. 334(11):707-714 (1996).
Bagatell et al., Effects of Endogenous Testosterone and Estradiol on Sexual Behavior in Normal Young Men, Journal of Clinical Endocrinology and Metabolism, vol. 78, No. 3, pp. 711-716 (1994).
Baillie et al., Pathogenesis of vertebral crush fractures in men. Age and Aging 21:139 (1992).
Bain, "Andropause—Testosterone Replacement Therapy for Aging Men," Can Fam Physician 47:91-97 (Jan. 2001), Abstract.
Baker et al., Changes in the pituitary-testicular system with age. Clin. Endocrinol. 5:349 (1976).
Balagopal P, Rooyackers OE, Adey DB, Ades PA, Nair KS: Effects of aging on in vivo synthesis of skeletal muscle myosin heavy-chain and sarcoplasmic protein in humans. Am J Physiol 273 :E790-800, 1997.
Bals-Pratsch et al., Substitution Therapy of Hypogonadal Men with Transdermal Testosterone Over One Year, ACTA Endocrinologica (COPENH), vol. 118, pp. 7-13 (1988).
Bals-Pratsch, et al., Transdermal Testosterone Substitution Therapy for Male Hypogonadism, Lancet, Oct. 25, 1986; 2(8513): 943-6.
Bancroft, Endocrinology of Sexual Function, Clinics in Obstetrics and Gynecology, vol. 7, No. 2, pp. 253-281 (Aug. 1980).
Bancroft, et al., Androgens and the Menopause; a Study of 40-60-Year-Old Women, Clin Endocrinol (Oxf), Nov. 1996; 45(5): 577-87.
Bancroft, et al., Mood, Sexuality, Hormones, and the Menstrual Cycle. III. Sexuality and the Role of Androgens, Psychosom Med, Dec. 1983; 45(6): 509-16.
Banker et al., Modern Pharmaceutics, $3^{rd}$ Edition (1996) Marcel Dekker, New York, p. 716.
Bardin et al., Androgens: Risks and benefits. J. Clin. Endocrinol. Metab. 73:4 (1991).
Barlow et al., In Vivo Observations on Testosterone and Estradiol-17beta Protein Binding in Women, Journal of Clinical Endocrinology and Metabolism, vol. 29 (No. 6), p. 767-776, (Jan. 22, 1969).
Barrett, C.W. et al., "The effect of particle size and vehicle on the percutaneous absoption of fluocinole acetonide," Br. J. Dermatol. (1965) 77:576-578.
Barrett, C.W. et al., "The influence of vehicles on skin penetration," J. Pharm. Pharmacol. (1964) 16 Supp.: 104T-107T.
Barrett-Connor E. Lower endogenous androgen levels and dyslipidemia in men with non-insulin dependent diabetes mellitus. Ann. Int. Med. 12/92 (1992).
Barrett-Connor, E., et al., Endogenous sex hormone levels in older adult men with diabetes mellitus. Am. J. Epidemiol., 132(5):895-901 (1990).
Barrett-Connor, Elizabeth et al. Bioavailable Testosterone and Depressed Mood in Older Men: The Rancho Bernardo Study. J. Clinical Endocrinology and Metabolism (1999); 84(2):573-577.
Barrett-Connor, et al., Cognitive Function and Endogenous Sex Hormones in Older Women, J. Am. Geriatr. Soc., vol. 47, No. 11, pp. 1289-1293 (Nov. 1999).
Barrett-Connor, et al., A Two-Year, Double-Blind Comparison of Estrogen-Androgen and Conjugated Estrogens in Surgically Menopausal Women. Effects Bone Mineral Density, Symptoms and Lipid Profiles, J Reprod Med, Dec. 1999; 44(12): 1012-20.
Barry, Dermatological Formulations, Percutaneous Absorption, Marcel Dekker (1983).
Barry, Low Testosterone Can Trigger Male Depression, Atlanta Business Chronicle, Feb. 14, 2002.
Barry, Prostate-Specific-Antigen Testing for Early Diagnosis of Prostate Cancer, N. Engl. J. Med., vol. 344, No. 18 , pp. 1373-1377 (May 23, 2001).
Barry, B.W. et al., "Effect of penetration enhancers on the permeation of mannitol, hydrocortisone and progesterone through human skin," J. Pharm. Pharmacol. (1987) 39:535-546.
Barry, B.W., "Mode of action of penetration enhancers in human skin," J. Contr. Rel. (1987) 6:85-97.
Bartnof, Testosterone Therapy Causes Menstruation to Return in Women with AIDS-Related Wasting, www.hivandhepatitis.com (Oct. 12, 1999).
Bartsch, et al., Sex Hormone Binding Globulin Binding Capacity, Testosterone, 5alpha-Dihydrotestosterone, Oestradiol and Prolactin in Plasma of Patients with Prostatic Carcinoma Under Various Types of Hormonal Treatment, ACTA Endocrinologica (COPENH), vol. 85, No. 3, pp. 650-664 (Jul. 1977).
Bartsch, et al., Interrelationships Between Sex Hormone-Binding Globulin and 17 beta-Estradiol, Testosterone, 5 alpha-Dihydrotestosterone, Thyroxine, and Triiodothyronine in Prepubertal and Pubertal Girls, J Clin Endocrinol Metab, Jun. 1980; 50(6): 1053-1056 (Jun. 1980).
Bartsch, Interrelationships Between Sex Hormone-Binding Globulin and Testosterone, 5 alpha-dihydrotestosterone and Oestradiol-17 beta in Blood of Normal Men, Maturitas, Jul. 1980; 2(2): 109-118.
Barzel, Recommended Testing Patients with Low Bone Density. J Clin Endocrinol Metab 88(3): 1403-1404(2003).
Basaria et al., "New Modalities of Transdermal Testosterone Replacement," Treat Endocrinol, 2(1): 1-9 (2003); Abstract.
Basson, et al., Androgen Replacement for Women, Canadian Family Physician, vol. 45, pp. 2100-2107 (Sep. 1999).
Baum, et., Effects of Testosterone, Dihydrotestosterone, or Estradiol Administered Neonatally on Sexual Behavior of Female Ferrets, Endocrinology, vol. III (No. 3), p. 773-780, (Jan. 22, 1982).
Baumgartner, et al., Predictors of Skeletal Muscle Mass in Elderly Men and Women, Mech Ageing Dev, Mar. 1, 1999; 107(2): 123-36.
Bazell, Male Hormone Gel May Pose Risks: Testosterone Therapy Promises Renewed Vigor, but Some Experts are Skeptical, NBC-TV NBC Nightly News Online (Jul. 31, 2002).
Beasley, Hormone Replacement Therapy for Men Gains Ground, Reuters, Jun. 21, 2002.
Behre HM, et al., Rationale, design and methods of the ESPIRIT study: Energy, Sexual desire and body Proportions with AndroGel, Testosterone 1% gel therapy, in hypogonadal men, Aging Male. Jun. 2008;11(2):101-6.
Behre, et al., Testosterone Buciclate (20 Aet-1) in Hypogonadal Men: Pharmacokinetics and Pharmacodynamics of the New Long-Acting Androgen Ester, Journal of Endocrinology and Metabolism, vol. 75, No. 5, pp. 1204-1210 (1992).
Behre, et al., Long-Term Effect of Testosterone Therapy on Bone Mineral Density in Hypogonadal Men, Journal of Clinical Endocrinology and Metabolism, vol. 82, No. 8, pp. 2386-90 (1997).
Behre, et al., Long-Term Substitution Therapy of Hypogonadal Men with Transscrotal Testosterone Over 7-10 Years, Clinical Endocrinology (1999) vol. 50, 629-635.
Behre, et al., Prostate Volume in Testosterone-Treated and Untreated Hypogonadal Men in Comparison to Age-Matched Normal Controls, Clin Endocrinol (OXF), Mar. 1994; 40(3): 341-9.
Behre, et al., Intramuscular Injection of Testosterone Undecanoate for the Treatment of Male Hypogonadism: Phase I Studies, European Journal of Endocrinology (1999);140:414-419.
Belgorosky, et al., Changes in Serum Sex Hormone-Binding Globulin and in Serum Non-Sex Hormone-Binding Globulin-Bound Testosterone During Prepuberty in Boys, J Steroid Biochem, 1987; 27(1-3): 291-295.
Belgorosky, et al., Dynamics of SHBG Response to Testosterone. Implications Upon the Immediate Biological Effect of Sex Hormones, J. Steroid Biochem., vol. 18, No. 6, pp. 783-787 (Jun. 1983).

(56) References Cited

OTHER PUBLICATIONS

Belgorosky, et al., Progressive Decrease in Serum Sex Hormone-Binding Globulin from Infancy to Late Prepuberty in Boys, J Clin Endocrinol Metab, Aug. 1986; 63(2): 510-512.

Belgorosky, Sex Hormone Binding Globulin Response to Testosterone. An Androgen Sensitivity Test, Acta Endocrinol (Copenh), May 1985; 109(1): 130-138.

Bennett, D., "It's no myth, scientists say—there really is a male menopause," Weekly World News (Jul. 18, 2000) 13.

Bennett, S.L. et al., "Optimization of bioavailability of topical steroids: non-occluded penetration enhancers under thermodynamic control," J. Pharm. Pharmacol (1985) 37:298-304.

Bentley Pharmaceuticals Announces License Agreement for Its Topical Testosterone Gel Formulation; Li, www.UVentures.com (Dec. 18, 2000).

Bentley Pharmaceuticals Announces Research and Licensing Agreements for Intranasal Pain Management and Topical Hormone Replacement Therapy, www.bentleypharm.com (downloaded Nov. 17, 2001).

Benzoyl peroxide. Wikipedia. http://en.wikipedia.org/wiki/Benzoyl_peroxide. pp. 1-3. Downloaded on Oct. 13, 2009.

Berger, RS et al., A reappraisal of the 21-day cumulative irritation test in man. J. Toxicol. Cut. and Ocular Toxicol. (1982) 1:109-115.

Berndt et al., "Consumption Externalities and Diffusion in Pharmaceutical Markets: Antiulcer Drugs," National Bureau of Economic Research Working Paper 7772 (2000).

Berndt et al., "Information, Marketing, and Pricing in the U.S. Antiulcer Drug Market," The American Economic Review 85(2): 100-105 (May 1995).

Berner, et al., Pharmacokinetic Characterisation of Transdermal Delivery System, Clin Pharmacokinet, Feb. 1994; 26(2): 121-34.

Bernini, et al., Endogenous Androgens and Carotid Intimal-Medical Thickness in Women, J Clin Endocrinol Metab, Jun. 1999; 84(6): 2008-12.

Berrie, "Testosterone Gel Addition Benefits Men With Erectile Dysfunction Who Do Not Respond to PDE5s Alone if Testosterone Levels Are Low," Presented at European Society for Sexual Medicine (ESSM/ISSM) 2008, Belgium.

Besins International Licenses Testogel to Schering, In Vivo: The Business & Medicine Report (Norwalk, CT), Sep. 2002.

Betamethasone dipropionate (Disprosone, Diprolene) MedicineNet.com. http:www.medicinenet.com/betamethasone_dipropionate/article.htm. pp. 1-3. Downloaded Oct. 13, 2009.

Bevier W et al., Aerobic capacity, muscle strength and bone density in elderly men and women. J. Bon. Miner. Res. 4:421 (1989).

Bhasin et al., The effects of supraphysiologic doses of testosterone on muscle size and strength. N. Eng. J. Med. 335: 1-7 (1996).

Bhasin S, et al., Testosterone replacement increases fat-free mass and muscle size in hypogonadal men J Clin Endocrinol Metab 82(2):407-13, 1997.

Bhasin S. et al., Editorial Commentary: Testosterone Supplementation for Cognitive Loss. J. Androl.: 45-46 (Jan./Feb. 2002).

Bhasin, Clinical Review 34—Androgen Treatment of Hypogonadal Men, Journal of Clinical Endocrinology and Metabolism, vol. 74, No. 6, pp. 1221-1225 (1992).

Bhasin, et al., Can Androgen Therapy Replete Lean Body Mass and Improve Muscle Function in Wasting Associated with Human Immunodeficiency Virus Infection?, J. of Parental and Enteral Nutrition, vol. 23, pp. S195-S201 (1999).

Bhasin, et al., Effects of Testosterone Replacement with a Nongenital, Transdermal System, Androderm, in Human Immunodeficiency Virus-Infected Men with Low Testosterone Levels, J. or Clinical Endocrinology and Metabolism, vol. 83, No. 9, pp. 3155-3162 (1998).

Bhasin, et al., Testosterone Supplementation in Older Men: A Rational Idea Whose Time Has Not Yet Come, J. of Andrology, vol. 22, No. 5, pp. 718-731 (2001).

Bhasin, et al., A Biodegradable Testosterone Microcapsule Formulation Providing Uniform Eugonadal Levels of Testosterone for 10-11 Weeks in Hypogonadal Men, J Clin Endocrinol Metab, Jan. 1992; 74(1): 75-83.

Bhasin, et al., Therapeutic Perspective—Issues in Testosterone Replacement in Older Men, Journal of Clinical Endocrinology and Metabolism, vol. 83, No. 10, pp. 3435-3448 (1998).

Bhowmick et al., Sexual Precocity in a 16-Month-Old Boy Induced by Indirect Topical Exposure to Testosterone, Clinical Pediatric, vol. 46(6), pp. 540-543 (2007).

Biopharmaceutical Firm Launched in Northbrook, Northbrook Star (Northbrook, IL), Aug. 29, 2002.

Biotech Business, "Testosterone Gel Restores Male Hormone Blood Levels" (Apr. 1999).

Biotech Business, "Unimed Submits NDA to Market "Androgel" Testosterone Gel" (Jun. 1999).

Bisschop, et al., Effects of Nandrolone Decanoate on Respiratory and Peripheral Muscles in Male and Female Rats, www.uth.tms.edu. (1996, Downloaded Oct. 8, 1998).

Bloch, et al., Pituitary-Adrenal Hormones and Testosterone Across the Menstrual Cycle in Women with Premenstrual Syndrome and Controls, Biol Psychiatry, Jun. 15, 1998; 43(12): 897-903.

Bocchinfuso, et al., Expression and Differential Glycosylation of Human Sex Hormone-Binding Globulin by Mammalian Cell Lines, Mol Endocrinol, Nov. 1991; 5(11): 1723-1729.

Bockserman, Med. Plastics and Biomaterials Mag., pp. 26-33 (Jul. 1996).

Bond, et al., Sex Hormone Binding Globulin in Clinical Perspective, Acta Obstet. Gynecol. Scand., vol. 66, pp. 255-262 (1987).

Bonithon-Kopp, et al., Relationship Between Sex Hormones and Haemostatic Factors in Healthy Middle-Aged Men, Atherosclerosis, vol. 71, pp. 71-76 (1988).

Bonney, Hormone Replacement Therapy for Men, American Clinical Laboratory, http://iscpubs.com/pubs/acl1197.html (Nov./Dec. 1997).

Booji, et al., Androgens as Adjuvant Treatment in Postmenopausal Female Patients with Rheumatoid Arthritis, Ann Rheum Dis, Nov. 1996; 55(11): 811-5.

Boots, et al., Measurement of Total Serum Testosterone Levels Using Commercially Available Kits: High Degree of Between-Kit Variability, Fertil Steril, Feb. 1988; 69(2): 286-292.

Borah et al., Risedronate preserves bone architecture in postmenopausal women with osteoporosis as measured by three-dimensional microcomputed tomography. Bone, 34:736-46 (2004).

Boyle, et al., Serum Testosterone Measurements, Am J Clin Pathol, Jun. 1984; 81(6): 754-761.

Brachet et al., Children's virilization and the use of a testosterone gel by their fathers, Eur J Pediatr, vol. 164, pp. 646-647 (2005).

Braunsteiner, et al., Essential Role of Post-Heparin Lipoprotein Lipase Activity and of Plasma Testosterone in Coronary Artery Disease, The Lancet, pp. 1242-1244 (Jun. 1, 1985).

Brawer MK. et al., Screening for prostatic carcinoma with prostate-specific antigen. J. Urol 147:841 (1992).

Brill, et al., Single and Joint Impact on One-Month of Transdermal Testosterone (T) and/or Recombinant Human Growth Hormone (rhGH) Supplementation on Body Composition, Strength, Balance, Function and Muscle IGF-1 and Androgen Gene Expression in Healthy Older Men: A Prospective Randomized Double-Blind Crossover, The Endocrine Society, No. 1647 (ENDO 2000).

Brinkmann, I. et al., "An attempt to clarify the influence of glycerol, propylene glycol, isopropyl myristate and a combination of propylene glycol and isopropyl myristate on human stratum corneum," Pharmazie (2005) 60:215-220.

Brinkmann, I. et al., "Role of isopropyl myristate, isopropyl alcohol and a combination of both in hydrocortisone permeation across the human stratum corneum," Skin Pharmacol. Appl. Skin Physiol. (2003) 16:393-404.

Brocks, et al., Pharmacokinetics of Testosterone in Hypogonadal Men After Transdermal Delivery: Influence of Dose, Journal of Clinical Pharmacology, vol. 36, pp. 732-739 (1996).

Brodsky IG, Balagopal P, Nair KS. Effects of testosterone replacement on muscle mass and muscle protein synthesis in hypogonadal men. J Clin Endocrinol Metab 1996;81(10) 3469-3475.

(56) References Cited

OTHER PUBLICATIONS

Brokaw, T, NBC-TV NBC Nightly News, Lifetime Transcript on NBC's Don Lemon Interview (Nov. 7, 2002).
Bronaugh et al., Vehicle effects on percutaneous absorption: in vivo and in vitro comparison with human skin, Br. J. Dermatol., vol. 11, pp. 1-11 (1986).
Broniarczyk-Dyla, et al., Aging of the Skin During Menopause, Medical Science Monitor vol. 5 (No. 5) 1024-1029. (Jan. 22, 1999).
Bross, et al., Androgen effects on body composition and muscle function: implications for the use of androgens as anabolic agents in sarcopenic states. Baillieres Clin. Endocrinol. Metab 12: 365-378 (1998).
Bruun, et al., Dihydrotestosterone Measured in Core Biopsies from Prostatic Tissues, Am J Clin Oncol, 1988; 11 Suppl 2:S27-9.
Buckler, et al., Pharmacokinetics of a Novel Transdermal Delivery System for Testosterone in Women Journal of Endocrinology, vol. 144 p. P329 (1995).
Buckler, et al., The Effects of Low-Dose Testosterone Treatment on Lipid Metabolism, Clotting Factors and U/trasonographic Ovarian Morphology in Women, Clinical Endocrinology, vol. 49, pp. 173-178 (1997).
Buckler, et al., Which Androgen Replacement Therapy for Women?, J Clin Endocrinol Metab, Nov. 1998; 83(11):3920-4.
Buhling et al., AIPPI Summary Report on Selection Inventions—The Inventive Step Requirement, Other Patentability and Scope of Protection (2009).
Bunch, et al., Pituitary Radiographic Abnormalities and Clinical Correlates of Hypogonadism in Elderly Males Presenting with Erectile Dysfunction, The Aging Male, vol. 5, pp. 38-46 (2002).
Burdet, et al., Administration of growth hormone to underweight patients with chronic obstructive pulmonary disease. A prospective, randomized, controlled study. Am. J. Respir. Crit Care Med. 156: 1800-1806 (1997).
Burge et al., "Idiopathic hypogonadotropic hypogonadism in a male runner is reversed by clomiphene citrate." Fertil. Steril. 67(4): 783-85 (1997).
Burger H. G. et al., The management of persistent menopausal symptoms with oestradiol-testosterone implants: clinical, lipid and hormonal results, Maturitas 1984; 6:351-358.
Burger, et al., Effect of Combined Implants of Oestradiol and Testosterone on Libido in Postmenopausal Women, British Medical Journal (Clin. Res. Ed.), vol. 294, No. 6577, pp. 936-937 (Apr. 11, 1987).
Business Wire, "Preliminary Data Show Topical Testosterone Replacement Gel May Effectively Restore Blood Levels of Male Hormone" (Feb. 11, 1999).
Business Wire, "Unimed Pharmaceuticals Submits NDA to Market Androgel—Testosterone Gel—for Men with Low Testosterone" (Apr. 29, 1999).
Buvat et al., Endocrine Screening in 1,022 Men with Erectile Dysfunction: Clinical Significance and Cost-Effective Strategy, The J. of Urology, vol. 158, pp. 1764-1767 (Nov. 1997).
Cable, C.G., "Oleic acid," Pharmaceutical Excipients (2009) 3 pages.
Calendar—It's a Guy Thing, Houston Chronicle, Sep. 11, 2002.
Calendar—Men's Health, Atlanta Journal-Constitution, Oct. 29, 2002.
Capaldini L. Fatigue and HIV Part II. Interview Interview with Lisa Capaldini, M.D. by John S. James. AIDS Treat News. Apr. 3, 1998, downloaded at http://www.thebody.com/content/art31526.html (Nov. 11, 2010).
Carey, et al., A Study to Evaluate Serum and Urinary Hormone Levels Following Short and Long Term Administration of Two Regimens of Progesterone Cream in Postmenopausal Women, British Journal of Obstetrics and Gynaecology, p. 722-726, (Jun. 22, 2000).
Carey, et al., Transdermal Testosterone Treatment of Hypogonadal Men, The Journal of Urology, vol. 140, pp. 76-79, (Jul. 1988).
Carlstrom, et al., Relationship Between Serum Testosterone and Sex Hormone-Binding Globulin in Adult Men with Intact or Absent Gonadal Function, International Journal of Andrology, vol. 13, pp. 67-73 (1990).
Carter, et al., Longitudinal evaluation of prostate-specific antigen levels in men with and without prostate disease. JAMA 267:2215 (1992).
Casaburi, et al., Anabolic therapies in chronic obstructive pulmonary disease. Monaldi Arch. Chest Dis. 53: 454-459 (1998).
Cascione, Evaluation of the use of a unique testosterone topical gel formulation and a transdermal testosterone patch (Androderm), Department of Veterans Affairs, Abstract, Jun. 5, 2001.
Cashdan, Hormones, Sex and Status in Women, Hormones and Behavior, vol. 29, pp. 354-366 (Sep. 1995).
Casson, et al., Testosterone Delivery Systems for Women: Present Status and Future Promise, Seminars in Reproductive Endocrinology, vol. 16 (No. 2). p. 153-159 (Jan. 22, 1998).
Casson, et al., Androgen Replacement Therapy in Women: Myths and Realities, Int J Fertil Menopausal Stud; Jul.-Aug. 1996; 41(4):412-22.
Castelo-Branco, et al., Circulating Hormone Levels in Menopausal Women Receiving Different Hormone Replacement Therapy Regimens, Journal of Reproductive Medicine, vol. 40 (No. 8), p. 556-560, (Aug. 22, 1995).
Catalona W. et al., Measurement of prostate-specific antigen in serum as a screening test for prostate cancer. N Engl J. Med 324:1156 (1991).
CBS Evening News, "More Men Take Testosterone," Transcript of CBS television broadcast (Aug. 25, 2002).
Cellegy Pharmaceuticals Market Opportunities, Cellegy Pharmaceuticals, Inc., http://www.cellegy.com/corp/market.html (1997).
Cellegy Pharmaceuticals, Inc Annual Report (Form 10-K) pursuant to The Securities Exchange Act of 1934 for the Fiscal Year Ended Dec. 31, 1998, filed on Mar. 22, 1999.
Cellegy Pharmaceuticals, Inc Annual Report (Form 10-K) pursuant to The Securities Exchange Act of 1934 for the Fiscal Year Ended Dec. 31, 1999, filed on Mar. 14, 2000.
Cellegy Pharmaceuticals, Inc. Annual Report (Form 10-KSB) pursuant to The Securities Exchange Act of 1934 for the Fiscal Year Ended Dec. 31, 1997, filed on Mar. 31, 1998.
Cellegy Pharmaceuticals, Inc. Annual Report (Form 10-KSB) pursuant to The Securities Exchange Act of 1934 for the Fiscal Year Ended Dec. 31, 1996, filed on Mar. 28, 1997.
Cellegy Pharmaceuticals, Inc. Investors: Press Releases, Cellegy Pharmaceuticals Receives FDA Nonapproval Letter for Fortigel, Jul. 7, 2003, www.cellegy.com.
Center, et al., Mortality After All Major Types of Osteoporotic Fracture in Men and Women: An Observational Study, The Lancet, vol. 353, pp. 878-882 (Mar. 13, 1999).
Chakravarti, et al., Endocrine Changes and Symptomatology After Oophorectomy in Premenopausal Women, Br J Obstet Gynaecol, Oct. 1977; 84(10): 769-75.
Chan, TC. Percutaneous penetration enhancers: An update. Prcdgs of 9th Bienniel Intl Conf of Perspectives in Percutaneous Penetration, La Grand Motte, France, Apr. 13, 2004; published Jan. 2005.
Chemana et al., Percutaneous absorption of 5-alpha-dihydrotestosterone in Man II. Percutaneous administration of 5-alpha-dihydrotestosterone in hypogonadal men with idiopathic haemochromatosis; clinical, metabolic and hormonal effectiveness. International Journal of Andrology 5:595-606 (1982).
Chemistry: The Central Science, 2d Edition, pp. 75-76, 84-86, 348-349 (1981).
Chen, et al., The Correlation Between Pretreatment Serum Hormone Levels and Treatment Outcome for Patients with Prostatic Cancer and Bony Metastasis, BJU Intl., vol. 89, pp. 710-713 (2002).
Chen, et al., Therapeutic Patents for Topical and Transdermal Drug Delivery Systems, Expert Opinion on Therapeutic Patents, vol. 10 (No. 7, pp. 1035-1043 (2000).
Cheng, R. Columbia Labs Reports Data on Testosterone Buccal Pdt, Dow Jones News Service, Jun. 20, 2002.
Cherrier, et al., Testosterone Supplementation Improves Spatial and Verbal Memory in Healthy Older Men, Neurology, vol. 57, pp. 80-88 (2001).
Cherrier, et al., T-Gel Study: Cognitive Effects of Exogenous Testosterone Manipulation in Hypogonadal Men, (Jun. 7, 1999), University of Washington.

(56) References Cited

OTHER PUBLICATIONS

Chevallier, et al., A double-blind, placebo-controlled study on the effects of transdermal testosterone replacement in hypogonadal men with type 2 diabetes or metabolic syndrome: the TIMES2 study, European Association of Urology, PosterSesseionOnline.com (2008).
Chiang HS, et al., Testosterone gel monotherapy improves sexual function of hypogonadal men mainly through restoring erection: evaluation by IIEF score.Urology. Apr. 2009;73(4):762-6. (Epub Date: Jan. 1, 2009).
Chik Z, et al., Correcting endogenous concentrations of testosterone influences bioequivalence and shows the superiority of TDS(R)-testosterone versus Androgel(R), Int J Clin Pharmacol Ther. Apr. 2009;47(4):262-8.
Chilcott et al., Transepidermal Water Loss Does not Correlate with Skin Barrier Function In Vitro, The Journal of Investigative Dermatology, vol. 118, No. 5, pp. 871-875, May 2002.
Choi, et al., Transdermal Dihydrotestosterone Therapy and its Effects on Patients with Microphallus, J Urol, Aug. 1993; 150(2 Pt 2): 657-660.
Christiansen, Behavioral Correlates of Testosterone, Testosterone: Action, Deficiency, Substitution, 109-111 (1998).
Chudakov B, et al., Transdermal testosterone gel prn application for hypoactive sexual desire disorder in premenopausal women: a controlled pilot study of the effects on the Arizona sexual experiences scale for females and sexual function questionnaire, J Sex Med. Jan. 2007;4(1):204-8.
Citron, et al., Prevalence of Hypothalmic-Pituitary Imaging Abnormalities in Impotent Men with Secondary Hypogonadism, The J. of Urol., vol. 155, pp. 529-533 (Feb. 1996).
Clarys, P. et al., "In vitro percutaneous penetration through hairless rat skin: influence of temperature, vehicle and penetration enhancers," Eur. J. Pharma. Biopharm. (1998) 46:279-283.
Cleary et al., The effect of intensive glycemic treatment on coronary artery calcification in type 1 diabetic participants of the Diabetes Control and Complications Trial/Epidemiology of Diabetes Interventions and Complications (DCCT/EDIC) Study. Diabetes. Dec. 2006;55(12):3556-65.
Clift, Let Us Pause, Brattleboro Reformer (Brattleboro, VT), Aug. 17, 2002.
Clift, Medicalizing Middle Age: Now Drug Companies Go After Men, The Keene Sentinel (Keene, NH), Aug. 18, 2002.
Cofrancesco, Jr., et al., Transdermal Testosterone Delivery Systems, The Endocrinologist, vol. 6, No. 3, pp. 207-213 (1996).
Cohan GR, et al., A prospective study of the safety and efficacy of a topical transdermal testosterone gel versus intramuscular injections of testosterone for the treatment of testosterone deficiency in male HIV-infected patients. Poster presentation #H-1912 at the Interscience Conference on Antimicrobial Agents and Chemotherapy Annual Meeting, Oct. 2002, Chicago, IL.
Colao, et al., Effect of GH and/or Testosterone Deficiency on the Prostate: An Ultrasonographic and Endorcrine Study in GH-deficient Adult Patients. Euro. J. of Endocrinology, vol. 143, pp. 61-69 (2000).
Colker, Q and A: Ask Dr. Colker, Muscular Development (Setauket, NY), Aug. 2002.
Columbia Laboratories Announces European Marketing Partnership With Ardana Bioscience for Testosterone Buccal Bioadhesive Product, www.bioexchange.com (Oct. 17, 2002).
Colvard DS et al., Identification of androgen receptors in normal human osteoblast-like cells. Proc Natn Acad Sci 86:854 (1989).
Company Interview: MacroChem Corporation (MCHM), The Wall Street Transcript (New York, NY), Jul. 8, 2002 at 201-205.
Conan, N. Men's Health Series, Part II: Male Menopause, National Public Radio Talk of the Nation Online (Oct. 15, 2002).
Confranceso Jr., et al., Testosterone Replacement Treatment Options for HHIV-Infected Men, J. of AIDS and Human Retrovirology, vol. 16, pp. 254-265 (1997).
Conway, et al., Randomized Clinical trial of Testosterone Replacement Therapy in Hypogonadal Men, Int J Androl, Aug. 1988; 11(4): 247-64.

Cooper, E.R., "Increased skin permeability for lipophilic molecules," J. Pharma. Sci. (1984) 73(8):1153-1156.
Cooper, et al., Epidemiology of Osteoporosis, Trends Endocrinol. Metab., vol. 3, pp. 224-229 (1992).
Cooper, et al., Effect of Fatty Acids and Alcohols on the Penetration of Acyclovir Across Human Skin in Vitro, Journal of Pharmaceutical Sciences, vol. 74, No. 6, pp. 688-689 (Jun. 1985).
Cornwell, P.A. et al., Modes of action of terpene penetration enhancers in human skin; differential scanning calorimetry, small-angle x-ray diffraction and enhancer uptake studies, Int. J. Pharmaceu. (1996) 127:9-26.
Corona G, et al., Six-month administration of 1% testosterone gel is able to restore erectile function in hypogonadal patients with erectile dysfunction, Arch Ital Urol Androl. Sep. 2008;80(3):103-8.
Corrales, et al., Partial Androgen Deficiency in Aging Type 2 Diabetic Men and Its relationship to Glycemic Control, Metabolism 53(5):666-72 (May 2004).
Correspondence to FDA from Testocreme® and Citizen Petition (Jul. 3, 2001).
Correspondence to Testocreme® from FDA regarding response to Citizen's Petition (Apr. 12, 2002).
Cortaid. RxList.com. http://www.rxlist.com/cortaid-drug.htm. pp. 1-2. Downloaded on Oct. 13, 2009.
Crols, Solvay Sees 2 Bln Euros in Drug Sales in 2002, Reuters, Jul. 5, 2002.
Cunningham, et al, Plasma Sex Hormone-Binding Globulin Levels Decrease During the Second Decade of Life Irresponsive of Pubertal Status, Journal of Clinical Endocrinology and Metabolism, vol. 58, No. 5, pp. 915-918 (1984).
Cunningham, et al, Testosterone Replacement Therapy and Sleep-Related Erections in Hypogonadal Men, Journal of Clinical Endocrinology and Metabolism, vol. 70, No. 3, 792-797 (1990).
Cunningham, et al., Testosterone Replacement with Transdermal Therapeutic System, Physiological Serum Testosterone and Elevated Dihydrotestosterone Levels, JAMA, May 5, 1989; 261(17): 2525-30.
Cunningham, et al., Testosterone Transdermal Delivery System, Pharmacology. Biology and Clinical Applications of Androgens. vol. 42, pp. 437-447 (1996 Wiley-Liss, Inc).
Cutolo, et al., Androgen Replacement Therapy in Male Patients with Rheumatoid Arthritis, Arthritis and Rheumatism, vol. 34, No. 1, pp. 1-5 (Jan. 1991).
Cutolo, et al., Hypothalamic-Pituitary-Adrenocortical Axis Function in Premenopausal Women with Rheumatoid Arthritis Not Treated with Glucocorticoids, J Rheumatol, Feb. 1999; 26(2): 282-8.
Cutter, Christopher, Compounded Percutaneous Testosterone Gel: Use and Effects in Hypogondal Men, JABFP, col. 14(1), pp. 22-32 (2001).
d'A Semple, P., W. S. Watson, R. Hume, and G. R Sutherland. Potassium studies in chronic obstructive airways disease. Thorax 33: 734-739 (1978).
Daly, R.C. et al., Testosterone's Effects Not Limited to Mood. Arch Gen Psychiatry 57: 403-404(Apr. 2001).
Damassa, et al., Sex Hormone-Binding Globulin and Male Sexual Development, Neuroscience and Biobehavioral Reviews, vol. 19, No. 2, pp. 165-175 (1995).
Data Supports Safety of Estratest for Men, Doctor's Guide, www.pslgroup.com (Mar. 9, 1998).
Davidson JM. et al., Effects of androgens on sexual behavior in hypogonadal men. J. Clin. Endocrinol. Metab. 48:955 (1979).
Davidson, et al., Hormonal Changes and Sexual Function in Aging Men, Journal of Clinical Endocrinology and Metabolism, vol. 57, No. 1, pp. 71-77 (1983).
Davidson, et al., Hormonal Replacement and Sexuality in Men, Clinics in Endocrinology and Metabolism, vol. 11, No. 3, pp. 599-623 (Nov. 1982).
Davis et al., Testosterone Enhances Estradiol's Effects on Postmenopausal Bone Density and Sexuality, Maturitas, vol. 21, No. 3, pp. 227-236 (Apr. 1995).
Davis, Androgen Treatment in Women, Medical Journal of Australia, vol. 170 (No. 11), p. 545-549. (Jun. 7, 1999).
Davis, The Clinical Use of Androgens in Female Sexual Disorders, Journal of Sex & Marital Therapy, vol. 24, pp. 153-163 (1998).

(56) References Cited

OTHER PUBLICATIONS

Davis, Androgen Replacement in Women: A Commentary, J Clin Endocrinol Metab, Jun. 1999; 84(6): 1886-91.
Davis, et al., Clinical Review 82: Androgens and the Postmenopausal Woman, J. Clin Endocrinol Metab, Aug. 1996; 81(8): 2759-63.
Davis, et al., Use of Androgens in Postmenopausal Women, Curr Opin Obstet Gynecol, Jun. 1997; 9(3): 177-80.
De Boer et al., Insulin therapy, hyperglycemia, and hypertension in type 1 diabetes mellitus. Arch Intern Med. Sep. 22, 2008;168(17):1867-73.
De Lignieres et al., Treatment of Male Hypogonadism by Topical Administration of Androgens. In: Mauvais-Jarvis et al. Eds. Percutaneous Absorption of Steroids, pp. 273-283 (1980).
De Lignieres, Transdermal Dihydrotestosterone Treatment of Andropause, Annals of Medicine 25: 235-241, (1993).
De Lunardo, et al., Determination of Acceptability of 2 Cutaneous Estradiol Gels, in a Dose of 1.5 mg Daily, J. Gynecol. Obstet. Bio. Reprod. (Paris), vol. 29, No. pp. 509-516, (Sep. 2000). (Abstract only).
De Ronde, Hyperandrogenism after transfer of topical testosterone gel: case report and review of published and unpublished studies, Human Reproduction, vol. 24(2), pp. 425-428 (2008).
De Ronde, Willem, Testosterone Gel for the Treatment of Male Hypogonadism, Expert Opin. Biol. Ther., vol. 9(2), pp. 249-253 (2009).
De Rose, et al., Combined Oral Therapy with Sildenafil and Doxazosin for the Treatment of Non-Organic Erectile Dysfunction Refractory to Sildenafil Monotherapy, Intl. J. of Impotence Research, vol. 14, pp. 50-53 (2002).
Definition of Isopropyl Myristate (5103), The Merck Index—An Encyclopedia of Chemicals, Drugs, and Biologicals, 11th edition, p. 821 (1989).
Delanoe et al., Androgenisation of Female Partners of Men on Medroxyprogesterone Acetate/Percutaneous Testosterone Contraception, The Lancet (Feb. 1984), p. 276.
Delatestryl BTG (testosterone cypionate), USP, Revised Dec. 2005.
Demery, A. Contraception Masculine Soins Gyn.-Obs.-Puer,-Ped No. 72 (May 1987) pp. 33-38.
Denis, Future Implications for the Management of Benign Prostatic Hyperplasia, Eur Urol, 1994; 25 Suppl 1:29-34.
Depo-Testosterone (testosterone cypionate), USP, Revised Aug. 2002.
Derogatis, The Derogatis Interview for Sexual Functioning (DISF/DISF-SR): an introductory report, J Sex Marital Ther. 1997 Winter;23(4):291-304.
Deslypere JP et al., Influence of age on pulsatile luteinizing hormone release and responsiveness of the gonadotrophs to sex hormone feedback in men. J. Clin. Endocrinol. Metab. 64:68 (1987).
Deslypere JP. et al., Leydig cell function in normal men: effect of age, life-style, residence, diet and activity. J. Clin. Endocrinol. Metab. 59:955-962 (1984).
Devogelaer et al., Low bone mass in hypogonadal males. Effect of testosterone substitution therapy, a densitometric study. Maturitas. Aug. 1992;15(1):17-23.
Diamond T. et al., Effects of testosterone and venesection on spinal and peripheral bone mineral in six hypogonadal men with hemochromatosis. J. Bone Min Res 6:39 (1991).
Ding, et al., Sex Hormone-Binding Globulin Mediates Prostate Androgen Receptor Action via a Novel Signaling Pathway, Endocrinology, vol. 139, No. 1, pp. 213-218 (Jan. 1998).
Dissemond, et al., Venous Leg Ulcers in a Patient with Klinefelter's Syndrome and Increased Activity of Plaminogen Activator Inhibitor-1, Acta. Derm. Venerol., vol. 83, pp. 149-150 (2002).
Dobs A, Clinical Trial of Testosterone Gel HRT in Hypogonal Men, Computer Retrieval of Information on Scientific Projects, downloaded at http://commons.ciLnih.gov/crisp3/CRISP_UB.getdoc?textkey=6457885&p_grant_num=5MO1RR000052-400738 (Feb. 19, 2002).
Dobs et al., Short-term pharmacokinetic comparison of a novel testosterone buccal system and a testosterone gel in testosterone deficient men. Current Med. Res. and Opns. 20(5):729-738 (2004).
Dobs et al., Pharmacokinetic Characteristics, Efficacy and Safety of Buccal Testosterone in Hypogonadal Males: A Pilot Study, J. Clinical Endocrinology & Metabolism 83:33-39 (1998).
Dobs, Androgen Therapy in AIDS Wasting, Bailliere's Clinical Endocrinology and Metabolism, vol. 12, No. 3, pp. 379-390 (Oct. 1998).
Dobs, A.S. Endocrine Disorders in Men Infected with Human Immunodeficiency Virus. Am. J. of Med. 84: 611-616 (Mar. 1988).
Dobs, et al., An Open Label Phase III Study of Fortigel (Testosterone) 2% Gels in Hypogondal Makes, ASA Poster (2009).
Dobs, et al., Pharmacokinetics, Efficacy and Safety of a Permeation-Enhanced Testosterone Transdermal System in Comparison with Bi-Weekly Injections of Testosterone Enanthate for the Treatment of Hypogonadal Men, J Clin Endocrinol Metab. Oct. 1999;84(10):3469-78.
Donahoe, et al., The effect of an aggressive nutritional support regimen on body composition in patients with severe COPD and weight loss. Am. J. Respir. Crit Care Med. 149(4):A3-A13 (1994).
Doren, Basic Principles of Hormone Replacement Therapy in the Postmenopause, Ther. Umsch Vo. 57 (No. 10). pp. 628-634 (Oct. 2000): (Abstract only).
Dosik et al., Tolerability comparison of adapalene gel, 0.3% versus tazarotene cream, 0.05% in subjects with healthy skin. (Clinical report). Journal of drugs in Dermatology. Jun. 1, 2007.
Douchi, et al., Serum Androgen Levels and Muscle Mass in Women with Polycystic Ovary Syndrome, Obstetrics & Gynecology, vol. 94, No. 3, pp. 337-340 (1999).
Douglas, et al., Effect of Exogenous Testosterone Replacement on Prostate-Specific Antigen and Prostate-Specific Membrane Antigen Levels in Hypogonadal Men, J. of Surg. Oncology, vol. 59, pp. 246-250 (1995).
Dr. N's Menopause & Hysterectomy Resource Page, http://www.menopausehysterectomy.com/methods.htm (accessed Jun. 22, 2000).
Drafta, et al., The Effects of Endocrine Therapy on Plasma Steroids in Prostatic Carcinoma Patients, Endocrinolgie, Jul.-Sep. 1984; 22(3): 191-7.
Drake, et al., Associations Between Circulating Sex Steroid Hormones and Cognition in Normal Elderly Women, Neurology, Feb. 2000; 54(3): 599-603.
Drobac et al., A workshop on pubertal hormone replacement options in the United States, Journal of Pediatric Endocrinology and Metabolism, 19(1):55-64 (2006).
Ducharme, Male Menopause: The Real Thing?, PN/Paraplegia News, Nov. 2002.
Duncan PW, et al., Functional reach: a new clinical measure of balance. J Geron 45:M192-7, 1990.
Earthman, CP, et al., A comparison of bioimpedance methods for detection of body cell mass change in HIV infection. J. Appl, Physiol 88: 944-956 (2000).
Echikson, Solvay CEO's Positive Outlook Breaks with Usual Caution, Dow Jones News Service, Jun. 6, 2002.
Edelstein, et al., The Latest Option and Future Agents for Treating Male Hypogonadism, Expert Opin. Pharmcaother., vol. 8(17), pp. 2991-3008 (2007).
Ehrenfeld, T. Health: A Loving Feeling, Newsweek (Nov. 11, 2002).
El Tribunal De Justicia De La Comunidad Andina, Oct. 27, 2000 (available at http://intranet.comunidadandina.org/Documentos/Procesos/21-ip-2000.doc).
ENDO 99: Testosterone Patch Effective for Diminished Sexual Function in Surgically Menopausal Women, Doctor's Guide to the Internet, www.docguide.com (Jun. 15, 1999).
Engelen, et al., Nutritional depletion in relation to respiratory and peripheral skeletal muscle function in out-patients with COPD. Eur. Respir. J. 7: 1793-1797 (1994).
English, et al., Low-Dose Transdermal Testosterone Therapy Improves Angina Threshold in Men with Chronic Stable Angina: A Randomized, Double-Blind, Placebo-Controlled Study, Circulation, vol. 102, pp. 1906-1911 (2000).

(56) References Cited

OTHER PUBLICATIONS

English, et al., Men with Coronary Artery Disease Have Lower Levels of Androgens than Men with Normal Coronary Angiograms, European Heart J., vol. 21, pp. 890-894 (2000).
English, et al., Testosterone Acts as Coronary Vasodilator by a Calcium Antagonistic Action, J. of Endocrinological Investigation, vol. 25, pp. 455-458 (2002).
Eriksson, et al., Serum Levels of Androgens are Higher in Women with Premenstrual Irritability and Dysphoria Than in Controls, Psychoneuroendocrinology, vol. 17, Nos. 2-3, pp. 195-204 (May-Jul. 1992).
Ernesti, et al., Absorption and Metabolism of Topically Applied Testosterone in an Organotypic Skin Culture, Skin Pharmacol, 1992; 5(3): 146-153.
Escoffier et al., Age-related mechanical properties of human skin: an in vivo study, the Society for Dermatology, Inc. 353 (1989).
Esposito, J, Rights to Market: Marketing Presence in Oncology, Med Ad News (West Trenton, NJ), Oct. 2002.
EstroGel® 0.06% (estradiol gel), 500123, 3E Rev Mar. 2004, pp. 1-16.
Estrogel, www.netdoktor.dk/medicin/Fakta/Estrogel (Downloaded Jun. 26, 2001).
Events Calendar: Events for the week of Dec. 13-19—Sportmart: Time Out for Men's Health, St. Paul Pioneer Press, Dec. 13, 2002.
Ewing, et al., Dihydrotestosterone Concentration of Beagle Prostatic Tissue: Effect of Age and Hyperplasia, Endocrinology, Dec. 1983; 113(6): 2004-9.
Experimental Abbott drug halts spread of prostate cancer. Chicago Tribune, Jun. 5, 2001.
Exton, et al., Cardiovascular and Endocrine Alternations after Masturbation-Induced Orgasm in Women, Psychosom Med, May-Jun. 1999; 61(3): 280-9.
Fabbri, et al., Testosterone Treatmet to Mimic Hormone Physiology in Androgen Replacement Therapy: A View on Testosterone Gel and Other Preparation Available, Expert Opin. Biol. Ther., vol. 7(7), pp. 1093-1106 (2007).
Fahmy, et al., Is the Measurement of Serum Testosterone Routinely Indicated in Men with Erectile Dysfunction?, BJU Intl., vol. 84, pp. 482-484 (1999).
Fahrner et al., Effects of Endurance Exercise on Free Testosterone Concentration and the Binding Affinity of Sex Hormone Binding Globulin (SHBG), International Journal of Sports Medicine, vol. 19, No. 1, pp. 12-15 (Jan. 1998). (Abstract only).
Farmer et al., Race and sex differences in hip fracture incidence. Am J. Public Health 74:1374 (1984).
FDA Guidance for Industry, Bioavailability and Bioequivalence Studies for Orally Administered Drug Products—General Considerations, Mar. 2003.
FDA Guidance for Industry, Developing Products for Weight Management (Draft Guidance), Feb. 2007.
FDA Guidance for Industry, Statistical Approaches to Establishing Bioequivalence, Jan. 2001.
FDA press release, Testosterone Gel Safety Concerns Prompt FDA to Require Label Changes, Medication Guide, May 7, 2009.
Fedorak et al., A novel colon-specific steroid prodrug enhances sodium chloride absorption in rat colitis, Am. J. Physiol, 269:G210-218 (1995).
Feigl, et al., Design of the Prostate Cancer Prevention Trial (PCPT), Controlled Clinical Trials, vol. 16, pp. 150-163 (1995).
Feldman, et al., Impotence and Its Medical and Psychosocial Correlates: Results of the Massachusetts Male Aging Study, The J. of Urology, vol. 151, pp. 54-61 (Jan. 1994).
Feldmann et al., Percutaneous Penetration of 14C Hydrocortisone in Man. Archives of Dermatology. 94:649-651 (1966).
Female Sexual Dysfunction and Andropause Could be Advisory Cmte. Topics, The Pink Sheet (Chevy Chase, MD), Mar. 18, 2002.
Female Testosterone in Phase II, Pharmaceutical Business News, vol. 12 (No. 279), p. 17 (Nov. 8, 1996).
Ferenchick, Are Androgenic Steroids Thrombogenic?, The New England Journal of Medicine, p. 476 (Feb. 15, 1990).
Ferreira, I. et al., The influence of 6 months of oral anabolic steroids on body mass and respiratory muscles in undernourished COPD patients. Chest 114: 19-28 (1998).
Fertility Industry News; Unimed Pharmaceuticals' Androgel Shows Solid Promise for Men. Aug. 19, 1998. http://staging.inciid.org/fertinews/androgel.html (Androgel Press Release Aug. 19, 1998).
Fiet J et al., Percutaneous absorption of 5a-dihydrotestosterone in man. I. Plasma androgen and gonadotropin levels in normal adult men after percutaneous administration of 5a-dihydrotestosterone. Int J. Androl 5:586 (1982).
Findlay et al., Journal of Clinical Endocrinology & Metabolishm, 64(2):266-68 (1987).
Findlay, et al., Treatment of Primary Hypogonadism in Men by the Transdermal Administration of Testosterone, J Clin Endocrinol Metab, Feb. 1989; 68(2): 369-373.
Finkelstein JK et al., Osteoporosis in men with idiopathic hypogonadotrophic hypogonadism. Ann Intern Med. 106:354 (1987).
Finkelstein JS, et al., Increases in bone density during treatment of men with idiopathic hypogonadotropic hypogonadism. J Clin Endocrinol Metab 1989; 69 ; 69:776-783.
First Phase of Testosterone TDS Trial Successful. Press release. Mar. 5, 2004.
Floter, et al., Administration of Testosterone Undecanoate in Postmenopausal Women: Effects on Androgens, Estradiol, and Gonadotrophins., Menopause, Jul.-Aug. 2000; 7(4): 251-6.
Flynn MA et al., Total body potassium in aging humans: longitudinal study. Am J. Clin. Nutr. 50:713 (1989).
Folstein MF, et al., Mini-mental state. A practical method for grading the cognitive state of patients for the clinician. J Psychiatr Res. 1975; 12: 189-198.
Forbes GB. et al., Age and sex trends in lean body mass calculated from 40K measurements: with a note on theoretical basis for the procedure Ann NY Acad Sci 110:225 (1963).
Fournier et al., Value of a Percutaneous Estrogen Solution in Stopping Lactation, Rev. Fr. Gynecol. Obstet., vol. 85, No. 12, pp. 715-719 (Dec. 1990). (Abstract only).
Fowler, et al., The Response of Metastatic Adenocarcinoma of the Prostate to Exogenous Testosterone, The J. of Urology, vol. 126, pp. 372-375 (Sep. 1981).
Francis RM et al., Osteoporosis in hypogonadal men: role of decreased plasma 1.21-dihydroxy vitamin D, calcium malabsorption and low bone formation. Bone 7:261 (1986).
Francoeur, M. et al., "The protein-lipid structure of stratum corneum in relation to its phase and permeability properties," Biophys. J. (1990) 57:188a.
Francoeur, M.L. et al., "Oleic acid: its effects on stratum corneum in relation to (trans)dermal drug delivery," Pharm. Res. (1990) 7(6):621-627.
Franklin, et al., Precocious Puberty Secondary to Topical Testosterone Exposure, Journal of Pediatric Endocrinology &Metabolism, vol. 16(1), pp. 107-110 (2003).
Fransen, et al., Excess Mortality or Institutionalization After Hip Fracture: Men Are at Greater Risk than Women, JAGS, vol. 50, pp. 685-690 (2002).
Free Health Screenings Offered Saturday for Men, The Tampa Tribune, Nov. 8, 2002.
Freidl KE et al., High density lipoprotein cholesterol is not decreased if an aromatizable androgen is administered. Metabolism 39:69-74 (1990).
Friday, Jul. 5—Men's Health, Arizona Republic (Phoenix, AZ), Jul. 5, 2002.
Friedl KE et al., The administration of pharmacological doses of testosterone or 19-nortestosterone to normal men is not associated with increased insulin secretion or impaired glucose tolerance. J. Clin. Endocrinol. Metab. 68:971 (1989).
Fugl-Myer, et al., On Life Satisfaction in Male Erectile Dysfunction, Intl. J. of Impotence Research, vol. 9, pp. 141-148 (1997).
Fukayama S. et al., Direct modulation by androgens of the response of human bone cells (SaOS-2) to human parathyroid hormone (PTH) and PTH related protein. Endocrinology 125:1789 (1989).
Furuyama et al., Radioimmunoassay for Plasma Testosterone, Steroids, vol. 16, No. 4, pp. 415-428 (1970).

(56) References Cited

OTHER PUBLICATIONS

Gabiga, H. et al., "Effect of penetration enhancers on isosorbide dinitrate penetration through rat skin from a transdermal therapeutic system," Int. J. Pharma. (2000) 199:1-6.

Gaidano et al., Dynamics of the Binding Capacity of Plasma Sex Hormone Binding Globulin (SHBG) for Testosterone and Dihydrotestosterone During Puberty, Clinical Chimica Acta, vol. 100, No. 2, pp. 91-97 (Jan. 15, 1980).

Gallagher JC. et al., Epidemiology of fractures of the proximal femur in Rochester, Minnesota. Clen. Orth. Rel.Res. 150:163 (1980).

Gallagher, et al., Androgens Contribute to the Stimulation of Cancellous Bone Formation by Ovarian Hormones in Female Rats, The American Physiological Society, pp. E407-E412 (1996).

Gann et al., Prospective Study of Sex Hormone Levels and Risk of Prostate Cancer, Journal of National Cancer Institute, vol. 88, No. 16, pp. 1118-1126 (Aug. 21, 1996).

Garban et al., Restoration of Normal Adult Penile Erectile Response in Aged Rats by Long-Term Treatment with Androgens, Biology of Reproduction, vol. 53, pp. 1365-1372 (1995).

Garnett et al., A Cross-Sectional Study of the Effects of Long-Term Percutaneous Hormone Replacement Therapy on Bone Density, Obstetrics & Gynecology, vol. 78, No. 6, pp. 1002-1007 (Dec. 1991).

Garnett et al., The Effects of Plasma Estradiol Levels on Increases in Vertebral and Femoral Bone Density Following Therapy with Estradiol and Estradiol with Testosterone Implants, Obstetrics and Gynecology. vol. 79, No. 6, pp. 968-972 (Jun. 1992).

Gearon, Dealing with Male Menopause, DiscoveryHealth.com (Jan. 2, 2002).

Gefael, Graeme's Testosterone Page, www.voyager.co.nz (May 12, 2000).

Geist S. H., Androgen therapy in the human female, J. Clin. Endocrinol. 1941; 1:154-161.

Gelfand et al., Androgen and estrogen-androgen hormone replacement therapy: a review of the safety literature, 1941-1996. Clinical Therapeutics, Excerpta Medica, Princeton, NJ, US vol. 19, No. 3, 1997, pp. 383-404.

Geller, Basis for Hormonal Management of Advanced Prostate Cancer, Cancer, Feb. 1, 1993; 71(3 Suppl): 1039-45.

Geller, et al., DHT in Prostate Cancer Tissue—a Guide to Management and Therapy, Prostate, 1985; 6(1):19-25.

Geller, Nonsurgical Treatment of Prostatic Hyperplasia, Cancer, Jul. 1, 1992; 70(1 Suppl): 339-45.

Geller, Pathogenesis and Medical Treatment of Benign Prostatic Hyperplasia, Prostate Suppl, 1989; 2:95-104.

Gennaro, Remington: The Science and Practice of Pharmacy, 20th Edition, "gels": pp. 745-747 (2000).

Gennaro, Remington: The Science and Practice of Pharmacy, 20th Edition, "sodium hydroxide": p. 1047 (2000).

Gennaro, Remington: The Science and Practice of Pharmacy, 20th Edition, Chapter 44, penetration enhancers,: pp. 842-843 (2000).

Gennaro, Remington: The Science and Practice of Pharmacy, 20th Edition, Chapter 57, Drug Absorption, Action, and Disposition, (2003).

Gennaro, et al., Remington's Pharmaceutical Sciences, Eighteenth Edition, pp. 1305, 1314-1315 (1990).

Genuth et al., Glycation and carboxymethyllysine levels in skin collagen predict the risk of future 10-year progression of diabetic retinopathy and nephropathy in the diabetes control and complications trial and epidemiology of diabetes interventions and complications participants with type 1 diabetes. Diabetes. Nov. 2005;54(11):3103-11.

Gerrity MS, Gaylord S. Williams ME. Short version of the timed manual performance test. Development, reliability and validity. Med Care 1993;31(7):617-628.

Gerstenbluth, Prostate-Specific Antigen Changes in Hypogonadal Men Treated with Testosterone Replacement, J. of Andrology, vol. 23, No. 6, pp. 922-926 (Nov./Dec. 2002).

Gertner, J.M., I-70, Hypogonadism is Uncommon in Men with Aids-Associated Wasting. 38th Annual ICAAC, Abstracts: 384, (1998).

Get it Checked! Radio: Audio News Release. Mens Health Network: Jun. 10-16, 2002?.

Ghosh et al., Methods of Enhancement of Transdermal Drug Delivery: Part I, Physical and Biochemical Approaches, Pharmaceutical Technology, pp. 73-90 (Mar. 1993).

Ghosh et al., Methods of Enhancement of Transdermal Drug Delivery: Part IIA, Chemical Permeation Enhancers, Pharmaceutical Technology, pp. 62-90 (Apr. 1993).

Ghosh et al., Methods of Enhancement of Transdermal Drug Delivery: Part IIB, Chemical Permeation Enhancers, Pharmaceutical Technology, pp. 68-76 (May 1993).

Ghusn et al., Evaluation and Treatment of Androgen Deficiency in Males. The Endocrinologist 1(6):399-408 (1991).

Goggin, et al., The Relationship of Mood, Endocrine, and Sexual Disorders in Human Immunodeficiency Virus Positive (Hiv+) Women: an Exploratory Study, Psychosom Med, Jan.-Feb. 1998; 60(1): 11-6.

Goldberg-Cettina et al., Enhanced transdermal delivery of estradiol in vitro using binary vehicles of isopropyl myristate and short-chain alkanols, Int'l J. Pharmaceutics (1995);114:237-245.

Golden GM, et al., "Role of stratum corneum lipid fluidity in transdermal drug flux," J Pharm Sci. Jan. 1987;76(1):25-8.

Goldstat, R. et al., "Transdermal testosterone therapy improves well-being, mood, and sexual function in premenopausal women," Menopause (2003) 10(5):390-398.

Gonzalez-Sagrado, et al., Reference Values and Methods Comparison of a New Testosterone Assay on the AxSYM System, Clin Biochem, Apr. 2000; 33(3): 175-9.

Gonzalo IT et al., Levonorgestrel implants (Norplant II) for male contraception clinical trials: combination with transdermal and injectable testosterone. J Clin Endocrinol Metab. Aug. 2002;87(8):3562-72.

Good, et al., Bone Mineral Density and Body Composition in Lean Women with Polycystic Ovary Syndrome, Fertil Steril, Jul. 1999; 72(1): 21-5.

Goodman & Gilman, Pharmacological Basis of Therapeutics, Ninth Edition (McGraw-Hill, New York, 1996), p. 8.

Goodman, et al., Action of Skin Permeation Enhancers Azone, Oleic Acid and Decylmethyl Sulphoxide: Permeation and DSC Studies. J Pharm Pharmacol 38(Supply): 71P, 1986.

Goodman, M. et al., "Action of penetration enhancers on human skin as assessed by the permeation of model drugs 5-fluorouracil and estradiol. I. Infinite dose technique," J. Invest. Dermatol. (1988) 91:323-327.

Goodman, M. et al., "Lipid-protein-partitioning (LPP) theory of skin enhancer activity: finitie dose technique," Int. J. Pharma. (1989) 57:29-40.

Gooren L J. G. and Polderman K. H., Safety aspects of androgens. In Testosterone: Action, Deficiency, Substitution, E. Nieschlag and H M. Behre, editors, Springer-Verlag, Heidelberg, p. 136 (1990).

Gooren, Androgen levels and sex function in testosterone-treated hypogonadal men, Archives of Sexual Behavior 16(6):463-473 (1987).

Gooren, Human male sexual functions do not require aromatization of testosterone: a study using tamoxifen, testolactone, and dihydrotestosterone, Arch. Sex. Behav. 14(6):539-48 (1985).

Gooren, A Ten-Year Safety Study of the Oral Androgen Testosterone Undecanoate, J Androl. May-Jun. 1994;15(3):212-5.

Gordon C L, et al., Relation between image-based assessment of distal radius trabecular structure and compressive strength, Canad. Assoc. Radiol. J., 49:390-7 (1998).

Gosker, et al., Skeletal muscle dysfunction in chronic obstructive pulmonary disease and chronic heart failure: underlying mechanisms and therapy perspectives. Am. J. Clin. Nutr. 71: 1033-1047 (2000).

Gouchie, et al., The Relationship Between Testosterone Levels and Cognitive Ability Patterns, Psychoneuroendocrinology, vol. 16, No. 4, pp. 323-334 (1991).

Gould, Duncan, A Novel Metered-Dose 2% Testosterone Gel Treatment for Male Hypogonadism, JMHG, vol. 4(4), pp. 419-427 (2007).

Graeme's Testosterone Page, http://www.voyager.co.nz/~gtuck/graeme/ (May 12, 2000).

Granger CV, et al., Functional assessment scales: a study of persons with multiple sclerosis. Arch Phys Med Rehab 71:870-5, 1990.

(56) References Cited

OTHER PUBLICATIONS

Gravholt, et al., Reduced Androgen Levels in Adult Turner Syndrome: Influence of Female Sex Steroids and Growth Hormone Status, Clinical Endocrinology, vol. 50(6), p. 791-800. (Jan. 22, 1999).

Gray A, et al., Age, disease, and changing sex hormone levels in middle-aged men: results of the Massachusetts Male Aging Study. J Clin Endocrinol Metab 73:1016-25, 1991.

Gray A. et al., An examination of research design effects on the association of testosterone and male aging: results of a meta-analysis. J. Clin Epidemiol 44:671 (1991).

Greendale, et al., Endogenous Sex Steroids and Bone Mineral Density in Older Women and Men: the Rancho Bernardo Study, J Bone Miner Res, Nov. 1997; 12(11): 1833-43.

Greenspan SL. et al., Osteoporosis in men with hyperprolactinemic hypogonadism. Ann Intern Med 104:777-82 (1986).

Gregory, et al., A Mechanism for Androgen Receptor-mediated Prostate Cancer Recurrence After Androgen Deprivation Therapy, Cancer Research, vol. 61, pp. 4315-4319 (Jun. 1, 2001).

Gregory, et al., Androgen Receptor Expression in Androgen-independent Prostate Cancer Is Associated with Increased Expression of Androgen-regulated Genes, Cancer Research, vol. 58, pp. 5718-5724 (Dec. 15, 1998).

Greider, "Experts Divided on Value of Testosterone Therapy for Men," AARP Bulletin Online (Jul.-Aug. 2003).

Griffin, J.E. "Hormonal Replacement Therapy at the Time of Expected Puberty in Patients With Gonadal Failure." The Endocrinologist (2003);13(3):211-213.

Griggs RC et al., Effect of testosterone on muscle mass and muscle protein synthesis. J. Appl Physiol 66:498 (1989).

Grignon, et al., College of American Pathologists Conference XXVI on Clinical Relevance of Prognostic Markers in Solid Tumors: Report of the Prostate Cancer Working Group, Arch. Pathol. Lab. Med., vol. 119, pp. 1122-1126 (Dec. 1995).

Grinspoon, et al, Body Composition and Endocrine Function in Women with Acquired Immunodeficiency Syndrome Wasting, J. Clin Endocrinol Metab, May 1997; 82(5): 1332-7.

Grinspoon, et al., Effects of Androgen Administration in Men with the AIDS Wasting Syndrome: A Randomized, Double-Blind, Placebo-Controlled Trial, Ann. Intern. Med., vol. 129, pp. 18-26 (1998).

Grinspoon, Scientific Project: AIDS Wasting in Women—Anabolic Effects of Testosterone, http://commons.cit.nih.gov/crisp3/CRISP_LIB.getdoc?textkey=6381169&p_grant_num=5R01DK054167-04 (downloaded at Feb. 19, 2002).

Grober ED, et al., Efficacy of changing testosterone gel preparations (Androgel or Testim) among suboptimally responsive hypogonadal men, Int J Impot Res. Mar.-Apr. 2008;20(2):213-7. (Epub Date: Sep. 27, 2007).

Gruber, et al., Effect of Percutaneous Androgen Replacement Therapy on Body Composition and Body Weight in Postmenopausal Women, Maturitas, vol. 29, pp. 253-259 (Jun. 1998).

Guay, et al., Testosterone Treatment in Hypogonadal Men: Prostate-Specific Antigen Level and Risk of Prostate Cancer, Endocrine Practice, vol. 6, No. 2, pp. 132-138 (Mar./Apr. 2000).

Guideline on Clinical Evaluation of Medical Products Used in Weight Control—Addendum on weight control in children. European Medicines Agency. Nov. 15, 2007.

Gunawardena, et al., Testosterone Is a Potential Augmentor of Antioxidant-induced Apoptosis in Human Prostate Cancer Cells, Cancer Detection and Prevention, vol. 26, pp. 105-113 (2002).

Guralnik JM, et al., A short physical performance battery assessing lower extremity function: Association with self-regulated disability and predictors of mortality and nursing home admission. J Gerontol Med Sci 1994;49:M85-M94.

Guzick, et al., Sex, Hormones, and Hysterectomies, The New England Journal of Medicine, vol. 343, No. 10, pp. 730-731 (Sep. 7, 2000).

Gwin et al., The effect of topical pilocarpine on intraocular pressure and pupil size in the normotensive and glaucomatous beagle. Investigative Ophthalmology and Visual Science 16:1143-1148 (1977).

Hadgraft et al., eds. "Transdermal Drug Delivery: Developmental Issues and Research Initiatives." Marcel Dekker: New York (1990). Ch. 10.

Hadigan, Scientific Project: AIDS Wasting in Women: Anabolic Effects of Testosterone Treatment Only, http://commons.cit.nih.gov/crisp3/CRISP_LIB.getdoc?textkey=6439601&p_grant_num=3M01RR000088-37S10365 (downloaded Feb. 19, 2001).

Hagenfeldt Y, Linde K, Sjoberg He, Zumkeller W, Arver S: Testosterone increases serum 1,25-dihydroxy vitamin D and insulin-like growth factor-1 in hypogonadal men. Int J Androl 15:93-102, 1992.

Hajjar, et al., Outcomes of Long-Term Testosterone Replacement in Older Hypogonadal Males: A Retrospective Analysis, J. of Clinical Endocrinology and Metabolism, vol. 82, No. 11, pp. 3793-3796 (1997).

Hak, Elisabeth A., Authors Response: Low Levels of Endogenous Androgens Increase the Risk of Atherosclerosis in Elderly Men—Further Supportive data. J Clin Endocrinol Metab 88(3): 1404(2003).

Hak, et al., Low Levels of Endogenous Androgens Increase the Risk of Atherosclerosis in Elderly Men: The Rotterdam Study, The J. of Endocrinology & Metabolism, vol. 87, No. 8, pp. 3632-3639 (2002).

Hall, et al., A Randomized Trial of Testosterone Therapy in Males with Rheumatoid Arthritis, Brit. J. of Rheumatology, vol. 35, pp. 568-573 (1996).

Hameed, A. et al. Delivery of testosterone replacement therapy. Curr Opin in Invest Drugs 2003. 4(1):1213-1219.

Handbook of Pharmaceutical Excipients, Third Edition, pp. 71-73, 85-90, 244-255, 263-266, 336-339, 465-467, 568-569, 599-601 (2000).

Handbook of Pharmaceuticals Excipients, Fourth Edition, pp. 89-92, 95-100, 289-296, 309-313, 543-545, 566-567, 654-656, 691-693 (2003).

Handelsman, et al., Pharmacokinetics and Pharmacodynamics of Testosterone Pellets in Man, Journal of Clinical Endocrinology and Metabolism, vol. 70, No. 1., pp. 216-222 (1990).

Hanke, et al., Effect of Testosterone on Plaque Development and Androgen Receptor Expression in the Arterial Vessel Wall, Circulation, vol. 103, No. 10, pp. 1382-1385 (Mar. 13, 2001).

Hansen, Nanette et al., Transcript of Early Today, (NBC television broadcast Jul. 31, 2002).

Hansen, R.P. et al., "The branched-chain fatty acids of mutton fat. 3. The isolation of 16 methylheptadecanoic acid," Methylheptadecanoic Acid in Mutton Fat, 16 (1956) 64:214-216.

Hanson DA et al., A specific immunoassay for monitoring human bone resorption: quantitation of type I collagen crosslinked n-telopeptides in urine. J. Bone Min Res 7:1251 (1992).

Hardy, et al., Endocrine Assessment of Impotence—Pitfalls of Measuring Serum Testosterone Without Sex-Hormone-Binding Globulin, Postgrad Med J (1994) 70, 836-837.

Harman SM. et al., Reproductive hormones in aging men. I. Measurement of sex steroids, basal luteinizing hormone, and Leydig cell response to human chorionic gonadotropin. J. Clin Endocrinol. Metab. 51:35 (1980).

Harman SM. et al., Reproductive hormones in aging men. II. Basal pituitary gonadotropins and gonadotropin responses to luteinizing hormone releasing hormone. J. Clin. Endocrinol. Metab. 54:547 (1982).

Hatch et al., Hirsutism: implications, etiology and management. Am. J. Obstet. Gynec. 140: 815-830 (1981).

Hecht, Ask Dr. Hecht, New York Daily News, Apr. 22, 2002.

Heikkila, et al., Serum Androgen-Anabolic Hormones and the Risk of Rheumatoid Arthritis, Ann Rheum Dis, May 1998; 57(5): 281-5.

Heiss, et al., Associations of Body Fat Distribution, Circulating Sex Hormones Bone Density in Postmenopausal Women, J Clin Endocrinol Metab, May 1995; 80(5): 1591-6.

Hendrick, Bill, Over the Hill? Atlanta Journal-Constitution, Healthy Living, Sep. 17, 2002.

Hengge, U. R., M. Baumann, R Maleba, N. H. Brockmeyer, and M. Goos. Oxymetholone promotes weight gain in patients with advanced human immunodeficiency virus (HIV-1) infection. Br. J. Nutr. 75: 129-138 (1996).

Herkenne, C. et al., "Effect of propylene glycol on ibuprofin absorption into human skin in vivo," J. Pharma. Sci. (2008) 97(1):185-197.

(56) References Cited

OTHER PUBLICATIONS

Hermens, WA. Delivery of hormones: some new concepts. Pharm. Weekbl Sci. 14(4A):253-7. 1992.

Herschberg AD., A new treatment of climacteric disorders, Gynecol Prat. 1965;16:433-42. (Article in French with English Summary).

Heymsfield SB et al., Dual photon absorptiometry: comparison of bone mineral and soft tissue mass measurements in vivo with established methods. Ann J Clin. Nutr 49:1283 (1989).

Hill, et al., Analysis of Relations Between Serum Levels of Epitestosterone, Estradiol, Testosterone, IGF-1 and Prostatic Specific Antigen in Men with Benign Prostatic Hyperplasia in Carcinoma of the Prostate, Physiol. Res., vol. 49 (Suppl. 1), pp. S113-S118 (2000).

HIV Wasting Syndrome, www.thebody.com (May 1997).

HIV Wasting Treatment: Nandrolone Decanoate, www.hivinsite. ucsf.edu (Aug. 1, 1995).

HIV/AIDS Clinical Trials in the New Orleans Area, ACTG 329, www.tmc.tulane.edu (Downloaded Oct. 8, 1998).

Hobbs CJ, Plymate SR, Rosen CJ, Adler RA: Testosterone administration increases insulin-like growth factor-1 levels in normal men. J Clin Endocrinol Metab 77:776-9, 1993.

Hochhaus, et al., A Selective HPLC/RIA for dexamethasone and its prodrug dexamethasone-21-sulphobenzoate sodium in biological fluids, Biomed. Chrom., 6:283-286 (1992).

Hoelgaard, A. et al., "Dermal drug delivery—improvement by choice of vehicle or drug derivative," J. Control. Release (1985) 2:111-120.

Hoffman, et al., Is Low Serum Free Testosterone a Marker for High Grade Prostate Cancer?, J. Urology, vol. 163, pp. 824-827 (Mar. 2000).

Holman et al., 10-year follow-up of intensive glucose control in type 2 diabetes. New England Journal of Medicine (2008);359(15):1577-1589.

Holownia, et al., A Clinical Evaluation of a Direct Radioimmunoassay of Testosterone; Clin Chim Acta, Jan. 31, 1993; 214(1): 31-43.

Hormone Therapy, BioSante Pharmaceuticals. Available at http://web.archive.org/web/20020607191414/biosantepharma.com/products/hrt.html (Downloaded in Oct. 2002).

Howell et al., "Testosterone Deficiency and Replacement," Horm Res, 56 Suppl 1: 86-92 (2001); Abstract.

Howland, The Other Hormone Replacement Therapy: Testosterone in Menopausal Women, HealthGate, www.bewell.com (Aug. 7, 2000).

Hsieh, et al., Risk Factors for Prostate Cancer: A Case-Control Study in Greece, Int. J. Cancer, vol. 80, pp. 699-703 (1999).

Humberstone et al., Comparison of pharmacokinetics and tolerability following application of an Estraderm 50® patch or a novel Estradiol Metered-Dose Transdermal Spray (MTDS®). Poster. Presented at the North American Menopause Society (NAMS) 13th Annual Meeting, Chicago, Oct. 2002.

Humberstone et al., Elevation of serum testosterone levels in oophorectomized women following application of a novel Metered-Dose Transdermal Spray (MTDS(RM)). Poster. Presented at the North American Menopause Society (NAMS) 13th Annual Meeting, Chicago, Oct. 2002.

Humberstone et al., Pharmacokinetics of estradiol after application of an Estradiol Metered-Dose Transdermal System (MDTS(RM)): Linearity and effect of washing the application site. Poster, Acrux Drug Delivery Solutions. Presented at American Association of Pharmaceutical Scientists (AAPS) (2002), Abstract published at AAPS PharmSci. 2002; 4(S1).

Husband Crabby, Sluggish, WebMD.com (May 6, 2002).

Hwang S N, et al., Probability-based structural parameters from three-dimensional nuclear magnetic resonance images as predictors of trabecular bone strength., Med. Phys., 24:1255-61 (1997).

Hydrocortisone (hydrocortisone cream 2.5%, and hydrocortisone ointment 2.5%). RxList.com. http://www.rxlist.com/hydrocortisone-drug.htm. pp. 1-2. Downloaded on Oct. 13, 2009.

Idson, et al., Percutaneous Absorption Enhancers, D&CI, pp. 30-33 (Jul. 1985).

Impotence Treatments, Impotence World Association, http://www.imootenceworld.org/treatment.htm (2000).

Industry News: Mens Health Effort, M M R/MASS Market Retailers (New York, NY), Sep. 23, 2002.

Information on TestoCreme® from www.testocreme.com. Downloaded on Oct. 21, 2002.

International Cosmetic Ingredient Dictionary and Handbook (2004) p. 912 Monographs—from "Isosteareth-25" to "Isostearic Acid".

Internet information on Bentley Pharmaceuticals, research.businessweek.com (Oct. 21, 2002).

Iqbal, et al., Binding of Testosterone and Oestradiol to Sex Hormone Binding Globulin, Human Serum Albumin and Other Plasma Proteins: Evidence for Non-Specific Binding of Oestradiol to Sex Hormone Binding Globulin, Clinical Science, vol. 64, No. 3, pp. 307-314 (Mar. 1983).

Isaacs, et al., Etiology and Disease Process of Benign Prostatic Hyperplasia, Prostate. Suppl 2:33-50 (1989).

Isaacs, Etiology of Benign Prostatic Hyperplasia, Eur Urol, 1994; 25 Suppl 1:6-9.

Isaia, et al., Effect of Testosterone on Bone in Hypogonadal Males, Maturitas, vol. 15, pp. 47-51 (1992).

Isidori et al.,Erectil dysfunction. Recent Prog. Med., Jul.-Aug. 1999; 90(7-8):396-402.

Itoh et al., The Assessment of Bioavailable Androgen Levels from the Serum Free Testosterone Level, Nippon Naibunpi Gakkai Zasshi, vol. 67, No. 1, pp. 23-32 (Jan. 20, 1991). (Abstract only).

Jackson JA et al., Bone histomorphometry in hypogonadal and engonadal men with spinal osteoporosis. J. Clin Endocrinol. Metab. 65:53 (1987).

Jackson JA, Riggs MW, Spiekerman AM: Testosterone deficiency as a risk factor for hip fractures in men: a case-control study. Am J Med Sci 304:4-8, 1992.

Jackson S A, et al., Vertebral fracture definition from population-based data: preliminary results from the Canadian Multicenter Osteoporosis Study (CaMos), Osteoporosis Int., 11:680-7 (2000).

Jaffa et al., Connective tissue growth factor and susceptibility to renal and vascular disease risk in type 1 diabetes. J Clin Endocrinol Metab. May 2008;93(5):1893-900. (Epub Date: Mar. 4, 2008).

Jaffe, et al., Effect of 5-Alpha-Reductase Inhibition on Sex-Hormone-Binding Globulin in Elderly Men, Horm. Res., vol. 41, pp. 215-217 (1994).

Jain, et al., Testosterone Supplementation for Erectile Dysfunction: Results of a Meta-Analysis, The J. or Urology, vol. 164, pp. 371-375 (Aug. 2000).

James JS. San Francisco area: testosterone replacement study, injection vs. patch. AIDS Treat News. Oct. 20, 1995(233):7-8.

Janowsky JS et al., Testosterone administration enhances spatial cognition in older men. Soc for Neurosci Ann Meeting, New Orleans, LA (1991).

Janowsky, et al., Sex Steroids Modify Working Memory, J. of Cognitive Neuroscience, vol. 12, No. 3, pp. 407-414 (2000).

Janowsky, et al., Testosterone Influences Spatial Cognition in Older Men, Behavioral Neuroscience, vol. 108, No. 2, pp. 325-332 (1994).

Jarkander-Rolff, et al., Transdermal Application of a Testosterone Gel—A Pharmacokinetic Study. Menopause (1997), vol. 4(4): 251.

Jarvinen et al., "Steady-state pharmacokinetics of oestraradiol gel in post-menopausal women: effects of application area and washing," British Journal of Obstetrics and Gynaecology 104(16): 14-18 (1997).

Javanbakht, et al., Pharmacokinetics of a Novel Testosterone Matrix Transdermal System in Healthy, Premenopausal Women and Women Infected with the Human Immunodeficiency Virus, Journal of Clinical Endocrinology and Metabolism, vol. 85, No. 7, pp. 2395-2401 (Jul. 2000).

Jenkins et al., Serum lipoproteins in the diabetes control and complications trial/epidemiology of diabetes intervention and complications cohort: associations with gender and glycemia. Diabetes Care. Mar. 2003;26(3):810-8.

Jiang Y, et al., Recombinant human parathyroid hormone (1-34) [teriparatide] improves both cortical and cancellous bone structure., J. Bone Miner. Res., 18:1932-41 (2003).

(56) References Cited

OTHER PUBLICATIONS

Jin, et al., Effects of Androgen Deficiency and Replacement on Prostate Zonal Volumes, Clinical Endocrinology, vol. 54, pp. 437-445 (2001).
Jockenhovel, at al., Pharmacokinetics and Pharmacodynamics of Subcutaneous Testosterone Implants in Hypogonadal Men, Clinical Endocrinology, vol. 45, pp. 61-71 (1996).
Johnson L. Spermatogenesis and aging in the human. J. Andro 7:331 (1986).
Jones, et al., Placebo Controlled Study on the Effects of Transdermal Testosterone Gel in Hypogonadal Men with Type II Diabetes (T2D) or Metabolic Syndrome(MS) in Diabetic Control and Insulin Sensitivity: The TIMES 2 Study, p. 3-422, Endo Society 2008.
Jones, et al., Pulmonary Vasodilatory Action of Testosterone: Evidence of Calcium Antagonistic Action, J. Cardiovasc. Pharmacol., vol. 39, No. 6, pp. 814-823 (Jun. 2002).
Jones, R. et al., Low Levels of Endogenous Androgens Increase the Risk of Atherosclerosis in Elderly Men: Further Supportive Data. J Clin Endocrinol Metab 88(3): 1403-1404(2003).
Jordan, Allergy and Topical Irritation Associated With Transdermal Testosterone Administration: A Comparison of Scrotal and Nonscrotal Transdermal Systems, American Journal o Contact Dermatitis. vol. 8 (No. 2).pp. 108-113 (Jun. 1997).
Joseph, et al., Relationship of Serum Sex-Steroid Hormones and Prostate Volume in African American Men, The Prostate, vol. 53, pp. 322-329 (2002).
Juenemann, et al., Androgen Deficiency in Prostate Carcinoma- and BPH-Patients?, American Urological Association, Abstract No. 193, (2002).
Kalantaridou, et al., Transdermal Testosterone Replacement for Young Women with Spontaneous Premature Ovarian Failure: A Pilot Study, No. 2322, www.abstracts-on-1 (Downloaded Aug. 7, 2000).
Kalman, Future Pharmacy: What's the T Team Up to?, Muscular Development (Setauken, NY), Sep. 2002.
Kang, et al., Effect of Oral Administration of Testosterone on Brachial Arterial Vasoreactivity in Men with Coronary Artery Disease, The Amer. J. of Cardiology, vol. 89, pp. 862-864 (Apr. 1, 2002).
Kanikkannan N, et al., "Structure-activity relationship of chemical penetration enhancers in transdermal drug delivery," Curr Med Chem. Jun. 2000;7(6):593-608.
Kanis J A, et al., The components of excess mortality after hip fracture, Bone, 32:468-73 (2003).
Kao, et al., Skin Absorption and Cutaneous First Pass Metabolism of Topical Steroids: in vitro Studies with Mouse Skin in Organ Culture, J Pharmacol Exp Ther, May 1987; 241(2): 482-487.
Karr, et al., Induction of Benign Prostatic Hypertrophy in Baboons, Urology, Mar. 1984; 23(3): 276-89.
Kasper, et al., Development, Progression, and Androgen-Dependence of Prostate Tumors in Probasin-Large T Antigen Transgenic Mice: a Model for Prostate Cancer, Lab Invest, Mar. 1998; 78(3): 319-333.
Kasperk CH et al., Androgens directly stimulate proliferation of bone cells in vitro. Endocrinology 124:1576 (1989).
Kasting, G.B. et al., "Skin penetration enhancement of triprolidine base by propylene glycol," J. Pharma. Sci. (1993) 82(5):551-552.
Katz, M. et al., "Absorption of drugs through the skin," Reprint from Handbook of Experimental Pharmacology, edited by O. Eichler et al., Chapter 7 (1971) 103-174.
Katznelson L, et al., Increase in bone density and lean body mass during testosterone administration in men with acquired hypogonadism, J. Clin. Endocrinol. Metab., 4358-4365 (1996).
Katznelson, Therapeutic Role of Androgens in the Treatment of Osteoporosis in Men, Bailliere's Clinical Endocrinology and Metabolism, vol. 12, No. 3:453-470 (Oct. 1998).
Kaufman JM, et al., Safety and efficacy of a testosterone (T) gel in a geriatric population. Abstract #1104 at the 97th Annual Meeting of the American Urological Association, May 25-30, 2002, Orlando, FL.
Kaufman, Efficacy and Safety of a New, Topical Testosterone Gel (T-gel) for Male Hormonal Supplementation, International Journal of Impotence Research, vol. 12, Supplement 3, p. S75 (B9) (Sep. 2000).
Kaufman, "Hormone Gel Stirs Debate," The Washington Post, p. A01 (May 27, 2000).
Kaufman, et al., Background for Studies on the Treatment of Male Osteoporosis: State of the Art, Ann. Rheum. Dis., vol. 59, pp. 765-772 (2000).
Kaufman, et al., Declining Gonadal Function in Elderly Men, Bailliere's Clinical Endocrinology and Metabolism, vol. 11, No. 2, pp. 289-307 (Jul. 1997).
Kellie S E, et al., Sex-specific and race-specific hip fracture rates, Am J. Public Health, 80:326-8 (1990).
Kelly PJ et al., Dietary calcium, sex hormones, and bone mineral density in men. Br. Med. J. 300:1361-4 (1990).
Kenny, et al., Determinants of Bone Density in Healthy Older Men With Low Testosterone Levels, J. of Gerontology, vol. 55A, No. 9, pp. M492-M497 (2000).
Kerr, Hormone Therapy a Risk for Men, Too: Testosterone Perils May Go Up With Age, Newsday (Melville, NY), Dec. 17, 2002.
Khan, et al., Radioimmunoassay for Human Testosterone-Estradiol Binding Globulin, J. Clinical Endocrinology and Metabolism, vol. 54, pp. 705-710 (1982).
Khosla S. et al., Relationship of serum sex steroid levels and bone turnover markers with bone mineral density in men and women: A key role for bioavailable estrogen, J Clin Endocrinol Metab. 1998;83(7): 2266-74.
Khosla, Oestrogen, Bones, and Men: When Testosterone Just Isn't Enough, Clinical Endocrinology, vol. 56, pp. 291-293 (2002).
Kim et al., "Preparation and evaluation of Eudragit gels. v. rectal gel preparations for sustained release and avoidance of first-pass metabolism of lidocaine." Chem. Pharm. Bull. 50(10): 2800-2804 (1992).
Kim et al., Formulation of a reservoir-type testosterone transdermal delivery system. International Journal of Pharmaceutics. 219:51-9 (2001).
Kim et al., Skin permeation of testosterone and its easier derivatives in rats. Journal of Pharmacy and Pharmacology. Apr. 2000; 52 (4) 369-75.
Kim, DD et al., Mutual hairless rat skin permeation-enhancing effect of ethanol/water system and oleic acid. J. Pharm. Sci. 85(11): 1191-1195 (1996).
Kirn, Testosterone Gel Promising in Hypoglandal Men (Benefits Seen at 29 Months), Family Practice News, Nov. 1, 2002.
Kirn, Testosterone Gel's Benefits Sustained at 29 Months, Internal Medicine News (Rockville, MD), Sep. 15, 2002.
Kirschner, et al., Androgen Production and Metabolism in Normal and Virilized Women, Metabolism, vol. 21 (7), pp. 667-688, (Jul. 22, 1972).
Kirschner, et al., Androgen-Estrogen Metabolism in Women with Upper Body Versus Lower Body Obesity, Journal of Clinical Endocrinology and Metabolism, vol. 70, No. 2, pp. 473-479 (Feb. 1990).
Klein et al., Fibrinogen is a marker for nephropathy and peripheral vascular disease in type 1 diabetes: studies of plasma fibrinogen and fibrinogen gene polymorphism in the DCCT/EDIC cohort. Diabetes Care. May 2003;26(5):1439-48.
Klinicheskaya endokrinologiya pod. Red. Prof. N.T. Starkovoy, M. Medicina, 1991, p. 426. [Russian; English machine translation included.].
Klose et al., Enhanced Percutaneous Penetration of Ethinyl Estradiol using Across(RM) Enhancers in Spray Formulations. Poster, Acrux Drug Delivery Solutions. Presented at American Association of Pharmaceutical Scientists (AAPS) (2002), Abstract published at AAPS PharmSci. 2002; 4(S1).
Klugo et al., Response of micropenis to topical testosterone and gonadotropin. J. Urol. 119(5):667-8 (May, 1978).
Knussmann, et al., Relations Between Sex Hormone Levels and Sexual Behavior in Men, Archives of Sexual Behavior, vol. 15, No. 5, p. 429-45 (1986).
Koenig HG, et al., Self-rated depression scales and screening for major depression in the older hospitalized patient with medical illness. J Am Geriatr Soc 36:699-706, 1988.
Kolata, Male Hormone Therapy Popular but Untested, N.Y. Times, Aug. 19, 2002.

(56) References Cited

OTHER PUBLICATIONS

Kong, et al., Testosterone Therapy in HIV Wasting Syndrome: Systematic Review and Meta-Analysis, The Lancet Infectious Diseases, vol. 2, pp. 692-699 (Nov. 2002).
Korbonits et al., A comparison of a novel testosterone bioadhesive buccal system, striant, with a testosterone adhesive patch in hypogonadal males. J. Clinical Endocrinology and Metabolism 89(5): 2039-2043 (2004).
Korenman SG et al., Secondary hypogonadism in older men: its relation to impotence. J. Clin Endocrinol Metab. 71:963 (1990).
Korenman, et al., Androgen Therapy of Hypogonadal Men with Transscrotal Testosterone Systems, Am J Med, Sep. 1987; 83(3): 471-478.
Kraemer, et al., Orgasmic Frequency and Plasma Testosterone Levels in Normal Human Males, Archives of Sexual Behavior, vol. 5, No. 2, p. 125 (1976).
Krahe, et al., Risk Factors for Decreased Bone Density in Premenopausal Women, Braz J Med Biol Res, Sep. 1997; 30(9): 1061-6.
Krotkieweski M et al., Impact of obesity on metabolism in men and women. Importance of regional adipose tissue distribution. J. Clin. Invest 72:1150 (1983).
Krumholtz, et al., Prostate-Specific Antigen Cutoff of 2.6 ng/mL for Prostate Cancer Screening is Associated with Favorable Pathologic Tumor Features, Urology, vol. 60, pp. 469-474 (2002).
Kuhn, et al., Gynecomastia: Effect of Prolonged Treatment with Dihydrotestosterone by the Percutaneous Route, Presse Medicine, vol. 12, No. 1, pp. 21-25 (Jan. 8, 1983). (Abstract only).
Kuhn, et al., Effects of 10 Days Administration of Percutaneous Dihydrotestosterone on the Pituitary-Testicular Axis in Normal Men, J Clin Endocrinol Metab, Feb. 1984; 58(2): 231-5.
Kuhn, et al., Traitement Androgenique Percutane des Hypogonadismes Masculins. Efficacite Comparee de la Testosterone et d la Dihydrotestosterone: Etude de 40 Observations, Contraception-Fertilite-Sexualite, vol. 14, No. 11, pp. 1031-1036 (1986).
Kuhnert, et al., Testosterone substitution with a new transdermal, hydroalcoholic gel applied to scrotal or non-scrotal skin: a multicentre trial, European Journal of Endocrinology, vol. 153, pp. 317-326 (2005).
Kunz, et al., Virilization of Young Children After Topical Androgen Use by Their Parents, Pediatrics, vol. 114(1), pp. 282-284 (2004).
Kwan et al., "The nature of androgen action on male sexuality: a combined laboratory-self-report study on hypogonadal men." J. Clin. Endocrinol Metab. 57(3): 557-562 (1983).
Kydonieus et al., Transdermal Delivery of Drugs vol. II. Drug and Cosmetic Industry, pp. 57-62 (1987).
Kyprianou, et al., Quantal Relationship Between Prostatic Dihydrotestosterone and Prostatic Cell Content: Critical Threshold Concept, The Prostate, vol. 11, pp. 41-50 (1987).
La Sexualite, L'Androgel, Le Gel Miracle, www.aci-multimedia.net/feminin/androgel (Downloaded May 9, 2001). [French; English machine translation included].
Labrie, et al., Physiological Changes in Dehydroepiandrosterone are not Reflected by Serum Levels of Active Androgens and Estrogens but of their Metabolites: Intracrinology, J Clin Endocrinol Metab, Aug. 1997; 82(8): 2403-2409.
Lacayo, Are You Man Enough?, Time Europe, www.Time.com, vol. 155, No. 16 (Apr. 24, 2000).
Lachin et al., Effect of glycemic exposure on the risk of microvascular complications in the diabetes control and complications trial—revisited. Diabetes. Apr. 2008; 57(4):995-1001. (Epub Date: Jan. 25, 2008).
Lagiou, et al., Serum Steroids in Relation to Benign Prostatic Hyperplasia, Oncology, vol. 54, No. 6, pp. 497-501 (Nov.-Dec. 1997).
Lammers, et al., Combination Therapy for Erectile Dysfunction: A Randomized, Double Blind, Unblended Active-Controlled, Cross-Over Study of the Pharmacodynamics and Safety of Combined Oral Formulations of Apomorphine Hydrochloride, Phentolamine Mesylate and Papaverine Hydrochloride in Men with Moderate to Severe Erectile Dysfunction, Intl. J. of Impotence Research, vol. 14, pp. 54-60 (2002).
Langtry, et al., Sildenafil: A Review of its Use in Erectile Dysfunction, Drugs, vol. 57, No. 6, pp. 967-989 (Jun. 1999).
Lanman BM et al., The role of human patch testing in a product development program. Joint Conference on Cosmetic Sciences, The Toilets Goods Association (currently the Cosmetic, Toiletry and Fragrance Association), Washington D.C., Apr. 21-23, 1968.
Larsen and H. Bundgaard, Prodrug forms for the sulfonamide group. I. Evaluation of N-acyl derivatives, N-sulfonylamidines, N-sulfonylsulfilimines and sulfonylureas as possible prodrug derivatives, Int. J. Pharmaceutics, 37:87-95 (1987).
Larsen et al., Int. J. Pharmaceutics, 47, 103 (1988).
Lawrence, J. Husband Crabby, Sluggish? MSN.com (May 6, 2002).
Lee KK, et al., A simple self-report diary for assessing psychosexual function in hypogonadal men, J Androl. Sep.-Oct. 2003;24(5):688-98.
Lee, Men's Health: Testosterone Gel Study Demonstrates Safety and Efficacy up to 42 Months in Men with Low Testosterone, Health & Medicine Week (Atlanta, GA), Aug. 5, 2002.
Lee, New Gel Treatment Proven and FDA Approved for Effective Treatment of Low Testosterone, 50+ Senior News (Bellport, NY), Dec. 2002.
Legro, et al., Role of Androgens in the Growth of Endometrial Carcinoma: An in Vivo Animal Model, American Journal of Obstetrics and Gynecology, vol. 184 (No. 3), p. 303-308, (2001).
Leiblum, et al., Vaginal Atrophy in the Postmenopausal Woman. The Important Sexual Activity and Hormones, JAMA, Apr. 22-29, 1983;249(16): 2195-8.
Leichtnam et al., "Identification of penetration enhancers for testosterone transdermal delivery from spray formulations," Journal of Controlled Relesae (2006);113:57-62.
Leifke, et al., Age-Related Changes of Serum Sex Hormones, Insulin-like Growth Factor-1 and Sex-hormone Binding Globulin Levels in Men: Cross-sectional Data from a Healthy Male Cohort, Clinical Endocrinology, vol. 53, pp. 689-695 (2000).
Leifke, et al., Effects of Testosterone Replacement Therapy on Cortical and Trabecular Bone Mineral Density, Verbetral Body Area and Paraspinal Muscle Area in Hypogonadal Men, European Journal of Endocrinology (1998);138:51-58.
Leigh, Antidote for Middle Age Met with Joy, Skepticism, San Mateo County Times, Nov. 25, 2002.
Leigh, Doctors Wary of Testosterone Drug Despite FDA's Approval, The Argus (Fremont, CA), Nov. 25, 2002.
Leigh, Some Doctors Question Use of Testosterone Gel: Despite FDA's Approval, Ointment for Men Might Increase Risk of Prostate Cancer, Alameda Times-Star (Oakland, CA), Nov. 25, 2002.
Leinonen, et al., Serum Sex Hormone Binding Globulin and Testosterone Binding After Estradiol Administration, Castration, and Their Combination in Men with Prostatic Carcinoma, Invest Urol, Jul. 1979; 17(1): 24-27.
Lemon, Testosterone Promises Renewed Vigor: Hormone Replacement Credited with Boosting Energy in Aging Men, MSNBC.com (Nov. 7, 2002).
Leopold, C.S. et al., "An attempt to clarify the mechanism of the penetration enhancing effects of lipophilic vehicles with differential scanning calorimetry (DSC)," J. Pharm. Pharmacol. (1995) 47:276-281.
Lesher EL, Berryhill J: Validation of the geriatric depression scale-short form among inpatients. J Clin Psychol40:256-60, 1994.
Letters to the Editor, J. Clin. Endocrinol. Metab., vol. 88, No. 3, pp. 1402-1405 (Mar. 2003).
Leucuta et al., abstract of Clujul Medical, 1983 ;56(4) :371-376.
Leuprorelin/testosterone—First Report of Heart Transplant Rejection: 3 Case Reports, Reactions, vol. 27, No. 912 (Jul. 2002).
Levy, Manopause: Experts Discuss Treatments for Testosterone Deficiencies in Older Men, Journal Inquirer (Manchester, CT), Aug. 26, 2002.
Lewis, et al, Serum 5.alpha.-Dihydrotestosterone and Testosterone Changes with Age in Man, Acta Endocrinologica, 82 (1976) 444-448.

(56) References Cited

OTHER PUBLICATIONS

Lewis, et al., Proceedings: Age-Related Changes in Serum 5aplhadihydrotestosterone and Testosterone in Normal Men, Journal of Endocrinology, vol. 67, No. 2, PQ. 15P (Nov. 1975).

Liao, J., Androgen Action: Molecular Mechanism and Medical Application, Formos Med. Assoc., vol. 93, No. 9, pp. 741-751 (Sep. 1994).

Lieberherr, et al., Androgens Increase Intracellular Calcium Concentration and Inositol 1,4,5-Triphosphate and Diacylglycerol Formation Via a Pertussis Toxin-sensitive G-protein, The J. of Biological Chemistry, vol. 269, No. 10, pp. 7217-7223 (Mar. 11, 1994).

Lieberman et al., eds. "Pharmaceutical Dosage Forms—Disperse Systems." vol. 2. Marcel Dekker: New York (1989). Ch. 13.

Lignieres, Effect of High Dihydrotestosterone Plasma Levels on Prostate of Aged Men. Second International Androgen Workshop, Long Beach, CA, USA (1995).

Lin, S. et al., Transdermal testosterone delivery: comparison between scrotal and nonscrotal delivery systems. Pharm Dev and Tech. 4(3): 405-414 (1999).

Linet, et al., Efficacy and Safety of Intracavernosal Alprostadil in Men with Erectile Dysfunction, The New England J. of Medicine, vol. 334, No. 14, pp. 873-877 (Apr. 4, 1996).

Ling, et al., Testosterone (T) Enhances Apoptosis-Related Damage in Human Vascular Endothelial Cells, Endocrinology, vol. 143, No. 3, pp. 1119-1125 (2002).

Liu, et al., Impact of Assay Parameters on the Accuracy of Free PSA Test: Source and Stability of Calibrator, Calibration Curve Fitting, and Level of Total PSA in the Serum. J Clinical Laboratory Analysis 12:304-309 (1998).

Lo, et al., Reproductive Function in Human Immunodeficiency virus Infection, The J. of Clinical Endocrinology & Metabolism, vol. 86, No. 6, pp. 2338-2343 (2001).

Lobel, B. et al., "Contraception in men: efficacy and immediate toxicity—a study of 18 cases," Acta Urologica Belgica (1989) 57(1):117-124.

Lobo R. A., Chapter 20: Androgen excess in Infertility, Contraception and Reproductive Endocrinology, Third Edition. D R Mishell, V. Davajan and R. Lobo, Editors. Blackwell Scientific Publications, Boston. pp. 422-446, 1991.

Loftsson T. et al., Cyclodextrins as Co-Enhancers in Dermal and Transdermal Drug Delivery, Pharmazie, vol. 2, pp. 137-139 (1998).

London Rubber Industries Ltd's Patent, Reports of Patent, Design, and Trade Mark Cases, No. 2, p. 31 (1968).

Longcope, et al., Androgens, Estrogens, and Sex Hormone-Binding Globulin in Middle-Aged Men, Journal of Clinical Endocrinology and Metabolism, vol. 71, No. 6, pp. 1442-1446 (Dec. 1990).

Longstreth, et al., Transdermal Testosterone Pharmacokinetics Remain Unchanged With Prolonged Treatment, Unimed Pharmaceuticals (Oct. 31, 2000).

Lopes-Virella et al., Risk factors related to inflammation and endothelial dysfunction in the DCCT/EDIC cohort and their relationship with nephropathy and macrovascular complications. Diabetes Care. Oct. 2008;31(10):2006-12. (Epub Date: Jul 15, 2008).

Louie, Transdermal Testosterone Replacement to Improve Women's Sexual 120 Functioning, Canadian Family Physician p. 1571-1573 ( Aug. 22, 2001).

Loyd. "Benzocaine 2% Anesthetic Gel." Int'l J. Pharm. Compounding. 2(4): 296 (1998).

Lucas, Finasteride Cream in Hirsutism, Endocrine Practice, 7(1):5-10 (2001).

Lugg et al., The Role of Nitric Oxide in Erectile Function, J. Andrology, vol. 16, pp. 2-4, (1995).

Luster, B. Sex Sells: But Buyers Should Beware of Natural Supplements that Haven't Been Tested and May Have Dangerous Side Effects, The Courier-Journal (Louisville, KY), Mar. 4, 2002.

Ly et al., A Double-Blind, Placebo-Controlled, Randomized Clinical Trial of Transdermal Dihydrotestosterone Gel on Muscular Strength, Mobility, and Quality of Life in Older Men with Partial Androgen Deficiency, The Journal of Clinical Endocrinology & Metabolism, vol. 86, No. 9, pp. 4078-4088 (2001).

Maclennan, et al., Hormone Replacement Therapies in Women at Risk of Cardiovascular Disease and Osteoporosis in South Australia in 1997, Medical Journal of Australia, vol. 170 (No. 11), p. 524-527, (Jun. 7, 1999).

MacroChem Accelerates Development of Top for Impotence, www.pslgroup.com (Apr. 10, 1997).

Macrochem announces initiation of next clinical trial of Opterone, first testosterone cream for male hypogonadism. Macrochem Press Release. Dec. 8, 2004.

MacroChem Awarded U.S. Patent Covering Transdermal Hormone Replacement Incorporating Proprietary SEPA® Technology and Hormonally Active Drugs Such as Testosterone, Estradiol and Progesterone, http://www.mchm.com/press/pr24.asp (Oct. 21, 1999).

Macrochem. Macrochem announces initiation of clinical trial of Opterone, first absorption-enhanced topical cream to treat testosterone deficiency. Press release. Dec. 16, 2003.

Macrochem. MCHM begins dose study for testosterone cream. Press Release. Dec. 16, 2003.

Macrochem. SEPA enhanced testosterone for topical applications: Macrochem investigational topical treatment for testosterone deficiency. Press Release. Dec. 8, 2004.

Magoha, East Afr. Med. J. (1997) vol. 74(10) pp. 642-644, East Afr. Med. J. (1997) vol. 74(10) pp. 642-644.

Mahabadi V, et al., Combined transdermal testosterone gel and the progestin nestorone suppresses serum gonadotropins in men, J Clin Endocrinol Metab. Jul. 2009;94(7):2313-20. (Epub Date: Apr. 14, 2009).

Maibach, et al., The Effect of DMSO on Percutaneous Penetration of Hydrocortisone and Testosterone in Man, Annals New York Academy of Sciences (Mar. 1967), pp. 423-427.

Majumdar S, et al., Correlation of trabecular bone structure with age, bone mineral density, and osteoporotic status: in vivo studies in the distal radius using high resolution magnetic resonance imaging, J. Bone Miner. Res., 12:111-8 (1997).

Mak, V.H.W. et al., "Oleic acid concentration and effect in human stratus corneum: non-invasive determination by attenuated total reflectance infrared spectroscopy in vivo," J. Control. Rel. (1990) 12:67-75.

Mak, V.H.W. et al., "Percutaneous penetration enhancement in vivo measured by attenuated total reflectance infrared spectroscopy," Pharm. Res. (1990) 835-841.

Male Hormone Patch Approved, Nuphann, http://www.nuoharm.com/malehorm.htm. (Jun. 16, 2000).

Male hypogonadism, Merck Index, pp. 1-6 (Jun. 2007).

Man, et al., Optimization of Physiological Lipid Mixtures for Barrier Repair, J Invest Dermatol, May 1996; 106(5): 1096-1101.

Manopause: Experts Seeking Treatments for Middle-Age Male Testosterone Deficiency, The Patriot Ledger (Quincy, MA),Jul. 9, 2002.

Manos, FDA Approves Gel to Treat Low Testosterone Levels, www.testocreme.com. Downloaded on May 9, 2001.

Mantzoros et al., Insulin-like Growth Factor 1 in Relation to Prostate Cancer and Benign Prostatic Hyperplasia, Brit. J. of Cancer, vol. 76, No. 9, pp. 1115-1118 (1997).

Mantzoros, et al, Contribution of Dihydrotestosterone to Male Sexual Behaviour, British Medical Journal, No. 6990, vol. 310, pp. 1289-1291 (May 20, 1995).

Mantzoros, et al., Leptin Concentrations in the Polycystic Ovary Syndrome, J Clin Endocrinol Metab, Jun. 1997; 82(6): 1687-91.

Mantzoros, et al., Serum Steroids in Relation to Benign Prostatic Hyperplasia, Oncology, Nov.-Dec. 1997; 54(6):497-501.

Marbury et al., Evaluation of the Pharmacokinetic Profiles of the New Testosterone Topical Gel Formulation, Testim(TM), Compared to AndroGel(R), Biopharm. Drug Dispos., 24:115-120 (2003).

Marin, et al., Androgen Treatment of Abdominally Obese Men, Obesity Research, vol. 1(4), pp. 245-251 (1993).

Marin, et al., Androgen Treatment of Middle-Aged, Obese Men: Effects on Metabolism, Muscle and Adipose Tissues, European Journal of Medicine, vol. 1, No. 6, pp. 329-336 (Oct. 1992).

(56) References Cited

OTHER PUBLICATIONS

Marin, et al., Androgen-dependent Nitric Oxide Release in Rat Penis Correlates with Levels of Constitutive Nitric Oxide Synthase Isoenzymes, Biology of Reproduction, vol. 61, pp. 1012-1016 (1999).
Marin, et al., The Effects of Testosterone Treatment on Body Composition and Metabolism in Middle-Aged Obese Men, Intl. J. of Obesity, vol. 16, pp. 991-997 (1992).
Marks, et al., Effect of Testosterone Replacement Therapy on Prostate Tissue in Men With Late-Onset Hypogonadism—A Randomized Controlled Trial, JAMA, vol. 296(19), pp. 2351-2361 (2006).
Marzulli FN. Photoirritation (Phototoxicity, Phototoxic Dermatitis) in Dermatotoxicology, 5th Ed., Eds. Marzulli et al., Washington D.C. 231-237 (1996).
Masi, Sex Hormones and Rheumatoid Arthritis: Cause or Effect Relationships in a Complex Pathophysiology?, Clin Exp Rheumatol, Mar.-Apr. 1995; 13(2): 227-40.
Masters, et al., Investigation of Sex-Hormone Binding Globulin Interference in Direct Radioimmunoassays for Testosterone and Estradiol, Clinical Chemistry, vol. 35, No. 6, pp. 979-984 (Jun. 1989).
Mather, et al., Free Plasma Testosterone Levels During the Normal Menstrual Cycle, Journal of Endocrinol. Invest., vol. 8, No. 5, pp. 437-441 (Oct. 1985).
Matsumoto A.M., Hormonal therapy of male hypogonadism. Endocrinology and Metabolism Clinics of North America, 23(4):857-875 (1994).
Mayorga, P. et al., "Formulation study of a transdermal delivery system of primaquine," Int. J. Pharm. (1996) 132:71-79.
Mazer N et al., Comparison of the steady-state pharmacokinetics, metabolism, and variability of a transdermal testosterone patch versus a transdermal testosterone gel in hypogonadal men, J Sex Med. Mar. 2005;2(2):213-26.
Mazer, et al., Enhanced Transdermal Delivery of Testosterone: A New Physiological Approach for Androgen Replacement in Hypogonadal Men, Journal of Controlled Release, vol. 19, pp. 347-361 (1992).
Mazer, New Clinical Applications of Transdermal Testosterone Delivery in Men and Women, J Controlled Release, Mar. 1, 2000; 65(1-2): 303-15.
Mazess, et al., Influence of Age and Body Weight on Spine and Femur Bone Density in U.S. White Men, J. of Bone and Mineral Research, vol. 5, No. 6; pp. 645-652 (1990).
Mccarthy, et al., Ventricular Thrombosis and Systemic Embolism in Bodybuilders: Etiology and Management, Ann. Thorac. Surg., vol. 70, pp. 658-660 (2000).
McClellan, et al., Transdermal Testosterone. ADIS New Drug Profile—Drugs, Feb. 1998 55(2): 253-258.
McClure et al., Hypogonadal impotence treated by transdermal testosterone. Urology 37(3):224-228 (1991).
Mccook, Testosterone Boost May Help Some with Parkinson's, ReutersHealth.com (Nov. 26, 2002).
McCoy, et al., A Longitudinal Study of the Effects of Menopause on Sexuality, Maturitas, Sep. 1985; 7(3): 203-10.
Mcdonnell, et al., A Survey of 2851 Patients with Hemochromatosis: Symptoms and Response to Treatment, The Am. J. Med., vol. 106, No. 6, pp. 619-624 (Jun. 1999).
McGraw-Hill Dictionary of Scientific and Technical Terms, 5th Edition, pp. 26, 1541 (1994).
McGuire M. Instant History: The Week, Chicago Tribune, Dec. 1, 2002.
McHorney CA, et al., The MOS 36-Item Short-Form Health Survey (SF-36): II. Psychometric and clinical tests of validity in measuring physical and mental health constructs, Med Care. Mar. 1993;31(3):247-63.
McLoed, et al., A glucocorticoid prodrug facilitates normal mucosal function in rat colitis without adrenal suppression. Gastroenterol., 106:405-413 (1994).
McMahon, et al., Treatment of Intracorporeal Injection Nonresponse with Sildenafil Alone or in Combination with Triple Agent Intracorporeal Injection Therapy, The J. of Urology, vol. 162, pp. 1992-1998 (Dec. 1999).
Mean, et al., Study on the Binding of Dihydrotestosterone, Testosterone and Oestradiol Sex Hormone Binding Globulin, Clin Chim Acta, Oct. 1, 1977; 80(1): 171-180.
Medline Plus, Drug Information: Testosterone Topical, available at www.nlm.nih.gov/medlineplus/druginfo/medmaster/a605020.html (retrieved Jun. 3, 2005).
Meier DE et al., Marked decline in male vertebral bone mineral content with age: association with free testosterone level. Clin. Res 32:705A (1984) [Abstract].
Meier DE et al., Marked disparity between trabecular and cortical bone loss with age in healthy men. Ann. Int. Med. 101:605 (1984).
Meikle, Prostate size in hypogonadal men treated with a nonscrotal permeation-enhanced testosterone transdermal system. Urology 49(2):191 (1997).
Meikle, et al., Androderm: A Permeation Enhanced Non-Scrotal Testosterone Transdermal System for the Treatment of Male Hypogonadism, Pharmacology Biology and Clinical Applications of Androgens, vol. 43, pp. 449-457 (1996 Wiley-Liss, Inc.).
Meikle, et al., Enhanced Transdermal Delivery of Testosterone Across Nonscrotal Skin Produces Physiological Concentrations of Testosterone and Its Metabolites in Hypogonadal Men, J Clin Endocrinol Metab, Mar. 1992; 74(3): 623-628.
Meikle, et al., Familial Effects on Plasma Sex-Steroid Content in Man: Testosterone, Estradiol and Sex-Hormone-Binding Globulin, Metabolism, Jan. 1982; 31(1): 6-9.
Meikle, et al., Familial Prostatic Cancer Risk and Low Testosterone, J Clin Endocrinol Metab, Jun. 1982; 54(6): 1104-8.
Meikle, et al., Pharmacokinetics and Metabolism of a Permeation-Enhanced Testosterone Transdermal System in Hypogonadal Men: Influence of Application Site—A Clinical Research Center Study, Journal of Clinical Endocrinology and Metabolism, (1996);81(5):1832-40.
Meilahn, et al., Association of Sex hormones and adiposity with plasma levels of fibrinogen and PAI-1 in Postmenopausal Women, American Journal of Epidemiology, vol. 143 (2) p. 159-166 (1996).
Men's Health Screenings, The Washington Post, Jun. 11, 2002.
Mendel, Rates of Dissociation of Sex Steroid Hormones from Human Sex Hormone-Binding Globulin: a Reassessment, J Steroid Biochem Mol Biol, Oct. 1990; 37(2): 251-255.
Mendenhall, Custom Fit: Compounding Pharmacies Tailor Hormone Replacement Therapies to Individual Women, Pittsburgh Post-Gazette, May 28, 2002.
Meneely GR. et al., Analysis of factors affecting body composition determined from potassium content in 915 normal Subjects. Ann NY Acad Sci 110:271 (1963).
Menopause and Testosterone, www.womenshealth.com (Downloaded Aug. 7, 2000).
Merhi, et al., Postmenopausal virilization after spousal use of topical androgens, Fertility and Sterility, vol. 87(4), pp. 976.e13-976.e15 (2007).
Mermall, et al., Temporal (Circadian) and Functional Relationship between Pro Specific Antigen and Testosterone in Healthy Men, Urology, Jul. 1995; 46(1): 45-53.
Merriam Webster's Collegiate Dictionary, 10th Edition, pp. 3, 9, 27, 39, 246, 291, 340, 398, 567, 622, 663, 702, 722, 870, 871, 1095, 1174, 1177, 1359 (1994).
Messing, et al., Immediate Hormonal Therapy Compared with Observation After Radical Prostatectomy and Pelvic Lymphadenectomy in Men with Node-Positive Prostate Cancer, N. Engl. J. Med., vol. 34, No. 1, pp. 1781-1788 (Dec. 9, 1999).
Methyltestosterone 1-2MG, Question No. 1151236.012. "Medi-Hut Clarifies Syntest Formula." Business Wire (accessed Apr. 16, 2002).
Methyltestosterone, http://www.mesomorphosis.com/steroid-profiles/methyltestosterone.htm, Apr. 15, 2002.
Methyltestosterone, http://www.rxlist.com/cgi/generic3/methyltes_ids.htm, Apr. 15, 2002, 2 pages.
Mettlin, et al., Characteristics of Prostate Cancer Detected in the American Cancer Society—National Prostate Cancer Detection Project, The J. of Urol., vol. 152, pp. 1737-1740 (Nov. 1994).

(56) References Cited

OTHER PUBLICATIONS

Miekle AW et al., Transdermal testosterone gel: pharmacokinetics, efficacy of dosing and application site in hypogonadal men. BJU Int. Apr. 2004 93(6): 789-95.
Miller, Benign Prostatic Hyperplasia: Nutritional and Botanical Therapeutic Options, Alt. Med. Rev., vol. 1, pp. 18-25 (1996) (Abstract only).
Miller, et al., Transdermal Testosterone Administration in Women with Acquired Immunodeficiency Syndrome Wasting: A Pilot Study, Journal of Clinical Endocrinology and Metabolism, vol. 83, No. 8, pp. 2717-2725 (1998).
Miller, et al., Androgen Deficiency in Women with Hypopituitarism, The Journal of Clinical Endocrinology & Metabolism, vol. 86, No. 2, pp. 561-567 (2001).
Miller, M et al., Contemporary Use of Complexed PSA and Calculated Percent Free PSA for Early Detection of Prostate Cancer: Impact of Changing Disease Demographics. Urology 57:1105-1111 (2001).
Minoxidil. Wikipedia. http://en.wikipedia.org/wiki/Minoxidil. pp. 1-3. Downloaded on Oct. 13, 2009.
Misra, et al., Biphasic Testosterone Delivery Profile Observed With Two Different Transdermal Formulations. Pharmaceutical Research, vol. 14, No. 9, pp. 1264-1268 (1997).
Mitchell, et al., Longitudinal Effects of Aging on Serum Total and Free Testosterone Levels in Healthy Men, The J. of Clinical Endocrinology and Metabolism, vol. 86, No. 2, pp. 724-731 (2001).
Mitchell, et al., Age Related Changes in the Pituitary-Testicular Axis in Normal Men; Lower Serum Testosterone Results from Decreased Bioactive LH Drive, Clin Endocrinol (Oxf), May 1995; 42(5): 501-507.
Moffat, et al., Longitudinal Assessment of Serum Free Testosterone Concentration Predicts Memory Performance and Cognitive Status in Elderly Men, The J. of Clin. Endocrinology & Metabolism, vol. 87, No. 11, pp. 5001-5007 (2002).
Moller, et al., Sex Hormone-Binding Globulin Mediates Prostate Androgen Receptor Action via a Novel Signaling Pathway, Endocrinology, Jan. 1998; 139(1):213-8.
Mollgaard, et al., Permeation of Estradiol Through the Skin—Effect of Vehicles, International Journal of Pharmaceutics, vol. 15, pp. 185-197 (1983).
Mollgaard, et al., Vehicle Effect on Topical Drug Delivery, Acta Pharm. Suec., vol. 20, pp. 433-442 (1983).
Monath, et al., Physiologic Variations of Serum Testosterone Within the Normal Range Do Not Affect Serum Prostate-Specific Antigen, Urology 46(1): 58-61 (1995).
Monga, et al., Patient Satisfaction with Testosterone Supplementation for the Treatment of Erectile Dysfunction, Arch. of Andrology, vol. 48, pp. 433-442 (2002).
Monnier et al., Skin collagen glycation, glycoxidation, and crosslinking are lower in subjects with long-term intensive versus conventional therapy of type 1 diabetes: relevance of glycated collagen products versus HbA1c as markers of diabetic complications. DCCT Skin Collagen Ancillary Study Group. Diabetes Control and Complications Trial. Diabetes. Apr. 1999;48(4):870-80.
Monterey, http://www.wellnessmd.com/testo.html (Jul. 10, 2000).
Mooney, Anabolic Steroids for AIDS Therapy: Differences Between Analogs, No. 1, www.digiweb.com. (Jul. 1998).
Mooney, Frequency of Administration—Testosterone & Nandrolone, vol. 1, No. 4, www.medibolics.com (Downloaded Oct. 8, 1998).
Mooney, M. et al., "Built to survive: a comprehensive guide to the medical use of anabolic therapies, nutrition, supplementation, and exercise for HIV(+) men and women," Program for Wellness Restoration (PoWeR) Anabolic Hormone Guidelines, Library of Congress (1999) Table of Contents, 63-85.
Mooradian, et al., Biological Actions of Androgens, Endocrine Reviews, vol. 8, No. 1, pp. 1-28 (1987).
Moreland, et al., "Sildenafil, A Novel Inhibitor of Phosphodiesterase Type 5 In Human Corpus Cavernosum Smooth Muscle Cells," Life Sciences (1998);62(20):PL309-318.

Morgan et al., An Ergonomic and Performance Evaluation of a Metered-Dose Transdermal Spray (MDTS(RM)) in Women of Postmenopausal Age. Poster, Acrux Drug Delivery Solutions. Presented at American Association of Pharmaceutical Scientists (AAPS) (2002), Abstract published at AAPS PharmSci. 2002; 4(S1).
Morgan et al., Enhanced Skin Permeation of Sex Hormones with Novel Topical Spray Vehicles, J. Pharm. Science (1998) vol. 87 No. 10, pp. 1213-1218.
Morgan et al., Enhanced Transdermal Delivery of Sex Hormones in Swine with a Novel Topical Aerosol, J. Pharm. Science (1998) vol. 87 No. 10, pp. 1219-1225.
Morgan et al., Photostabilization of Estradiol by Padimate O or Octyl Salicylate When Added to a Transdermal S[ray as Dermal Penetration Enhancing Excipients. Poster, Acrux Drug Delivery Solutions. Presented at American Association of Pharmaceutical Scientists (AAPS) (2002), Abstract published at AAPS PharmSci. 2002; 4(S1).
Morgentaler A, Response to: Efficacy of changing testosterone gel preparations (Androgel or Testim) among suboptimally responsive hypogonadal men, Int J Impot Res. May-Jun. 2008;20(3):331; author reply 332.
Morgentaler, A. Transcript of CBS-TV Interview with the Early Show, (CBS television broadcast Aug. 30, 2002).
Morgentaler, et al., Occult Prostate Cancer in Men with Low Serum Testosterone Levels, vol. 276, No. 23, pp. 1904-1906 (Dec. 18, 1996).
Morgentaler, et al., Letters to the Editor, Testosterone's Uses The New Yorker, Aug. 19 & 26, 2002.
Morley JE. et al., Validation of a screening questionnaire for androgen deficiency in aging males. Metabolism, 2000;49(9):1239-1242.
Morley, Testosterone Treatment in Older Men: Effects on the Prostate, Endocr. Pract., vol. 6, No. 2, pp. 218-221 (2000).
Morley, "Testosterone Replacement in Older Men and Women," J Gend Specif Med, 4(2): 49-53 (2001); Abstract.
Morley, et al., Androgen Deficiency in Aging Men: Role of Testosterone Replacement Therapy, J. Lab. Clin. Med., vol. 135, No. 5, pp. 370-378 (May 2000).
Morley, et al., Longitudinal Changes in Testosterone, Luteinizing Hormone, and Follicle-Stimulating Hormone in Healthy Older Men, Metabolism, vol. 46, No. 4 (Apr. 1997), pp. 410-413.
Morley, J. E., et al., Effects of testosterone replacement therapy in old hypogonadal males: a preliminary study. J. Am. Geriatr. 41: 149-152 (1993).
Morris, et al., Marital Sex Frequency and Midcycle Female Testosterone, Arch Sex Behav, Feb. 1987; 16(1):27-37.
Morrison and Boyd Organic Chemistry, 3rd Edition, Boston, US (1973), pp. 36-37.
Morrison, Androgens in the Elderly: Will Androgen Replacement Therapy Improve Mood, Cognition, and Quality of Life in Aging Men and Women, Psychopharmacology Bulletin, vol. 33, No. 2, pp. 293-296 (1997).
Mother Molly's Guide for Living: Daddy, Too. Post-Messenger (New Glarus, WI), Aug. 7, 2002.
Moynihan, R., "Drug maker urges group to lobby FDA on testosterone for women," BMJ (2004) 329:1255.
Mukherjee, et al., Testosterone Attenuates Expression of Vascular Cell Adhesion Molecule-1 by Conversion to Estradiol by Aromatase in Endothelial Cells: Implications in Atherosclerosis, PNAS, vol. 99, No. 6, pp. 4055-4060 (Mar. 19, 2002).
Mulhall, et al., Effect of testosterone supplementation on sexual function in hypogonadal men with erectile dysfunction. Urology; 63:348-353, 2004.
Müller et al., Testosterontherapie des Hypogonadismus , Schweizerische Arztezeitung, vol. 81, No. 46, pp. 2589-2593 (2000) [German; English Summary Machine Translated].
Mulligan, K., et al., Use of growth hormone and other anabolic agents in AIDS wasting. JPEN J. Parenter. Enteral Nutr. 23: S202-S209 (1999).
Mussoline M E, et al., Risk factors for hip fracture in white men: the NHANES I Epidemiologic Follow-up Study. J. Bone Miner. Res. 13: 918-24 (1998).
Mydlo, et al., Initial Results Utilizing Combination Therapy for Patients with a Suboptimal Response to Either Alprostadil or Sildenafil Monotherapy, Eur. Urol., vol. 38, pp. 30-34 (2000).

(56) References Cited

OTHER PUBLICATIONS

Mydlo, et al., Results from Different Patient Populations Using Combined Therapy with Alprostadil and Sildenafil: Predictors of Satisfaction, BJU Intl., vol. 86, pp. 469-473 (2000).
Myers, et al., Effects of Estrogen, Androgen, and Progestin on Sexual Psychophysiology and Behavior in Postmenopausal Women, Journal of Clinical Endocrinology and Metabolism, vol. 70, No. 4, pp. 1124-1131 (Apr. 1990).
Mylonakis, et al., Clin. Infect. Dis., 2001, 33, p. 857-864.
N.N. AIDS Alert, American health consultants, Jun. 1999.
Nagelberg, et al., Cerebrovascular Accident Associated with Testosterone Therapy in a 21-year-old Hypogonadal Man, N. Engl. J. Med., vol. 314, No. 10, pp. 649-650 (Mar. 6, 1986).
Naik, A. et al., "Mechanism of oleic acid-induced skin penetration enhancement in vivo in humans," J. Control Rel. (1995) 37:299-306.
Nakhla, et al, Stimulation of Prostate Cancer Growth by Androgens and Estrogens Through the Intermediacy of Sex Hormone-Binding Globulin, Endocrinology, vol. 137, No. 10, pp. 4126-4129 (Oct. 1996).
Nankin HR et al., The aging Leydig cell III. Gonadotropin stimulation in men. J. AndroI 2:181 (1981).
Nankin, et al., Daytime Titers of Testosterone, LH, Estrone, Estradiol, and Testosterone-Binding Protein: Acute Effects of LH and LH-Releasing Hormone in Men, Journal of Clinical Endocrinology Metabolism, vol. 41, pp. 271-281 (1975).
Nankin, et al., Decreased Bioavailable Testosterone in Aging Normal and Impotent Men, J Clin Endocrinol Metab, Dec. 1986; 63(6):1418-1420.
Naps, Hey Men, It's Time for a Health Tune-Up. Available at http://www.wscare.com/viewArticle?ID=374714, Date published: Jul. 10, 2002.
Nathorst-Boos, J, et al., Treatment with percutaneous testosterone gel in postmenopausal women with decreased libido—effects on sexuality and psychological general well-being, Maturitas (2006);53(1):11-8 (Abstract only).
Navarro, et al., Salivary Testosterone in Postmenopausal Women with Rheumatoid Arthritis, J Rheumatol, Jun. 1998; 25(6): 1059-62.
Need, et al., Double-Blind Placebo-Controlled Trial of Treatment of Osteoporosis with the Anabolic Nandrolone Decanoate, Osteoporosis Int. Supplement 1: S218-222 (1993).
Need, et al., Effects of Nandrolone Therapy on Forearm Bone, www.medmedia.com (Downloaded Oct. 8, 1998).
Nehra, et al., Rationale for Combination Therapy of Intraurethral Prostaglandin $E_1$ and Sildenafil in the Salvage of Erectile Dysfunction Patients Desiring Noninvasive Therapy, Intl. J. of Impotence Research, vol. 14, Suppl. 1, pp. S38-S42 (2002).
Neugarten BL, Havigurst RJ, Tobin SS. The measurement of life satisfaction. J Gerontol 16:134-43, 1961.
Nevalainen, et al., Hormone Regulation of Human Prostate in Organ Culture, Cancer Res, Nov. 1, 1993; 53(21):5199-207.
Never Too Buff, Time Europe, www.time.com, vol. 155, No. 16 (Apr. 24, 2000).
New Drug Application for Testosterone Gel Accepted for Review by FDA Represents First NDA with Bentley's Proprietary CPE-215 Technology, Business Wire (Mar. 6, 2002).
New Treatment Approved for Low Testosterone, Not Born Yesterday (La Canada Flintridge, CA), Dec. 2002.
Ng. Martin et al., Prospective Study of Effect of Androgens on Serum Inflammatory Markers in Men, Arterioscler. Thromb. Vasc. Biol., vol. 22, pp. 1136-1141 (2002).
Nicolazzo, J.A. et al., "Synergistic enhancement of testosterone transdermal delivery," J. Contr. Rel. (2005) 103:577-585.
Nicoli, S. et al., "Dermatopharmacokinetics: factor influencing drug clearance from the stratum corneaum," Pharm. Res. (2009) 26(4):865-871.
Nieschlag E. et al., Reproductive functions in young fathers and grandfathers. J. Clin. Endocrinol. Metab. 55:876 (1982).
Nieschlag et al., Testosterone: Action, Deficiency, Substitution, Chapters 1, 6-16 (1999).
Nieschlag, Eberhard, Testosterone Treatment Comes of Age: New Options for Hypogonadal Men, Clinical Endocrinology, vol. 65, pp. 275-281 (2006).
Nieschlag, et al., eds., Testosterone: Action—Deficiency—Substitution (2d ed.), pp. 335-337.
Nilas, et al., Bone Mass and its Relationship to Age and the Menopause, J Clin Endocrinol Metab, Oct. 1987; 65(4): 697-702.
Nishimura, Y., M. Tsutsumi, H. T. Tsunenari, H. Maeda, and M. Yokoyama. Relationship between respiratory muscle strength and lean body mass in men with COPD. Chest 107: 1232-1236 (1995).
Notice of NDA No. 202763 Concerning Testosterone Gel, 1% with Paragraph IV Certification Concerning US Patent No. 6,503,894 dated Mar. 16, 2011 (Teva).
Notification of Certification of Invalidity, Unenforceability and/or Non-Infringement for U.S. Patent No. 6,503,894 B1 Pursuant to Section 505(b)(3) of the Federal Food, Drug and Cosmetic Act dated Sep. 20, 2011 (Perrigo).
Novelli, et al., Pharmacogenetics of Human Androgens and Prostatic Diseases, Pharmacogenomics, vol. 2, No. 1, pp. 65-72 (2001).
Noveon Bulletin 10: Neutralization Procedures (Jan. 2002).
Noveon Bulletin 11: Thickening Properties (Jan. 2002).
Noveon Bulletin 14: Formulating Topical Properties (Jan. 2002).
Noveon Product Specification: Carbopol 1342 NF (Jan. 2003).
Noveon Product Specification: Carbopol 674 Polymer (Nov. 2001).
Noveon Product Specification: Carbopol 676 Polymer (Nov. 2001).
Noveon Product Specification: Carbopol 934 NF Polymer (Jan. 2003).
Noveon Product Specification: Carbopol 940 NF Polymer (Jan. 2003).
Noveon Product Specification: Carbopol 941 NF Polymer (Jan. 2003).
Noveon Product Specification: Carbopol 971P NF Polymer (Jan. 2003).
Noveon Product Specification: Carbopol 974P NF Polymer (Jan. 2003).
Noveon Product Specification: Carbopol 980 NF Polymer (Jan. 2003).
Noveon Product Specification: Carbopol Aqua 30 Polymer (Nov. 2002).
Noveon Product Specification: Carbopol ETD 2020 Polymer (Nov. 2001).
Noveon Product Specification: Carbopol ETD 2623 Polymer (Nov. 2001).
Noveon Product Specification: Carbopol ETD 2691 Polymer (Nov. 2001).
Noveon Product Specification: Carbopol EZ-2 Polymer (Aug. 2003).
Noveon Product Specification: Carbopol EZ-3 Polymer (Aug. 2003).
Noveon Product Specification: Carbopol Ultrez 10 NF Polymer (May 2003).
Noveon Product Specification: Carbopol Ultrez 21 Polymer (Sep. 2003).
Noveon Standard Test Procedure SA-051A: Determination of Waiting Time & Brookfield Viscosity of Carbopol Ultrez and EZ Polymers (Aug. 2002).
Noveon TDS-207: Carbopol ETD Polymers: Formulation Tips (Jan. 2002).
Noveon TDS-297: Carbopol Ultrez 21 Polymer, Technical Data Sheet (Feb. 2003).
Noveon TDS-60: Applications Technology for Carbopol Resins and Cosmetic Formulations (2001).
Noveon TDS-64: Typical Properties of Carbopol Polymers (Jan. 2002).
Noveon, Formulating Hydroalcoholic Gels with Carbopol Polymers, Noveon TDS-255, Dec. 1999.
Noveon, Neutralizing Carbopol and Pemulen Polymers in Aqueous and Hydroalcoholic Systems, Commercial Brochure TDS-237 (Oct. 1998) by Noveon Inc. of Cleveland, Ohio.
O'Carrol & Bancroft, Testosterone Therapy for Low Sexual Interest and Erectile Dysfunction in Men: A Controlled Study, Brit. J. Psychiatry 145:146-151 (1984).
O'Carroll et al., "Androgens, behaviour and nocturnal erection in hypogonadal men: the effects of varying the replacement dose." Clin. Endocrinol. 23: 527-538 (1985).

(56) References Cited

OTHER PUBLICATIONS

O'Connor, Managing Menopause—Part 2: What Are the Choices in Treatment? Medicine Today, vol. 2 (No. 2), p. 30-39, (Feb. 22, 2001).
Oden Z M, et al., the effect of trabecular structure on DXA-based predictions of bovine bone failure. Calcif. Tissue Int., 63:67-73 (1998).
Okun, et al., Beneficial Effects of Testosterone Replacement for the Nonmotor Symptoms of Parkinson Disease, Arch. Neurol., vol. 59, pp. 1750-1753 (Nov. 2002).
Okun, et al., Refractory Nonmotor Symptoms in Male Patients with Parkinson Disease Due to Testosterone Deficiency: A Common Unrecognized Comorbidity, Arch. Neurol., vol. 59, pp. 807-811 (May 2002).
O'Neill T W, et al., the prevalence of vertebral deformity in European men and women: the European Vertebral Osteoporosis Study. J. Bone Miner. Res., 11:1010-8 (1996).
Ongpipattanakul, B. et al., "Evidence that oleic acid exists in a separate phase within stratum corneum lipids," Pharm. Res. (1991) 8(3):350-354.
Openbrier, D. R., M. M. Irwin, R. M. Rogers, G. P. Gottlieb, J. H. Daubner, D. H. Van Theil and B. E. Pennock. Nutritional status and lung function in patients with emphysema and chronic bronchitis. Chest 83: 11-22 (1983).
Oppermann, Testosterone Replacement Carries Definite Risks for Men, Chicago Daily Herald, Jun. 3, 2002.
Options, Alt Med. Rev., (vol. 1, pp. 18-25 (1996). (Abstract only).
Orwell ES et al., The impact of osteophytic and vascular calcifications on vertebral mineral density measurements in men. J. Clin. Endocrinol. Metab. 70:1202 (1990).
Orwoll ES et al., The rate of bone mineral loss in normal men and the effects of calcium and cholecalciferol supplementation. Ann. Int. Med. 112:29 (1990).
Orwoll, E. S., Oviatt, S., Biddle, J., and Janowsky, J. Transdermal testosterone supplementation in normal older men. Proc. 74th Endocr. Soc. Meetings, San Antonio, TX. Jun. 24, 1992.
Osborne et al., Skin Penetration Enhancers Cited in Technical Literature, Pharmaceutical Technology. pp. 58, 60, 62, 64 and 66, Nov. 1997.
Ostrenga, et al., Significance of Vehicle Composition I: Relationship Between Topical Vehicle Composition, Skin Penetrability, and Clinical Efficacy, Journal of Pharmaceutical Sciences, vol. 60, No. 8, pp. 1175-1179 (Aug. 1971).
Ostrenga, et al., Significance of Vehicle Composition II: Prediction of Optimal Vehicle Composition, Journal of Pharmaceutical Sciences, vol. 60, No. 8, pp. 1180-1183 (Aug. 1971).
Oxford Dictionary of Biochemistry and Molecular Biology, "ethanol": p. 218 (1997).
Pabla D, Zia H, A comparative permeation/release study of different testosterone gel formulations, Drug Deliv. Aug. 2007;14(6):389-96.
Package insert for Estrogel, (Mar. 2004).
Padova, et al., Pubarche Induction with Testosterone Treatment in Women with Panhypopituitarism, Fertil Steril, Feb. 1996; 65(2): 437-9.
Page ST et al., Testosterone gel combined with depomedroxyprogesterone acetate is an effective male hormonal contraceptive regimen and is not enhanced by the addition of a GnRH antagonist, J Clin Endocrinol Metab. Nov. 2006;91(11):4374-80. (Epub Date: Aug. 29, 2006).
Pannek, et al., The Role of PSA and Percent Free PSA for Staging and Prognosis Prediction in Clinically Localized Prostate Cancer, Seminars in Urologic Oncology, vol. 16, No. 3, pp. 100-105 (Aug. 1998).
Parfitt A M, Implications of architecture for the pathogenesis and prevention of vertebral fracture. Bone, 13:S41-7 (1992).
Parfitt A M, et al., Relationships between surface, volume, and thickness of iliac trabecular bone in aging and in osteoporosis. Implications for the microanatomic and cellular mechanisms of bone loss. J. Clin. Invest., 72:1396-409 (1983).
Park, et al., Effects of Androgens on the Expression of Nitric Oxide Synthase mRNAs in Rat Corpus Cavernosum, BJU Int'l vol. 83, pp. 327-333 (1999).

Parker, et al., Experience with Transdermal Testosterone Replacement in Hypogonadal Men, Clinical Endocrinology (OXF), vol. 50, pp. 57-62 (1999).
Patch Ups Women's Sex Drive. ABCNEWS.com: http://abcnews.go.com/sections/living/DailyNews/testosterone990615.html (Sep. 8, 2000).
Pavlov. "Indications and technique of intra-articular administration of hydrocortisone to patients with infectious nonspecific polyarthritis." Soviet Medicine (1964). [in Russian with English Abstract].
Pedersen, et al., Relationship Between Sex Hormones, Body Composition and Metabolic Risk Parameters in Premenopausal Women, Eur J Endocrinol, Aug. 1995; 133(2): 200-6.
Pena, Topical Drug Delivery Formulations, ed. Osborne and Amann, vol. 42, pp. 381-388 (1990).
Penson, et al., Androgen and Pituitary Control of Penile Nitric Oxide Synthase and Erectile Function in the Rat, Biology of Reproduction, vol. 55, pp. 567-574 (1996).
Percutacrine Strong Androgenic Testosterone Percutacrine Androgenique Forte from VIDAL dictionary (1985).
Peres, Clinical Trials to Test Efficacy of Testosterone-Replacement Therapy for Men, Knight-Ridder Tribune Business News, Nov. 29, 2002.
Peres, Hormones Now a Men's Issue, Chicago Tribune, Nov. 29, 2002.
Peres, Replacement Hormones New Issue for Men, Pittsburgh Post-Gazette, Jan. 5, 2003.
Peres, Researchers Consider Benefits of Male Hormone Replacement, Houston Chronicle, Jan. 3, 2002.
Perez CA, I love my Androgel, Posit Aware. Nov.-Dec. 2003;14(6):42-3.
Perry, et al., Osteoporosis in Men: Are We Ready to Diagnose and Treat?, Curr. Rheumatol. Res., vol. 3, No. 3, pp. 240-244 (Jun. 2001).
Pershing, L.K. et al., "Disparity of in vitro and in vivo oleic acid-enhanced beta-estradiol percutaneous absorption across human skin," Pharm. Res. (1993) 10(12):1745-1750.
Persky, et al., The Relation of Plasma Androgen Levels to Sexual Behaviors and Attitudes of Women, Psychosomatic Medicine, vol. 44, No. 4, pp. 305-319 (Sep. 1982).
Persky, et al., Plasma Testosterone Level and Sexual Behavior of Couples. Arch Sex Behav, May 1978; 7(3): 157-73.
Petra, The Plasma Sex Steroid Binding Protein (SBP or SHBG): A Critical Review of Recent Developments of the Structure, Molecular Biology, and Function, J. Steroid Biochem. Mol. Biol. vol. 40, pp. 735-753 (1991).
Petrangeli, et al., Effects of Two Different Medical Treatments on Dihydrotestosterone Content and Androgen Receptors in Human Benign Prostatic Hyperplasia. J Steroid Biochem, 1988; 30(1-6): 395-9.
Petrow, The Dihydrotestosterone (DHT) Hypothesis of Prostate Cancer and its Therapeutic Implications. Prostate, 1986; 9(4): 343-61.
Pfeilschifter, et al., Osteoporosis Due to Cancer Treatment: Pathogenesis and Management, J. of Clin. Oncology, vol. 18, No. 7, pp. 1570-1593 (Apr. 2000).
Phillips GB, Pinkernell BH, Jinh TY: The association of hypotestosteronemia with coronary artery disease in men. Arteriosclerosis & Thrombosis 14:701-6, 1994.
Phillips L et al., A comparison of rabbit and human skin response to certain irritants. Toxicol. Appl. Pharmacol. 21, 369-82 (1972).
Pilepich, et al., Androgen Deprivation with Radiation Therapy Compared with Radiation Therapy Alone for Locally Advanced Prostatic Carcinoma: A Randomized Comparative Trial of the Radiation Therapy Oncology Group, Urology, vol. 45, No. 4, pp. 616-623 (Apr. 1995).
Pirke KM et al., Age related changes in free plasma testosterone, dihydrotestosterone and oestradiol. Acta Endocrinol. 80: 171 (1975).
Pirke, et al., Age Related Changtes and Interrelationships Between Plasma Testosterone, Oestradiol and Testosterone-Binding Globulin in Normal Adult Males, Acta Endocrinologica (COPENH), vol. 74, No. 4, pp. 792-800 (Dec. 1973).
Place, et al., Transdermal Delivery of Testosterone with Testoderm to Provide Normal Circadian Pattern of Testosterone. Ann NY Acad Sci, 1991; 618:441-9.

(56) References Cited

OTHER PUBLICATIONS

Plymate, et al., Androgens, Lipids, and Cardiovascular Risk, Annals of Internal Medicine, vol. 117, No. 10, pp. 871-872 (Nov. 15, 1992).
Plymate, et al., Circadian Variation in Testosterone, Sex Hormone-Binding Globulin and Calculated Non-Sex Hormone-Binding Globulin Bound Testosterone in Healthy Young and Elderly Men. J Androl, Sep.-Oct. 1989; 10(5): 366-71.
Plymate, et al., Effects of Sex Hormone Binding Globulin (SHBG) on Human Prostatic Carcinoma. J Steroid Biochem Mol Biol, 1991; 40(4-6): 833-839.
Pollard et al., Dihydrotestosterone does not induce prostate adenocarcinoma in L-W rats, Prostate 10:325-331 (1987).
Polsy, et al., HIV-Associated Wasting in the HAART Era: Guidelines for Assessment, Diagnosis, and Treatment, AIDS Patient Care and STDs, vol. 15, No. 8, pp. 411-423 (2001).
Poor, et al., Determinants of Reduced Survival Following Hip Fractures in Men, Clinical Orthopaedics and Related Research, No. 319, pp. 260-265 (Oct. 1995).
Pope Jr., et al., Testosterone Gel Supplementation for Men with Refractory Depression: A Randomized, Placebo-Controlled Trial. Am. J. Psychiatry, 160(1): 105-111 (2003).
Porche DJ. Treatment review. Testosterone (Testoderm). J Assoc Nurses AIDS Care. Jul.-Aug. 1995;6(4):43-5.
Porter, et al., Humoral Mechanisms in Prostate Cancer: A Role for FSH, Urologic Oncology, vol. 6, pp. 131-138 (2001).
Postma, et al., Effects of Testosterone Administration on Selective Aspects of Object-Location Memory in Healthy Young Women, Psychoneuroendocrinology, vol. 25, pp. 563-575 (2000).
Poteat, et al., Appropriateness of Prostate-Specific Antigen Testing, Am. J. Clin. Pathol., vol. 113, pp. 421-428 (2000).
Poulsen, B.J. et al., "Effect of topical vehicle composition on the in vitro release of fluocinolone acetonide and its acetate ester," J. Pharm. Sci. (1968) 57(6):928-933.
Preidt, Testosterone: Shot in the Arm for What Ails Aging Males, HealthScoutNews.com (Aug. 5, 2002).
Press Release, "Schering AG—Male Hormone Therapy" (Jul. 2, 2002).
Press Release, "The Endocrine Society Responds to the Institute of Medicine Report on Testosterone Therapy for Older Men" (Nov. 17, 2003).
Press Release, Cellegy Announces Settlement of PDI Litigation (Apr. 12, 2005).
Press Release, FDA Approves Androgel, First Gel to Treat Male Testosterone Deficiency (Feb. 29, 2000) from www.androgel.com/media/press_release000229.htm.
Prince RL et al., Prevention of postmenopausal osteoporosis: A comparative study of exercise, calcium supplementation and hormone-replacement therapy. N Engl J. Med 325:1189 (1991).
Procter & Gamble, TheraTech Plan Testosterone Patch for Use by Women. The Wall Street Journal, p. B6 (Dec. 4, 1997).
Product information—Testoderm TTS, Physicians' Desk Reference, Alza pp. 517-520 (1999).
Prospectus—Cellegy Pharmaceuticals, Inc., Oppenheimer & Co., pp. 1-4, 20821-28 (it is 21-28 on U.S. Appl. No. 10/153,468) (1997).
Quincey et al., The metabolism of [1,2-3H]17 {alpha}-methyltestosterone in human subjects, J. Endocrinol. 37(1):37-35 (1967).
R&D Directions, "Products Filed for Approval: Androgel—Unimed Applies for FDA Approval for Androgel Gel for the Treatment of Low Testosterone Levels in Hypogonadal Men," 5(7) (Jul. 1999).
Rabkin, et al., Testosterone Therapy for Human Immunodeficiency Virus-Positive Men With and Without Hypogonadism, J. Clin. Psychopharmacol., vol. 19, No. 1, pp. 19-27 (Feb. 1999).
Rabkin, et al., Treatment of Depression in HIV+ Men: Literature Review and Report of an Ongoing Study of Testosterone Replacement Therapy, Ann. Behav. Med., vol. 18, No. 1, pp. 24-29 (1996).
Rabkin, J et al., A double-blind, Placebo-Controlled Trial of Testosterone Therapy for HIV-Positive Men With Hypogonadal Symptoms. Arch Gen Psychiatry 57: 141-147 (Feb. 2000).

Radio: Public Service Announcement: Transcripts for Advertisements: Low Testosterone in Men, an Easily Diagnosed and Treated Condition. PSA. :15, :30, :60 Versions, (2003).
Raisz, et al., Comparison of the Effects of Estrogen Alone and Estrogen Plus Androgen on Biochemical Markers of Bone Formation and Resorption in Postmenopausal Women, Journal of Clinical Endocrinology and Metabolism, vol. 81, No. 1, pp. 37-43 (Jan. 1996).
Rako, Testosterone Deficiency: a Key Factor in the Increased Cardiovascular Risk to Women Following Hysterectomy or with Natural Aging? J Womens Health, Sep. 1998; 7(7): 825-9.
Ramzy, P. I., S. E. Wolf, and D. N. Herndon. Current status of anabolic hormone administration in human burn injury. JPEN J. Parenter. Enteral Nutr. 23: S190-S194 (1999).
Random House Webster's Unabridged Dictionary, 2d Edition, "ethanol": p. 665 and "alcohol": p. 49 (2005).
Random House Webster's Unabridged Dictionary, 2d Edition, "pharmaceutical": p. 1451 and "drug": p. 600 (2005).
Raudaskoski, et al., Sex-Hormone Binding Globulin As an Indicator of the Hepatic Impacts of Continuous Combined Hormone Replacement Regimens, Maturitas, vol. 29 (No. 1), p. 87-92, (Jan. 22, 1998).
Ray Fox et al., Medical Expenditures for the Treatment of Osteoporotic Fractures in the United States in 1995: Report from the National Osteoporosis Foundation, J. of Bone and Mineral Research, vol. 12, No. 1, pp. 24-35 (1997).
Ray, et al., ISATT Series 2007, Men's Health Information (Presentation).
Rebora, Baldness and Coronary Artery Disease: The Dermatologic Point of View of a Controversial Issue, Arch Dermatol. 137:943-947 (2001).
Reed RL et al., The relationship, between muscle mass and muscle strength in the elderly. J. Am Ger Soc 39:555 (1991).
Rehm, Testosterone and Andropause, National Public Radio, The Diane Rehm Show Summary Introduction (Aug. 14, 2002).
Reichardt, J. Prostatic Steroid 5α-Reductase, an Androgen Metabolic Gene. Mayo Clin Proc. 75(suppl):S36-S39 (2000).
Reilly et al., Androgenic Regulation of NO Availability in Rat Penile Erection, 18 J. Andrology 110 (1997): 110-115.
Research & Education Institute at Harbor-UCLA Medical Center, Testosterone Gel (AndroGel(R)) Study Demonstrates Safety and Efficacy Persists Up to 42 Months in Men with Low Testosterone, Yahoo!Finance.com (Jun. 20, 2002).
Retin-A (tretinoin) Cream; Retin-A (tretinoin) Gel; Retin-A (tretinoin) Liquid. Daily Med. http://dailymed.nlm.nih.gov/dailymed/drugInfo.cfm?id=3734. pp. 1-13. Downloaded on Oct. 13, 2009.
Retinopathy and nephropathy in patients with type 1 diabetes four years after a trial of intensive therapy. Am J Ophthalmol. May 2000;129(5):704-5.
Retinopathy and nephropathy in patients with type 1 diabetes four years after a trial of intensive therapy. NEJM. 2000. 342:381-9.
Retnakaran et al., Risk factors for renal dysfunction in type 2 diabetes: U.K. Prospective Diabetes Study 74. Diabetes. Jun. 2006;55(6):1832-9.
Reuters News, "Unimed Files to Market Gel to Treat Impotence" (Apr. 29, 1999).
Reynolds, Do women with impaired sexual function following oophorectomy benefit from transdermal testosterone at a physiologic dose? The Journal of Family Practice, vol. 49 (No. 12n), p. 1075 (Dec. 2000).
Rheology Modifiers Handbook, 2000, p. 81-88, published by William Andrew Publishing.
Rhoden et al., "Risks of Testosterone-Replacement Therapy and Recommendations for Monitoring," N Engl J Med 350:5, 482-492 (2004).
Rhoden, et al., The Relationship of Serum Testosterone to Erectile Function in Normal Aging Men, The J. of Urol., vol. 167, pp. 1745-1748 (Apr. 2002).
Rich JB, Brandt J. Lesh K, Dobs AS. The effect of testosterone on cognition in hypogonadal men. ICE the endocrine society p. 734 #OR58-6 (1996).
Richmond et al., Male pubertal development and the role of androgen therapy, Nature Clinical Practice Endocrinology and Metabolism, 3(4):338-344 (2007).

(56) References Cited

OTHER PUBLICATIONS

Rietschel, et al., Prevalence of Hypogonadism among Men with Weight Loss Related to Human Immunodeficiency Virus Infection Who Were Receiving Highly Active Antiretroviral Therapy, Clinical Infectious Diseases, vol. 31, pp. 1240-1244 (2000).
Riggs, et al., A Unitary Model for Involutional Osteoporosis: Estrogen Deficiency Causes Both Type I and Type II Osteoporosis in Postmenopausal Women and Contributes to Bone Loss in Aging Men, J. of Bone and Mineral Research, vol. 13, No. 5, pp. 763-773 (1998).
Riggs, Unimed Begins Pivotal Clinical Trial for Innovative Testosterone Gel, Unimed News Release, pp. 1-2 (Mar. 31, 1997).
Ringham, et al., Dose Proportionality and Systemic Bioavailability of a Testosterone Topical Gel in Hypogonadal Men, Unimed Pharmaceuticals (Oct. 31, 2000).
Rizzo, "Advertising and Competition in the Ethical Pharmaceutical Industry: The Case of Antihypertensive Drugs," J Law & Econ 42(1): 89-116 (Apr. 1999).
Roberts, et al., PSA Doubling Time as a Predictor of Clinical Progression After Biochemical Failure Following Radical Prostatectomy for Prostate Cancer, Mayo Clin. Proc., vol. 76, pp. 576-581 (2001).
Roberts, More Men Take Testosterone, CBS-TV CBS Morning News Online (Aug. 25, 2002).
Robinson, M.K. et al., "Evaluation of the primary skin irritation and allergic contact sensitization potential of transdermal triprolidine," Fund. Appl. Toxico. (1991) 17:103-119.
Rodriguez, Study of Drug to Preserve Lean Muscle Mass Recruiting Patients, ALPA 9701: Study Recruiting Patients, www.apla.org (Downloaded Oct. 8, 1998).
Rogol A.D., New facets of androgen replacement therapy during childhood and adolescence. Expert Opinion on Pharmacotherapy, 6(8):1319-1336 (2005).
Rogol, Nature clinical practice endocrinology and metabolism vol. 3, No. 4, Apr. 2007, pp. 338-344.
Rogol, Pubertal androgen therapy in boys. Pediatr. Endocrinol. Rev., Mar. 2005; 2(3):383-90.
Rolf, et al., Interpersonal testosterone transfer after topical application of a newly developed testosterone gel preparation, Clinical Endocrinology, vol. 56, pp. 637-641 (2002).
Rolf, et al., Pharmacokinetics of a new transdermal testosterone gel in gonadotrophin-suppressed normal men, European Journal of Endocrinology, vol. 146, pp. 673-679 (2002).
Rosano et al., Acute Anti-Ischemic Effect of Testosterone in Men with Coronary Artery Disease, Circulation, vol. 99, No. 13, pp. 1666-1670 (Apr. 6, 1999).
Rosano, et al., Antianginal and Lipid Lowering Effect of Chronic Oral Androgen Supplementation in Elderly Male Patients with Coronary Heart Disease. JACC, Abstract No. 835-4 (Feb. 2001).
Rosen, et al., The International Index of Erectile Function (IIEF): A Multidimensional Scale for Assessment of Erectile Dysfunction, Urology, vol. 49, pp. 822-830 (1997).
Rosenthal BD, et al., Adjunctive use of AndroGel (testosterone gel) with sildenafil to treat erectile dysfunction in men with acquired androgen deficiency syndrome after failure using sildenafil alone, Urology. Mar. 2006;67(3):571-4.
Rosner et al., Sex Hormone-Binding Globulin Mediates Steroid Hormone Signal Transduction at the Plasma Membrane, J. Steroid Biochem. Mol. Biol. vol. 69:481-5 (1999).
Roubenoff, et al., Role of Cytokines and Testosterone in Regulating Lean Body Mass and Resting Energy Expenditure in HIV-infected Men, Am. J. Physiol. Endocrinol. Metab., vol. 283, pp. E138-E145 (2002).
Rouru, et al., Serum Leptin Concentrations in Women with Polycystic Ovary Syndrome. J Clin Endocrinol Metab, Jun. 1997; 82(6): 1697-700.
Rousseau, et al, Inhibition of Steroid-Protein Interactions by Dicyclohexane Derivatives. J Steroid Biochem, vol. 31, No. 4B, pp. 691-697 (1988).
Rowe et al., Handbook of Pharmaceutical Excipients, 2d ed. (1994).

Rubens RM et al., Further studies on Leydig cell function in old age. J. Clin. Endocrinol. Metab. 39:40 (1974).
Rudman D, Drinka PJ, Wilson CR, Mattson DE, Scherrnan F, Cuisinier MC, Schults S: Relations of endogenous anabolic hormones and physical activity to bone mineral density and lean body mass in elderly men. Clin Endocrinol 40:653-61, 1994.
Saad F, et al., A dose-response study of testosterone on sexual dysfunction and features of the metabolic syndrome using testosterone gel and parenteral testosterone undecanoate, J Androl. Jan.-Feb. 2008;29(1):102-5. (Epub Date: Oct. 3, 2007).
Saad F, et al., Effects of testosterone gel followed by parenteral testosterone undecanoate on sexual dysfunction and on features of the metabolic syndrome, Andrologia. Feb. 2008;40(1):44-8.
Saar, B.G. et al., "Imaging drug delivery to skin with stimulated raman scattering microscopy," Mol. Pharm. (2011) 8:969-975.
Saeedi M et al., A randomized, double-blind, controlled trial of testosterone gel treatment versus vehicle control on the facial hair of young men with beta-thalassemia major, J Dermatolog Treat. 2007;18(5):271-4.
Salehian et al., Pharmacokinetics, bioefficacy and safety of sublingual testosterone cyclodextrin in hypogonadal men: comparison to testosterone enanthate—a clinical research center study. J. Clin. Endocrinol. Metab. 80: 3567-75 (1995).
Sanctis et al., Clinical experience using the Androderm testosterone transdermal system in hypogonadal adolescents and young men with beta-thalassemia major. J. Ped. Endocrinol. Metab. 11, Supp. 3, 891-900 (1998) (abstract only).
Sands, et al., Exogenous Androgens in Postmenopausal Women, Am J Med, Jan. 16, 1995; 98(1A): 76S-79S.
Santavirta S et al., Determinants of osteoporotic thoracic vertebral fracture. Screening of 57,000 Finnish women and men. Acta Orthop Scand 63:198 (1992).
Santos, P. et al., "Oxybutinin permeation in skin: the influence of drug and solvent activity," Int. J. Pharma. (2010) 384:67-72.
Santus G. C. et al., Transdermal enhancer patent literature, Journal of Controlled release, Elsevier Science Publishers, (1993);25:1-20.
Sarrel P. et al., Estrogen and estrogen-androgen replacement in postmenopausal women dissatisfied with estrogen-only therapy, sexual behavior and neuroendocrine responses, Journal of Reproductive Medicine, Oct. 1998;43(10):847-856.
Sasagawa I, et al., Serum levels of total and free testosterone in men undergoing hemodialysis. Arch Androl 1998;40(20):153-158.
Sato, K. et al., "Effect and mode of action of aliphatic esters on the in vitro skin permeation of nicorandil," Int. J. Pharma. (1988) 43:31-40.
Sattler FR, et al., Effects of pharmacological doses of nandrolone decanoate and progressive resistance training in immunodeficient patients infected with Human Immunodeficiency Virus. J Clin Endocrinol Metab 84:1268-76, 1999.
Sauvez et al., "Cutaneously applied 4-hydroxytamoxifen is not carcinogenic in female rats." Carcinogenesis. 20(5): 843-850 (1999).
Savvas, et al., Increase in Bone Mass after One Year of Percutaneous Oestradiol and Testosterone Implants in Post-Menopausal Women Who Have Previously Received Long-Term Oral Oestrogens, British Journal of Obstetrics Gynecology, vol. 99, No. 9, pp. 757-760 (Sep. 1992).
Schaefer et al., Skin Barrier, Principles of Percutaneous Absorption, ed. Kager, pp. 164-171 (1996).
Schaison et al., Testosterone,: Percutaneous dihydrotestosterone treatment, Ch. 15, pp. 423-435 (1999).
Schaison G, Nahoul K, Couz B) Percutaneous dihydrotestosterone (DHT) treatment. Testosterone: Action. Deficiency and Substitution E. Nieschlag, H.M. Behre (Eds.). Springer-Verlag, New York, pp. 155-164 (1990.
Schaison, et al., On the Role of Dihydrotestosterone in Regulating Luteinizing Hormone Secretion in Man, J Clin Endocrinol Metab, Nov. 1980; 51(5): 1133-1137.
Schatzl, et al., Endocrine Patterns in Patients with Benign and Malignant Prostatic Diseases, The Prostate, vol. 44, pp. 219-224 (2000).
Schatzl, et al., High-Grade Prostate Cancer is Associated With Low Serum Testosterone Levels, The Prostate, vol. 47, pp. 52-58 (2001).
Schering AG Business: Reproductive, Metabolic. Biocentury Part II, Belmont, CA (Jul. 8, 2002).

(56) References Cited

OTHER PUBLICATIONS

Schiavi RC, et al., Effect of Testosterone Administration on Sexual Behavior and Mood in Men with Erectile Dysfunction. Arch. Sex Behav., Jun. 1997, 26(3):231-41.
Schols, A. M., P. B. Soeters, R. Mostert, R. J. Pluymers, and E. F. Wouters. Physiologic effects of nutritional support and anabolic steroids in patients with chronic obstructive pulmonary disease. A placebo-controlled randomized trial. Am. J. Respir. Crit Care Med. 152: 1268-1214 (1995).
Schoor, M., Livening Up Libidos: Testosterone Patches Can Help Revive Women's Sex Drive, www.abcnews.com, Sep. 6, 2000.
Schottner, et al., Lignans Intefering with 5 alph-Dihydrotestosterone Binding to Human Sex Hormone-Binding Globulin, J Natl Prod, Jan. 1988; 61(1): 119-121.
Schreiner-Engel, et al., Low Sexual Desire in Women: the Role of Reproductive Hormones, Hormones and Behavior, vol. 23, No. 2, pp. 221-234 (Jun. 1989).
Schreiner-Engel, et al., Sexual Arousability and the Menstrual Cycle, Psychosom Med Jun. 1981; 43(3): 199-214.
Schulthesis, D et al., Pilot study of the transdermal application of testosterone gel to the penile skin for the treatment of hypogonadotropic men with erectile dysfunction Abstract. World J Urol 18: 431-435 (2000).
Schurmeyer, et al., Comparative Pharmacokinetics of Testosterone Enanthate and Testosterone Cyclohexanecarboxylate as Assessed by Serum and Salivary Testosterone Levels in Normal Men, International Journal of Andrology, (1984);vol. 7, pp. 181-187.
Schustack A, Meshiaj D, Waiss Z, Gottloib L. L. Intramuscular iron replenishment and replacement combined with testosterone enanthoate in maintenance hemodialysis anemia: a follow up of up to 8 years in 16 patients. Clin Nephrol 1985; 23(6):303-306.
Schwartz RS et al., "Body Fat Distribution in Healthy Young and Older Men" Journal of Gerontology: Medical Sciences, 1990. vol. 45. No. 6. M18I-I85.
Scott JD et al., Prospective study of topical testosterone gel (AndroGel) versus intramuscular testosterone in testosterone-deficient HIV-infected men, HIV Clin Trials. Nov.-Dec. 2007;8(6):412-20.
Seeman E, et al., Risk factors for spinal osteoporosis in men. Am J. Med 75:977 (1983).
Seidenfeld, M.A. et al., "The general properties, actions and toxicity of propyvene glycol," J. Pharm. Exp. Ther. (1932) 109-121.
Seidman SN, Rabkin JG. Testosterone replacement therapy for hypogonadal men with SSRI-refractory depression . Journal of Affective Disorder 4H: 157-161 (1998).
Seidman, et al., J Clin Psychiatry 2001 ;62:406-412.
Seki, T. et al., Percutaneous absorption enhancer applied of membrane permeation-controlled transdermal delivery of nicardipine hydrochloride in drug design and delivery (1989) 4:69-75.
Sepa Testosterone Transdermal Gel Receives Application by FDA, Doctor's Guide Global Edition, http://pslgroup.com/dg/123aa.htm (Jan. 15, 1997).
Sexual Dysfunction in the Male—Sexual Arousal Disorder, The Merck Manual, Sixteenth Edition, Ch. 139, pp. 1575-1576 (1992).
Shabsigh R, et al., Randomized study of testosterone gel as adjunctive therapy to sildenafil in hypogonadal men with erectile dysfunction who do not respond to sildenafil alone, J Urol. May 2008;179(5 Suppl):S97-S102.
Shabsigh R, et al., Testosterone replacement therapy with testosterone gel 1% converts sildenafil non-responders to responders in men with hypogonadism and erectile dysfunction who failed prior sildenafil therapy. Abstract #954 at the 98th Annual Meeting of the American Urological Association, Apr. 26-May 1, 2003, Chicago, Il.
Shabsigh, Recent Developments in Male Sexual Dysfunction, Curr Psychiatry Rep. Jun. 2000;2(3):196-200.
Shabsigh, The Effects of Testosterone on the Cavernous Tissue and Erectile Dysfunction, World J. of Urol., vol. 15, pp. 21-26 (1997).
Shabsigh, et al., Intracavernous Alprostadil Alfadex (Edex/Viridal) is Effective and Safe in Patients with Erectile Dysfunction After Failing Sildenafil (Viagra), Urology, vol. 55, pp. 477-480 (2000).

Shanbhag, et al., The Temperature Dependence of the Binding of 5 Alpha-Dihydrotestosterone and Estradiol to the Sex Hormone Globulin (SHBG) of Human Plasma, J Steroid Biochem, Feb. 1986; 24(2): 549-555.
Shaneyfelt et al., Hormonal Predictors of Prostate Cancer: A Meta-Analysis, Journal of Clinical Oncology, vol. 18, No. 4, pp. 847-853, 2000.
Shapiro et al., Testosterone and Other Anabolic Steroids as Cardiovascular Drugs, Am. J. of Therapeutics, vol. 6, No. 3 May 1999, pp. 167-174.
Sheffield-Moore M, Urban RJ, Wolf SE, Jiang J, Catlin DH, Herndon DN, Wolfe RR, Ferrando AA: Short-term oxandrolone administration stimulates net muscle protein synthesis in young men. J Clin Endocrinol Metab 84:2705-11, 1999.
Sheikh VI, Yesavage VA: Geriatric Depression scale (GDS): recent evidence and development of a shorter version. Clinical Gerontology: A Guide to Assessment and intervention. New York: Haworth Press, 1986, 165-74.
Sherwin B. B. and Gelfand M. M., Differential symptom response to parenteral estrogen and/or androgen administration in the surgical menopause, Am. J. Obstet. Gynecol. 1985; 151:153-160.
Sherwin, Affective Changes with Estrogen and Androgen Replacement Therapy in Surgically Menopausal Women, Journal of Affective Disorders, vol. 14, pp. 177-187 (1988).
Sherwin, Estrogen and/or Androgen Replacement Therapy and Cognitive Functioning in Surgically Menopausal Women, Psychoneuroendocrinology, vol. 13, No. 4, pp. 345-357 (Mar. 1988).
Sherwin, Sex Hormones and Psychological Functioning in Postmenopausal Women, Experimental Gerontology, vol. 29, Nos. 3&4, pp. 423-430 (May-Aug. 1994).
Sherwin, et al., Androgen Enhances Sexual Motivation in Females: a Prospective Crossover Study of Sex Steroid Administration in the Surgical Menopause, Psychosom Med, Jul.-Aug. 1985; 47(4): 339-51.
Sherwin, et al., Postmenopausal Estrogen and Androgen Replacement and Lipoprotein Lipid Concentrations, Am J Obstet Gynecol, Feb. 1987; 156(2): 414-9.
Sherwin, et al., The Role of Androgen in the Maintenance of Sexual Functioning in Oophorectomized Women, Psycosomatic Medicine, 49: 397-409 (1987).
Shibasaka, Effect of Testosterone Replacement Therapy on Serum PSA in Patients with Klinefelter Syndrome, Archives of Andrology, vol. 47, pp. 173-176 (2001).
Shifren, et al, Transdermal Testosterone Treatment in Women with Impaired Sexual Function After Oophorectomy, The New England Journal of Medicine, vol. 343, No. 10, pp. 682-688 (Sep. 7, 2000). (Abstract only).
Shifren, et al., Do women with impaired sexual function following oophorectomy benefit from transdermal testosterone at a physiologic dose? The Journal of Family Practice, vol. 49 (No. 12), pp. 1148 (Dec. 2000).
Shimizu, et al., Androgen-Induced Production of Colony-Stimulating Factor (CSF) and Colony-Inhibitory Factor (CIF) in the Submandibular Gland in Female Mice, Journal of Pharrnacobio-Dyn., vol. 12 (6), pp. 352-356, (Jan. 22, 1989).
Shin, S-C. et al., "Enhancing effects of fatty acids on piroxicam permeation through rat skins," Drug Dev. Ind. Pharma. (2000) 26(5):563-566.
Shirai, et al., Effects of Testosterone, Dihydrotestosterone and Estrogen on 3,2'-Dimethyl-4-Aminobiphenyl-Induced Rat Prostate Carcinogenesis, Int J Cancer, Apr. 15, 1994; 57(2):224-8.
Shouls, et al., Contact Allergy to Testosterone in an Androgen Patch: Control of Symptoms by Pre-Application of Topical Corticosteroid, Contact Dermatitis, p. 124-125, ( Aug. 22, 2001).
Shuster et al., The influence of age and sex on skin thickness, skin collagen and density. British Journal of Dermatology 93:639 (1975).
Sidh, et al., Adenocarcinoma of Prostate: Role of 17beta-Estradiol and 5alpha-Dihydrotestosterone Binding Proteins, Urology, Jun. 1979; 13(6): 597-603.
Signorello, et al., Serum Steroids in Relation to Prostate Cancer Risk in a Case-Control Study (Greece), Cancer Causes Control, Jul. 1997; 8(4): 632-636.

(56) References Cited

OTHER PUBLICATIONS

Simms, Use of Male Sex Hormone is Growing, Wisconsin State Journal (Jul. 29, 2002).
Simon et al., Androgen Therapy Improves Insulin Sensitivity and Decreases Leptin Level in Healthy Adult Men with Low Plasma Total Testosterone, Diabetes Care, vol. 24, No. 12, pp. 2149-2151 (Dec. 2001).
Simon HB, On call. My wife and I are both 62 and healthy. She started taking Prempro during her menopause eight years ago but has now decided to stop the hormones. I began taking DHEA five years ago, but I switched to AndroGel when my doctor gave me a prescription last year. Should I stay on AndroGel, go back to DHEA, or stop hormones? Harv Mens Health Watch. Jan. 2003;7(6):8.
Simon, et al., Association Between Plasma Total Testosterone and Cardiovascular Risk Factors in Healthy Adult Men: The Telecom Study, J. of Clin. Endocrinology and Metabolism, vol. 82, No. 2, pp. 682-685 (1997).
Simon, et al., Safety Profile: Transdermal Testosterone Treatment of Women After Oophorectomy, Obstetrics & Gynecology, vol. 97 (Suppl. 4), DD. 10S-11S (Apr. 2001).
Simon, et al., Percutaneous Absorption of 17 Beta-Estradiol in Ovariectomized Rhesus Monkeys: Skin and Serum Pharmacokinetics. Fertility and Sterility, vol. 53, No. 3, pp. 561-565 (Mar. 1990).
Simon, et al., The Absorption of Oral Micronized Progesterone: The Effect of Food, Dose Proportionality, and Comparison With Intramuscular Progesterone. Fertility and Sterility, vol. 60, No. 1, pp. 26-33 (Jul. 1993).
Sinaki M et al., Relationship between bone mineral density of spine and strength of back extensors in healthy postmenopausal women. Mayo Clint Proc 61:116 (1986).
Sinaki M. Exercise and osteoporosis. Arch Phy Med Rehab 70:220 (1989).
Singh, et al., Pharmacokinetics of a Transdermal Testosterone System in Men with End Stage Renal Disease Receiving Maintenance Hemodialysis and Healthy Hypogonadal Men, The J. of Clinical Endocrinology & Metabolism, vol. 86, No. 6, pp. 2437-2445 (2001).
Singh, et al., The Effects of Varying Doses of T on Insulin Sensitivity, Plasma Lipids, Apolipoproteins, and C-Reactive Protein in Healthy Young Men, The J. of Clin. Endocrinology & Metabolism, vol. 87, No. 1, pp. 136-143 (2002).
Sinha-Hikim et al., The Use of a Sensitive Equilibrium Dialysis Method for the Measurement of Free Testosterone Levels in Healthy, Cycling Women and in HIV-Infected Women, J. Clinical Endocrinology & Metabolism 83:1312-18. (1998).
Sinkula et al., Rationale for design of biologically reversible drug derivatives: prodrugs. J. Pharm. Sci., 64:181-210 (1975).
Sitruk-Ware, Percutaneous and Transdermal Oestrogen Replacement Therapy, Annals of Medicine, vol. 25, pp. 77-82 (1993).
Sitruk-Ware, R., "Transdermal delivery of steroids," Contraception (1989) 39(1):1-20.
Skakkebaek, et al., Androgen Replacement with Oral Testosterone Undecanoate in Hypogonadal Men: A Double Blind Controlled Study, Clinical Endocrinology (1981) 14, 49-61.
Slater, et al., Pharmacokinetics of Testosterone After Percutaneous Gel or Buccal Administration Fertility and Sterility, vol. 76 (No. 1), D. 32-37 (Jul. 22, 2001).
Slayden SM., Risks of menopausal androgen supplementation, Semin Reprod Endocrinol. 1998;16(2): 145-52.
Smerdely, et al., Predictors of Bone Mass in Healthy Older Men in the Community, MJA, vol. 173, pp. 183-186 (Aug. 21, 2000).
Smith et al., Percutaneous Penetration Enhancers, pp. 21-28 (1995).
Smith, et al., The Nature of Prostate Cancer Detected Through Prostate Specific Antigen Based Screening, The J. of Urol., vol. 152, pp. 1732-1736 (Nov. 1994).
SmithKline Beecham's New 5 mg Androderm Testosterone Transdermal System Now Available, International Association of Physicians in AIDS Care, .http://www.iapac.org/clinmgt/compnews/sb061297.html(Jun. 12, 1997).

Snitker T. The Nation Takes a 'Time Out for Men's Health'—Free Health Screenings for Men Across the U.S., WCNC-TV (NBC) Online (Jun. 11, 2002).
Snow-Harter C et al., Muscle strength as a predictor of bone mineral density in young women. J. Bone Miner Res 5:589 (1990).
Snyder et al., Effect of testosterone treatment on body composition and muscle strength in, men over 65 years of age. J Clin Endocrinol Metab 84:2647-53 (1999).
Snyder et al., Effects of Testosterone Replacement in Hypogonadal Men, J. Clin. Endocrinol. Metab., 85:2670-7 (2000).
Snyder et al., Treatment of Male Hypogonadism with Testosterone Enanthate. J. Clinical Endocrinology and Metabolism 51(5): 1335-9 (1980).
Snyder, Effects of Age on Testicular Function and Consequences of Testosterone Treatment, The J. of Clinical Endocrinology & Metabolism, vol. 86, No. 6, pp. 2369-2372 (2001).
Snyder, et al., Effect of Testosterone Treatment of Bone Mineral Density in Men Over 65 Years of Age, The Journal of Clinical Endocrinology and Metabolism, vol. 84, No. 6, pp. 1966-1972 (1999).
Sobel, S. Clinical Considerations of Transdermal Drugs. Chapter 24, pp. 431-436. Topical Drug Bioavailability, Bioequivalence, and Penetration (eds. Shah, VP and Maibach, HI).1993.
Solvay Eyes Acquisitions, Confirms FY Double-Digit Growth, Dow Jones News Service, Jul. 31, 2002.
Solvay Pharmacueticals, Estratest Prescribing and Safety Information and Patient Information (2005).
Solvay Pharmacueticals; AndroGel 1%, Dec. 2000, pp. 1-2.
Southren A. L., et al., Further study of factors-affecting the metabolic clearance rate of testosterone in man, J. Clin. Endocrinol. Metab. 1968; 28:1105-1112.
Spark et al., Dihydrotestosterone gel: a novel androgen for AIDS wasting syndrome. 79th Annual Meeting of the Endocrine Society (Abstract) 1997.
Sparrow D et al., The influence of age, alcohol consumption, and body build on gonadal function in men. J. Clin. Endocrinol. Metab. 51: 508 (1980).
Spector, et al., Free and Serum Testosterone Levels in 276 Males: A Comparative Study of Rheumatoid Arthritis, Ankylosing Spondylitis and Healthy Controls, Clinical Rheumatology, vol. 8, No. 1, pp. 37-41 (1989).
Spector, et al., Low Free Testosterone Levels in Rheumatoid Arthritis, Annals of the Rheumatic Diseases, vol. 47, pp. 65-68 (1988).
Stafford, et al., Androgen Deficiency and Bone Mineral Density in Men with Rheumatoid Arthritis, The J. of Rheumatology, vol. 27, No. 12, pp. 2786-2790 (2000).
Stahl, et al., Effects of Tamoxifen on the Levels of Luteinizing Hormone (LH), Follicle Stimulating Hormone (FSH), Prolactin (PRL), 17 beta-oestradiol (E2), Total and Free Testosterone (T) and Total and Free Dihydrotestosterone (DHT) in blood of Patients with benign prostatic hyperplasia, Exp Clin Endocrinol Jul. 1983;82(1):21-8, (Abstract only).
Stanley HL et al., Does hypogonadism contribute to the occurrence of a minimal trauma hip fracture in elderly men. J. Am Ger Soc 39:766 (1991).
Steams EL et al., Declining testicular function with age, hormonal and clinical correlates. Am J. Med 57:761 (1974).
Stedman's Concise Medical Dictionary, 4th Edition, "formula": p. 376 (2001).
Stehli, et al., Info—Androgel, www.mageos.ifrance.com/nade38/androgel (Downloaded May 9, 2001). [French; English machine translation included].
Steidle et al., AA2500 Testosterone Gel Normalizes Androgen Levels in Aging Males with Improvements in Body Composition and Sexual Function. J. Clinical Endocrinology & Metabolism 88(6):2673-2681 (2003).
Stepan JJ et al., Castrated men exhibit bone loss: effect of calcitonin treatment on biochemical indices of bone remodeling. J. Clin Endocrinol. Metab. 69:528 (1989).
Stephan, et al., Prostate-Specific Antigen, Its Molecular Forms, and Other Kallikrein Markers for Detection of Prostate Cancer, Urology, vol. 59, pp. 2-8 (2002).
Stephenson, As Genes Differ, So Should Interventions for Cancer, JAMA, vol. 285, No. 14, pp. 1829-1830 (Apr. 11, 2001).

(56) References Cited

OTHER PUBLICATIONS

Sternbach, Age-Associated Testosterone Decline in Men: Clinical Issues for Psychiatry. Am. J. Psychiatry (1998) vol. 155(10), pp. 1310-1318.

Stineman MG, Shea JA, Jette A, Tassoni CJ, Ottenbacher KJ, Fiedler R, Granger CV: The functional independence measure: tests of scaling assumptions, structure, and . reliability across 20 diverse; impairment categories. Arch Phys Med Rehab 77:1101-8, 1996.

Stomati, et al., Effects of Hormonal Replacement Therapy on Plasma Sex Hormone-Binding Globulin, Androgen and Insulin-Like Growth Factor-1 Levels in Postmenopausal Women, Journal of Endocrinological Investigation, vol. 19 (No. 8), p. 535-541, ( Jan. 22, 1996).

Stomati, et al., Endocrine, Neuroendocrine and Behavioral Effects of Oral Dehydroepiandrosterone Sulfate Supplementation in Postmenopausal Women, Gynecological Endocrinology, vol. 13 (No. 1), p. 134 15-25, (Jan. 22, 1999).

Strategy for Change: Pharmaceuticals Represent a Major Direction of Solvay's Growth Strategy and the Objective is to Have the Pharmaceutical Business Grow More Rapidly, Med Ad News (West Trenton, NJ), Sep. 2002.

Straub, et al., Involvement of the Hypothalmic-Pituitary-Adrenal/Gonadal Axis and the Peripheral Nervous System in Rheumatoid Arthritis: Viewpoint Based on a Systemic Pathogenetic Role, Arthritis & Rheumatism, vol. 44, No. 3, pp. 493-507 (Mar. 2001).

Strawford, et al., Effects of Nandrolone Decanoate Therapy in Borderline Hypogonadal Men with HIV-Associated Weight Loss, J. of AIDS and Human Retrovirology, vol. 20, pp. 137-146 (1999).

Studd, et al., The Relationship Between Plasma Estradiol and the Increase in Bone Density in Postmenopausal Women After Treatment with Subcutaneous Hormone Implants, American Journal of Obstetrics and Gynecology, vol. 163, No. 5 (Part 1), pp. 1474-1479 (Nov. 1990).

Stuenkel, et al, Sublingual Administration of Testosterone-Hydroxypropyl-.beta.-Cyclodextrin Inclusion Complex Simulates Episodic Androgen Release in Hypogonadal Men, Journal of Clinical Endocrinology and Metabolism, vol. 72, No. 5, pp. 1054-1059 (1991).

Sturdee, D. W., et al., Br. J. Obstet. Gynecol. (1997) 104:109-115.

Styne, D., Puberty, Basic and Clinical Endocrinology, 6th Edition, Greenspan F S and Gardner D G, ed. McGraw-Hill, New York, 2001.

Suchner, U., M. M. Rothkopf, G. Stanislaus, D. H. Elwyn, V. Kvetan, and J. Askanazi. Growth hormone and pulmonary disease—Metabolic effects in patients receiving parenteral nutrition. Arch. Intern. Med. 150: 1225-1230 (1990).

Suenderhauf et al., Therapy of menopausal syndrome with a combination of ovocyclin and perandren. Schweizerische Medizinische Wochenschrift, vol. 32, No. 22, May 31, 1952, pp. 589-590. [German; English machine translation included.].

Suh, H. et al., "Effectiveness and mode of action of isopropyl myristate as a permeation enhancer for naproxin through shed snake skin," J. Pharm. Pharma. (1996) 48:812-816.

Supac-ss, Guidance for Industry: Nonsterile Semisolid Dosage Forms—Scale-Up and Postapproval Changes: Chemistry, Manufacturing, and Controls; In Vitro Release Testing and In Vivo Bioequivalence Documentation (May 1997).

Surber et al., Optimization of Topical Therapy: Partitioning of Drugs into Stratum Corneum, Pharmaceutical Res., vol. 7(12), pp. 1320-1324 (1990).

Susman, 'Male Menopause' Therapy Hotly Debated, The Palm Beach Post, Aug. 28, 2002.

Svetec, et al., The Effect of Parenteral Testosterone Replacement on Prostate Specific Antigen in Hypogonadal Men with Erectile Dysfunction, The J. of Urol., vol. 158, pp. 1775-1777 (Nov. 1997).

Swerdloff RS et al., Androgen replacement therapy. In Current Therapy in Endocrinology and Metabolism (4th edition), Bardin C.W. (Ed) Decker, Philadelphia pp. 255 (1991).

Swerdloff RS, et al., Transdermal testosterone (T) gel is efficacious and safe in older compared to young men. Poster presentation #P2-648 at the 84th Annual Meeting of the Endocrine Society, Jun. 19-22, 2002, San Francisco, CA.

Swerdloff RS, et al., "Long-term pharmacokinetics of transdermal testosterone gel in hypogonadal men," J Clin Endocrinol Metab. Dec. 2000;85(12):4500-10.

Szadurski. "The application of a galvanic penetration test for the rapid determination of skin resistance to bases." Przeglad dermatologiczny [Dermatological Review]. 55(1):20-3 (1968).

Sznitowska, M. et al., "The effect of sorption promoters on percutaneous permeation of a model switterion—baclofen," Int. J. Pharm. (1996) 137:125-132.

Tan KC et al., Alterations in hepatic lipase and lipoprotein subfractions with transdermal testosterone replacement therapy. Clin Endocrinol (Oxf). 51(6):765-9 (1999).

Tangredi, et al., Hypertension as a Complication of Topical Testosterone Therapy. The Annals of Pharmacotherapy, vol. 35 (No. 10), p. 1205-1207 (Oct. 22, 2001).

Tanojo, H. et al., "In vivo human skin permeability enhancement by oleic acid: a laser Doppler velocimetry study," J. Cont. Rel. (1999) 58:97-104.

Taylor, A.K., "Isopropyl myristate," Pharmaceutical Excipients (2009) 348-349.

TDS Delivers Testosterone safely and effectively. Press release. Oct. 1, 2004.

Teichert, A Man's Pain: Age-Related Testosterone Loss in Men, Coined by One Doctor as Mano-Pause, Fuels Medical Debate, The Montgomery Journal (Rockville, MD), Jul. 9, 2002.

Tennant, PSA Levels, IPPS Scores Normal: Transdermal Testosterone Gel Safe Over Long Term, Urology Times (Cleveland, OH), Oct. 2002.

Tenover JL: Testosterone and the aging male. J Androl 18:103-106, 1997.

Tenover JS et al., Serum bioactive and immunoreactive follicle-stimulating hormone levels and the response to clomiphene in healthy young and elderly men. J. Clin. Endocrinol. Metab. 64:1103 (1987).

Tenover JS. Effects of testosterone supplementation in the aging male. J. Clin Endocrinol. Metab. 75:1092-1098 (1992).

Tenover, et al., Age-Related Alterations in the Circadian Rhythms of Pulsatile Luteinizing Hormone and Testosterone Secretion in Healthy Men. J Gerontol, Nov. 1988; 43(6): M163-9.

Tenover, et al., The Effects of Aging in Normal Men on Bioavailable Testosterone and Luteinizing Hormone Secretion: Response to Clomiphene Citrate, J Clin Endocrinol Metab, Dec. 1987; 65(6): 1118-1126.

Tenover. "Male Hormone Replacement Therapy Including 'Andropause.'" Endocrinol. Metab. Clin. North. Am. 27(4): 969-987 (1998).

Testim 1% (Testosterone Gel) CIII Medication Guide, Sep. 2009, available at http://www.auxilium.com/PDFs/20090918%20Testim%2OPI%20DPT%20FDA%20approved.pdf.

Testim 1% (Testosterone Gel), Physician Desk Reference, pp. 711-713 (2004).

TestoCreme—A Natural Transdermal Testosterone Replacement Therapy, www.testocreme.com, (2002).

Testocreme—No Shots, No Pills, No Patches, www.testocreme.com (Downloaded Jul. 10, 2000).

Testocreme Transdermal Testosterone Is New, Preventive Medicine Clinic of Monterey http://www.wellnessmd.com/testo.html (Jul. 10, 2000).

Testosterone Aids Post-Menopausal Women, BBC News Online: Health, www.bbc.co.uk. (Jun. 14, 1999).

Testosterone and Aging: Clinical Research Directions, Institute of Medicine of the National Academies (Liverman and Blazer, eds. )(2004).

Testosterone Gel May Help Men with Low Sex Drive, WRAL Online, http://www.wral-tv.com/features/healthteam/1997/0814-tgel/ (Aug. 14, 1997).

Testosterone Patch Treats Sexual Dysfunction in Women, Biomedical Technology Information Service vol. 23 (No. 21), pp. 244 (Dec. 1996).

Testosterone Patch Trial for Women with AIDS, Pharmaceutical Business News. vol. 12 (No. 275), p. 19 (Sep. 14, 1996).

Testosterone Replacement Therapy: Effective Treatments Are Available, MayoClinic.com (Feb. 26, 2002).

(56) References Cited

OTHER PUBLICATIONS

Testosterone Therapy—for Women?, Health News, www.onhealth.com (May 7, 1996).
Testosterone Undecanoate—Schering AG. Drugs RD. 2004; 5(6):368-9.
Testosterone's Role in the Female Sex Drive, USA Today News, www.usatoday.com (Apr. 8, 1996).
Testosterone-Topical Fortigel—Cellegy: Fortigel Tostrex, BioDrugs, vol. 17(4), pp. 299-300 (2003) (No authors listed).
Textbook of Dermatology, 6th Edition, vol. 4, p. 3524 (Chapman et al., eds.)(1998).
The Endocrine Society, Summary from the Second Annual Andropause Consensus Meeting (2001).
The Male Body: A Physician's Guide to What Every Man Should Know About His Sexual Health. CBC-TV The Early Show Online:Eye on Health (Aug. 30, 2002).
The Merck Index, 13th Edition, "Testosterone": p. 1638 and "Stanolone": p. 1566 (2001).
The Nation Takes a 'Time Out for Men's Health'—Free Health Screenings for Men Across the U.S., Yahoo!Finance.com (Jun. 11, 2002).
The Testosterone Source, http://www.testosteronesource.com (1998).
The United States Pharmacopeia, "alcohol": pp. 42-43 (1995).
The United States Pharmacopeia, "viscosity" (2002).
The United States Pharmacopeia, pp. 958, 2213-2225, 2568, 2619 (2002).
Thompson, ed. "The Concise Oxford Dictionary." 9th ed. Oxford: Oxford University Press, 1995, pp. 1014.
Thompson, et al., Effect of Intravenous Testosterone on Myocardial Ischemia in Men with Coronary Artery Disease, Am. Heart J., vol. 143, pp. 249-256 (2002).
Thompson, Hey Guys, If You Have Your Health . . . , HealthScoutNews, http://www.healthscoutnews.com/view.cfm?id=507614 (Jun. 12, 2002).
Time Out for Men's Health, The Weekly Planet (Tampa, FL), Nov. 4, 2004.
Tirassa, et al., High-Dose Anabolic Androgenic Steroids Modulate Concentrations of Nerve Growth Factor and Expression of its Low Affinity Receptor (p75-NGFr) in Male Rat Brain, Journal of Neuroscience Research, vol. 47, No. 2, pp. 198-207 (Jan. 15, 1997).
Tostran 2% Gel Medicinal Guide, available at http://emc.medicines.org.uk/printfriendlydocument.aspx?documentid=19702&companyid (Jul. 13, 2009).
Toutiou E. et al., Enhanced Delivery of Drugs Into and Across the Skin by Ethosomal Carriers, Drug Development Research, vol. 50 pp. 406-415 (2000).
Toutiou E. et al., Ethosomes—Novel Vesicular Carriers for Enhanced Delivery: Characterization and Skin Penetration Properties, Journal of Controlled Release, vol. 65 pp. 403-418 (2000).
Traish et al., Effects of Castration and Androgen Replacement on Erectile Function in a Rabbit Model, Endocrinology 140:1861 (1999).
Transdermal Technologies Profile. Available at pharmalicensing.com/company/dc/2252. (Dec. 16, 2004).
Transdermal Testosterone, Cellegy Pharmaceuticals, www.Cellegy.com. Downloaded on Oct. 21, 2002.
Transpharma Medical, Product Applications: Testosterone, www.transpharma-medical.com/product_apps_testosterone.html (downloaded Dec. 16, 2004).
Trbovich, Drug Development & Biotechnology Companies, The Wall Street Transcript (New York, NY), Feb. 4, 2002, at 18-24.
Tremblay et al., "Plasma concentrations of free and non-TeBG bound testosterone in women on oral contraceptives." Contraception. 10(6): 599-605 (1974). (Abstract only).
Trials for the Treatment of Wasting, AIDS Treatment Data Network, www.aidsinfonyc.org (Downloaded Oct. 8, 1998).
Trottet, L. et al., "Effect of finite doses of propylene glycol on enhancement of in vitro percutanous permeation of loperamide hydrochloride," Int. J. Pharma. (2004) 274:213-219.
Truelove, "Widening Range of Hormone Drugs; Rights to Market; Schering AG Reacquired Sales, Distribution Rights for Testogel; Brief Article," Med Ad News 10(21): 5 (2002).
Tsai et al., Effect of Barrier Disruption by Acetone Treatment on the Permeability of Compounds with Various Lipophilicities: Implications for the Permeability of Compromised Skin, Journal of Pharmaceutical Sciences, vol. 90, pp. 1242-1254, 2001.
Tsai, et al., Metabolic Approaches to Enhance Transdermal Drug Delivery. 1. Effect of Lipid Synthesis Inhibitors, J Pharm Sci, Jun. 1996; 85(6): 643-648.
Tsitouras, Effects of Age on Testicular Function, Endocrinology and Metabolism Clinics, vol. 16, No. 4, p. 1045-1059 (Dec. 1987).
Tuiten, et al., Time Course of Effects of Testosterone Administration on Sexual Arousal in Women, Arch Gen Psychiatry, Feb. 2000; 57(2): 149-53.
Tuller, Competitors to Viagra Get Ready to Rumble, N.Y. Times, Sep. 23, 2002.
Tutten, et al., Discrepancies Between Genital Responses and Subjective Sexual Function during Testosterone Substitution in Women with Hypothalamic Amenorrhea, Psychosom Med, May-Jun. 1996; 58(3): 234-41.
Tymchuk, et al., Role of Testosterone, Estradiol, and Insulin in Diet- and Exercise Induced Reductions in Serum-Stimulated Prostate Cancel Cell Growth in Vitro, Nutrition and Cancer, vol. 42, No. 1, pp. 112-116 (2002).
UK Prospective diabetes study group, Effect of intensive blood-glucose control with metformin on complications in overweight patients with type 2 diabetes (UKPDS 34) The Lancet, vol. 352, Sep. 12, 1998, pp. 854-865.
UK Prospective diabetes study group, Intensive blood-glucose control with sulphylureas or insulin compared with conventional treatment and risk complications in patients with type 2 diabetes (UKPDS 33) The Lancet, vol. 352, Sep. 12, 1998, pp. 837-853.
Ullis, K., Super T: The Complete Guide to Creating an Effective, Safe and Natural Testosterone Supplement Program for Men and Women, Simon & Schuster, New York (1999) Table of Contents.
Ulrich D, et al., The ability of three-dimensional structural indices to reflect mechanical aspects of trabecular bone, Bone, 25:55-60 (1999).
Unimed Pharmaceuticals' Androgel Shows Solid Promise for Men, Fertility Industry News, www.INCIID.com (Aug. 19, 1998).
Unimed pharmaceuticals initiates phase III geriatric hypogonadism study in elderly men: Broad US patent covering DHT delivery for androgen therapy is issued. Unimed News Release, Sep. 10, 1997.
Unimed Products, "Androgel™ (testosterone gel) 1% CIII," internet article May 11, 2000 [Retrieved from internet: http://web.archieve.org/web/20000511171938/http://www.unimed.com/proddisc2.html, retrieved on Jun. 14, 2012].
Urban RJ, et al., Testosterone administration to elderly men increases skeletal muscle strength and protein synthesis. Am J Physiol 269:E820-6, 1995.
Urman B., et al., Elevated serum testosterone, hirsutism and virilism associated with combined androgen-estrogen hormone replacement therapy, Obstet. Gynecol., 1991; 77:595-598.
USP Drug Information—Anabolic Steroids (Systemic), Mayo Clinic, www.mayohealth.org (Downloaded Oct. 8, 1998).
Valero-Politi, et al., Annual Rhythmic Variations of Follitropin, Lutropin, Testosterone and Sex-Hormone-Binding Globulin in Men, Clinica Chimica Acta, vol. 271, No. 1, pp. 57-71 (Mar. 9, 1998).
Valero-Politi, et al., Daily Rhythmic and Non-Rhythmic Variations of Follitropin, Lutropin, Testosterone, and Sex-Hormone-Binding Globulin in Men, Eur J Clin Chem Clin Biochem, Jun. 1996; 34(6): 455-462.
Van Den Beld AW, Huhtaniemi IT, Pettersson KSL, Pols HAP, Grobbee DE, De Jong FH, Lamberts SWJ: Luteinizing hormone and different genetic variants, as indicators of frailty in healthy elderly men. J Clin Endocrinol Metab 84:1334-9, 1999.
Van Gaal, et al., Sex Hormones, Body Fat Distribution, Resting Metabolic Rate and Glucose-Induced Thermogenesis in Premenopausal Obese Women, Int J Obes Relat Metab Disord, May 1994; 18(5): 333-8.

(56) References Cited

OTHER PUBLICATIONS van Honk, et al., Correlations Among Salivary Testosterone, Mood, and Selective Attention to Threat in Humans. Horm Behav. Aug. 1999; 36(1): 17-24.
Van Scott et al., Hyperkeratinization, Corneocyte Cohesion, and Alpha Hydroxy Acids, J. Am Acad Dermatol11:867-879 (1984).
Vaubourdolle, et al., Effect of Dihydrotestosterone on the Rate of Ethanol Elimination in Healthy Men. Alcohol Clin. Exp. Res., vol. 15, No. 2, pp. 238-240 (Mar. 1991).
Vedi S, et al., Effects of hormone replacement therapy on cancellous bone microstructure in postmenopausal women. Bone, 19:69-72 (1996).
Velazquez et al., "Testosterone Replacement Therapy," Arch Androl 41(2): 79-90 (Sep.-Oct. 1998); Abstract.
Veldhuis JD et al., Attenuation of luteinizing hormone secretory burst amplitude as a proximate basis for the hypoandrogenism of healthy aging in men. J. Clin. Endocrinol. Metab. 75:707-713 (1992).
Veldhuis, et al., Muting of Androgen Negative Feedback Unveils Impoverished Gonadotropin-Releasing Hormone/Luteinizing Hormone Secretory Reactivity in Healthy Older Men, The Journal of Clinical Endocrinology & Metabolism, vol. 86, No. 2, pp. 529-535. (2001).
Vergel, Anabolic Steroids: A Practical Guide, CRIA Update, vol. 7, No. 3 (Summer 1998).
Vermeulen A et al., Testosterone secretion and metabolism in male senescence. J. Clin. Endocrinol. Metab. 34:730 (1972).
Vermeulen A. Androgens in aging male. J. Clin. Endocrinol. Metab. 73:221 (1991).
Vermeulen A. Nyctohemeral growth hormone profiles in young and aged men: correlation with somatomedin-C levels. J. Clin. Endocrinol. Metab. 64:884 (1987).
Vermeulen, et al., Long-Term Transdermal Dihydrotestosterone Therapy: Effects on Pituitary Gonadal Axis and Plasma Lipoproteins, Maturitas, vol. 7, pp. 281-287 (1985).
Vetter et al., Quantitative Determination of Isostearic Acid Isomers in Skin Creams by GC-MS-SIM, Chromatographia 2009, 70, July (No. 1/2). pp. 157-164.
Viagra and Testocreme Together, www.testocreme.com (downloaded Feb. 28, 2002).
Vijayakumar, et al., Results of a Study to Correlate Serum Prostate Specific antigen Reproductive Hormone Levels in Patients with Localized Prostate Cancer. J Natl Med Assoc, Nov. 1995; 87(11): 813-9.
Vogel W, Klaiber EL, Broverman DM. Roles of gonadal steroid hormones in psychiatric depression in men and women. Prog. Neuro-Psychopharrnocol 2: 487-503 (1978).
Voigt, et al., The Role of Tissue Steroids in Benign Hyperplasia and Prostate Cancer, Urologe [A], Nov. 1987; 26(6):349-57.
Wagner, et al., Testosterone as a Treatment for Fatigue in HIV+ Men, Gen. Hospital Psychiatry, vol. 20, pp. 209-213 (1998).
Wagner, et al., A Comparative Analysis of Standard and Alternative Antidepressants in the Treatments of Human Immunodeficiency Virus Patients, Comprehensive Psychiatry, vol. 37, No. 6, pp. 402-408 (Nov./Dec. 1996).
Wagner, et al., Exercise as a Mediator of Psychological and Nutritional Effects of Testosterone Therapy in HIV+ Men, Official Journal of the American College of Sports Medicine, pp. 811-817 (1998).
Walters, Penetration Enhancers and Their Use in Transdermal Therapeutic Systems, pp. 202-227 (1990).
Wandell, et al., Assessing Sexual Functioning in Patients with Chronic Disorders by Using a Generic Health-Related Quality of Life Questionnaire, Quality of Life Research, vol. 9, pp. 1081-1092 (2001).
Wang & Swerdloff, "Androgen Replacement Therapy," The Finnish Medical Society DUODECIM, Ann. Med. 29: 365-370 (1997).
Wang C, et al., Does pretreatment testosterone affect responsiveness to long term transdermal testosterone gel (Androgel) in hypogonadal men. Poster presentation #P2-166 at the 85th Annual Meeting of the Endocrine Society, Jun. 19-22, 2003, Philadelphia, PA.
Wang C, et al., Long term efficacy and safety of transdermal testosterone gel (Androgel) in hypogonadal men. Poster presentation #P2-646 at the 84th Annual Meeting of the Endocrine Society, Jun. 19-22, 2002, San Francisco, CA.
Wang et al. "Transdermal Testosterone Gel Improves Sexual Function, Mood, Muscle Strength, and Body Composition Parameters in Hypogonadal Men." J. Clin. Endocrin. Metab. (2000);85(8):2839-53.
Wang et al., Long-Term Testosterone Gel (Androgel) Treatment Maintains Beneficial Effects on Sexual Function and Mood, Lean, and Fat Mass, and Bone Mineral Density in Hypogonadal Men , J. Clin. Endocrinol. Metab., vol. 85, No. 5, pp. 2085-2098 (May 2004).
Wang et al., Male Reproductive Function, Kluwer Acad. Publ. (May 1999). Table of Contents.
Wang J. et al., Body fat from body density: underwater weighing vs dual-photon absorptiometry. Am J. Physiol 256:E829 (1989).
Wang, et al., Effects of Transdermal Testosterone Gel on Bone Turnover Markers and Bone Mineral Density in Hypogonadal Men, Clinical Endocrinology, vol. 54, No. 6, pp. 739-750 (2001). (Abstract only).
Wang, et al., Effects of Transdermal Testosterone Gel on Bone Turnover Markers and Bone Mineral Density in Hypogonadal Men, Clinical Science: Reproduction (Male)-Prostate, Male Reproduction Poster Session, No. 2348 , Board 579 (Jun. 22, 2000).
Wang, et al., Pharmacokinetics of Transdermal Testosterone Gel in Hypogonadal Men, Abstract P2-51, 80th Annual Meeting of the Endocrine Society, New Orleans, Louisiana, Jun. 1998 (ENDO '98).
Wang, et al., Salivary Testosterone in Men: Further Evidence of a Direct Correlation with Free Serum Testosterone, Journal of Clinical Endocrinology and Metabolism, vol. 53, No. 5, pp. 1021-1024 (Nov. 1981).
Wang, et al., Transdermal Testosterone Gel Improves Sexual Function, Mood, Muscle Strength, and Body Composition Parameters in Hypogonadal Men, Basic Science: Reproduction-Gonadal Control (Male), Male Reproduction Oral Session, The Endo Society No. 1360 Endo 2000) (Jun. 24, 2000).
Wang, et al., "Comparative Pharmacokinetics of Three Doses of Percutaneous Dihydrotestosterone Gel in Healthy Elderly Men—A Clinical Research Center Study," Journal of Clinical Endocrinology and Metabolism Aug. 1998;83(8):2749-2757.
Wang, et al., "Pharmacokinetics of Transdermal Testosterone Gel in Hypogonadal Men: Application of Gel at One Site Versus Four Sites: A General Clinical Research Center Study," The Journal of Endocrinology and Metabolism, Mar. 2000;85(3):964-969.
Wang, et al., New Androgen Formulations, The Endocrine Society, No. 167 (Endo 2000).
Wang, et al., Sublingual Testosterone Replacement Improves Muscle Mass and Strength, Decreases Bone Resorption, and Increases Bone Formation Markers in Hypogonadal Men—A Clinical Research Center Study, J Clin Endocrinol Metab. Oct. 1996;81(10):3654-62.
Wang, et al., Testosterone Replacement Therapy Improves Mood in Hypogonadal Men—A Clinical Research Center Study, Journal of Clinical Endocrinology and Metabolism, vol. 81, No. 10, pp. 3578-3583 (1996).
Ware et al., "The MOS 36-Item Short-Form Health Survey." Med. Care. 30(6): 473-83 (1992).
Warner BA et al., Effects of aging and illness on the pituitary testicular axis in men: qualitative as well as quantitative changes in luteinizing hormone. J. Clin. Endocrinol. Metab. 60:263-268 (1985).
Warnock et al., "Female Hypoactive sexual disorder: Case studies of physiologic androgen replacement," J. Sex and Marital Therapy (1999);25:175-182.
Warnock JK, et al., Female hypoactive sexual desire disorder due to androgen deficiency: clinical and psychometric issues, Psychopharmacol Bull. 1997;33(4):761-6.
Watts, et al., Comparison of Oral Estrogens and Estrogens Plus Androgen on Mineral Density, Menopausal Symptoms, and Lipid-Lipoprotein Profiles in Surgical Menopause, Obstet Gynecol, Apr. 1995; 85(4):529-37.
Webb et. al., "Sildenafil citrate and blood-pressure-lowering drugs: results of drug interaction studies with an organic nitrate and a calcium antagonist." American Journal of Cardiology (1999);83(5A):21C-28C.

(56) References Cited

OTHER PUBLICATIONS

Webb, et al., Effect of Acute Testosterone on Myocardial Ischemia in Men with Coronary Artery Disease, Am. J. of Cardiol., vol. 83, No. 3, pp. 437-439, A9 (Feb. 1, 1999).
Webb, et al., Effects of Testosterone on Coronary Vasomotor Regulation in Men with Coronary Heart Disease, Circulation, vol. 100, pp. 1690-1696 (1999).
Webster's New Collegiate Dictionary. 2000. Definition of Prevention. p. 933.
Weekend datebook: Nov. 14-17—Time Out for Men's Health, The Seattle Times, Nov. 14, 2002.
Weinbauer et al., Pharmacokinetics and Pharmacodymanics of testosterone enanthate and dihydrotestosterone enanthate in non-human primates. ACTA Endocrinologica (COPENH) 122(4):432-444 (1990).
Weiner DK, et al., Does functional reach improve with rehabilitation? Arch Phys Med Rehabil 74:796-800, 1993.
Weiner DK, et al., Functional reach: a marker of physical frailty. J Amer Geriatr Soc 40:203-7, 1991.
Weinstein et al., Topical methotrexate therapy for psoriasis. Arch Dermatol. 1989; 125(2):227-230.
Weissberger AJ and Ho KKY: Activation of the somatotropic axis by testosterone in adult males: evidence for the role of aromatization. J Clin Endocrinol Metab 76:1407-1412, 1993.
Weller, P.J., "Propylene glycol," Pharmaceutical Excipients (2009) 592-594.
Wellner et al., "Systemic therapy with dermal application: Transdermal therapeutic systems (TTS)," Dermatologie in Beruf und Umwelt (Dermatol. Beruf Umwelt) (Germany) Mar. 1, 2006, 54/1 (13-18) [Article in German, English Abstract submitted only].
Westaby et al., Liver damage from long-term methyltestosterone, The Lancet, vol. 310, Issue 8032, pp. 261-263, (1977).
Wheeler, M D, Endocrinol and Metab Clin N. Am., 20(1):1-14 (1991).
Whittaker, J. S., C. F. Ryan, P.A. Buckley, and J. D. Road. The effects of refeeding on peripheral and respiratory muscle function in malnourished chronic obstructive pulmonary disease patients. Am. Rev. Respir. Dis. 142: 283-288 (1990).
Willemse, et al., No Change in Plasma Free Testosterone Ratio and Plasma Sex Hormone-Binding Globulin Concentration During hCG Stimulation, Journal of Clinical Endocrinology and Metabolism, vol. 58, No. 6, pp. 1193-1196 (Jun. 1984).
Williams AC and Barry BW, "Penetration enhancers," Adv Drug Deliv Rev. Mar. 27, 2004;56(5):603-18.
Williams Textbook of Endocrinology, 10th Ed., pp. 720-725 (Larsen et al., eds)(2002).
Wilson JD, Androgen abuse by athletes. Endocr Rev 9:181 (1988).
Wilson, et al., Nutrition and chronic lung disease. Am. Rev. Respir. Dis. 132: 1347-1365 (1999).
Wilson, et al., Use of Topical Corticosteroid Pretreatment to Reduce the Incidence and Severity of Skin Reactions Associated with Testosterone Transdermal Therapy, Clinical Therapeutics vol. 20 (No. 2), p. 299-306, (Jan. 22, 1998).
Wilson, The Pathogenesis of Benign Prostatic Hyperplasia, Am J Med, May 1980; 68(5): 745-56.
Winter et al., Serum LH Concentrations in Hypogonadal Men During Transdermal Testosterone Replacement Through Scrotal Skin: Further Evidence That Ageing Enhances Testosterone Negative Feedback. The Testoderm Study Group, Clinical Endocrinology (OXF), vol. 47, No. 3, pp. 317-322 (Sep. 1997).
Winters et al., LH, Non-SHBC Testosterone and Estradiol Levels During Testosterone Replacement of Hypogonadal Men: Further Evidence that Steroid Negative Feedback Increases as Men Grow Older, Journal of Andrology, Dec. 3, 2009 (Published-Ahead-of-Print).
Winters et al., Pituitary-Testicular Function in Men with Testicular Failure Treated with a 2% Testosterone Gel: Further Evidence that Increased Testosterone Negative Feedback Contributes to the Gonadotropin Disturbances as Men Grow Older, p. 3-639, Endo Society 2008.
Winters SJ et al., Episodic luteinizing hormone (LH) secretion and the response of LH and follicle-stimulating hormone to LH-releasing hormone in aged men: evidence for coexistent primary testicular insufficiency and an impairment in gonadotropin secretion. J. Clin Endocrinol. Metab. 55:560 (1982).
Winters, Current Status of Testosterone Replacement Therapy in Men, Arch. Fam. Med., vol. 8, pp. 257-263 (1999).
Winters, The Gonadotropin-Suppressive Activity of Androgen is Increased in Elderly Men; Metabolism, Nov. 1984; 33(11): 1052-1059.
Wittert et al., Androgen Deficiency in Aging Men, The Endocrine Society, No. 126 (ENDO 2000).
Wolf et al., Testosterone and Cognition in Elderly Men: A Single Testosterone Injection Blocks the Practice Effect in Verbal Fluency, But Has No Effect on Spatial or Verbal Memory, Biol. Psychiatry, vol. 47, pp. 650-654 (2000).
Wolk et al., Insulin-like Growth Factor 1 and Prostate Cancer Risk: A Population-Based, Case-Control Study, J. of the Natl. Cancer Inst., vol. 90, No. 12, pp. 911-915 (Jun. 17, 1998).
Women and HIV, Women and HIV Discussion Paper, pp. 1-12 (Jan. 1998).
Women's Hormones: Testosterone, the Other Female Hormone, Harvard Women's Health Watch, Sep. 2002, at 4-5.
Wong TK et al., Bone mass response to testosterone replacement in hypogonadal men. J. Bone and Min Res Suppl 1., p. S390, Abstract 1092 (Sep. 4, 1989).
Woodford, et al., Optimization of Bioavailability of Topical Steroids: Thermodynamic Control, The Journal of Investigative Dermatology, vol. 79, No. 6, pp. 388-391 (Dec. 1982).
Worboys, et al., Testosterone Therapy improves endothelium-dependent and endothelium-independent vasodilation in postmenopausal women on established hormone replacement therapy, The Endocrine Society (ENDO 2000).
World Health Organization. Guidelines for the use of androgens in men. World Health Organization: Geneva (1992).
Woznicki, Feature: Doctors Debate Hormones for Men, United Press International, Aug. 8, 2002.
Wu SZ & Weng XZ: Therapeutic effects of an androgenic preparation on myocardial ischemia and cardiac function in 62 elderly male coronary heart disease patients. Chinese Med J 106:415-8, 1993.
Xie et. al., "Induction of high incidence of mammary tumour in female Noble rats with a combination of 17β-oestradiol and testosterone," Carcinogenesis (1999); 20(6):1069-1078.
Yaffe et al., Sex Hormones and Cognitive Function in Older Men, JAGS, vol. 50, pp. 707-712 (2002).
Yesavage JA, Brink TL, Rose TL, Lum O, Huang V. Adey M, Leirer VO: Development and validation of a geriatric depression screening scale: a preliminary report. J Psychiatr Res 17:37-49, 1983.
Yesavage JA, Davidson J. Widrow L, Berger PA. Plasma testosterone levels, depression. sexuality and age. Biological Psychiatry 20: 199-225 (1985).
Your health and Well-Being, SF-36v2™ survey, 2000 by Quality Metric Incorporated and Medical Outcomes Trust. 6 pages.
Yu et al., Sexual Development in a Two-Year-Old-Boy Induced by Topical Exposure to Testosterone, Pediatrics, vol. 104(2), e23 (1999).
Yu et al., Testosterone Pharmacokinetics after Application of an Investigational Transdermal System in Hypogonadal Men, Journal of Clinical Pharmacology, vol. 37, pp. 1139-1145 (1997).
Yu et al., Transdermal Testosterone Administration in Hypogonadal Men:Comparison of Pharmacokinetics at Different Sites of Application and at the First and Fifth Days of Application, Journal of Clinical Pharmacology, vol. 37, pp. 1129-1138 (1997).
Yu Z et al., DeMonS—a new deconvolution method for estimating drug absorbed at different time intervals and/or drug disposition model parameters using a monotonic cubic spline. Biopharm Drug Dispos. Aug. 1997;18(6):475-87.
Zagars, et al., Serum Testosterone—A Significant Determinant of Metastatic Relapse for Irradiated Localized Prostate Cancer, Urology, vol. 49, No. 3, pp. 327-334 (1997).
Zartarian, et al., Comparative Evaluation of the Acceptability of a New Estradiol Gel TX11323(A) and a Reference Gel, J. Gynecol. Obstet. Biol. Reprod. (Paris), Vo. 25, No. 5, pp. 451-456 (1996). (Abstract only).

(56) References Cited

OTHER PUBLICATIONS

Zatz JL et al., Topical Protective and Cosmetic Products. Transdermal and Topical Drug Delivery Systems. Eds. Ghosh et al., Interpharm Press Inc., Illinois 1997.
Zatz, J.L. et al., "Evaluation of solvent-skin interaction in percutanous absorption," J. Soc. Cos. Chem. (1983) 34:327-334.
Zeginiadou, et al., NonLinear Binding of Sex Steroids to Albumin and Sex Hormone Binding Globulin, Eur J Drug Metab Pharmacokinet, Jul. 1997; 22(3): 229-235.
Zetterberg C et al., Epidemiology of hip fractures in Goteborg, Sweden, 1940-1983. Clen Orth Rel Res 191:43 (1984).
Zhang et al., Association Between Prostate Cancer and Serum Testosterone Levels, The Prostate, vol. 53, pp. 179-182 (2002).
Zhao H et al., The effects of pressure-sensitive adhesives and solubilizers on the skin permeation of testosterone from a matrix-type transdermal delivery system. Drug Dev Ind Pharm. Oct. 2002;28(9):1125-31.
Ziegler et al., Interactions between nutrients and peptide growth factors in intestinal growth, repair, and function. JPEN J. Parenter. Enteral Nutr. 23: S174-S183 (1999).
Zimulti (rimonabant), NDA 21-888, Briefing Information for FDA Advisory Committee Meeting. May 10, 2007, available at http://www.fda.gov/ohrms/dockets/ac/07/briefing/2007-4306b1-01-sponsor-backgrounder.htm (Feb. 9, 2011).
Zmuda, et al., Exercise Increases Serum Testosterone and Sex Hormone-Binding Globulin Levels in Older Men, Metabolism, vol. 45, No. 8, pp. 935-939 (Aug. 1996).
Zonagen Product Pipeline, www.zonagen.com/html/product_pipeline.htm (downloaded Dec. 17, 2004).
Zonagen reports initial findings comparing Androxal to Androgel form from US Phase I/II safety and efficacy study in men with low testosterone. Press release Jul. 15, 2004.
Zumoff B. et al., Age variation of the 24-hour mean plasma concentrations of androgens, estrogens and gonadotropins in normal adult men. J. Clin. Endocrinol. Metab. 54:534 (1982).
Docket Report for *Unimed Pharmaceuticals, Inc.* v. *Watson Pharmaceuticals, Inc.* (retrieved from PACER Jan. 4, 2011).
Complaint by Unimed Pharmaceuticals filed Aug. 21, 2003.
Plaintiff Unimed Pharmaceutical, Inc.'s Rule 7.1 Corporate Ownership Disclosure Statement filed Aug. 21, 2003.
First Amended Complaint by Unimed Pharmaceuticals filed Aug. 22, 2003.
Answer and Counterclaim by Watson Pharmaceuticals filed Oct. 27, 2003.
Answer to Counterclaim by Unimed Pharmaceuticals filed Nov. 17, 2003.
Joint Preliminary Report and Discovery Plan filed Nov. 26, 2003.
Certificate of Interested Persons filed Nov. 26, 2003.
Letter by Watson Pharmaceuticals directed to Judge Thrash as a Response to the Letter Motion to Compel filed Oct. 21, 2004.
Watson Pharmaceutical's Motion to Issue Letter of Request for International Judicial Assistance dated Dec. 2, 2004.
Request for International Judicial Assistance by Judge Thrash dated Dec. 22, 2004.
Unimed Pharmaceuticals, Inc.'s Objections to Watson Pharmaceuticals, Inc.'s Notice of Depositions filed Mar. 17, 2005.
Watson's Principal Claim Construction Brief filed Jul. 25, 2005.
Plaintiff's Memorandum on Claim Construction (Redacted Version) filed Jul. 25, 2005.
Watson's Reply to Plaintiff's Principal Claim-Construction Brief dated Aug. 12, 2005.
Plaintiff's Opposition Brief on Claim Construction (Redacted Version) dated Aug. 12, 2005.
Watson's Motion to Strike Section VI of Plaintiffs' Memorandum on Claim Construction filed Aug. 12, 2005.
Plaintiff's Response to Watson's Motion to Strike Section VI of Plaintiff s Claim Construction Memorandum filed Aug. 26, 2005.
Watson's Reply in Support of Its Motion to Strike Section VI of Plaintiffs' Claim-Construction Memorandum filed Sep. 9, 2005.
Defendant Watson Pharmaceuticals. Inc.'s Motion for Partial Summary Judgment filed Sep. 9, 2005.
Plaintiffs' Consolidated Memorandum of Law in Opposition to Defendants' Motions for Partial Summary Judgment filed Oct. 17, 2005.
Unimed Pharmaceuticals, Inc.'s Statement of Additional Facts which are Material and Present a Genuine Issue for Trial filed Oct. 17, 2005.
Plaintiffs' Consolidated Response to Defendants Watson's and Paddock's Statement of Material Facts as to Which There are No Genuine Issues to be Tried filed Oct. 17, 2005.
Watson's Response to Plaintiffs' Statement of Additional Facts which are Material and Present a Genuine Issue for Trial filed Nov. 11, 2005.
Watson's Reply to Plaintiffs' Consolidated Opposition to Defendants' Motions for Partial Summary Judgment filed Nov. 11, 2005.
Defendant Watson Pharmaceuticals, Inc.'s Motion for Partial Summary Judgment of Invalidity of Claims 1-30 for Failure to Comply with the Written Description Requirement filed Nov. 23, 2005.
Plaintiffs' Consolidated Memorandum of Law in Opposition to Defendants' Motions for Partial Summary Judgment of Invalidity of Claims 1-30 filed Dec. 19, 2005.
Unimed Pharmaceuticals, Inc.'s Statement of Additional Facts which are Material and Present a Genuine Issue for Trial filed Dec. 19, 2005.
Plaintiffs' Consolidated Response to Defendants Watson's and Paddock's Statements of Material Facts as to Which There are No Genuine Issues to be Tried Regarding Invalidity of Claims 1-30 of the '894 Patent Lacking a Written Description under 35 U.S.C. § 112 filed Dec. 19, 2005.
Watson's Reply Memorandum of Law in Support of its Motion for Partial Summary Judgment of Invalidity of Claims 1-30 for Failure to Comply with the Written Description Requirement filed Jan. 19, 2006.
Watson's Response to Plaintiff's Statement of Additional Facts which are Material and Present a Genuine Issue for Trial filed Jan. 19, 2006.
Docket Report for *Unimed Pharmaceuticals, Inc.* v. *Paddock Laboratories, Inc.* (retrieved from PACER Jan. 4, 2011).
Complaint by Unimed Pharmaceuticals dated Aug. 21, 2003.
Plaintiff Unimed Pharmaceuticals, Inc.'s Rule 7.1 Corporate Ownership Disclosure Statement filed Aug. 21, 2003.
Answer and Counterclaim by Paddock Laboratories filed Oct. 22, 2003.
Answer to Counterclaims by Unimed Pharmaceuticals filed Nov. 12, 2003.
Certificate of Interested Persons filed Nov. 21, 2003.
Joint Preliminary Report and Discovery Plan filed Nov. 21, 2003.
Defendant's Rule 26 Disclosures filed Dec. 12, 2003.
Paddock's Motion to Issue Letters of Request for International Judicial Assistance filed Dec. 1, 2004.
Request for International Judicial Assistance by Judge Thrash dated Dec. 9, 2004.
Unimed Pharmaceuticals, Inc.'s Objections to Paddock Laboratories, Inc.'s Notices of Depositions Under Rule 30(b)(6) dated Mar. 17, 2005.
Paddock's Opening Claim Construction Brief (Redacted Version) filed Jul. 25, 2005.
Paddock's Opposition Claim Construction Brief filed Aug. 12, 2005.
Defendant Paddock Laboratories, Inc.'s Motion for Partial Summary Judgment filed Sep. 27, 2005.
Memorandum in Support of Paddock's Motion for Partial Summary Judgment of Invalidity of Claims 1-30 of the '894 Patent as Lacking a Written Description as Required by 35 U.S.C. § 112, First Paragraph with Respect to the Claimed Ranges of Sodium Hydroxide filed Oct. 18, 2005.
Paddock's Reply Memorandum in Further Support of its Motion for Partial Summary Judgment as to the Inapplicability and Invalidity of the Certificate of Correction filed Nov. 11, 2005.
Paddock's Response to Plaintiffs' Statement of Additional Facts which are Material and Present a Genuine Issue for Trial filed Nov. 11, 2005.
Defendant Paddock Laboratories, Inc.'s Motion in Limine to Exclude Unimed's Argument and Expert Testimony on the Basis of,

(56) References Cited

OTHER PUBLICATIONS and Support in the Specification for, the Sodium Hydroxide Ranges Recited in Certain Claims of the '894 Patent filed Nov. 28, 2005.
Plaintiffs' Memorandum of Law in Opposition to Paddock's Motion in Limine to Exclude Plaintiffs' Argument and Expert Testimony on the Sodium Hydroxide Ranges filed Jan. 13, 2006.
Paddock's Reply memorandum in Further Support of its Motion for Partial Summary Judgment as to the Invalidity of Claims 1-30 under 35 U.S.C. § 112 filed Jan. 19, 2006.
Paddock's Response to Unimed's Statement of Additional Facts which are Material and Present a Genuine Issue for Trial with Respect to Paddock's motion of Summary Judgment that Claims 1-30 of the '894 Patent are Invalid under 35 U.S.C. § 112 filed Jan. 19, 2006.
Paddock's Reply Brief in Further Support of its Motion In Limine to Exclude Unimed's Argument and Expert Testimony on the Basis of, and Support in the Specification for, the Sodium Hydroxide Ranges Recited in Certain Claims of the '894 Patent filed Jan. 31, 2006.
Consent Judgment and Order of Permanent Injunction dated Sep. 15, 2006.
Docket Report for In re Androgel Antitrust Litigation (No. II) (retrieved from PACER Jan. 5, 2011).
Complaint, *Meijer, Inc.* v. *Unimed Pharmaceuticals, Inc.* (originally filed in C.D. Cal. on Feb. 2, 2009).
Complaint, *Louisiana Wholesale Drug Co.* v. *Unimed Pharmaceuticals, Inc.* (originally filed in C.D. Cal. on Feb. 3, 2009).
Complaint, *Rochester Drug Co-operative, Inc.* v. *Unimed Pharmaceuticals, Inc.* (originally filed in C.D. Cal. on Feb. 3, 2009).
First Amended Complaint, *Federal Trade Commission* v. *Watson Pharmaceuticals, Inc.*, Case No. CV 09-598 MRP (originally filed in C.D. Cal. on Feb. 12, 2009).
Complaint, *Stephen L. LaFrance Pharmacy, Inc.* v. *Unimed Pharmaceuticals, Inc.* (originally filed in D.N.J. on Mar. 31, 2009).
Complaint, *Fraternal Order of Police* v. *Unimed Pharmaceuticals, Inc.* (originally filed in D.N.J. on Apr. 17, 2009).
Complaint, *Scurto* v. *Unimed Pharmaceuticals, Inc.* (originally filed in D.N.J. on Apr. 21, 2009).
Complaint, *United Food and Commercial Workers Unions and Employers Midwest Health Benefits Fund* v. *Unimed Pharmaceuticals, Inc.* (originally filed in D. Minn. 2009).
Complaint, *Rite Aid Corp.* v. *Unimed Pharmaceuticals, Inc.* (originally filed in M.D. Penn. on Jun. 17, 2009).
Complaint, *Walgreen Co.* v. *Unimed Pharmaceuticals, Inc.* (originally filed in M.D. Penn. on Jun. 29, 2009).
Complaint, *Jabo's Pharmacy, Inc.* v. *Solvay Pharmaceuticals, Inc.* (originally filed in Circuit Court for Cocke County, Tennessee on Oct. 30, 2009).
Complaint, *Supervalu Inc.* v. *Unimed Pharmaceuticals, Inc.* (originally filed in N.D. Ga. on Apr. 7, 2010).
Complaint, *LeGrand* v. *Unimed Pharmaceuticals, Inc.* (originally filed in N.D. Ga. on Sep. 10, 2010).
Order Granting in Part and Denying in Part Defendant's Motions to Dismiss dated Feb. 22, 2010.
Amended Class Action Complaint and Jury Demand, *Fraternal Order of Police* v. *Unimed Pharmaceuticals, Inc.*, Case No. 09-md-2084-TWT (filed Mar. 5, 2010).
Plaintiff's Answer to Teva's Counterclaims (Redacted) dated Jun. 27, 2011.
United States Patent Office Action for U.S. Appl. No. 13/942,245 dated Nov. 22, 2013 (25 pages).
United States Patent Office Action for U.S. Appl. No. 13/965,499 dated Nov. 21, 2013 (23 pages).
United States Patent Office Action for U.S. Appl. No. 13/831,217 dated Dec. 13, 2013 (32 pages).
United States Patent Office Action for U.S. Appl. No. 13/831,189 dated Dec. 11, 2013 (11 pages).
United States Patent Office Action for U.S. Appl. No. 13/831,207 dated Dec. 11, 2013 (10 pages).

\* cited by examiner

TESTOSTERONE GEL AND METHOD OF USE

CROSS-REFERENCE TO RELATED APPLICATIONS

This application is a continuation of U.S. patent application Ser. No. 13/180,327 filed on Jul. 11, 2011, which is a continuation of U.S. patent application Ser. No. 11/549,083, filed on Oct. 12, 2006, which is now abandoned, which claims priority to U.S. Provisional Application No. 60/725,276, filed on Oct. 12, 2005, the entire contents of each of which are hereby incorporated by reference their references herein.

BACKGROUND OF THE INVENTION

Testosterone, the major circulating androgen in men, is synthesized from cholesterol. The approximately 500 million Leydig cells in the testes secrete more than 95% of the 6-7 mg of testosterone produced per day. Two hormones produced by the pituitary gland, luteinizing hormone ("LH") and follicle stimulating hormone ("FSH"), are required for the development and maintenance of testicular function and negatively regulate testosterone production. Circulating testosterone is metabolized to various 17-keto steroids through two different pathways. Testosterone can be metabolized to dihydrotestosterone ("DHT") by the enzyme 5α-reductase or to estradiol ("E2") by an aromatase enzyme complex.

Testosterone circulates in the blood 98% bound to protein. In men, approximately 40% of the binding is to the high-affinity sex hormone binding globulin ("SHBG"). The remaining 60% is bound weakly to albumin. Thus, a number of measurements for testosterone are available from clinical laboratories. The term "free" testosterone as used herein refers to the fraction of testosterone in the blood that is not bound to protein. The term "total testosterone" or "testosterone" as used herein means the free testosterone plus protein-bound testosterone. The term "bioavailable testosterone" as used herein refers to the non-SHBG bound testosterone and includes testosterone weakly bound to albumin.

The following table from the UCLA-Harbor Medical Center summarizes the hormone concentrations in normal adult men range:

TABLE 1

Hormone Levels in Normal Men

| Hormone | Normal Range |
| --- | --- |
| Testosterone | 298 to 1043 ng/dL |
| Free testosterone | 3.5 to 17.9 ng/dL |
| DHT | 31 to 193 ng/dL |
| DHT/T Ratio | 0.052 to 0.33 |
| DHT + T | 372 to 1349 ng/dL |
| SHBG | 10.8 to 46.6 nmol/L |
| FSH | 1.0 to 6.9 mIU/mL |
| LH | 1.0 to 8.1 mIU/mL |
| $E_2$ | 17.1 to 46.1 pg/mL |

There is considerable variation in the half-life of testosterone reported in the literature, ranging from 10 to 100 minutes. Researchers do agree, however, that circulating testosterone has a diurnal variation in normal young men. Maximum levels occur at approximately 6:00 to 8:00 a.m. with levels declining throughout the day. Characteristic profiles have a maximum testosterone level of 720 ng/dL and a minimum level of 430 ng/dL. The physiological significance of this diurnal cycle, if any, however, is not clear.

Male hypogonadism results from a variety of patho-physiological conditions in which testosterone concentration is diminished below the normal range. The hypogonadic condition is sometimes linked with a number of physiological changes, such as diminished interest in sex, impotence, reduced lean body mass, decreased bone density, lowered mood, and decreased energy levels.

Researchers generally classify hypogonadism into one of three types. Primary hypogonadism includes the testicular failure due to congenital or acquired anorchia, XYY Syndrome, XX males, Noonan's Syndrome, gonadal dysgenesis, Leydig cell tumors, maldescended testes, varicocele, Sertoli-Cell-Only Syndrome, cryptorchidism, bilateral torsion, vanishing testis syndrome, orchiectomy, Klinefelter's Syndrome, chemotherapy, toxic damage from alcohol or heavy metals, and general disease (renal failure, liver cirrhosis, diabetes, myotonia dystrophica). Patients with primary hypogonadism show an intact feedback mechanism in that the low serum testosterone concentrations are associated with high FSH and LH concentrations. However, because of testicular or other failures, the high LH concentrations are not effective at stimulating testosterone production.

Secondary hypogonadism involves an idiopathic gonadotropin or LH-releasing hormone deficiency. This type of hypogonadism includes Kallman's Syndrome, Prader-Labhart-Willi's Syndrome, Laurence-Moon-Biedl's Syndrome, pituitary insufficiency/adenomas, Pasqualini's Syndrome, hemochromatosis, hyperprolactinemia, or pituitary-hypothalamic injury from tumors, trauma, radiation, or obesity. Because patients with secondary hypogonadism do not demonstrate an intact feedback pathway, the lower testosterone concentrations are not associated with increased LH or FSH levels. Thus, these men have low testosterone serum levels but have gonadotropins in the normal to low range.

Hypogonadism may be age-related. Men experience a slow but continuous decline in average serum testosterone after approximately age 20 to 30 years. Researchers estimate that the decline is about 1-2% per year. Cross-sectional studies in men have found that the mean testosterone value at age 80 years is approximately 75% of that at age 30 years. Because the serum concentration of SHBG increases as men age, the fall in bioavailable and free testosterone is even greater than the fall in total testosterone. Researchers have estimated that approximately 50% of healthy men between the ages of 50 and 70 have levels of bioavailable testosterone that are below the lower normal limit. Moreover, as men age, the circadian rhythm of testosterone concentration is often muted, dampened, or completely lost. The major problem with aging appears to be within the hypothalamic-pituitary unit. For example, researchers have found that with aging, LH levels do not increase despite the low testosterone levels. Regardless of the cause, these untreated testosterone deficiencies in older men may lead to a variety of physiological changes, including sexual dysfunction, decreased libido, loss of muscle mass, decreased bone density, depressed mood, and decreased cognitive function. The net result is geriatric hypogonadism, or what is commonly referred to as "male menopause." Today, hypogonadism is the most common hormone deficiency in men, affecting 5 in every 1,000 men. At present, it is estimated that only five percent of the estimated four to five million American men of all ages with hypogonadism currently receive testosterone replacement therapy.

SUMMARY OF THE INVENTION

The present invention relates to an improved transdermal hydroalcoholic testosterone gel formulation that provides, among other things, a desirable pharmacokinetic hormone profile, and methods of use.

DETAILED DESCRIPTION OF THE INVENTION

Figure 1:
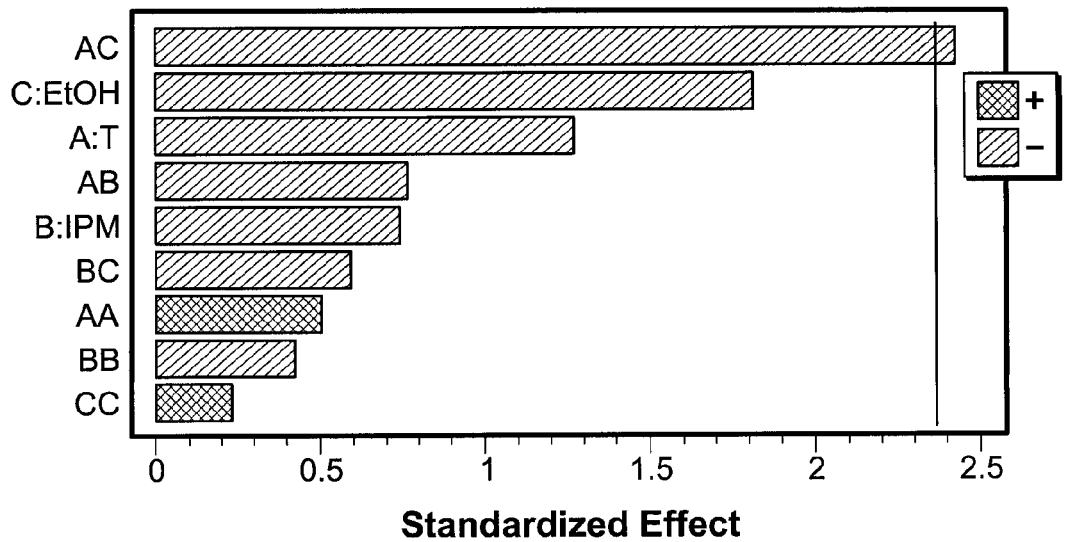
FIG. 1 is a standardized Pareto Chart demonstrating the effect of test factors testosterone, isopropyl myristate and ethyl alcohol on response variable-viscosity.

While the present invention may be embodied in many different forms, several specific embodiments are discussed herein with the understanding that the present disclosure is to be considered only as an exemplification of the principles of the invention, and it is not intended to limit the invention to the embodiments illustrated. Where the invention is illustrated herein with particular reference to testosterone, it will be understood that any other steroid in the testosterone synthetic pathway can, if desired, be substituted in whole or in part for testosterone in the methods, kits, combinations, and compositions herein described.

The present invention relates to an improved testosterone gel formulation and methods of use.

In one embodiment, the present invention is directed to a method for percutaneous administration of testosterone in a hydroalcoholic gel. The gel comprises testosterone (or a testosterone derivative), one or more lower alcohols, such as ethanol or isopropanol; a penetration enhancing agent such as isopropyl myristate; a thickener; and water. Additionally, the present invention may optionally include salts, emollients, stabilizers, antimicrobials, fragrances, and propellants.

The present invention also includes kits, methods, combinations, and pharmaceutical compositions for treating, preventing, reversing, halting or slowing the progression of hypogonadism or other low-testosterone-associated disorders in a subject once it becomes clinically evident, or treating the symptoms associated with, or related to the hypogonadism or low-testosterone-associated disorder. The subject may already have a diagnosis of hypogonadism and/or low testosterone at the time of administration, or be at risk of developing hypogonadism and/or low testosterone. The present invention preferably is for treatment of adult subjects over 18 years of age. Even more preferably the present invention is for treatment of adult subjects over 21 years of age.

The term "derivative" refers to a compound that is produced from another compound of similar structure by the replacement of substitution of one atom, molecule or group by another. For example, a hydrogen atom of a compound may be substituted by alkyl, acyl, amino, etc., to produce a derivative of that compound.

As used herein, the term "lower alcohol," alone or in combination, means a straight-chain or branched-chain alcohol moiety containing one to about six carbon atoms. In one embodiment, the lower alcohol contains one to about 4 carbon atoms, and in another embodiment the lower alcohol contains two to about 3 carbon atoms. Examples of such alcohol moieties include methanol, ethanol, ethanol USP (i.e., 95% v/v), n-propanol, isopropanol, n-butanol, isobutanol, sec-butanol, and tert-butanol.

As used herein, the term "ethanol" refers to $C_2H_5OH$. It may be used as dehydrated alcohol USP, alcohol USP, or in any common form including in combination with various amounts of water.

The composition is used in a "pharmacologically effective amount." This means that the concentration of the drug administered is such that in the composition it results in a therapeutic level of drug delivered over the term that the drug is to be used. Such delivery is dependent on a number of variables including the time period for which the individual dosage unit is to be used, the flux rate of the drug from the composition, for example, testosterone, from the gel, surface area of application site, etc. For testosterone, for example, the amount of testosterone necessary can be experimentally determined based on the flux rate of testosterone through the gel, and through the skin when used with and without enhancers.

In one embodiment, the present invention is directed to a method for percutaneous administration of testosterone in a hydroalcoholic gel. The gel comprises one or more lower alcohols, such as ethanol or isopropanol; a penetration enhancing agent; a thickener; and water. In one embodiment, the gel comprises an anionic polymer thickening agent precursor neutralized with a hydroxide releasing agent, such as, e.g, sodium hydroxide. Additionally, the present invention may optionally include salts, emollients, stabilizers, antimicrobials, fragrances, and propellants.

Included in the methods and pharmaceutical compositions of the present invention are the isomeric forms and tautomers of the described compounds and the pharmaceutically-acceptable salts thereof. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, b-hydroxybutyric, galactaric and galacturonic acids.

The thickening agents (aka gelling agents) suitable for use in the present invention include neutralized anionic polymers such as polyacrylic acid. Preferred are the carbomer polyacrylic acids, especially those made and sold by Noveon Inc. of Cleveland, Ohio under the trademark CARBOPOL® (carbomer, or cross-linked polyacrylic acid polymer, The Lubrizol Corporation, Wickliffe, Ohio). (See information at http://www.noveon.com, incorporated herein by reference.) Particularly preferred are CARBOPOLS® Ultrez 10, 940, 941, 954, 980, 981, ETD 2001, EZ-2 and EZ-3. Most preferred are CARBOPOL® 940 and CARBOPOL® 980. Other suitable anionic polymers include carboxypolymethylene and carboxymethyl cellulose. Also suitable are other known polymeric thickening agents such as PEMULEN® polymeric emulsifiers (crosslinked copolymers of acrylic acid and $C_{10}$-$C_{30}$ alkyl acrylate, The Lubrizol Corporation, Wickliffe, Ohio), and NOVEON® polycarbophils (acrylic acid polymers crosslinked with divinyl glycol, The Lubrizol Corporation, Wickliffe, Ohio). Additional thickening agents, enhancers and adjuvants may generally be found in Remington's The Science and Practice of Pharmacy, Meade Publishing Co., United States Pharmacopeia/National Formulary, all incorporated herein by reference.

In one embodiment, the formulation is a gel, an ointment, a cream or a patch and is comprised of testosterone; a penetration enhancing agent, such as isopropyl myristate; a thickening agent, such as a neutralized carbomer; a lower alcohol, such as ethanol or isopropanol; and water.

In another embodiment, the formulation contains an anionic polymer thickening agent precursor such as a carbomer which has been combined with a neutralizer in an amount sufficient to form a gel in the course of forming the composition.

In another embodiment, the formulation contains an anionic polymer thickening agent precursor such as a carbomer which has been combined with a neutralizer in an amount sufficient to form a gel with a viscosity greater than 9000 cps as measured by a Brookfield RV DVII+ Viscometer with a spindle equal to RV6, RPM (rotations per minute) equal to 10, and the temperature maintained at 20° C.

In yet a further embodiment, the formulation contains an anionic polymer thickening agent precursor such as a carbomer which has been combined with a neutralizer selected from the group consisting of sodium hydroxide, ammonium hydroxide, potassium hydroxide, arginine, aminomethyl propanol, tetrahydroxypropyl ethylenediamine, triethanolamine ("TEA"), tromethamine, PEG-15 cocamine, diisopropanolamine, and triisopropanolamine, or combinations thereof in an amount sufficient to neutralize the anionic polymer thickening agent precursor to form a gel in the course of forming the composition. Suitable neutralizing agents and their use with selected anionic polymer thickening agent precursors are disclosed in "Neutralizing CARBOPOL® and PEMULEN® Polymers in Aqueous and Hydroalcoholic Systems," Commercial Brochure TDS-237 (October 1998) by Noveon Inc. of Cleveland, Ohio, incorporated by reference herein.

In yet a further embodiment, the formulation contains an anionic polymer thickening agent precursor such as a carbomer which has been combined with a neutralizer which is an aqueous solution of sodium hydroxide such as 0.1 N sodium hydroxide, or 1.5 N sodium hydroxide, or 2.0 N sodium hydroxide or any other convenient strength aqueous solution in an amount sufficient to form a gel. In one embodiment, the composition was prepared using between about 1.0% and 10.0% 0.1 N sodium hydroxide. Accordingly, embodiments employing any percentage between about 1.0% and about 10.0% 0.1N NaOH may be used, such as, e.g., 1.0%, 2.0%, 3.0%, 4.0%, 5.0%, 6.0%, 7.0%, 8.0%, 9.0% or 10.0% 0.1N NaOH.

In one embodiment the formulation is a gel and is obtained by combining the following substances in approximate percentages:

TABLE 2

Ingredients Combined to Yield Testosterone Formulations (% w/w)

| T (Testosterone) | Alcohol (95% v/v) | Isopropyl Myristate | CARBOPOL® 980 (carbomer) | 0.1N NaOH | Purified Water |
|---|---|---|---|---|---|
| 1.20 | 73.5 | 1.00 | 1.0 | 7.00 | 16.3 |
| 1.40 | 73.5 | 1.00 | 1.0 | 7.00 | 16.1 |
| 1.60 | 73.5 | 1.00 | 1.0 | 7.00 | 15.9 |

In one embodiment, the composition comprises from about 1.22% testosterone to about 1.62% testosterone, such as, e.g, about 1.22% testosterone, about 1.42% testosterone, or about 1.62% testosterone.

In another embodiment, the composition comprises from about 1.15% to about 1.22% (w/w) testosterone.

In another embodiment, the composition comprises from about 1.30% to about 1.45% (w/w) testosterone.

In another embodiment, the composition comprises from about 1.50% to about 1.70% (w/w) testosterone.

In one embodiment, the composition comprises about 1.15% to about 1.8% (w/w) testosterone; about 0.6% to about 1.2% (w/w) isopropyl myristate; about 60% to about 80% (w/w) alcohol selected from the group consisting of ethanol and isopropanol; a sufficient amount of a thickening agent to give the composition a viscosity in excess of about 9000 cps; and water.

In another embodiment, the composition comprises about 1.15% to about 1.8% (w/w) testosterone; about 0.6% to about 1.2% (w/w) isopropyl myristate; about 67% to about 74% (w/w) alcohol selected from the group consisting of ethanol and isopropanol; a sufficient amount of a thickening agent to give the composition a viscosity in excess of about 9000 cps; and water.

The composition of the present invention can comprise about 1.15% to about 1.25% (w/w) testosterone, about 1.30% to about 1.45% (w/w) testosterone, or about 1.50% to about 1.70% (w/w) testosterone.

In an embodiment, the viscosity of the composition of the present invention is about 13,000 cps to about 33,000 cps. Accordingly, the viscosity of the composition of the present invention may be any amount between about 13,000 cps and 33,000 cps, such as, e.g., 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, or 33,000 cps.

In one embodiment of the present invention, the composition is obtained by combining about 1.30% to about 1.45% (w/w) testosterone; about 0.6% to about 1.4% (w/w) isopropyl myristate; about 67% to about 74% (w/w) ethanol; about 0.6% to about 1.4% (w/w) carbomer; about 6.5% to about 7.5% (w/w) 0.1N NaOH; and additional water.

In another embodiment of the present invention, the composition is obtained by combining about 1.50% to about 1.70% (w/w) testosterone; about 0.6% to about 1.4% (w/w) isopropyl myristate; about 67% to about 74% (w/w) ethanol; about 0.6% to about 1.4% (w/w) carbomer; about 6.5% to about 7.5% (w/w) 0.1N NaOH; and additional water.

In yet another embodiment of the present invention, the composition is obtained by combining about 1.15% to about 1.25% (w/w) testosterone; about 0.6% to about 1.4% (w/w) isopropyl myristate; about 67% to about 74% (w/w) ethanol;

about 0.6% to about 1.4% (w/w) carbomer; about 6.5% to about 7.5% (w/w) 0.1N NaOH; and additional water.

The gel is rubbed or placed onto an area of skin of the subject and allowed to dry. The gel dries rapidly, i.e., within about 30 seconds to about 3 minutes after application. Illustratively, the gel is rubbed onto an area of skin, for example, on the upper outer thigh and/or hip once daily. Following application the subject washes his or her hands. Application of the gel results in an increased testosterone level having a desirable pharmacokinetic profile and is effective to treat or prevent hypogonadism and/or low testosterone, or the symptoms associated with, or related to hypogonadism and/or low testosterone in the subject. The composition is thus useful for treating a number of conditions or diseases.

In one embodiment, the present invention employs a packet having a polyethylene liner compatible with the components of a testosterone gel, as described below. The packet may hold a unit dose or multiple dose.

In another embodiment, the methods and compositions employ a composition that is dispensed from a rigid multi-dose container (for example, with a hand pump) having a larger foil packet, for example, of the composition inside the container. Such larger packets can also comprise a polyethylene liner as above. In one embodiment, the multi-dose container comprises an airless pump that comprises a polyethylene lined foil pouch within a canister with a hand pump inserted. In one embodiment, the polyethylene lined foil pouch comprises 44 g or 88 g of product. In one embodiment, the pump is capable of dispensing a total amount of about 75 g of gel. In one embodiment, the pump is primed before use, such as, e.g., by fully depressing the pump three times and discarding the gel. In one embodiment, the pump contains enough product to allow for priming and a set number of precise doses. In one embodiment, each full pump depression delivers 1.25 g of testosterone gel. In this embodiment, a 3.75 g dose of gel would require 3 pump depressions. A 5 g dose of gel would require 4 pump depressions. A 7.5 g dose of gel would require 6 pump depressions. A 10 g dose of gel would require 8 depressions, and so on. Of course, each pump depression can deliver any amount of testosterone gel suitable for delivering the desired dose. The pouch size, amount dispensed and the delivery volume per depression are not limited to these embodiments and may be changed or adjusted to meet the needs of the patient population.

The methods and compositions of the present invention provide enhanced treatment options for treating, preventing, reversing, halting or slowing the progression of hypogonadism or another low-testosterone-associated disorder in a subject, for example, a man, as compared to those currently available.

In one embodiment, the pharmaceutical composition of the present invention is administered once, twice, or three times a day, or as many times necessary to achieve the desired therapeutic effect. In another embodiment the composition of the present invention is administered once, twice, or three times a day on alternate days. In another embodiment the composition of the present invention is administered once, twice, or three times a day on a weekly, biweekly, or monthly basis.

In one embodiment, a therapeutically effective dose is between about 1.0 g and 10.0 g, preferably between about 1.25 g and 6.25 g.

Besides being useful for human treatment, the present invention is also useful for veterinary treatment of mammals, reptiles, birds, exotic animals and farm animals, including mammals, rodents, and the like. In one embodiment, the mammal includes a primate, for example, a human, a monkey, or a lemur, a horse, a dog, a pig, or a cat. In another embodiment, the rodent includes a rat, a mouse, a squirrel or a guinea pig.

The composition is capable of releasing the steroid after applying the composition to the skin at a rate and duration that delivers in one embodiment of the present invention at least about 10 μg per day of the steroid to the blood serum of the subject.

In another embodiment of the present invention, the composition is capable of releasing the testosterone after applying the composition to the skin of a subject at a rate and duration that achieves a circulating serum concentration of testosterone greater than about 300 ng per dl serum.

In another embodiment of the present invention, the composition is capable of releasing the testosterone after applying the composition to the skin of a subject at a rate and duration that achieves a circulating serum concentration of testosterone greater than about 300 ng per dl serum during a time period beginning about 0.5 hours after administration and ending about 24 hours after administration.

In another embodiment of the present invention, the composition is capable of releasing the testosterone after applying the composition to the skin of a subject at a rate and duration that achieves a circulating serum concentration of the testosterone between about 298 ng testosterone per dl serum to about 1043 ng testosterone per dl serum.

In another embodiment of the present invention, after administration of the composition, the serum testosterone concentration is maintained between about 400 and 1050 ng testosterone per dl serum.

In yet another embodiment of the present invention, after administration of the composition, the serum testosterone concentration is maintained between about 200 and 1800 ng testosterone per dl serum.

In another embodiment of the present invention, after administration of the composition, an obtained $C_{max}$ is between about 300 and 5000 ng/dl.

In another embodiment of the present invention, the composition is provided to a subject for daily administration in about a 1.25 g to about a 3.75 g dose, such as, e.g., about 1.25 g, or about 2.50 g, or about 3.75 g. Any other suitable dose may be also be administered.

In yet another embodiment of the present invention, the subject in need of treatment has a serum testosterone level before the first application (pretreatment) of the composition of the present invention of less than about 300 ng/dl.

In another embodiment of the present invention, where after at least about 30 days of daily administration of the composition of the present invention the serum testosterone concentration in a subject is at least about 300 ng/dl to about 1050 ng/dl, such as, for example, about 300 ng/dl to about 400 ng/dl, about 300 ng/dl to about 500 ng/dl, about 500 ng/dl to about 700 ng/dl, about 700 ng/dl to about 900 ng/dl, about 400 ng/dl to about 500 ng/dl, about 500 ng/dl to about 600 ng/dl, about 600 ng/dl to about 700 ng/dl, about 700 ng/dl to about 800 ng/dl, about 800 ng/dl to about 900 ng/dl, about 900 ng/dl to about 1000 ng/dl, about 1000 ng/dl to about 1100 ng/dl, about 400 ng/dl to about 1050 ng/dl, about 500 ng/dl to about 1050 ng/dl, about 600 ng/dl to about 1050 ng/dl, or about 700 ng/dl to about 1050 ng/dl.

In still another embodiment of the present invention, where after daily administration of the composition of the present invention the total testosterone concentration in a subject is greater than about 300 ng/dl. In one embodiment, the total serum testosterone concentration in the subject is greater than about 400 ng/dl, about 500 ng/dl, about 600 ng/dl or about 700 ng/dl. In one embodiment, the total testosterone concentration is measured after 24 hours of administration. In one embodiment, the total testosterone concentration is measured after more than 2 days of daily administration, such as, for example, after 10 days, 14 days, 20 days, or 30 days.

In another embodiment of the methods, kits, combinations, and compositions of the present invention, the composition of the present invention is administered once, twice, or three times daily to a subject for at least about 7 days. In one embodiment, the composition is administered once a day.

Example 1

Development of Improved Testosterone Gel(s)

Introduction

In order to develop a new testosterone gel formulation, a number of exploratory studies were conducted to prepare and test gel formulations containing different levels of testosterone, isopropyl myristate and ethyl alcohol. Preliminary studies have demonstrated that viscosity of the gel can be increased by slightly increasing the concentrations of gelling and neutralizing agents. A statistical program was used to generate a design to study the effect of 3 ingredients, testosterone, ethyl alcohol and isopropyl myristate on viscosity and in vitro permeation of testosterone from hydroalcoholic gels. In vitro permeation studies were conducted using Franz diffusion cells. The concentration of testosterone present in receptor samples was analyzed by HPLC technique or beta scintillation counter (for radiolabeled technique). Based on results from these studies three optimized formulations were prepared and tested for skin permeation using HPLC method. All three optimized formulations showed significant improvement in viscosity and in vitro skin permeation compared to currently marketed formulation (1% testosterone gel).

Objectives

The present disclosure summarizes studies conducted to develop testosterone gel formulation(s) with improved viscosity, reduced volume of application, and improved in vitro skin permeation compared to currently marketed formulation (1% testosterone gel), and potentially reduce the volume of gel application.

Procedure a. Statistical Design

A statistical design was created (StatGraphics Plus 5.1) to study the effect of 3 ingredients, testosterone, ethyl alcohol and isopropyl myristate on viscosity and in vitro permeation of testosterone from hydroalcoholic gels. Concentration of two other ingredients, CARBOPOL® 980 (carbomer) and 0.1N sodium hydroxide solution were kept constant. Following is the design summary:

Design class: Response Surface
Design name: Box-Behnken design
Number of experimental factors: 3 (all continuous)
Number of blocks: 1; Number of runs: 15 (randomized)
Error degrees of freedom: 5

| Factors | Low (%) | High (%) |
|---|---|---|
| Testosterone | 1.33 | 2.0 |
| Isopropyl myristate | 0.5 | 1.0 |
| Alcohol (95% v/v) | 72.5 | 76.1 |

The following table summarizes the ingredients of test formulations as created by the statistical design. These formulations were prepared at 1 kg size and packaged in to glass jars for analytical and skin permeation tests.

TABLE 3

Ingredients Combined to Yield Test Formulations and Control Formulation (% w/w)

| F# (Formulation) | T (Testosterone) | Alcohol (95% v/v) | Isopropyl Myristate | CARBOPOL® 980 (carbomer) | 0.1N NaOH | Purified Water |
|---|---|---|---|---|---|---|
| 41 | 1.665 | 74.3 | 0.75 | 1.0 | 7.00 | 15.3 |
| 42 | 1.665 | 72.5 | 0.50 | 1.0 | 7.00 | 17.3 |
| 43 | 1.665 | 76.1 | 0.50 | 1.0 | 7.00 | 13.7 |
| 44 | 2.000 | 74.3 | 0.50 | 1.0 | 7.00 | 15.2 |
| 45 | 1.330 | 74.3 | 0.50 | 1.0 | 7.00 | 15.9 |
| 46 | 1.330 | 76.1 | 0.75 | 1.0 | 7.00 | 13.8 |
| 47 | 2.000 | 74.3 | 1.00 | 1.0 | 7.00 | 14.7 |
| 48 | 1.665 | 74.3 | 0.75 | 1.0 | 7.00 | 15.3 |
| 49 | 1.330 | 74.3 | 1.00 | 1.0 | 7.00 | 15.4 |
| 50 | 2.000 | 72.5 | 0.75 | 1.0 | 7.00 | 16.8 |
| 51 | 1.665 | 76.1 | 1.00 | 1.0 | 7.00 | 13.2 |
| 52 | 2.000 | 76.1 | 0.75 | 1.0 | 7.00 | 13.2 |
| 53 | 1.665 | 72.5 | 1.00 | 1.0 | 7.00 | 16.8 |
| 54 | 1.330 | 72.5 | 0.75 | 1.0 | 7.00 | 17.4 |
| 55 | 1.665 | 74.3 | 0.75 | 1.0 | 7.00 | 15.3 |
| 56 (control) | 1.000 | 72.5 | 0.50 | 0.9 | 4.75 | 20.4 | b. Analytical Testing

All test formulations and control samples were analyzed for physical (appearance, pH and viscosity) and chemical (assays for testosterone, isopropyl myristate and alcohol) attributes.

c. In Vitro Skin Permeation Studies

Permeation of testosterone was studied quantitatively with human skin placed on the Franz diffusion cell. The skin was mounted horizontally between the donor and receptor half. The surface area of the skin exposed to the formulation in the donor chamber was 0.64 $cm^2$, and the receptor volume was 5.0 mL. Temperature was maintained at 37° C. with the help of a double water circulation jacket surrounding the lower part of the cell. The donor chamber was open on the top.

Radiolabel Method

Test formulations were spiked with $^{14}C$ labeled testosterone. Spiked (radiolabeled) formulation (5-15 mg of gel containing 0.125-0.250 µCi) was applied over the surface of the epidermis gravimetrically. Periodic samples (0, 1, 2, 4, 6, 8, 10, 22 and 24 h) were taken from the receptor cell to measure the radioactivity/amount of drug permeated across the skin. In addition the amount of radiolabel/drug remaining on the skin, in the skin samples was also determined. Further details of these experiments and results are presented in Example 2.

HPLC Method

Formulation (300 mg ±5% which contains 3000 µg of the drug based on 1% gel) was applied over the surface of the epidermis gravimetrically. Aliquots were collected periodically (0, 1, 2, 4, 6, 8, 10, 22 and 24 h) and replaced with fresh buffer. Later aliquots were analyzed for testosterone content. Further details of these experiments and results are presented in Example 3.

d. Data Analysis

In addition to data reported in corresponding examples, data from both radiolabel and HPLC methods was analyzed further by statistical program (StatGraphics Plus 5.1). StatGraphics program was also used to predict optimum levels of different factors which could provide maximum response.

Results and Discussion

Analytical Data

All test formulations were clear and have pH between 5.68-5.82. The contents of testosterone, isopropyl myristate and alcohol were close to the target. The following table summarizes analytical test results after 1 month storage at 40° C./75% RH.

TABLE 4

Analytical Results for Test Formulations and Control Formulation*

| F# (Formulation) | Appearance | pH | Viscosity (cps) | Assay-T (%) | Assay-Alcohol (95% v/v) | Assay-IPM (%) |
|---|---|---|---|---|---|---|
| 41 | Clear gel | 5.79 | 23567 | 1.69 | 73.8 | 0.67 |
| 42 | Clear gel | 5.76 | 26900 | 1.66 | 71.8 | 0.45 |
| 43 | Clear gel | 5.82 | 23000 | 1.69 | 75.5 | 0.44 |
| 44 | Clear gel | 5.75 | 26700 | 2.00 | 74.1 | 0.44 |
| 45 | Clear gel | 5.76 | 25467 | 1.32 | 73.7 | 0.44 |
| 46 | Clear gel | 5.69 | 30233 | 1.40 | 74.5 | 0.74 |
| 47 | Clear gel | 5.78 | 24733 | 2.02 | 73.3 | 0.92 |
| 48 | Clear gel | 5.79 | 24767 | 1.66 | 74.3 | 0.68 |
| 49 | Clear gel | 5.76 | 24300 | 1.33 | 73.8 | 0.93 |
| 50 | Clear gel | 5.72 | 26133 | 2.02 | 71.7 | 0.68 |
| 51 | Clear gel | 5.82 | 20700 | 1.75 | 75.4 | 0.93 |
| 52 | Clear gel | 5.83 | 19733 | 2.00 | 75.5 | 0.68 |
| 53 | Clear gel | 5.72 | 26033 | 1.68 | 71.7 | 0.95 |
| 54 | Clear gel | 5.69 | 28267 | 1.34 | 71.9 | 0.69 |
| 55 | Clear gel | 5.77 | 23233 | 1.67 | 74.0 | 0.68 |
| 56 (control) | Clear gel | 5.59 | 22033 | 1.01 | 72.4 | 0.44 |

*test results after 1 month storage at 40° C./75% RH
T = testosterone,
IPM = isopropyl myristate As one of the objectives for this study is to increase the viscosity of the gel, statistical analysis was performed to assess the effect of test factors testosterone, isopropyl myristate and ethyl alcohol on response variable-viscosity. The following is an analysis summary:

TABLE 5

ANOVA for Viscosity
Analysis of Variance for Viscosity

| Source | Sum of Squares | Df | Mean Square | F-Ratio | P-Value |
|---|---|---|---|---|---|
| A:T | 9.41613E6 | 1 | 9.41613E6 | 1.58 | 0.2488 |
| B:IPM | 3.16945E6 | 1 | 3.16945E6 | 0.53 | 0.4892 |
| C:EtOH | 1.94337E7 | 1 | 1.94337E7 | 3.27 | 0.1137 |
| AA | 1.43962E6 | 1 | 1.43962E6 | 0.24 | 0.6379 |
| AB | 3.37413E6 | 1 | 3.37413E6 | 0.57 | 0.4760 |
| AC | 3.50601E7 | 1 | 3.50601E7 | 5.89 | 0.0456 |
| BB | 1.00605E6 | 1 | 1.00605E6 | 0.17 | 0.6933 |
| BC | 1.95303E6 | 1 | 1.95303E6 | 0.33 | 0.5847 |
| CC | 286812.0 | 1 | 286812.0 | 0.05 | 0.8325 |
| Total error | 4.16608E7 | 7 | 5.95155E6 | | |
| Total (corr.) | 1.17733E8 | 16 | | | |

Referring now to FIG. 1, where in the chart A represents testosterone, B represents isopropyl myristate, C represents EtOH, and joint letters represents a combination of factors, it is clear that the combination of alcohol and testosterone (i.e., AC) has a significant negative effect on viscosity. This observation is consistent with earlier studies with alcohol; to maximize the viscosity the level of alcohol should be at the lowest level possible.

Permeation Data: Radiolabel Technique

Skin samples from two donors were used in this study. To minimize variability between skins, permeation data, % label permeated (% LP), from test formulations was normalized to control formulation tested with corresponding donor skin. Additional statistical analysis was performed on the ratio of % LP (test/control, Ratio % LP) to obtain trends and optimal concentrations of testosterone, isopropyl myristate and ethyl alcohol. Following is the analysis summary:

TABLE 6

Radiolabel Data Table used for Statistical Analysis *

| F# (Formulation) | Donor | T | IPM | Alcohol (95% v/v) | % LP | Ratio % LP |
|---|---|---|---|---|---|---|
| 41 | 8127 | 1.665 | 0.75 | 74.3 | 4.86 | 0.83 |
| 42 | 8127 | 1.665 | 0.50 | 72.5 | 3.45 | 0.59 |
| 43 | 8127 | 1.665 | 0.50 | 76.1 | 2.7 | 0.46 |
| 44 | 8127 | 2.000 | 0.50 | 74.3 | 3.8 | 0.65 |
| 45 | 8300 | 1.330 | 0.50 | 74.3 | 3.51 | 0.46 |
| 46 | 8300 | 1.330 | 0.75 | 76.1 | 6.37 | 0.84 |
| 47 | 8300 | 2.000 | 1.00 | 74.3 | 3.57 | 0.47 |
| 48 | 8300 | 1.665 | 0.75 | 74.3 | 5.38 | 0.71 |
| 49 | 8300 | 1.330 | 1.00 | 74.3 | 9.47 | 1.25 |
| 50 | 8300 | 2.000 | 0.75 | 72.5 | 5.69 | 0.75 |
| 51 | 8300 | 1.665 | 1.00 | 76.1 | 6.73 | 0.89 |
| 52 | 8300 | 2.000 | 0.75 | 76.1 | 2.22 | 0.29 |
| 53 | 8300 | 1.665 | 1.00 | 72.5 | 4.61 | 0.61 |
| 54 | 8300 | 1.330 | 0.75 | 72.5 | 4.33 | 0.57 |
| 55 | 8300 | 1.665 | 0.75 | 74.3 | 4.33 | 0.57 |
| 56 (control) | 8127 | 1.000 | 0.50 | 72.5 | 5.87 | 1.00 |
| 56 (control) | 8300 | 1.000 | 0.50 | 72.5 | 7.56 | 1.00 |

* % LP data from Example 2. Ratio % LP calculated from % LP values.
T = testosterone,
IPM = isopropyl myristate,
LP = label permeated

TABLE 7

ANOVA for Ratio of % Label Permeated (Ratio % LP)
Analysis of Variance for Viscosity

| Source | Sum of Squares | Df | Mean Square | F-Ratio | P-Value |
|---|---|---|---|---|---|
| A:T | 0.213314 | 1 | 0.213314 | 7.19 | 0.0315 |
| B:IPM | 0.107294 | 1 | 0.107294 | 3.62 | 0.0990 |
| C:EtOH | 0.00430679 | 1 | 0.00430679 | 0.15 | 0.7145 |
| AA | 0.119589 | 1 | 0.119589 | 4.03 | 0.0847 |
| AB | 0.131132 | 1 | 0.131132 | 4.42 | 0.0736 |
| AC | 0.0554353 | 1 | 0.0554353 | 1.87 | 0.2140 |
| BB | 0.00724917 | 1 | 0.00724917 | 0.24 | 0.6363 |
| BC | 0.0800686 | 1 | 0.0800686 | 2.70 | 0.1445 |
| CC | 0.00941549 | 1 | 0.00941549 | 0.32 | 0.5908 |
| Total error | 0.207716 | 7 | 0.0296737 | | |
| Total (corr.) | 0.947084 | 16 | | | |

Figure 2:
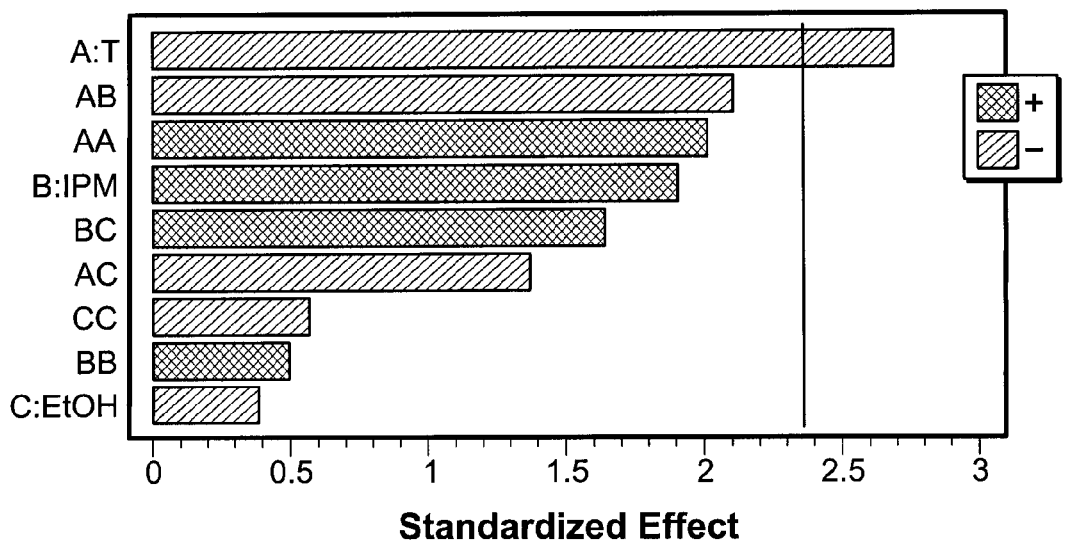
FIG. 2 is a standardized Pareto Chart demonstrating the effect of test factors testosterone, isopropyl myristate and ethyl alcohol on percent label permeated.

The Pareto chart in FIG. 2 shows that the level of testosterone has significant negative effect, and the level of isopropyl myristate has a positive (not statistically significant) effect on % label permeated. Above analysis suggests that the maximum level of testosterone in gel formulation should be less than highest level studied. This analysis also suggests that the maximum level of isopropyl myristate in gel formulation should be close to the highest level studied.

Permeation Data: HPLC Technique

Same skin samples (two donors) used in radiolabel study were used in this study. To minimize variability between skins, permeation data (flux or cumulative amount released, CAR) from test formulations was normalized to control formulation tested with corresponding donor skin. Additional statistical analysis was performed on the ratio of CAR (test/control, Ratio CAR) to obtain trends and optimal concentrations of testosterone, isopropyl myristate and ethyl alcohol. Following is the analysis summary:

TABLE 8

HPLC Data Table used for Statistical Analysis *

| F# (Formulation) | Donor | T | IPM | Alcohol (95% v/v) | CAR | Ratio CAR |
|---|---|---|---|---|---|---|
| 41 | 8127 | 1.665 | 0.75 | 74.3 | 189.81 | 1.02 |
| 42 | 8127 | 1.665 | 0.50 | 72.5 | 188.21 | 1.01 |
| 43 | 8127 | 1.665 | 0.50 | 76.1 | 50.11 | 0.27 |
| 44 | 8127 | 2.000 | 0.50 | 74.3 | 151.95 | 0.82 |
| 45 | 8300 | 1.330 | 0.50 | 74.3 | 74.13 | 0.69 |
| 46 | 8300 | 1.330 | 0.75 | 76.1 | 117.87 | 1.09 |
| 47 | 8300 | 2.000 | 1.00 | 74.3 | 114.61 | 1.06 |
| 48 | 8300 | 1.665 | 0.75 | 74.3 | 208.82 | 1.94 |
| 49 | 8127 | 1.330 | 1.00 | 74.3 | 298.76 | 1.61 |
| 50 | 8127 | 2.000 | 0.75 | 72.5 | 94.71 | 0.51 |
| 51 | 8127 | 1.665 | 1.00 | 76.1 | 254.57 | 1.37 |
| 52 | 8127 | 2.000 | 0.75 | 76.1 | 113.93 | 0.61 |
| 53 | 8127 | 1.665 | 1.00 | 72.5 | 326.46 | 1.76 |
| 54 | 8127 | 1.330 | 0.75 | 72.5 | 200.45 | 1.08 |
| 55 | 8127 | 1.665 | 0.75 | 74.3 | 240.61 | 1.30 |
| 56 (control) | 8127 | 1.000 | 0.50 | 72.5 | 185.71 | 1.00 |
| 56 (control) | 8300 | 1.000 | 0.50 | 72.5 | 107.79 | 1.00 |

* T = testosterone,
IPM = isopropyl myristate,
CAR = cumulative amount released

TABLE 9

ANOVA for Ratio of Cumulative Amount Released (Ratio CAR)
Analysis of Variance for Viscosity

| A:T | 0.452519 | 1 | 0.452519 | 3.27 | 0.1135 |
|---|---|---|---|---|---|
| B:IPM | 1.01713 | 1 | 1.01713 | 7.35 | 0.0302 |
| C:EtOH | 0.18431 | 1 | 0.18431 | 1.33 | 0.2864 |
| AA | 0.164241 | 1 | 0.164241 | 1.19 | 0.3120 |
| AB | 0.0291287 | 1 | 0.0291287 | 0.21 | 0.6603 |
| AC | 0.0600202 | 1 | 0.0600202 | 0.43 | 0.5312 |
| BB | 0.000234383 | 1 | 0.000234383 | 0.00 | 0.9683 |
| BC | 0.0737582 | 1 | 0.0737582 | 0.53 | 0.4891 |
| CC | 0.200542 | 1 | 0.200542 | 1.45 | 0.2678 |
| Total error | 0.968701 | 7 | 0.138386 | | |
| Total (corr.) | 3.03859 | 16 | | | |

The results in Table 8 were subjected to a regression analysis and generated the following algorithm:

Ratio CAR=5.1239−0.4403*T+1.5781*IPM−0.0607*EtOH where T is an amount of testosterone % (w/w), IPM is an amount of isopropyl myristate % (w/w), and EtOH is an amount (w/w) of alcohol 95% v/v.

In one embodiment of the invention, values of T, IPM and EtOH are selected from within the ranges given below such that the above algorithm gives a Ratio CAR value greater than 1, preferably greater than 1.1, or most preferably greater than 2. The ranges are: between 1.0 and 2.0% (w/w) testosterone, preferably between 1.15 and 1.8% (w/w) testosterone; between 0.2% and 2.0% (w/w) isopropyl myristate, preferably between 0.6 and 1.2% (w/w) isopropyl myristate; and between about 60.0% and 80% (w/w) alcohol 95% v/v, preferably between about 72.5% and 76.1% (w/w) alcohol 95% v/v.

Figure 3:
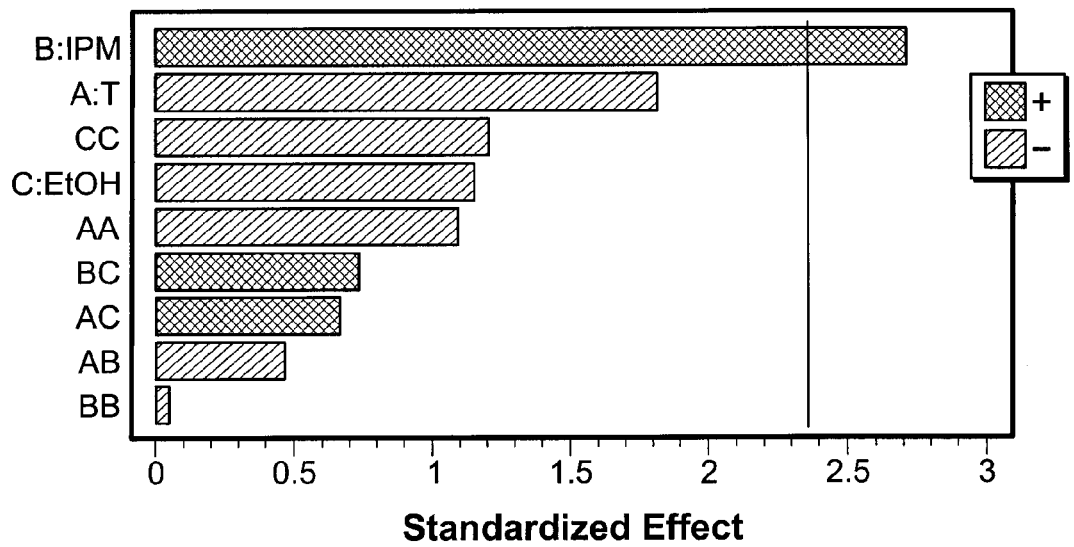
FIG. 3 is a standardized Pareto Chart demonstrating the effect of test factors testosterone, isopropyl myristate and ethyl alcohol on Ratio CAR.

Referring now to the Pareto chart in FIG. 3, statistical analysis clearly shows that the level of isopropyl myristate has significant positive effect and the level of testosterone has negative (not statistically significant) effect on Ratio CAR. FIG. 3 suggests that the maximum level of testosterone in gel formulation should be less than highest level studied. This analysis also suggests that the maximum level of isopropyl myristate in gel formulation should be close to the highest level studied. Permeation results from HPLC method are qualitatively consistent with results from radiolabel method.

Response Optimization

Permeation results from HPLC method are qualitatively similar to those from radiolabel method. For convenience, data from HPLC study was used to predict (statistical optimization) optimum levels of testosterone, isopropyl myristate and alcohol for a given response. The statistical program produced the following combination of factor levels which maximizes the ratio of cumulative amount released (Ratio CAR).

TABLE 10

Optimized Factor Levels for Cumulative
Amount Released (Ratio CAR)

| Goal: maximize Ratio CAR | | Optimum Value = 1.81748 | |
|---|---|---|---|
| Factor | Low | High | Optimum |
| T | 1.0 | 2.0 | 1.28995 |
| IPM | 0.5 | 1.0 | 1.0 |
| EtOH | 72.5 | 76.1 | 73.7366 |

Figure 4:
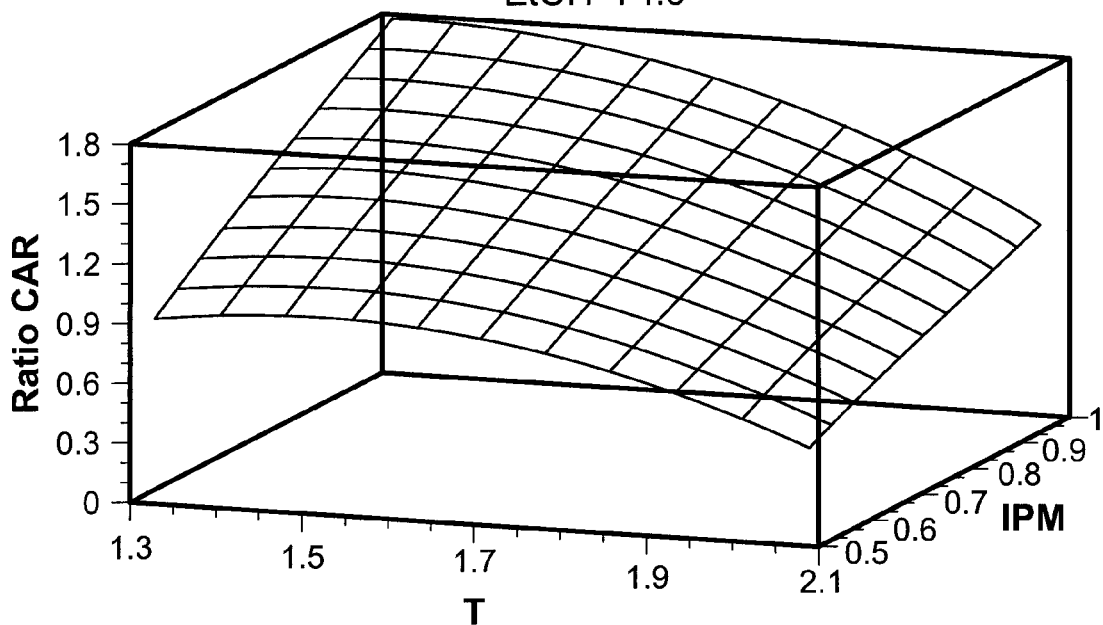
FIG. 4 is an Estimated Response Surface Plot illustrating estimated response (Ratio CAR) for a given combination of testosterone and isopropyl myristate for an alcohol (95% v/v) content of 74.3 wt %.
Figure 5:
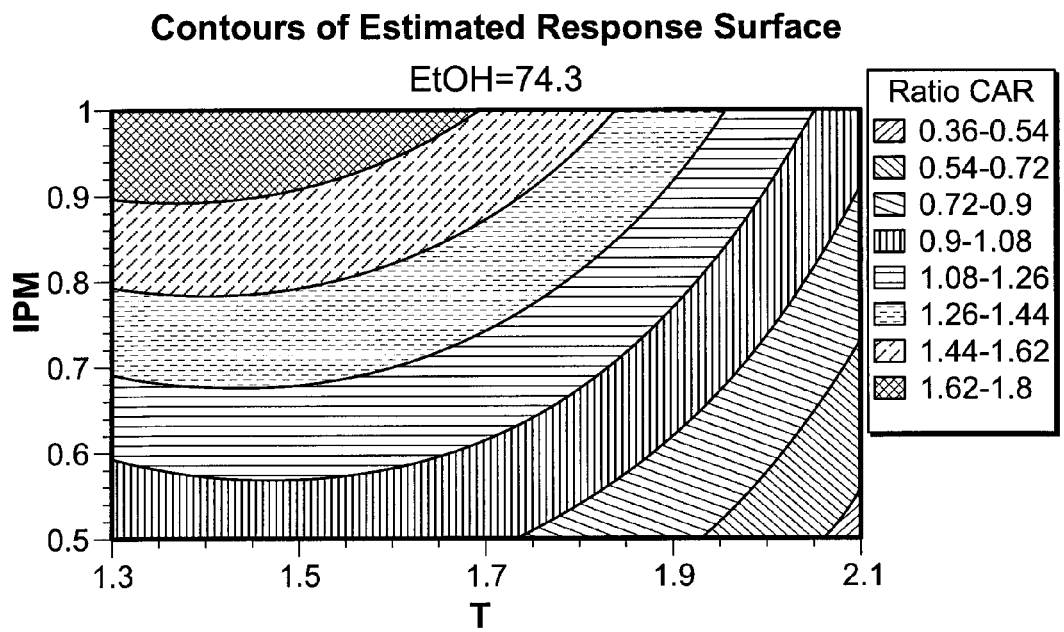
FIG. 5 is a Contour Plot illustrating the contours of the Estimated Response Surface Plot in FIG. 4.

FIGS. 4 and 5 illustrate estimated response (Ratio CAR) for a given combination of testosterone and isopropyl myristate at an alcohol 95% v/v level of 74.3% (w/w).

a. Formulation Selection

Based on response surface plots and predicted optimum factor levels, the following 3 formulations were selected for further permeation studies. Again for convenience these 3 formulations were tested by HPLC method only.

TABLE 11

Ingredients Combined to Yield Selected Formulations
and Control Formulation (% w/w)

| F# (Formulation) | T (Testosterone) | Alcohol (95% v/v) | Isopropyl Myristate | CAR-BOPOL® 980 (carbomer) | 0.1N NaOH | Purified Water |
|---|---|---|---|---|---|---|
| 57 | 1.20 | 73.5 | 1.00 | 1.0 | 7.00 | 16.3 |
| 58 | 1.40 | 73.5 | 1.00 | 1.0 | 7.00 | 16.1 |
| 59 | 1.60 | 73.5 | 1.00 | 1.0 | 7.00 | 15.9 |
| 56 (control) | 1.00 | 72.5 | 0.50 | 0.9 | 4.75 | 20.4 |

The following table summarizes initial (after preparation) analytical test results for selected formulations.

TABLE 12

Analytical Test Results for Selected
Formulations and Control Formulation

| F# (Formulation) | Appearance | pH | Viscosity (cps) | Assay-T (%) | Assay-Alcohol (95% v/v) | Assay-IPM (%) |
|---|---|---|---|---|---|---|
| 57 | Clear gel | 5.66 | 24500 | 1.21 | 73.1 | 0.94 |
| 58 | Clear gel | 5.71 | 25533 | 1.42 | 72.7 | 0.94 |
| 59 | Clear gel | 5.68 | 24800 | 1.61 | 73.3 | 0.94 |
| 56 (control) | Clear gel | 5.57 | 20267 | 1.02 | 71.8 | 0.43 |

Figure 6:
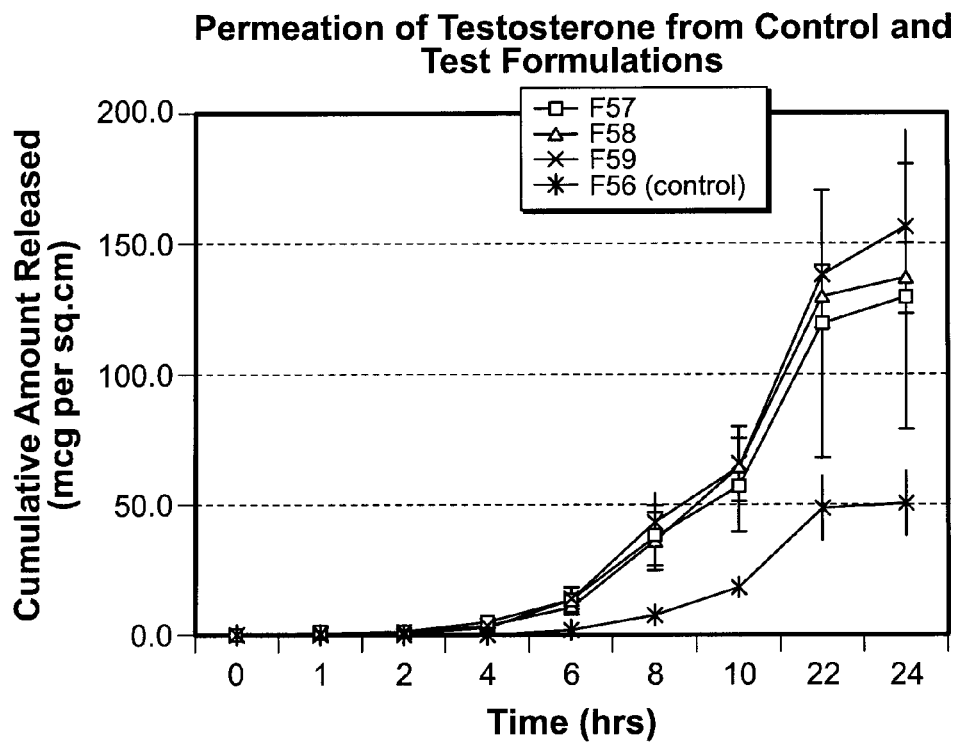
FIG. 6 is a graph showing the cumulated amount testosterone released as a function of time for various testosterone formulations (F57 to F59) in comparison to reference formulation (F56).

The following table and FIG. 6 summarize permeation data from 3 selected formulations (data points for FIG. 6 and the table were obtained from Example 4, Tables 17-20).

TABLE 13

HPLC Data Table used for Statistical Analysis*

| Time (hr) | F56 (1% gel) CAR | SD | F57 (1.2% gel) CAR | SD | F58 (1.4% gel) CAR | SD | F59 (1.6% gel) CAR | SD |
|---|---|---|---|---|---|---|---|---|
| 0 | 0 | 0 | 0.0 | 0 | 0.0 | 0.00 | 0.0 | 0 |
| 1 | 0 | 0 | 0.5 | 0.7 | 0.0 | 0.00 | 0.0 | 0 |
| 2 | 0 | 0 | 1.3 | 0.5 | 1.3 | 1.2 | 0.5 | 0.3 |
| 4 | 0.40 | 0.1 | 4.3 | 1.3 | 4.0 | 1.0 | 2.9 | 1.3 |
| 6 | 1.52 | 0.3 | 14.2 | 4.5 | 11.0 | 2.7 | 13.8 | 4.6 |
| 8 | 6.96 | 1.5 | 38.0 | 11.5 | 35.9 | 11.0 | 43.5 | 10.8 |
| 10 | 18.35 | 3.4 | 57.0 | 17.9 | 65.4 | 14.3 | 64.5 | 10.4 |
| 22 | 48.20 | 12.5 | 119.2 | 51.0 | 129.1 | 11.8 | 137.5 | 30.6 |
| 24 | 50.76 | 12.3 | 129.7 | 50.4 | 137.0 | 13.9 | 156.3 | 36.4 |

*Data points obtained from Example 4, tables 17-20.

All 3 selected formulations showed significantly improved permeation (2-3× cumulative amount released) than control. These results further support the observations from initial screening of formulations and formed the basis for selection of final formulations.

Conclusions

Statistical program was used to design the experiments based on 3 key factors i.e., testosterone, isopropyl myristate and ethyl alcohol. The program was also used to analyze the analytical and in vitro skin permeation data, and identify trends and optimum levels of each of the factors to maximize response (permeation).

Three selected testosterone gel formulations have higher viscosity (~4,000 cps) than control formulation.

Significantly improved in-vitro permeation of testosterone (2-3 times than control) through the dermatomed human skin was observed with the three selected testosterone gel formulations.

Example 2

In Vitro Percutaneous Absorption of Experimental Testosterone Gel Formulations through Human Skin by Radiolabel Method Materials Formulations were prepared and supplied by Solvay Pharmaceuticals. Testosterone ($^{14}$C) was procured from American Radiolabeled Chemicals Inc, (St Louis, Mo.). All other chemicals and reagents were procured from approved vendors and were of highest quality and purity available.

Methods

Description of Transdermal Diffusion Cell Apparatus

The transdermal diffusion cell apparatus used in this study (PermeGear, Bethlehem, Pa.) holds up to 9 diffusion cells in series and the receptor fluid is stirred by the magnetic bead at 600 rpm. Percutaneous absorption in vitro was studied quantitatively with human skin placed in the Franz diffusion cell. The skin was mounted horizontally between the donor and receptor halves of the diffusion cell. The surface area of the skin exposed to the formulation in the donor chamber was 0.64 cm$^2$, and the receptor cell volume was 5.0 ml.

The receptor compartment was filled with phosphate buffered saline pH 7.4 (PBS) and propylene glycol (1:1) and gentamicin sulphate (50 µg/ml). A double water circulation jacket (37° C.) surrounds the receptor cell in order to have the skin temperature maintained at physiologic level. The donor chamber was open towards the external environment, thus exposing the surface of the skin to the surrounding air of the laboratory. The relative humidity (RH) of the experimental area (around the diffusion cell setup) was monitored for every experiment and this was found to be in the range of 35 to 45% for all the experiments.

Skin Permeation Study

Human skin (thigh region) dermatomed to 0.3 mm thickness was obtained from a tissue bank (US Tissue and Cell, Salt Lake City, Utah) from cadavers. The skin was collected within 8 h of donor death and frozen in 10% w/v glycerol in normal saline. The skin was stored at −80° C. until use. Skin from two different donors was used in the experiments. Each experiment was carried out with each formulation for at least 6 times using the skin from one donor. The skin permeation data of formulations was compared with that of permeation of 1% marketed gel (in 6 replicates) tested on the skin of same donor as test formulations and all data were normalized to the reference (marketed) formulation.

Radiolabeled Testosterone ($^{14}$C, specific activity 50-60 mCi/mmol) was used for this purpose. This is supplied by American Radiolabeled Chemicals and is 99.5% pure as ascertained by HPLC.

Radioactive gels were prepared in order to apply 0.125 to 0.250 µCi in a minimum amount of the gel that spreads 0.64 cm$^2$ of the diffusion area of Franz cell (0.64 cm$^2$). The minimum quantity was at least 5.0 to 15.0 mg. An appropriate amount of radioactive testosterone (12.5 µCi per 125 µl of ethanol) was evaporated in a round bottom flask until the solvent is completely evaporated to dryness. To this flask, 500 mg of cold gel formulation was added and vortexed for 5 minutes and allowed to equilibrate over night (12 to 16 h). This gel was further vortexed for 30 minutes to obtain homogenous gels. Homogeneity of the formulation's radioactivity was determined by the counting level of 9 exactly weighted (~5 mg) samples (standards).

The frozen skin was thawed to room temperature by keeping the skin at ambient temperature for about 30 to 45 minutes. This was then rinsed with water to remove glycerol. The skin was then put in PBS pH 7.4 and gently agitated in a shaker (100 rpm) for 20 min to remove traces of glycerol. The washed skin was mounted on the cells approximately 30 minutes before the application of the formulations. The formulation (5 to 15 mg) was applied over the surface of the epidermis gravimetrically using a syringe (for each determination sufficient gel was dispensed to cover the test surface and the weight of the gel dispensed was determined). Periodic samples were taken from the receptor cell to measure the amount of drug transporting across the skin (1, 2, 4, 6, 8, 10, 22 and 24 h).

Washing Procedures:

At the end of the test (24 hours), the residual drug remaining at the surface of the skin was removed by washing the surface with 200 µl of different solvents according to the following protocol:

1st wash: Cetavlon™ alcoholic (10/90 v/v)
2nd wash: water
3rd wash: Cetavlon™ alcoholic (10/90 v/v)
4th wash: water
5th wash: water.

The application area was then wiped with a cotton wool stick (Q-tip). The washings, cotton stick and the donor cell were collected in 20 ml of ethanol and allowed to extract all radioactivity in to ethanol. The exposed area was collected by a biopsy punch. To account for lateral diffusion, lateral portions of skin were collected and counted for radioactivity to account for Mass balance for the experiments.

The skin of the active diffusion area as well as the lateral skin were minced into pieces with a pair of sharp point dissecting scissors (Sigma) and digested for extraction of radioactivity, with 3 ml of Soluene 350™ (PACKARD) for overnight.

The radioactivity contained in the samples obtained as previously described, was measured in the totality or in weighed aliquots using a scintillating liquid beta counter equipped with dedicated software.

The evaluation was performed for the standards (0.5 ml/5 ml picofluor40™), for the receptor fluid (1.0 ml/10 ml Picofluor 40™) and for an aliquot exactly weighed of the ethanolic solution containing the washing solvents (0.5 ml/5 ml Picofluor 40™).

For the epidermis and dermis, after digestion, 15 ml of Hionic Fluor 30™ (PACKARD) were added. The background of the count is automatically deducted from the counting rate of each sample in counts per minute (dpm).

Data Analysis:

The results were expressed in quantities or in percentages of applied testosterone, found in the different compartments. Applied quantities of testosterone were determined from the counting levels of diluted standards. Each result represents the mean value of 6 experimental determinations and is associated with its standard error of mean.

1. The quantity of testosterone and the % of the dose absorbed in the receptor fluid for each time were calculated as follows:

$$\% = (Qt/Qi) \times 100$$

where Qt represents absorbed amount at time t, and Qi, applied quantity at time 0, 2. The total quantity and corresponding % of the dose absorbed as a function of the time (cumulated values), 3. The mean flux of testosterone permeated was calculated from the slope of the linear portion of the Q versus time plot and expressed as µCi/cm2/h 4. The quantity and % of the administered dose, which was found in the skin and in the washing solvents.

The validity of the test was checked by balancing the radioactivity which is found in the different samples (this summarization should be comprised, for each test, between 90% and 110% of the applied dose).

Results and Conclusion

Table 14 shows that formulations F45, F47, F52, F53, F54 and F55 permeate significantly lower amount of testosterone than F56 (P<0.001). For formulations F41, 42, 43, 44, 46, 48, 50, 51 the permeated amounts appear to be lower than F56. However, the difference between these formulations and F56 were not statistically significant (P>0.05). However F49 permeated higher than F56 but the difference between these two formulations were not statistically significant (P>0.05). The mass balance data indicate variable levels of skin retention of testosterone. Furthermore, this data also demonstrates that the total mass balance is in between 90 to 110% of the initial quantity of $^{14}$C Testosterone applied (Table 14).

The flux of formulations F41, F42, 46, F49 and F50, albeit appearing to be higher than F56, the differences were not statistically significant (P>0.05). The flux of the all other formulations, were although appearing to be lower than control, the differences among the formulations versus F56 were not statistically significant except for F45 (P>0.05).

From this study, it is clear that the rate and extent of permeation of testosterone through human skin of all the test formulations were lower (or similar in some cases) than the reference formulation and none of the test formulation demonstrated significantly higher permeation than the reference formulation (F56).

Constraints for Flux studies: The studies conducted here were based on a finite dose kinetics where the rate limiting step is amount of gel used. Due to our using a finite dose, a non-linear permeation profile was obtained for most of the formulations which made us difficult to calculate the steady state flux. Nevertheless, a 2-10 h time points were used to calculate the flux values which is an assumption of a linear progression of flux but in actuality, the steady state was not achieved in these experiments. Hence the AUC values are a better representation to compare the formulations than flux values.

TABLE 14

Mass Balance Studies

DONOR 8127

|  | F41 | | F42 | | F43 | | F44 | | F56 | |
| --- | --- | --- | --- | --- | --- | --- | --- | --- | --- | --- |
|  | Mean | SD | Mean | SD | Mean | SD | Mean | SD | Mean | SD |
| % IN WASH | 72.84 | 19.88 | 82.63 | 12.27 | 95.46 | 8.71 | 92.22 | 3.68 | 92.01 | 13.45 |
| % LATERAL SK. | 1.15 | 2.14 | 0.27 | 0.18 | 0.31 | 0.41 | 0.36 | 0.29 | 0.59 | 0.40 |
| % CTRL SKIN | 10.57 | 4.50 | 6.38 | 5.27 | 4.18 | 1.14 | 5.80 | 2.28 | 3.52 | 2.39 |
| % PERMEATED | 4.86 | 1.53 | 3.45 | 0.43 | 2.70 | 0.70 | 3.80 | 2.05 | 5.87 | 5.05 |
| % TOTAL | 89.42 | | 92.73 | | 102.65 | | 102.18 | | 101.99 | |

DONOR 8300

|  | F45 | | F46 | | F47 | | F48 | | F56 | |
| --- | --- | --- | --- | --- | --- | --- | --- | --- | --- | --- |
|  | Mean | SD | Mean | SD | Mean | SD | Mean | SD | Mean | SD |
| % IN WASH | 95.41 | 5.29 | 86.91 | 3.16 | 87.98 | 13.59 | 79.68 | 7.41 | 86.08 | 3.67 |
| % LATERAL SK. | 0.24 | 0.14 | 0.42 | 0.17 | 0.14 | 0.08 | 0.25 | 0.10 | 0.21 | 0.09 |
| % CTRL SKIN | 4.09 | 2.05 | 4.67 | 1.84 | 2.29 | 0.84 | 4.88 | 2.76 | 4.07 | 1.59 |
| % PERMEATED | 3.51 | 1.65 | 6.37 | 3.98 | 3.57 | 1.25 | 5.38 | 3.81 | 7.56 | 1.78 |
| % TOTAL | 103.25 | | 98.37 | | 93.98 | | 90.19 | | 97.92 | |

TABLE 14-continued

Mass Balance Studies

DONOR 8300

| | F49 | | F50 | | F51 | | F52 | | F56 | |
|---|---|---|---|---|---|---|---|---|---|---|
| | Mean | SD | Mean | SD | Mean | SD | Mean | SD | Mean | SD |
| % IN WASH | 79.64 | 5.61 | 88.34 | 2.30 | 91.04 | 8.28 | 95.51 | 4.07 | 86.08 | 3.67 |
| % LATERAL SK. | 0.41 | 0.24 | 0.29 | 0.25 | 0.54 | 0.59 | 0.23 | 0.21 | 0.21 | 0.09 |
| % CTRL SKIN | 8.29 | 2.69 | 5.70 | 2.12 | 6.58 | 1.92 | 2.67 | 0.84 | 4.07 | 1.59 |
| % PERMEATED | 9.47 | 2.14 | 5.69 | 1.72 | 6.73 | 2.28 | 2.22 | 0.40 | 7.56 | 1.78 |
| % TOTAL | 97.82 | | 100.01 | | 104.89 | | 100.64 | | 97.92 | |

DONOR 8300

| | F53 | | F54 | | F55 | | F56 | |
|---|---|---|---|---|---|---|---|---|
| | Mean | SD | Mean | SD | Mean | SD | Mean | SD |
| % IN WASH | 85.33 | 4.58 | 87.39 | 4.37 | 90.02 | 2.64 | 86.08 | 3.67 |
| % LATERAL SK. | 0.20 | 0.08 | 0.35 | 0.33 | 0.09 | 0.05 | 0.21 | 0.09 |
| % CTRL SKIN | 9.14 | 2.93 | 5.88 | 3.69 | 4.37 | 3.29 | 4.07 | 1.59 |
| % PERMEATED | 4.61 | 0.62 | 4.33 | 0.68 | 4.33 | 0.68 | 7.56 | 1.78 |
| % TOTAL | 99.28 | | 97.95 | | 98.81 | | 97.92 | |

Example 3

In Vitro Percutaneous Absorption of Experimental Testosterone Gel Formulations through Human Skin by HPLC Method Methods Human Skin: Human frozen skin was supplied by U.S. Tissue and Cell (Cincinnati, Ohio). Skin was shipped over dry ice and once received, it was stored at −80° C. until use. The average thickness of the dermatomed skin was 540 µm. Each experiment was carried out in replicates of six (n=6) using the same donor for any given formulation. Also, each donor was tested for permeation of 1% marketed gel (F56) in triplicate and all data was normalized to this measurement.

Formulations: Formulations were prepared and supplied by Solvay Pharmaceuticals. Formulations were blinded except for control/marketed product formula (F56).

Transport Studies: Percutaneous absorption in vitro was studied quantitatively with human skin placed on the Franz diffusion cell. The skin was mounted horizontally between the donor and receptor half. The surface area of the skin exposed to the formulation in the donor chamber was 0.64 cm$^2$, and the receptor volume was 5.0 mL. Temperature was maintained at 37° C. with the help of a double water circulation jacket surrounding the lower part of the cell. This enabled the skin temperature to be maintained at physiological level. The donor chamber was open on the top.

The receptor compartment was filled with receptor fluid consisting of phosphate buffered saline pH 7.4 (PBS) and propylene glycol (1:1). The skin was mounted on the cells approximately 30 minutes before the application of the formulations. Formulation (300 mg±5% which contains 3000 µg of the drug based on 1% gel) was applied over the surface of the epidermis gravimetrically. Samples of 0.3 ml were collected periodically (0, 1, 2, 4, 6, 8, 10, 22 and 24 h) and replaced with fresh buffer.

Assay: Samples were analyzed for testosterone content using HPLC assay. The conditions/details were as follows:

Mobile phase: Acetonitrile:Water (50:50)

Column: C18, 3µ, 150 mm Phenomenex (Nucleosil)

Injection volume: 30 µl

Flow rate: 1 ml/min

UV detection: 239 nm

Results

Referring to Table 15, the results were expressed as cumulative amounts of testosterone permeated as a function of time for the different formulations. The table shows the cumulative amount permeated relative to control/marketed product formula using the same human skin donor. The mean flux of testosterone permeated was calculated from the slope of the linear portion of the CAR (Cumulative amount released) versus time plot and expressed as µg/cm$^2$/h. The results were expressed as a ratio of flux of test formulation and Control formulation (test/control). The cumulative amount of drug permeated through the skin per sq. cm area was also compared with that of marketed formulation and expressed as a ratio (test/control). Therefore, each formulation was compared to the marketed product formula for its cumulative permeation and flux value and the results are compiled in Table 15. The comparison of each formulation to the marketed product formula was assessed for statistical significance using ANOVA. Mean differences with p<0.05 were considered to be statistically significant. Raw data for each formulation relative to marketed product formula shows the Ratio Flux and Ratio CAR as well as the statistical conclusions.

Conclusions

Permeation of testosterone through the dermatomed human skin was observed with all the formulations and permeation ranged from 1 to 7% with various formulations.

Referring again to Table 15, it is shown that improved permeation relative to marketed product formulation as determined by a comparison of cumulative amount of drug permeated after 24 hrs and/or flux at statistically significant levels was observed for Formulations F 48, F 49 and F 53.

TABLE 15

| Formulation | Donor | Flux (µg/cm2/h) | Cum Amt Rel (CAR) (µg) | Relative Standard Deviation ((SD/Mean)* 100) | Ratio Flux | Ratio CAR | Statistically better than marketed formulation? Ratio Flux | Ratio CAR |
|---|---|---|---|---|---|---|---|---|
| F41(n = 4) | 8127 | 13.03 | 189.81 | 11.87 | 0.65 | 1.02 | No | No |
| F42(n = 5) | 8127 | 10.944 | 188.21 | 55.52 | 0.54 | 1.01 | No | No |
| F43(n = 6) | 8127 | 3.44 | 50.11 | 23.91 | 0.17 | 0.27 | No | No |
| F44(n = 6) | 8127 | 10.57 | 151.95 | 22.05 | 0.53 | 0.82 | No | No |
| F45(n = 6) | 8300 | 5.95 | 74.13 | 29.00 | 0.47 | 0.69 | No | No |
| F46(n = 6) | 8300 | 11.16 | 117.87 | 22.60 | 0.88 | 1.09 | No | No |
| F47(n = 6) | 8300 | 10.85 | 114.61 | 22.57 | 0.86 | 1.06 | No | No |
| F48(n = 6) | 8300 | 20.53 | 208.82 | 39.5 | 1.62 | 1.94 | Yes | Yes |
| F49(n = 6) | 8127 | 20.34 | 298.76 | 18.70 | 1.01 | 1.61 | No | Yes |
| F50(n = 6) | 8127 | 6.78 | 94.71 | 28.76 | 0.34 | 0.51 | No | No |
| F51(n = 6) | 8127 | 21.37 | 254.57 | 29.68 | 1.06 | 1.37 | No | No |
| F52(n = 4) | 8127 | 8.18 | 113.93 | 40.08 | 0.41 | 0.61 | No | No |
| F53(n = 6) | 8127 | 24.04 | 326.46 | 28.49 | 1.19 | 1.76 | No | Yes |
| F54(n = 6) | 8127 | 14.75 | 200.45 | 37.80 | 0.73 | 1.08 | No | No |
| F55(n = 4) | 8127 | 16.67 | 240.61 | 27.58 | 0.83 | 1.30 | No | No |
| F56(n = 3) | 8127 | 20.13 | 185.71 | 23.15 | NA | NA | NA | NA |
| F56(n = 3) | 8300 | 12.69 | 107.79 | 7.00 | NA | NA | NA | NA |

Example 4

In Vitro Percutaneous Absorption of Three Testosterone Gel Formulations through Human Skin by HPLC Method Methods Human Skin: Human frozen skin was supplied by U.S. Tissue and Cell (Cincinnati, Ohio). Skin was shipped over dry ice and once received; it was stored at −80° C. until use. The average thickness of the dermatomed skin was about 700 µm. Each experiment was carried out in replicates of six (n=6) using the same donor for any given formulation. Permeation of marketed formula testosterone gel (1%, F56) was also carried out in replicates of six (n=6) and all data was normalized to this measurement.

Formulations: Formulations were prepared and supplied by Solvay Pharmaceuticals. Formulations were blinded except for control/marketed product formula (F56).

Transport Studies: Percutaneous absorption in vitro was studied quantitatively with human skin placed on the Franz diffusion cell. The skin was mounted horizontally between the donor and receptor half. The surface area of the skin exposed to the formulation in the donor chamber was 0.64 cm$^2$, and the receptor volume was 5.0 mL. Temperature was maintained at 37° C. with the help of a double water circulation jacket surrounding the lower part of the cell. This enabled the skin temperature to be maintained at physiological level. The donor chamber was open on the top.

The receptor compartment was filled with receptor fluid consisting of phosphate buffered saline pH 7.4 (PBS) and propylene glycol (1:1). The skin was mounted on the cells approximately 30 minutes before the application of the formulations. Formulation (300 mg ±5% which contains 3000 µg of the drug based on 1% gel) was applied over the surface of the epidermis gravimetrically. Samples of 0.3 ml were collected periodically (0, 1, 2, 4, 6, 8, 10, 22 and 24 h) and replaced with fresh buffer.

Figure 7:
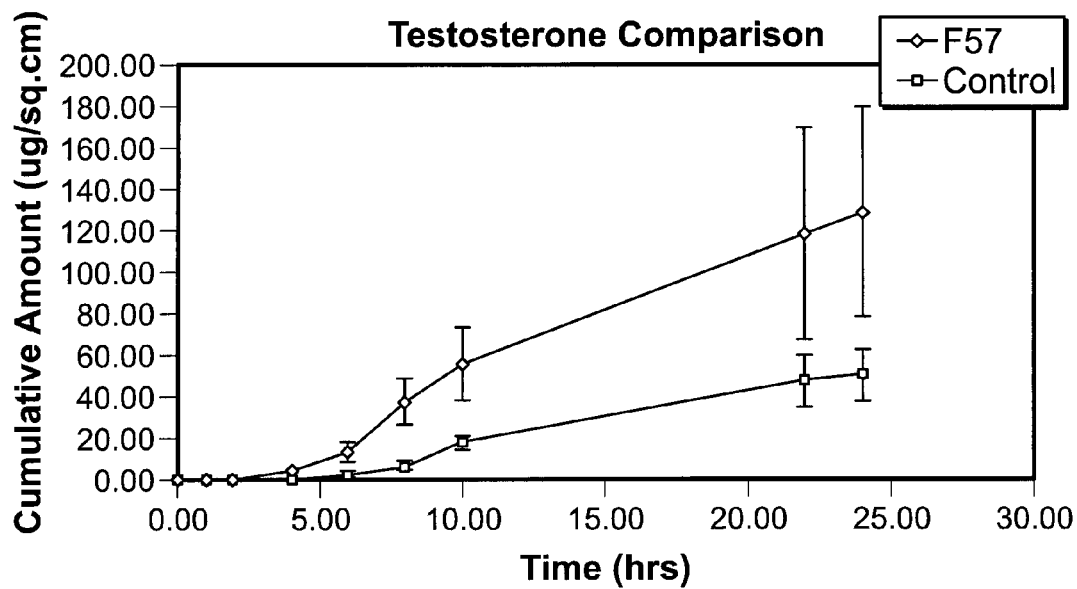
FIG. 7 is a graph showing cumulative amounts of testosterone permeated as a function of time for formulation F57.
Figure 8:
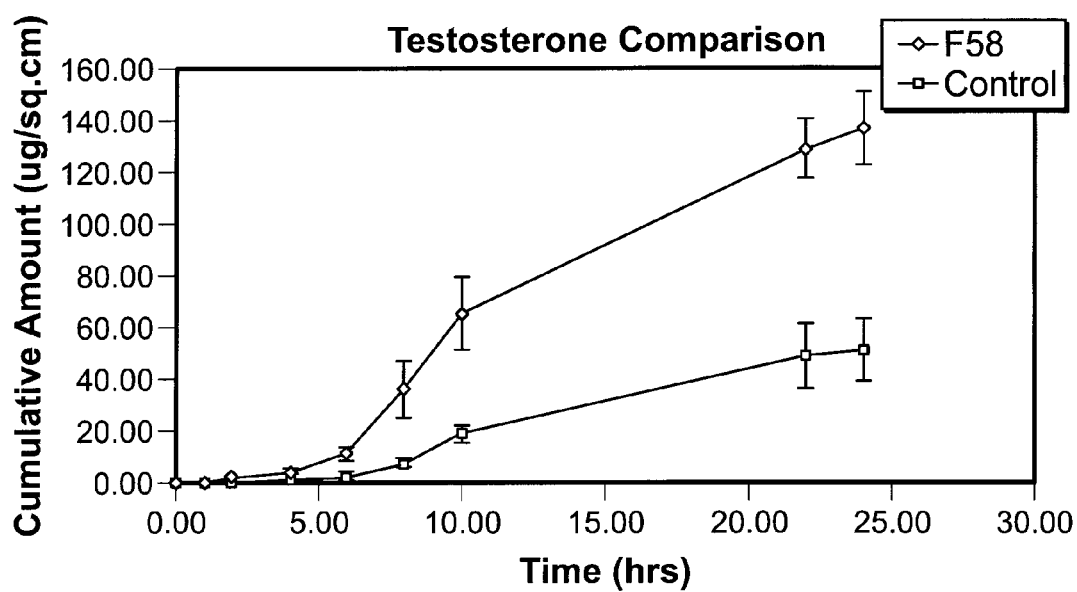
FIG. 8 is a graph showing the cumulative amounts of testosterone permeated as a function of time for formulation F58.
Figure 9:
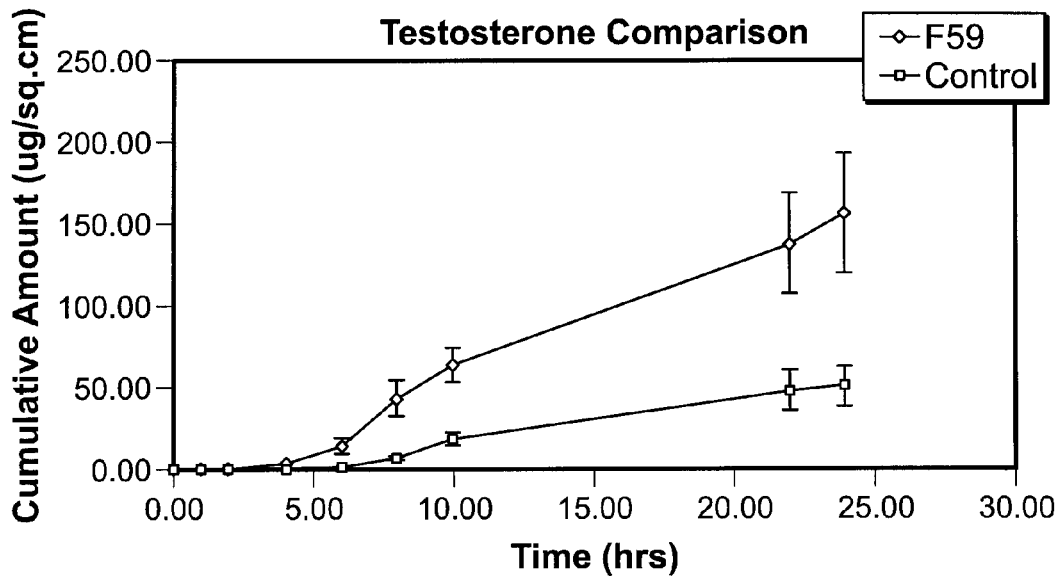
FIG. 9 is a graph showing the cumulative amounts of testosterone permeated as a function of time for formulation F59.

Assay: Samples were analyzed for testosterone content using HPLC assay. The conditions/details were as follows:
Mobile phase: Acetonitrile:Water (50:50)
Column: C18, 3µ, 150 mm Phenomenex (Nucleosil)
Injection volume: 30 µl
Flow rate: 1 ml/min
UV detection: 239 nm Results Referring to FIGS. 7-9 and Tables 17-20, the results were expressed as cumulative amounts of testosterone permeated as a function of time for the different formulations. Each table shows the cumulative amount permeated relative to control/marketed product formula using the same human skin donor. The mean flux of testosterone permeated was calculated from the slope of the linear portion of the CAR (Cumulative amount released) versus time plot and expressed as µg/cm$^2$/h. The result was expressed as a ratio of flux of test formulation and Control formulation (test/control). The cumulative amount of drug permeated through the skin per sq. cm area was also compared with that of marketed formulation and expressed as a ratio (test/control). Therefore, each formulation was compared to the marketed product formula for its cumulative permeation and flux value and the results are compiled in Table 16. The comparison of each formulation to the marketed product formula was assessed for statistical significance using ANOVA. Mean differences with p<0.05 were considered to be statistically significant.

Conclusions

Permeation of testosterone through the dermatomed human skin was observed with the three formulations and permeation was about 3% (CAR)

Improved permeation relative to marketed product formulation as determined by a comparison of cumulative amount of drug permeated after 24 hrs and/or flux at statistically significant levels was observed for all test formulations F57, F58 and F59.

Accordingly, utilizing the teachings of the present disclosure, a hydroalcoholic gel comprising testosterone, isopropyl myristate, ethanol, water and a sufficient amount of a thickening agent to give the gel a viscosity in excess of about 9000 cps can be prepared such that when is applied to human skin mounted in a Frantz cell in an amount of about 300 mg, after 24 hours the flux ratio is in excess of 1, or preferably in excess of 1.5 where the flux ratio is the ratio of flux of testosterone expressed in amount per unit area and per unit time which permeates the skin when the gel is so tested to the flux of testosterone which permeates the skin when a gel of similar viscosity comprising 1 wt % testosterone, 0.5 wt % isopropyl myristate and 72.5 wt % alcohol 95% v/v is so tested. The hydroalcoholic gel has between 1.15 and 1.8% (w/w) testosterone; between 0.6 and 1.2% (w/w) isopropyl myristate, and between about 72.0 and 78.0% (w/w) alcohol 95% v/v.

TABLE 16

Summary of Testosterone Skin Permeation Data at 24 hours from Test Formulations (F57, F58 and F59) and Control (F56)

| Formulation | Donor | Flux (µg/cm2/h) | Cumulative Amount Rel (CAR, µg) | Relative Standard Deviation ((SD/Mean)* 100) | Ratio Flux | Ratio CAR | Statistically better than marketed formulation? Ratio Flux | Ratio CAR |
|---|---|---|---|---|---|---|---|---|
| Control-F56 (n = 6) | 8126 | 4.20 | 50.76 | 26.08 | — | — | — | — |
| F57 (n = 6) | 8126 | 10.69 | 129.66 | 41.77 | 2.55 | 2.55 | Yes | Yes |
| F58 (n = 6) | 8126 | 8.70 | 136.98 | 10.88 | 2.07 | 2.70 | Yes | Yes |
| F59 (n = 6) | 8126 | 12.67 | 156.32 | 15.25 | 3.02 | 3.08 | Yes | Yes |

TABLE 17

Testosterone Skin Permeation Data from Control Formulation (F56)

| Time(hrs) | Control (area counts) | Conc(µg/ml) | Conc X Dil | Conc*0.3 | Total (5 ml) | Cum. (µg) | Cum-Sqcm | SD | Flux (mcg/cm2/hr) |
|---|---|---|---|---|---|---|---|---|---|
| 0.00 | 0.00 | 0.00 | 0.00 | 0.00 | 0.00 | 0.00 | 0.00 | 0.00 | 0.00 |
| 1.00 | 0.00 | 0.00 | 0.00 | 0.00 | 0.00 | 0.00 | 0.00 | 0.00 | 0.00 |
| 2.00 | 0.00 | 0.00 | 0.00 | 0.00 | 0.00 | 0.00 | 0.00 | 0.00 | 0.00 |
| 4.00 | 4137.83 | 0.05 | 0.05 | 0.02 | 0.25 | 0.25 | 0.40 | 0.10 | 0.20 |
| 6.00 | 15522.67 | 0.19 | 0.19 | 0.06 | 0.96 | 0.97 | 1.52 | 0.30 | 0.56 |
| 8.00 | 71183.00 | 0.88 | 0.88 | 0.26 | 4.38 | 4.46 | 6.96 | 1.49 | 2.72 |
| 10.00 | 185241.67 | 2.28 | 2.28 | 0.68 | 11.41 | 11.74 | 18.35 | 3.37 | 5.69 |
| 22.00 | 484302.17 | 5.97 | 5.97 | 1.79 | 29.83 | 30.85 | 48.20 | 12.49 | 2.49 |
| 24.00 | 481870.50 | 5.94 | 5.94 | 1.78 | 29.68 | 32.49 | 50.76 | 12.29 | 1.28 |

TABLE 18

Testosterone Skin Permeation Data from Test Formulation-F57

| Time(hrs) | F57 (area counts) | Conc(µg/ml) | Conc X Dil | Conc*0.3 | Total (5 ml) | Cum. (µg) | Cum-Sqcm | SD | Flux (mcg/cm2/hr) |
|---|---|---|---|---|---|---|---|---|---|
| 0.00 | 0.00 | 0.00 | 0.00 | 0.00 | 0.00 | 0.00 | 0.00 | 0.00 | 0.00 |
| 1.00 | 5171.20 | 0.06 | 0.06 | 0.02 | 0.31 | 0.31 | 0.48 | 0.73 | 0.48 |
| 2.00 | 13574.00 | 0.16 | 0.16 | 0.05 | 0.81 | 0.83 | 1.30 | 0.53 | 0.82 |
| 4.00 | 45117.33 | 0.54 | 0.54 | 0.16 | 2.71 | 2.77 | 4.33 | 1.29 | 1.52 |
| 6.00 | 147837.67 | 1.77 | 1.77 | 0.53 | 8.87 | 9.10 | 14.21 | 4.45 | 4.94 |
| 8.00 | 393201.67 | 4.72 | 4.72 | 1.42 | 23.58 | 24.35 | 38.04 | 11.49 | 11.91 |
| 10.00 | 571442.33 | 6.86 | 6.86 | 2.06 | 34.28 | 36.45 | 56.96 | 17.86 | 9.46 |
| 22.00 | 1201173.50 | 14.41 | 14.41 | 4.32 | 72.05 | 76.28 | 119.19 | 50.99 | 5.19 |
| 24.00 | 1240824.00 | 14.89 | 14.89 | 4.47 | 74.43 | 82.98 | 129.66 | 50.45 | 5.24 |

TABLE 19

Testosterone Skin Permeation Data from Test Formulation-F58

| Time(hrs) | F58 (area counts) | Conc(µg/ml) | Conc X Dil | Conc*0.3 | Total (5 ml) | Cum. (µg) | Cum-Sqcm | SD | Flux (mcg/cm2/hr) |
|---|---|---|---|---|---|---|---|---|---|
| 0.00 | 0.00 | 0.00 | 0.00 | 0.00 | 0.00 | 0.00 | 0.00 | 0.00 | 0.00 |
| 1.00 | 0.00 | 0.00 | 0.00 | 0.00 | 0.00 | 0.00 | 0.00 | 0.00 | 0.00 |
| 2.00 | 13377.80 | 0.16 | 0.16 | 0.05 | 0.80 | 0.80 | 1.25 | 1.23 | 1.25 |
| 4.00 | 41996.33 | 0.50 | 0.50 | 0.15 | 2.52 | 2.57 | 4.01 | 1.03 | 1.38 |
| 6.00 | 114316.00 | 1.37 | 1.37 | 0.41 | 6.86 | 7.06 | 11.03 | 2.71 | 3.51 |
| 8.00 | 372728.67 | 4.47 | 4.47 | 1.34 | 22.36 | 22.97 | 35.89 | 10.99 | 12.43 |
| 10.00 | 665420.00 | 7.98 | 7.98 | 2.39 | 39.91 | 41.86 | 65.41 | 14.32 | 14.76 |
| 22.00 | 1304913.50 | 15.65 | 15.65 | 4.70 | 78.27 | 82.62 | 129.09 | 11.80 | 5.31 |
| 24.00 | 1123168.83 | 15.72 | 15.72 | 4.72 | 78.62 | 87.67 | 136.98 | 13.89 | 3.95 |

TABLE 20

Testosterone Skin Permeation Data from Test Formulation-F59

| Time(hrs) | F59 (area counts) | Conc(µg/ml) | Conc X Dil | Conc*0.3 | Total (5 ml) | Cum. (µg) | Cum-Sqcm | SD | Flux (mcg/cm2/hr) |
|---|---|---|---|---|---|---|---|---|---|
| 0.00 | 0.00 | 0.00 | 0.00 | 0.00 | 0.00 | 0.00 | 0.00 | 0.00 | 0.00 |
| 1.00 | 0.00 | 0.00 | 0.00 | 0.00 | 0.00 | 0.00 | 0.00 | 0.00 | 0.00 |
| 2.00 | 5610.17 | 0.07 | 0.07 | 0.02 | 0.35 | 0.35 | 0.54 | 0.25 | 0.54 |
| 4.00 | 30049.67 | 0.37 | 0.37 | 0.11 | 1.86 | 1.88 | 2.94 | 1.34 | 1.20 |
| 6.00 | 140427.33 | 1.74 | 1.74 | 0.52 | 8.69 | 8.82 | 13.79 | 4.64 | 5.42 |
| 8.00 | 439193.83 | 5.44 | 5.44 | 1.63 | 27.18 | 27.83 | 43.49 | 10.80 | 14.85 |
| 10.00 | 629849.83 | 7.80 | 7.80 | 2.34 | 38.98 | 41.26 | 64.47 | 10.42 | 10.49 |
| 22.00 | 1346943.00 | 16.67 | 16.67 | 5.00 | 83.36 | 87.98 | 137.47 | 30.64 | 6.08 |
| 24.00 | 1461065.83 | 18.08 | 18.08 | 5.43 | 90.42 | 100.05 | 156.32 | 36.38 | 9.43 |

Example 5

The Single and Multiple Dose Pharmacokinetics of Testosterone After Administration of 1.62% Hydro-Alcoholic Gel at Dose Levels of 1.25, 2.50, 3.75, 5.00, and 6.25 g in Hypogonadal Males Objectives To determine the single and multiple dose pharmacokinetics of testosterone after administration of testosterone gel 1.62% at doses of 1.25 g (20.3 mg), 2.50 g (40.5 mg), 3.75 g (60.8 mg), 5.00 g (81.0 mg), and 6.25 g (101.3 mg).

To assess the dose proportionality and accumulation of testosterone over the dose range of 1.25 g (20.3 mg) to 6.25 g (101.1 mg) of testosterone gel 1.62%.

Methods

Formulations: Formulations were prepared and supplied by Solvay Pharmaceuticals. Formulations were blinded except for control/marketed product formula.

Design: A single center, open-label, randomized, single and multiple dose, parallel group study in hypogonadal male subjects. Subjects were randomized to one of five treatment groups. Each group was to be composed of 12 subjects, for a total of 60 subjects.

Subjects who consented to participate in this study and met the inclusion/exclusion criteria were randomized to one of the following treatment groups:

TABLE 21

Treatment Groups

| Treatment Group | Gel Dose (g) | Testosterone Dose (mg) |
|---|---|---|
| A | 1.25 | 20.3 |
| B | 2.50 | 40.5 |
| C | 3.75 | 60.8 |
| D | 5.00 | 81.0 |
| E | 6.25 | 101.3 |

Each subject received single (Day 1) and multiple (Days 2-14) doses of testosterone gel 1.62% over a 14-day treatment period. Study drug was applied topically once daily in the morning. The total duration of the study was 17 days, not including the screening period. Subjects were confined to the clinic for the entire 17-day study period. The following table lists the ingredients combined to yield the study formulation used.

TABLE 22

Ingredients Combined to Yield Study Formulation (% w/w)

| Component | Function | % w/w |
|---|---|---|
| Testosterone | Active pharmaceutical ingredient | 1.62 |
| Alcohol (95% v/v)* | Absorption enhancer | 73.5 |
| Isopropyl myristate | Absorption enhancer | 1.00 |
| CARBOPOL ® 980 (carbomer) | Thickening agent precursor | 1.00 |
| 0.1N Sodium hydroxide | Neutralizer | 7.00 |
| Purified water | Solvent | 15.9 |

*Equivalent to about 68.1% of absolute alcohol in the formulation.

Subjects: Fifty-six (56) hypogonadal males.

Main Criteria for Inclusion: Male subjects 18-75 years of age, inclusive; serum total testosterone <300 ng/dL at screening as measured by the clinical site laboratory; and subjects with a Body Mass Index (BMI) of 20-35 kg/m^2, inclusive.

Procedures and Assessments

Dose Administration: Testosterone gel 1.62% was applied topically once daily in the morning on Days 1-14. The site of application was either the shoulder/upper arm area or the abdomen. The study drug was applied in 1.25 g increments until the total target dose was reached using maximum surface area possible.

Twenty (20) minutes prior to the targeted time of dose application, subjects showered and washed the application site with soap and water. Subjects were not allowed to remain in the shower for longer than 10 minutes. The designated area for gel application was thoroughly dried.

Site personnel directly involved with the dosing procedures wore gloves when handling the study gel. A fresh pair of gloves was used for each subject. Each incremental gel dose of 1.25 g +/−0.02 g was weighed on a sheet of weighing paper on a balance. Immediately after measuring the appropriate amount of gel, the weighing paper with the measured gel dose was wiped directly onto the subject's designated site of application by the study personnel. The subject then rubbed the product into the skin of the designated application site using his hand. This process was repeated until the total target dose (1.25 g to 6.25 g) was reached.

Pharmacokinetic Sampling: Whole blood samples (10 mL each) were obtained from each subject for determination of total testosterone, dihydrotestosterone, and estradiol at the following time points:

Day-1: predose, 0.5, 1, 2, 4, 6, 8, 10, 12, and 16 hours relative to the projected time of gel application on subsequent study days;

Day 1: predose, 0.5, 1, 2, 4, 6, 8, 10, 12, and 16 hours postdose;

Days 2-13: predose;

Day 14: predose, 0.5, 1, 2, 4, 6, 8, 10, 12, 16, and 24 hours postdose.

Bioanalysis: Serum concentrations of total testosterone, dihydrotestosterone, and estradiol were determined using validated LC-MS/MS methodology.

Criteria for Evaluation

Safety: Vital signs, ECG, physical examination, clinical laboratory determinations (including PSA measurement), DRE and IPSS, safety testosterone and hematocrit measurements.

Pharmacokinetics: For this preliminary report, pharmacokinetic parameters (AUC(0-24), $C_{max}$, $C_{avg}$, $C_{min}$, peak to trough fluctuation, $T_{min}$ and $T_{max}$) derived from both observed and baseline adjusted serum concentrations for testosterone.

Statistical methods: Descriptive statistics (n, mean, SD, CV, median, geometric mean, minimum, maximum) and graphical representations.

TABLE 23

Subject Demographics (Mean (range))

| Treatment Group | N | Age (years) | BMI (kg/m^2) |
|---|---|---|---|
| A (1.25 g) | 11 | 50 (27-69) | 30.4 (25.6-33.6) |
| B (2.50 g) | 11 | 50 (31-66) | 31.0 (25.9-36.1) |
| C (3.75 g) | 11 | 52 (38-65) | 29.3 (21.8-35.3) |
| D (5.00 g) | 12 | 55 (37-68) | 29.6 (22.6-34.0) |
| E (6.25 g) | 11 | 48 (27-68) | 30.2 (27.3-32.7) |
| All Groups | 56 | 51 (27-69) | 30.1 (21.8-36.1) |

TABLE 24

Ethnicity of the Subjects (N (%))

| Treatment Group | N | White Not Hispanic or Latino | White Hispanic or Latino | Black | Asian |
|---|---|---|---|---|---|
| A | 11 | 5 | 5 | 0 | 1 |
| B | 11 | 5 | 6 | 0 | 0 |
| C | 11 | 5 | 5 | 1 | 0 |
| D | 12 | 5 | 7 | 0 | 0 |
| E | 11 | 2 | 9 | 0 | 0 |
| All Groups | 56 | 22 (39.3%) | 32 (57.1%) | 1 (1.8%) | 1 (1.8%) |

Screening Testosterone Baseline Values

All subjects at screening had testosterone concentrations <300 ng/dL, confirming the hypogonadal status of all subjects prior to exposure to study drug. The local clinical laboratory used chemiluminescence methodology for these evaluation. Mean screening baseline serum total testosterone concentrations ranged from 215 to 232 ng/dL for the five individual dose groups. Table 25 provides the screening baseline mean (range) by treatment group.

TABLE 25

Mean Screening Testosterone Baseline Values

| Treatment Group | N | Mean Baseline Testosterone (ng/dL) | Range |
|---|---|---|---|
| A | 11 | 215 | 73-286 |
| B | 11 | 231 | 132-293 |
| C | 11 | 230 | 93-295 |
| D | 12 | 232 | 132-293 |
| E | 11 | 225 | 158-282 |
| All | 56 | 227 | 23-295 |

Testosterone Concentration-Time Data

Figure 10:
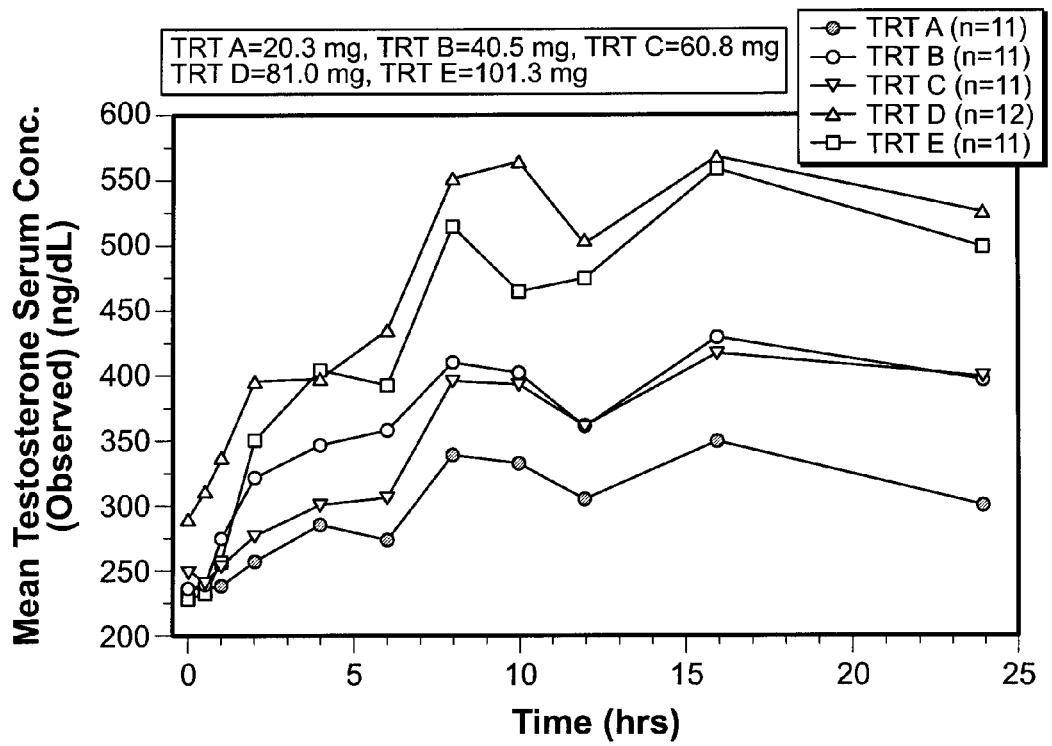
FIG. 10 is a graph showing mean serum concentration-time profiles for observed testosterone on Day 1.
Figure 11:
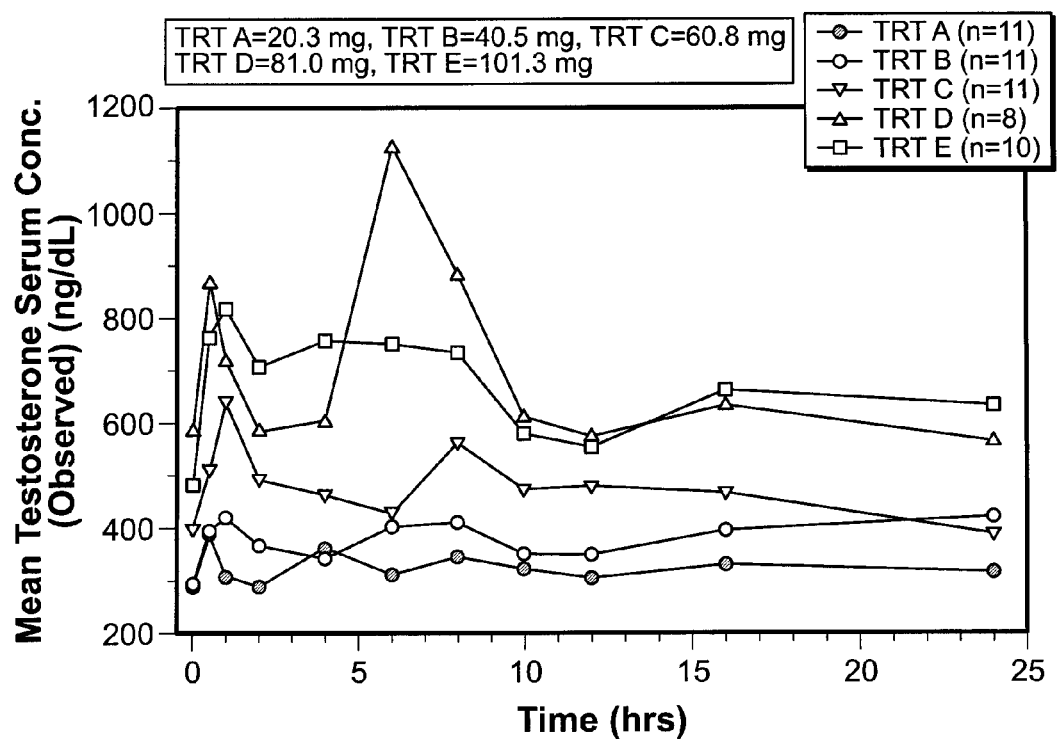
FIG. 11 is a graph showing mean serum concentration-time profiles for observed testosterone on Day 14.

The mean concentration-time profiles for observed testosterone on Day 1 and Day 14 are provided in FIGS. 10 and 11, respectively.

Referring to FIG. 10, on Day 1, a continuous increase in testosterone concentrations occurred in all treatments for approximately 8 hours postdose. Testosterone concentrations then remained consistent over the remainder of the 24-hour dosing interval. Based on the mean concentration-time profiles, all treatments provided sufficient testosterone exposure to increase levels above the lower limit of the eugonadal range (>300 ng/dL) after a single dose on Day 1.

Consistent testosterone levels were observed throughout the majority of the 24-hour concentration-time profiles after multiple dosing of testosterone gel 1.62%. The exception to this is Treatment D, 5.00 g, where a significant peak was observed at 6 hours postdose. This increase in the mean profile was due to the results of one subject who had a reported testosterone concentration of 4980 ng/dL at 6 hours postdose.

Referring now to FIG. 11, the mean profiles on Day 14 demonstrate testosterone concentrations remain above the lower limit of the eugonadal range (>300 ng/dL) over the 24-hour dose interval for all five doses. An increase in testosterone exposure was observed with increased dose over the 1.25 g to 6.25 g range, with the exception of the second profile peak in Treatment D, 5.00 g.

Testosterone Pharmacokinetic Results

The pharmacokinetic results for observed and baseline adjusted testosterone are provided in Table 26 below after subjects received a single dose of 1.62% testosterone gel on Day 1.

TABLE 26

Single Dose Pharmacokinetic Parameters for Testosterone Gel 1.62% on Day 1

| Parameter | Treatment Group | Gel Dose (g) | Testosterone Dose (mg) | N | Arithmetic Mean (SD) Observed | N | Baseline Adjusted |
|---|---|---|---|---|---|---|---|
| AUC(0-24) (ng*h/dl) | A | 1.25 | 20.3 | 11 | 7376 (1465) | 11 | 1934 (1005) |
| | B | 2.50 | 40.5 | 11 | 9112 (3354) | 9 | 3168- (1845) |
| | C | 3.75 | 60.8 | 11 | 8719 (2831) | 10 | 3330 (1875) |
| | D | 5.00 | 81 | 12 | 11933 (3188) | 12 | 5329 (3296) |
| | E | 6.25 | 101.3 | 11 | 11137 (3024) | 11 | 5573 (2602) |

TABLE 26-continued

Single Dose Pharmacokinetic Parameters for Testosterone Gel 1.62% on Day 1

| Parameter | Treatment Group | Gel Dose (g) | Testosterone Dose (mg) | N | Observed Arithmetic Mean (SD) | N | Baseline Adjusted Arithmetic Mean (SD) |
|---|---|---|---|---|---|---|---|
| $C_{avg}$ (ng/dl) | A | 1.25 | 20.3 | 11 | 307 (61) | 11 | 81 (42) |
|  | B | 2.50 | 40.5 | 11 | 380 (140) | 9 | 132 (77) |
|  | C | 3.75 | 60.8 | 11 | 363 (118) | 10 | 139 (78) |
|  | D | 5.00 | 81 | 12 | 497 (133) | 12 | 222 (137) |
|  | E | 6.25 | 101.3 | 11 | 464 (265) | 11 | 232 (108) |
| $C_{max}$ (ng/dL) | A | 1.25 | 20.3 | 11 | 387 (80) | 11 | 159 (57) |
|  | B | 2.50 | 40.5 | 11 | 479 (161) | 9 | 234 (102) |
|  | C | 3.75 | 60.8 | 11 | 533 (211) | 10 | 305 (178) |
|  | D | 5.00 | 81 | 12 | 698 (231) | 12 | 424 (200) |
|  | E | 6.25 | 101.3 | 11 | 657 (215) | 11 | 424 (210) |
| $T_{max}$[a] (h) | A | 1.25 | 20.3 | 11 | 12 (4-24) | 11 | 12 (4-24) |
|  | B | 2.50 | 40.5 | 11 | 12 (4-24) | 9 | 16 (8-24) |
|  | C | 3.75 | 60.8 | 11 | 16 (8-24) | 10 | 16 (8-24) |
|  | D | 5.00 | 81 | 12 | 12 (2-24) | 12 | 12 (6-24) |
|  | E | 6.25 | 101.3 | 11 | 12 (8-24) | 11 | 12 (8-24) |

[a]median (range).

Observed mean $C_{avg}$ on Day 1 was in the eugonadal range of 300-1000 ng/dL for all dose levels. Mean AUC and $C_{avg}$ generally increased over the 1.25 g to 6.25 g dose range, with similar values for Treatments B and C, and Treatments D and E, respectively. Mean $C_{max}$ increased with dose from 1.25 g to 5.00 g, then leveled off. Median $T_{max}$ for all groups, except 5.00 g, was 12 hours and ranged from 2 to 24 hours.

Observed $C_{max}$ values on Day 1 for 1.25 g, 2.50 g, and 3.75 g remained below the upper limit of the eugonadal range (<1000 ng/dL). In treatment D, 5.00 g, one subject had a $C_{max}$ value of 1070 ng/dL. In treatment E, 6.25 g, one subject had a $C_{max}$ value of 1020 ng/dL. All other Day 1 $C_{max}$ values were <1000 ng/dL in Treatment groups D and E.

Baseline adjusted mean AUC and $C_{avg}$ parameter values increased with dose over all five treatment levels. Baseline adjusted mean $C_{avg}$ indicates endogenous testosterone concentrations increased from 81 to 232 ng/dL over the 1.25 g to 6.25 g dose range after single dose administration of testosterone gel 1.62%.

The multiple dose pharmacokinetic results for observed and baseline adjusted testosterone are provided in Table 27 below for testosterone gel 1.62% on Day 14.

TABLE 27

Multiple Dose Pharmacokinetic Parameters for Testosterone Gel 1.62% on Day 14

| Parameter | Treatment Group | Gel Dose (g) | Testosterone Dose (mg) | N | Observed Arithmetic Mean (SD) | N | Baseline Adjusted Arithmetic Mean (SD) |
|---|---|---|---|---|---|---|---|
| AUC(0-24) (ng*h/dl) | A | 1.25 | 20.3 | 11 | 7731 (2914) | 9 | 3149 (2909) |
|  | B | 2.50 | 40.5 | 11 | 9232 (4146) | 11 | 3174- (2628) |
|  | C | 3/75 | 60.8 | 11 | 11132 (2950) | 11 | 5346 (3834) |
|  | D | 5.00 | 81 | 8 | 16115 (11345) | 8 | 9646 (12002) |
|  | E | 6.25 | 101.3 | 10 | 15250 (4123) | 10 | 10005 (4474) |
| $C_{avg}$ (ng/dl) | A | 1.25 | 20.3 | 11 | 322 (121) | 9 | 131 (121) |
|  | B | 2.50 | 40.5 | 11 | 385 (173) | 11 | 132 (110) |
|  | C | 3.75 | 60.8 | 11 | 464 (123) | 11 | 223 (160) |
|  | D | 5.00 | 81 | 8 | 671 (473) | 8 | 402 (500) |
|  | E | 6.25 | 101.3 | 9 | 634 (182) | 9 | 413 (197) |
| $C_{max}$ (ng/dL) | A | 1.25 | 20.3 | 11 | 464 (158) | 9 | 293 (170) |
|  | B | 2.50 | 40.5 | 11 | 506 (195) | 11 | 266 (119) |
|  | C | 3.75 | 60.8 | 11 | 750 (221) | 11 | 523 (241) |
|  | D | 5.00 | 81 | 8 | 1422 (1450) | 8 | 1145 (1466) |
|  | E | 6.25 | 101.3 | 10 | 1179 (520) | 10 | 965 (527) |
| $T_{max}$[a] (h) | A | 1.25 | 20.3 | 11 | 8 (0-16) | 9 | 4 (0.5-16) |
|  | B | 2.50 | 40.5 | 11 | 4 (0-16) | 11 | 8. (0.5-24) |
|  | C | 3.75 | 60.8 | 11 | 8 (1-12) | 11 | 1 (1-12) |
|  | D | 5.00 | 81 | 8 | 1.5 (0.5-24) | 8 | 1.5 (0.5-24) |
|  | E | 6.25 | 101.3 | 10 | 6 (0.5-24) | 10 | 6 (0.5-24) |
| $C_{min}$ (ng/dl) | A | 1.25 | 20.3 | 11 | 209 (91) | 9 | 46 (77) |
|  | B | 2.50 | 40.5 | 11 | 263 (138) | 11 | 29 (70) |
|  | C | 3.75 | 60.8 | 11 | 310 (106) | 11 | 89 (152) |
|  | D | 5.00 | 81 | 8 | 414 (184) | 8 | 154 (203) |
|  | E | 6.25 | 101.3 | 10 | 351 (43) | 10 | 102 (74) |
| Fluctuation | A | 1.25 | 20.3 | 11 | 81 (20) | 9 | 271 (166) |
|  | B | 2.50 | 40.5 | 11 | 66 (18) | 11 | 262 (188) |
|  | C | 3.75 | 60.8 | 11 | 97 (43) | 11 | 252 (149) |
|  | D | 5.00 | 81 | 8 | 129 (66) | 8 | 355 (306) |
|  | E | 6.25 | 101.3 | 9 | 117 (52) | 9 | 201 (69) |

[a]median (range).

Observed AUC, $C_{avg}$, and $C_{max}$ parameter values on Day 14 increased across the dose range of 1.25 g to 5.00 g, with an apparent leveling off with the 6.25 g dose. In the 5 g dose level group, one subject (#25791) on Day 14 had $C_{max}$ and $C_{avg}$ values of 4980 ng/dL and 1801 ng/dL, respectively. These values were approximately 4-fold higher than the other subjects in this same treatment group. The cause of elevated levels in this subject is unknown. When this subject's values are removed from the group mean presented in the table above, the pharmacokinetic parameters for the 5.00 g dose group are reduced from 1422 to 914 ng/dL for $C_{max}$ and 671 to 510 ng/dL for $C_{avg}$, respectively. Using these revised mean values, a trend of increased $C_{avg}$ and $C_{max}$ values over the entire dose range of 1.25 g to 6.25 g is observed.

Observed mean $C_{min}$ values remained above the lower limit of the eugonadal range (>300 ng/dL) with multiple dosing at the 3.75 g, 5.00 g, and 6.25 dose levels. Observed mean $C_{avg}$ for all dose levels ranged from 322 to 671 ng/dL and were in the eugonadal testosterone range of 300 to 1000 ng/dL.

Observed $C_{max}$ values on Day 14 for the 1.25 g dose level remained below the upper limit of the eugonadal range (<1000 ng/dL). In the other dose groups, a total of 12 subjects had observed $C_{max}$ values above 1000 ng/dL. At the 2.50 dose level, one subject had a $C_{max}$ value of 1010 ng/dL. At the 3.75 dose level, one subject had a $C_{max}$ value of 1070 ng/dL. At the 5.00 g dose level, four subjects had $C_{max}$ values >1000 ng/dL ranging from 1050 to 4980 ng/dL. At the 6.25 dose level, six subjects had $C_{max}$ values >1000 ng/dL ranging from 1110 to 2080 ng/dL. These observations are based on the bioanalytical results from the LC-MS/MS assay. These values were not identified during the predose testosterone safety testing conducted at the clinical site.

Baseline adjusted mean $C_{avg}$ values increased with dose across the entire dose range. Baseline adjusted mean $C_{avg}$ indicates endogenous testosterone concentrations increased from 131 to 413 ng/dL over the 1.25 g to 6.25 g dose range after fourteen days of multiple dose administration of testosterone gel 1.62%.

Conclusions

Based on the preliminary review of adverse event data, safety testosterone and hematocrit laboratory measures, and application site evaluation, testosterone gel 1.62% was safe and well tolerated at dose levels ranging from 1.25 to 6.25 g of gel (20.3 to 101.1 mg of testosterone). After single and multiple dose administration of testosterone gel 1.62% at dose levels ranging from 1.25 g to 6.25 g (20.3 to 101.1 mg of testosterone), mean $C_{avg}$ values in the eugonadal range of 300-1000 ng/dL are obtained.

At the highest dose levels of 5.00 g and 6.25 g (81.0 and 101.3 mg of testosterone, respectively) a greater incidence of $C_{max}$ values exceeding the upper limit of normal for eugonadal men was observed. Appropriate monitoring in Phase 3 clinical development is indicated.

All references, including publications, patent applications, and patents, cited herein are hereby incorporated by reference to the same extent as if each reference were individually and specifically indicated to be incorporated by reference and were set forth in its entirety herein.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the particular subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it there individually recited herein.

Use of the phrase 'the invention' or 'the present invention' is not meant to limit the claims in any manner and no conclusion should be drawn that any description or argument associated with a particular use of the phrase 'the invention' or 'the present invention' applies to each and every claim. The use of the phrase 'the invention' or 'the present invention' has been used solely for linguistic or grammatical convenience and not to effect a limitation of any nature on any of the claims.

Alternative embodiments of the claimed invention are described herein, including the best mode known to the inventors for carrying out the claimed invention. Of these, variations of the disclosed embodiments will become apparent to those of ordinary skill in the art upon reading the foregoing disclosure. The inventors expect skilled artisans to employ such variations as appropriate, and the inventors intend for the claimed invention to be practiced otherwise than as specifically described herein. Accordingly, the claimed invention includes all modifications and equivalents of the subject matter recited in the claims appended hereto as permitted by applicable law. Moreover, any combination of the above-described elements in all possible variations thereof is encompassed by the claimed invention unless otherwise indicated herein or otherwise clearly contradicted by context.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

The use of the terms "a" and "an" and "the" and similar referents in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the claimed invention.

What is claimed is:

1. A method of treating hypogonadism in a human male comprising applying a therapeutically effective dose of a gel pharmaceutical composition consisting of:
   a) 1.3% to 1.7% (w/w) testosterone;
   b) 0.9% to 1.0% (w/w) isopropyl myristate;
   c) 67.0% to 74.0% (w/w) of a lower alcohol selected from the group consisting of methanol, ethanol, n-propanol, isopropanol, n-butanol, isobutanol, sec-butanol, and tert-butanol;
   d) 0.6% to 1.4% (w/w) of a gelling agent, which gelling agent is an anionic polymer that has been neutralized with an amount of neutralizer sufficient to form a gel; and
   e) water,
to an area of skin of the human male.

2. The method of claim 1, wherein the lower alcohol is ethanol.

3. The method of claim 2, wherein the ethanol is absolute ethanol.

4. The method of claim 2, wherein the ethanol is 95% (v/v) ethanol.

5. The method of claim 1, wherein the anionic polymer is a carbomer.

6. The method of claim 1, wherein the neutralizer is selected from the group consisting of: sodium hydroxide, ammonium hydroxide, potassium hydroxide, arginine, aminomethyl propanol, tetrahydroxypropyl ethylenediamine, triethanolamine, tromethamine, PEG-15 cocamine, diisopropanolamine and triisopropanolamine and combinations thereof.

7. The method of claim 6, wherein the neutralizer is sodium hydroxide.

8. The method of claim 1, wherein the testosterone in the gel pharmaceutical composition is in the range of 1.50% to 1.70% (w/w) testosterone.

9. The method of claim 1, wherein the gel pharmaceutical composition consists of:
   a) 1.3% to 1.7% (w/w) testosterone;
   b) 0.9% to 1.0% (w/w) isopropyl myristate;
   c) 67.0% to 74.0% (w/w) of absolute ethanol;
   d) 0.6% to 1.4% (w/w) of a carbomer which has been neutralized with sodium hydroxide; and
   e) water.

10. The method of claim 1, wherein the gel pharmaceutical composition consists of:
   a) 1.3% to 1.7% (w/w) testosterone;
   b) 0.9% to 1.0% (w/w) isopropyl myristate;
   c) 67.0% to 74.0% (w/w) of absolute ethanol;
   d) 0.6% to 1.4% (w/w) of a carbomer;
   e) an amount of sodium hydroxide sufficient to form a gel; and
   f) water.

11. The method of claim 1, wherein the therapeutically effective dose of the gel pharmaceutical composition is 2.5 grams.

12. The method of claim 11, wherein the amount of testosterone applied in the applying step is 40.5 milligrams.

13. The method of claim 1, wherein a circulating serum concentration of testosterone greater than about 300 ng per dl serum is achieved in the human male during a time period beginning about 0.5 hours after said applying and ending about 24 hours after said applying.

14. A method of treating hypogonadism in a human male comprising applying a therapeutically effective dose of a gel pharmaceutical composition consisting of:
   a) 1.62% (w/w) testosterone;
   b) 1.0% (w/w) isopropyl myristate;
   c) 68.1% (w/w) dehydrated ethanol;
   d) 1.0% (w/w) of a gelling agent, which gelling agent is an anionic polymer that has been neutralized with an amount of neutralizer sufficient to form a gel; and
   e) water
to an area of skin of the human male.

15. The method of claim 14, wherein the gel pharmaceutical composition consists of:
   a) 1.62% (w/w) testosterone;
   b) 1.0% (w/w) isopropyl myristate;
   c) 68.1% (w/w) absolute ethanol;
   d) 1.0% (w/w) of a carbomer which has been neutralized with sodium hydroxide; and
   e) water.

16. The method of claim 14, wherein the gel pharmaceutical composition consists of:
   a) 1.62% (w/w) testosterone;
   b) 1.0% (w/w) isopropyl myristate;
   c) 68.1% (w/w) absolute ethanol;
   d) 1.0% (w/w) of a carbomer;
   e) an amount of sodium hydroxide sufficient to form a gel; and
   f) water.

17. The method of claim 14, wherein the amount of testosterone applied in the applying step is 40.5 milligrams.

18. The method of claim 14, wherein the ethanol is 95% (v/v) ethanol.

19. The method of claim 14, wherein the anionic polymer is a carbomer.

20. The method of claim 14, wherein the neutralizer is selected from the group consisting of: sodium hydroxide, ammonium hydroxide, potassium hydroxide, arginine, aminomethyl propanol, tetrahydroxypropyl ethylenediamine, triethanolamine, tromethamine, PEG-15 cocamine, diisopropanolamine and triisopropanolamine and combinations thereof.

21. The method of claim 20, wherein the neutralizer is sodium hydroxide.

22. The method of claim 14, wherein the therapeutically effective dose of the gel pharmaceutical composition is 2.5 grams.

23. The method of claim 14, wherein a circulating serum concentration of testosterone greater than about 300 ng per dl serum is achieved in the human male during a time period beginning about 0.5 hours after said applying and ending about 24 hours after said applying.

24. The method of claim 15, wherein the therapeutically effective dose of the gel pharmaceutical composition is 2.5 grams.

25. The method of claim 24, wherein the amount of testosterone applied in the applying step is 40.5 milligrams.

26. The method of claim 15, wherein a circulating serum concentration of testosterone greater than about 300 ng per dl serum is achieved in the human male during a time period beginning about 0.5 hours after said applying and ending about 24 hours after said applying.

27. The method of claim 16, wherein the therapeutically effective dose of the gel pharmaceutical composition is 2.5 grams.

28. The method of claim 26, wherein the amount of testosterone applied in the applying step is 40.5 milligrams.

29. The method of claim 16, wherein a circulating serum concentration of testosterone greater than about 300 ng per dl serum is achieved in the human male during a time period beginning about 0.5 hours after said applying and ending about 24 hours after said applying.

* * * * *